United States Patent
Almstetter et al.

(10) Patent No.: US 10,752,624 B2
(45) Date of Patent: *Aug. 25, 2020

(54) KINASE INHIBITORS

(71) Applicant: Origenis GmbH, Martinsried (DE)

(72) Inventors: Michael Almstetter, Martinsried (DE);
Michael Thormann, Martinsried (DE);
Andreas Treml, Martinsried (DE);
Roland Koestler, Martinsried (DE);
Nasser Yehia, Martinsried (DE)

(73) Assignee: ORIGENIS GMBH, Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/983,423

(22) Filed: May 18, 2018

(65) Prior Publication Data
US 2018/0305356 A1    Oct. 25, 2018

Related U.S. Application Data

(63) Continuation of application No. 14/436,152, filed as application No. PCT/EP2013/003147 on Oct. 18, 2013, now Pat. No. 10,000,482.

(60) Provisional application No. 61/795,571, filed on Oct. 19, 2012.

(51) Int. Cl.
*C07D 471/04*    (2006.01)
*A61K 31/444*    (2006.01)

(52) U.S. Cl.
CPC .......... *C07D 471/04* (2013.01); *A61K 31/444* (2013.01)

(58) Field of Classification Search
CPC .......................... C07D 471/04; A61K 31/444
USPC ........................................................ 514/212
See application file for complete search history.

(56) References Cited

U.S. PATENT DOCUMENTS

| | | | |
|---|---|---|---|
| 6,531,475 B1 | 3/2003 | Haddach et al. | |
| 9,449,535 B2 | 9/2016 | Henderson | |
| 9,499,535 B2 * | 11/2016 | Thormann | ............ C07D 471/04 |
| 10,000,482 B2 | 6/2018 | Almstetter et al. | |
| 2006/0094707 A1 | 5/2006 | Chaturvedula et al. | ...... 514/250 |
| 2011/0257137 A1 * | 10/2011 | Borchardt | ............ C07D 471/04 514/171 |

FOREIGN PATENT DOCUMENTS

| | | |
|---|---|---|
| CA | 1148159 | 6/1983 |
| JP | 2008519074 | 6/2008 |
| JP | 2010143829 | 7/2010 |
| WO | WO 98/029413 A1 | 7/1998 |
| WO | WO 02/074774 A1 | 9/2002 |
| WO | WO 05/079195 A2 | 9/2005 |
| WO | WO 06/107771 A2 | 10/2006 |
| WO | WO2006107851 | 10/2006 |
| WO | WO 08/144253 A1 | 11/2008 |
| WO | WO 09/152133 A1 | 12/2009 |
| WO | WO 09/155527 A2 | 12/2009 |
| WO | WO 10/030785 A2 | 3/2010 |
| WO | WO-2010030785 A2 * | 3/2010 ........... C07D 471/04 |
| WO | WO 10/106333 A1 | 9/2010 |
| WO | WO 11/068881 A1 | 6/2011 |
| WO | WO 11/068899 A1 | 6/2011 |
| WO | WO 11/112731 A2 | 9/2011 |
| WO | WO 12/143143 A1 | 10/2012 |
| WO | WO-2012143143 A1 * | 10/2012 ........... C07D 471/04 |

OTHER PUBLICATIONS

Ombretta Lenzi et al . Synthesis, structural-Affinity, and molecular modeling studies of novel pyrazol0 [3,4c] quinoline derivative as adosonine receptor antagonists , (Year: 2011).*
Colotta et al. "Synthesis and Structure-Activity Relationships of a New Set of 2-Arylpyrazolo[3,4-c] quinoline Derivatives as Adenosine Receptor Antagonists" Journal of Medicinal Chemistry 2000 43:3118-3124 [XP002717138].
Lenzi et al. "Synthesis, Structure-Affinity Relationships, and Molecular Modeling Studies of Novel Pyrazolo[3,4-c] quinoline Derivatives as Adenosine Receptor Antagonists" Bioorganic & Medicinal Chemistry 2011 19:3757-3768 [XP028378041].
Nagarajan, K. and Shah, R. K. "Condensed Heterotricycles: Synthesis of Pyrazolo[3,4-c] quinoline Derivatives" Indian Journal of Chemistry 1992 31B:316-321 [XP009174674].
Database Registry [Online] Chemical Abstracts Service, Columbus, Ohio: XP-002658260 retrieved from Registry Database Accession No. 304872-03-5 Nov. 29, 2000.
Database Registry [Online] Chemical Abstracts Service, Columbus, Ohio: XP-002658261 retrieved from Registry Database Accession No. 327100-02-7 Mar. 14, 2011.
Database Registry [Online] Chemical Abstracts Service, Columbus, Ohio: XP-002658262 retrieved from Registry Database Accession No. 368839-23-0 Nov. 11, 2001.

(Continued)

*Primary Examiner* — Rita J Desai
(74) *Attorney, Agent, or Firm* — Licata & Tyrrell P.C.

(57) ABSTRACT

The present invention relates to novel compounds of formula (I)

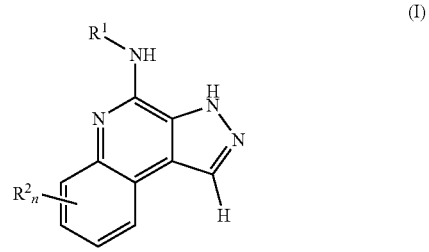

that are capable of inhibiting one or more kinases, especially SYK (Spleen Tyrosine Kinase), LRRK2 (Leucine-rich repeat kinase 2) and/or MYLK (Myosin light chain kinase) or mutants thereof. The compounds find applications in the treatment of a variety of diseases. These diseases include autoimmune diseases, inflammatory diseases, bone diseases, metabolic diseases, neurological and neurodegenerative diseases, cancer, cardiovascular diseases, allergies, asthma, alzheimer's disease, parkinson's disease, skin disorders, eye diseases, infectious diseases and hormone-related diseases.

7 Claims, No Drawings

(56) References Cited

OTHER PUBLICATIONS

Database Registry [Online] Chemical Abstracts Service, Columbus, Ohio: XP-002658263 retrieved from Registry Database Accession No. 382610-70-0 Jan. 14, 2002.
Database Registry [Online] Chemical Abstracts Service, Columbus, Ohio: XP-002658264 retrieved from Registry Database Accession No. 383161-12-4 Jan. 15, 2002.
Office Communication dated Sep. 29, 2014 from U.S. Appl. No. 13/506,509, filed Apr. 23, 2012.
Office Communication dated Feb. 26, 2015 from U.S. Appl. No. 13/506,509, filed Apr. 23, 2012.
Office Communication dated May 18, 2015 from U.S. Appl. No. 13/506,509, filed Apr. 23, 2012.
European Search Report from EP11003373.5, dated Sep. 26, 2011.
International Search Report from PCT/EP2012/001736, dated Apr. 23, 2012.
International Search Report from PCT/EP2013/003147, dated Dec. 16, 2013.
Office Communication dated Nov. 2, 2015 from U.S. Appl. No. 13/506,509, filed Apr. 23, 2012.
Office Communication dated Jan. 11, 2016 from U.S. Appl. No. 13/506,509, filed Apr. 23, 2012.
Office Communication dated Mar. 28, 2016 from U.S. Appl. No. 13/506,509, filed Apr. 23, 2012.
Office Communication dated May 20, 2016 from U.S. Appl. No. 13/506,509, filed Apr. 23, 2012.
Database Registry [Online] Chemical Abstracts Service, Columbus, Ohio: XP-002658260 retrieved from Registry Database Accession No. 304879-41-2.
Office Communication dated Jun. 21, 2016 from U.S. Appl. No. 14/436,152, filed Apr. 16, 2015.
Office Communication dated Sep. 30, 2016 from U.S. Appl. No. 14/436,152, filed Apr. 16, 2015.
Office Communication dated Apr. 10, 2017 from U.S. Appl. No. 14/436,152, filed Apr. 16, 2015.
Office Communication dated Sep. 18, 2017 from U.S. Appl. No. 14/436,152, filed Apr. 16, 2015.
Office Communication dated Feb. 22, 2018 from U.S. Appl. No. 14/436,152, filed Apr. 16, 2015.

* cited by examiner

KINASE INHIBITORS

This application is a continuation of U.S. Serial application Ser. No. 14/436,152 filed Apr. 16, 2015, which is the U.S. National Phase of International Application No. PCT/EP2013/003147 filed Oct. 18, 2013, which claims priority from U.S. Provisional Application No. 61/795,571 filed Oct. 19, 2012, the teachings of which are incorporated herein by reference in their entireties.

The present invention relates to novel compounds that are capable of inhibiting one or more kinases, especially SYK (Spleen Tyrosine Kinase), LRRK2 (Leucine-rich repeat kinase 2) and/or MYLK (Myosin light chain kinase) or mutants thereof. The compounds find applications in the treatment of a variety of diseases. These diseases include autoimmune diseases, inflammatory diseases, bone diseases, metabolic diseases, neurological and neurodegenerative diseases, cancer, cardiovascular diseases, allergies, asthma, alzheimer's disease, parkinson's disease, skin disorders, eye diseases, infectious diseases and hormone-related diseases.

The present invention provides one or more compounds of formula (I):

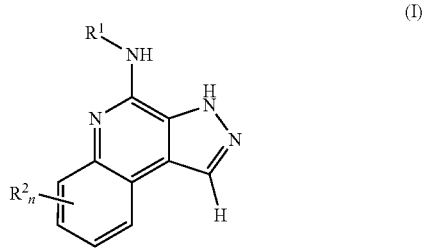

wherein
n is 1, 2, 3 or 4;
$R^1$ is an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group; and
the groups $R^2$ are independently from each other selected from halogen, OH, $C_{1-6}$ alkyl, $C_{1-6}$ heteroalkyl (such as e.g. —OMe, —SMe, —SOMe, —$SO_2Me$) or $C_{3-6}$ cycloalkyl;
or a pharmaceutically acceptable salt, ester, solvate or hydrate or a pharmaceutically acceptable formulation thereof.

The expression alkyl refers to a saturated, straight-chain or branched hydrocarbon group that contains from 1 to 20 carbon atoms, preferably from 1 to 12 carbon atoms, especially from 1 to 6 (e.g. 1, 2, 3 or 4) carbon atoms, for example a methyl, ethyl, propyl, iso-propyl, n-butyl, iso-butyl, sec-butyl, tert-butyl, n-pentyl, iso-pentyl, n-hexyl, 2,2-dimethylbutyl or n-octyl group.

The expressions alkenyl and alkynyl refer to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulfur atom (preferably by an oxygen, sulfur or nitrogen atom) or by a SO or a $SO_2$ group. The expression heteroalkyl furthermore refers to a carboxylic acid or to a group derived from a carboxylic acid, such as, for example, acyl, acylalkyl, alkoxy-carbonyl, acyloxy, acyloxyalkyl, carboxyalkylamide or alkoxycarbonyloxy.

Preferably, a heteroalkyl group contains from 1 to 12 carbon atoms and from 1 to 4 hetero atoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2 or 3 (especially 1 or 2) hetero atoms selected from oxygen, nitrogen and sulphur (especially oxygen and nitrogen). The term $C_1$-$C_6$ heteroalkyl refers to a heteroalkyl group containing from 1 to 6 carbon atoms and 1, 2 or 3 heteroatoms selected from 0, S and/or N (especially O and/or N). The term $C_1$-$C_4$ heteroalkyl refers to a heteroalkyl group containing from 1 to 4 carbon atoms and 1, 2 or 3 heteroatoms selected from 0, S and/or N (especially O and/or N). Furthermore, the term heteroalkyl refers to groups in which one or more hydrogen atoms have been replaced by a halogen atom (preferably F or Cl).

Examples of heteroalkyl groups are groups of formulae:
$R^a$—O—$Y^a$—, $R^a$—S—$Y^a$—, $R^a$—SO—$Y^a$—, $R^a$—$SO_2$—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—(=$NR^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$, $R^a$—N($R^b$)—CO—S—$Y^a$—, $R^a$—S—CO—O—$Y^a$—, $R^a$—C—S—Y, —S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—,
wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; Rd being a hydrogen atom, a $C_1$-$C_6$ alkyl, a $C_2$-$C_6$ alkenyl or a $C_2$-$C_6$ alkynyl group and $Y^a$ being a bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, —$CH_2CH_2OH$, —$CH_2OH$, —$SO_2Me$, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, $=$O, SH, $=$S, $NH_2$, $=$NH, $N_3$ or $NO_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulfur atom (preferably by an oxygen, sulfur or nitrogen atom) or a SO group or a $SO_2$ group. A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups that are substituted by fluorine, chlorine, bromine or iodine atoms or by OH, $=$O, SH, $=$S, $NH_2$, $=$NH, $N_3$ or $NO_2$ groups. Examples are a piperidyl, prolinyl, imidazolidinyl, piperazinyl, morpholinyl, urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom) or a SO group or a $SO_2$ group. A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenylheterocycloalkyl, allkynylheterocycloalkyl, hetero-alkylcycloallkyl, heteroalkylheterocycloalkyl and heteroalkylheterocycloalkenyl, the cyclic groups being saturated or mono-, di- or tri-unsaturated.

The expression aryl refers to an aromatic group that contains one or more rings containing from 6 to 14 ring carbon atoms, preferably from 6 to 10 (especially 6) ring carbon atoms. The expression aryl refers furthermore to groups that are substituted by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6 or 9 or 10) ring atoms, and contains one or more (preferably 1, 2, 3 or 4) oxygen, nitrogen, phosphorus or sulfur ring atoms (preferably O, S or N). The expression heteroaryl refers furthermore to groups that are substituted by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms have been replaced by an oxygen, nitrogen, silicon, selenium, phosphorus, boron or sulfur atom (preferably oxygen, sulfur or nitrogen), that is to say to groups containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylallkynylheterocycloalkyl, arylalkylhetero-cycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, hetero-arylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylhetero-cycloalkyl groups, the cyclic groups being saturated or mono-, di- or tri-unsaturated. Specific examples are a tetrahydroisoquinolinyl, benzoyl, 2- or 3-ethylindoyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups that are substituted by fluorine, chlorine, bromine or iodine atoms or by OH, =O, SH, =S, $NH_2$, =NH, $N_3$ or $NO_2$ groups.

The expression "optionally substituted" especially refers to groups that are optionally substituted by fluorine, chlorine, bromine or iodine atoms or by OH, =O, SH, =S, $NH_2$, =NH, $N_3$ or $NO_2$ groups. This expression refers furthermore to groups that may be substituted by one, two, three or more unsubstituted $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl groups. This expression refers furthermore especially to groups that may be substituted by one, two, three or more unsubstituted $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

Preferred substituents are F, Cl, Br, OH, SH, =O, $NH_2$, $C_{1-4}$ alkyl, $C_{1-4}$ heteroalkyl cyclopropyl, $SF_5$, NO and $NO_2$.

Moreover preferred substituents are F, Cl, Br, OH, SH, =O, $NH_2$, $C_{1-4}$ alkyl (e.g. methyl, ethyl, t-butyl), $NMe_2$, $CONH_2$, $CH_2NMe_2$, $NHSO_2Me$, $C(CH_3)_2CN$, COMe, OMe, SMe, COOMe, COOEt, $CH_2COOH$, $OCH_2COOH$, COOH, SOMe, $SO_2Me$, cyclopropyl, $SO_2NH_2$, $SO_2NHMe$, $SO_2CH_2CH_2OH$, $NHCH_2CH_2OH$, $CH_2CH_2OCH_3$, $SF_5$, $SO_2NMe_2$, NO, $NO_2$, $OCF_3$, $SO_2CF_3$, CN or $CF_3$.

Especially preferred substituents are F, Cl, Br, Me, OMe, CN or $CF_3$.

The term halogen preferably refers to F, Cl, Br or I.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

Preferred are compounds of formula (I) wherein n is 1 or 2, especially wherein n is 1.

Further preferred are compounds of formula (I) wherein $R^2$ is selected from —OMe, —F, —SOMe, —$SO_2Me$, cyclopropyl, methyl and —SMe.

Moreover preferred are compounds of formula (I) wherein $R^2$ is selected from —$SO_2Me$, —SOMe, cyclopropyl, methyl and —SMe.

Especially preferred are compounds of formula (I) wherein $R^2$ is —$SO_2Me$.

Moreover preferred are compounds of formula (I) wherein $R^2$ is Br or I which are preferably bound to the compound of formula (I) at position 7 or 8.

Further preferred are compounds of formula (I) wherein $R^1$ is an aryl, heteroaryl, cycloalkyl, heterocycloalkyl, alkylcycloalkyl, heteroalkylcycloalkyl, aralkyl or heteroaralkyl group, all of which may optionally be substituted.

Further preferred are compounds of formula (I) wherein $R^1$ is an aryl, heteroaryl, $CH_2$-aryl or $CH_2$-heteroaryl group, all of which may optionally be substituted.

Moreover preferred are compounds of formula (I) wherein $R^1$ is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three rings (especially two annullated rings) and 9 to 20 (especially 9 or 10) ring atoms. Preferably, the heteroatoms are selected from S, O and N, especially from N and O. Further preferably, the number of heteroatoms is 1 to 6 (especially 1, 2, 3 or 4).

Especially preferably, $R^1$ is an optionally substituted phenyl group or an optionally substituted heteroaryl group having one ring containing 5 or 6 ring atoms. Preferably this phenyl or heteroaryl group is substituted by one or more (especially one) $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl group(s). Preferably, the heteroatoms are selected from S, O and N, especially from N and O. Especially preferably, the phenyl or heteroaryl group is substituted by one or more (especially one) $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl group(s). Preferably, the heteroatoms are selected from S, O and N, especially from N and O.

Further preferred are compounds of formula (I) wherein $R^1$ is a group of formula —$CH_2$—Ar wherein Ar is an optionally substituted phenyl or naphthyl group or an optionally substituted heteroaryl group having one or two rings containing 5, 6, 7, 8, 9 or 10 ring atoms, or an optionally substituted arylheterocycloalkyl, heteroarylcycloalkyl or heteroarylheterocycloalkyl group containing two or three rings (especially two annullated rings) and 9 to 20 (especially 9 or 10) ring atoms. Preferably, the heteroatoms are selected from S, O and N, especially from N and O. Further preferably, the number of heteroatoms is 1 to 6 (especially 1, 2, 3 or 4).

Especially preferably, Ar is an optionally substituted phenyl group or an optionally substituted heteroaryl group having one ring containing 5 or 6 ring atoms. Preferably this phenyl or heteroaryl group is substituted by one or more (especially one) $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl group(s). Preferably, the heteroatoms are selected from S, O and N, especially from N and O. Especially preferably the phenyl or heteroaryl group is substituted by one or more (especially one) $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl group(s). Preferably, the heteroatoms are selected from S, O and N, especially from N and O.

Further preferably, $R^1$ is a group of formula $X^1$-$L^1$-$Y^1$ or a group of formula $X^1$-$L^1$-$Y^1$-$L^2$-$Z^1$ wherein $X^1$ is an optionally substituted phenyl group or an optionally substituted heteroaryl group containing 5 or 6 ring atoms and 1, 2, 3 or 4 heteroatoms selected from O, S and N;

$L^1$ is a bond or a group of formula —$CH_2$—, —C(=O)—, —SO—, —$SO_2$—, —NH—C(=O)—, —C(=O)—NH—; —C(=O)—O—, —O—C(=O)—, —NH—C(=O)—O—, —O—C(=O)—NH—, —NH—$SO_2$—NH—, —$CH_2$—NH—$CH_2$—, —NH—$SO_2$—, —$SO_2$—NH— or —NH—C(=O)—NH— (preferably, L is a bond or a group of formula —$CH_2$—, —C(=O)—, —$SO_2$— or —NH—C(=O)—NH—);

Y[1] is an optionally substituted phenyl group, an optionally substituted heteroaryl group containing 5 or 6 ring atoms and 1, 2, 3 or 4 heteroatoms selected from O, S and N, an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N (preferably, Y[1] is an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N);

L[2] is a bond or a group of formula —CH$_2$—, —C(=O)—, —SO—, —SO$_2$—, —NH—C(=O)—, —C(=O)—NH—; —C(=O)—O—, —O—C(=O)—, —NH—C(=O)—O—, —O—C(=O)—NH—, —NH—SO$_2$—NH—, —CH$_2$—NH—CH$_2$—, —NH—SO$_2$—, —SO$_2$—NH— or —NH—C(=O)—NH— (preferably, L[2] is a bond or a group of formula —CH$_2$—, —C(=O)—, —SO$_2$— or —NH—C(=O)—NH—; especially preferably, L[2] is a bond); and Z[1] is an optionally substituted phenyl group, an optionally substituted heteroaryl group containing 5 or 6 ring atoms and 1, 2, 3 or 4 heteroatoms selected from O, S and N, an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N (preferably, Z[1] is an optionally substituted $C_3$-$C_7$ cycloalkyl group or an optionally substituted heterocycloalkyl group containing 3, 4, 5, 6 or 7 ring atoms and 1, 2, 3 or 4 heteroatoms selected from O, S and N).

Especially preferably, R[1] is selected from the following groups:

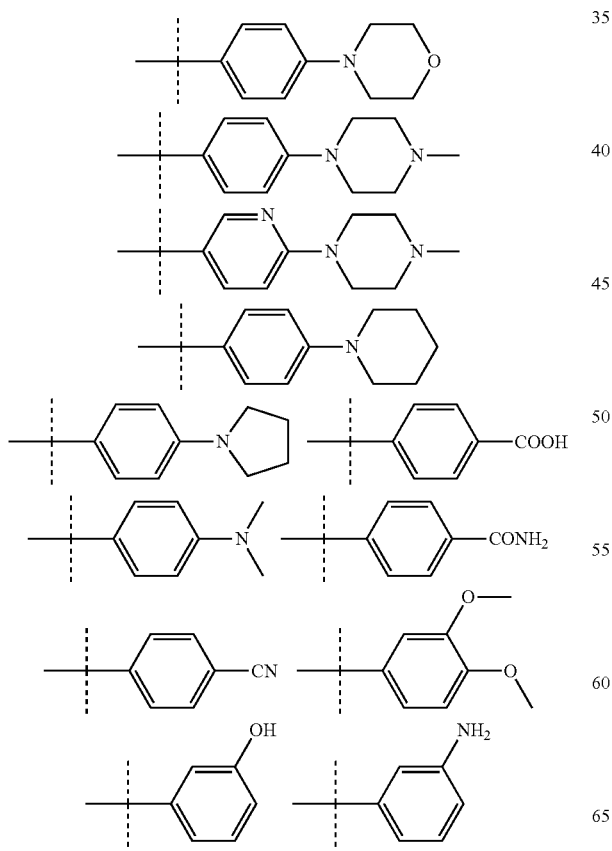

-continued

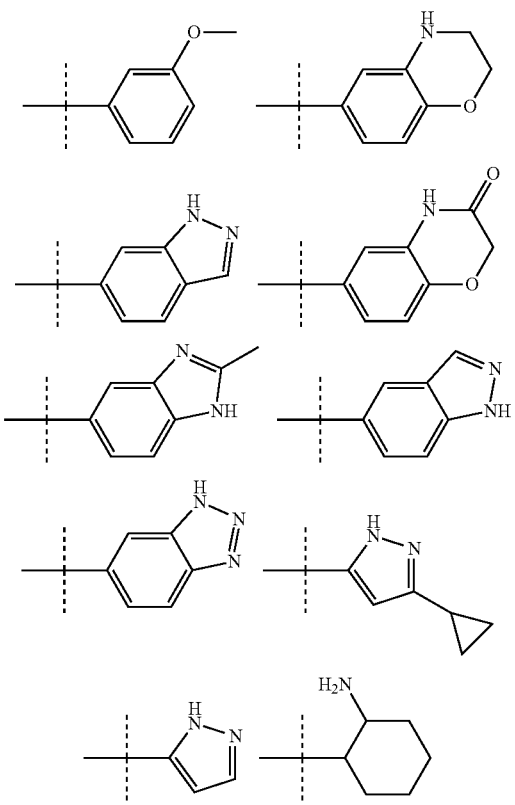

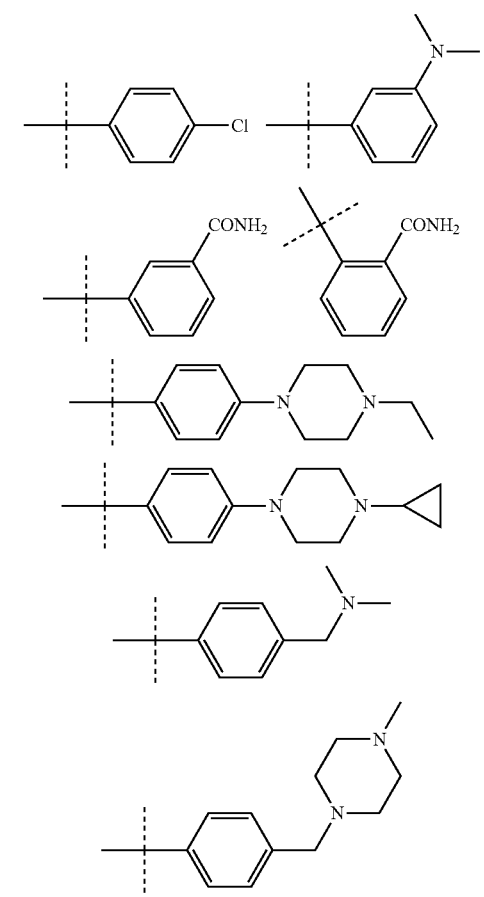

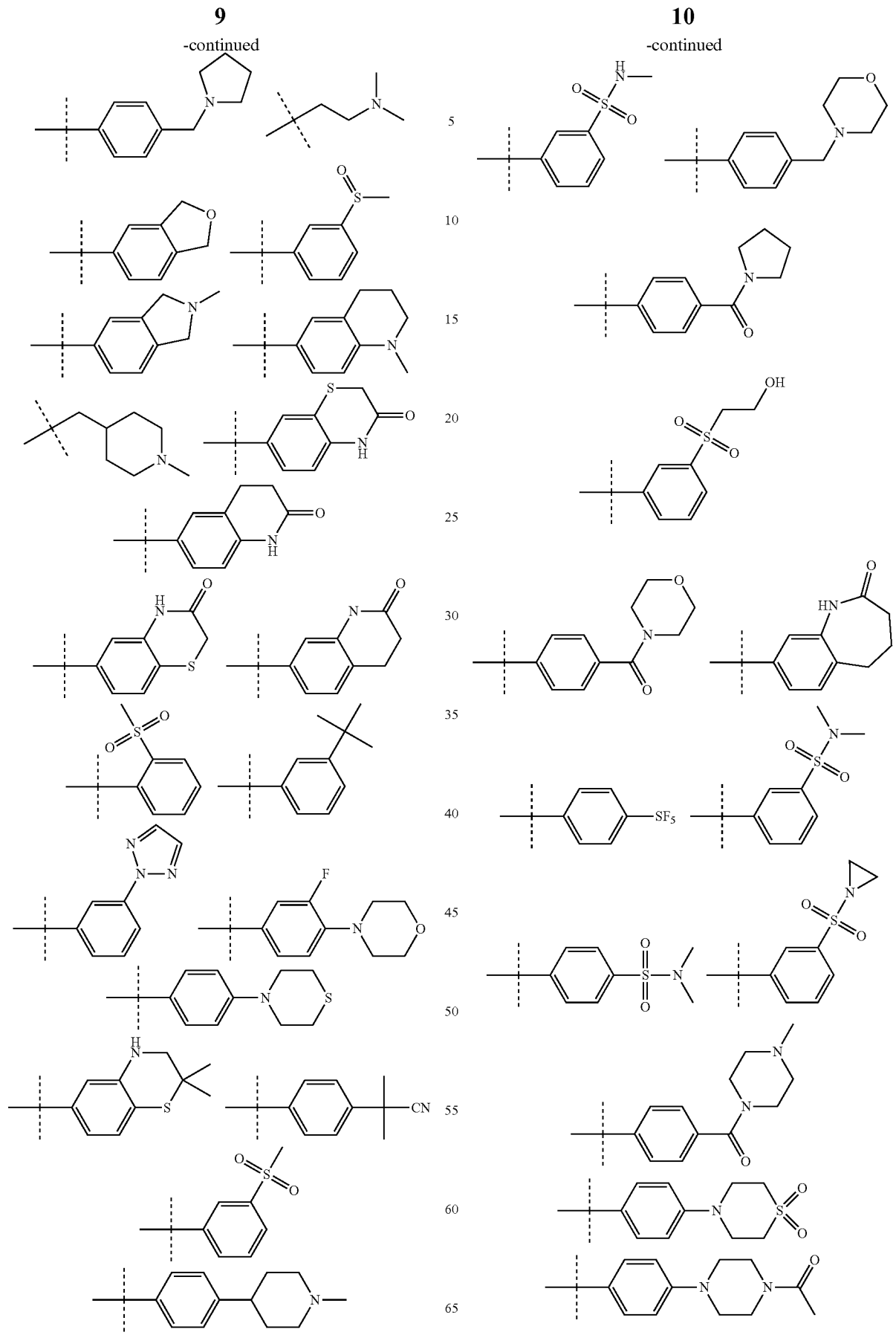

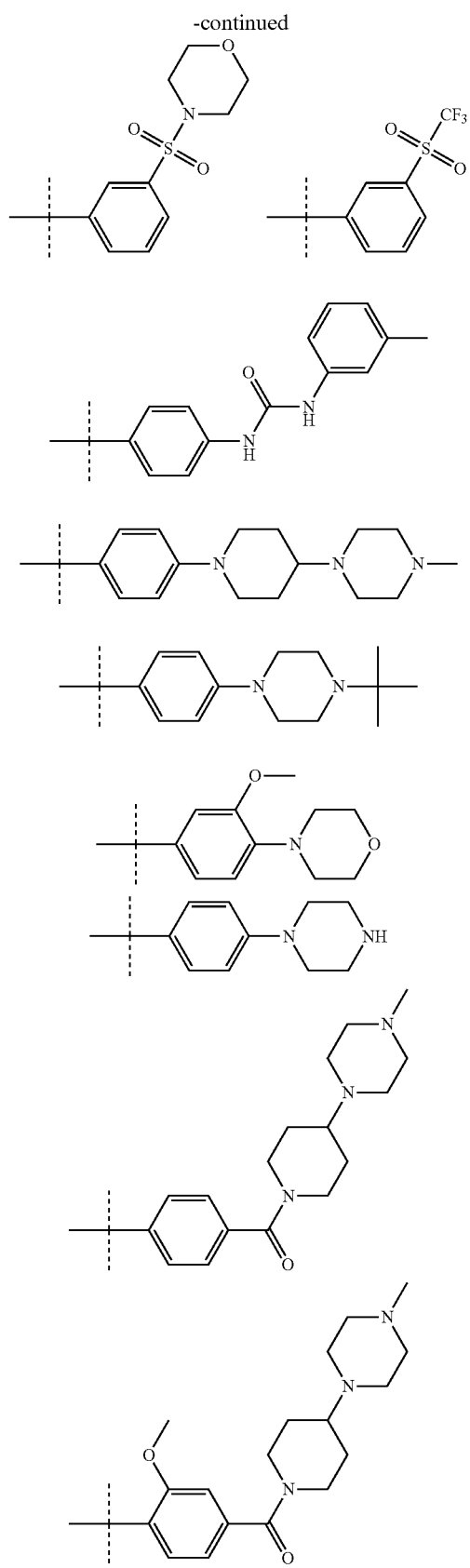
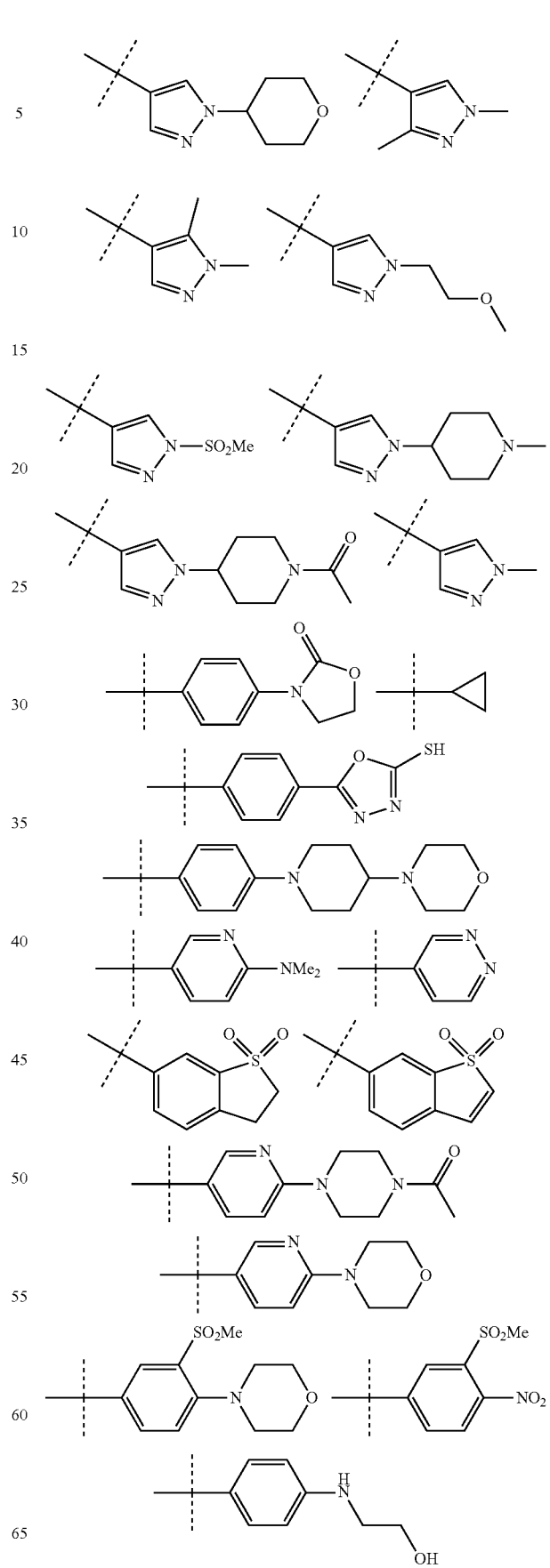
Moreover especially preferably, $R^1$ is selected from the following groups:

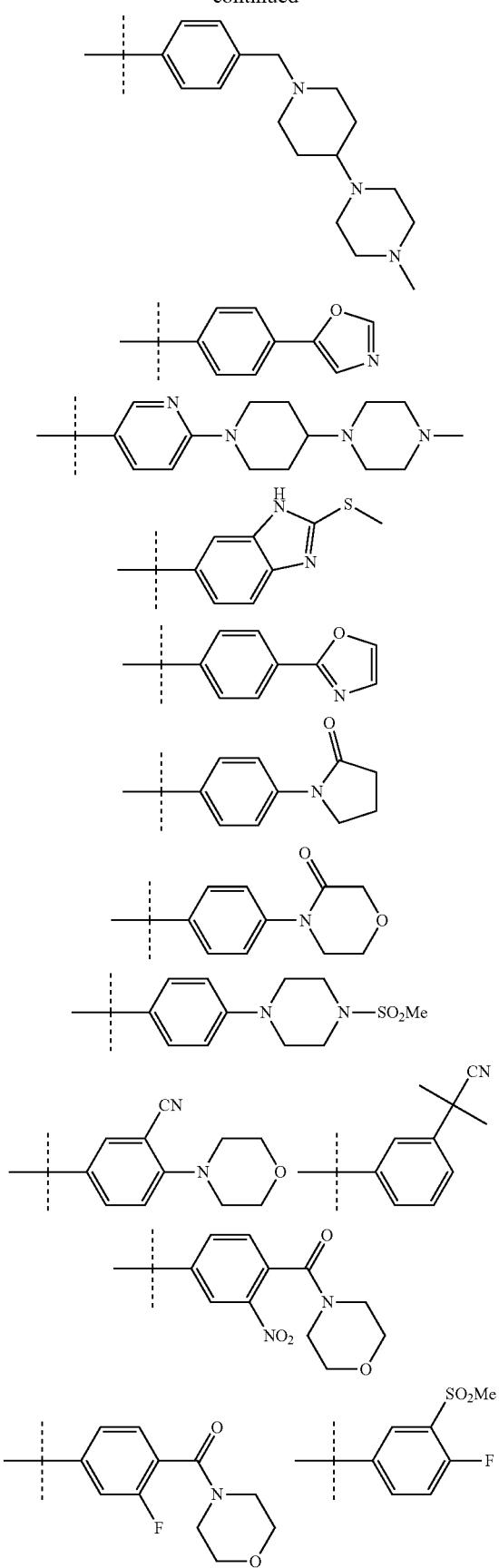
Moreover especially preferably, R¹ is selected from the following groups:
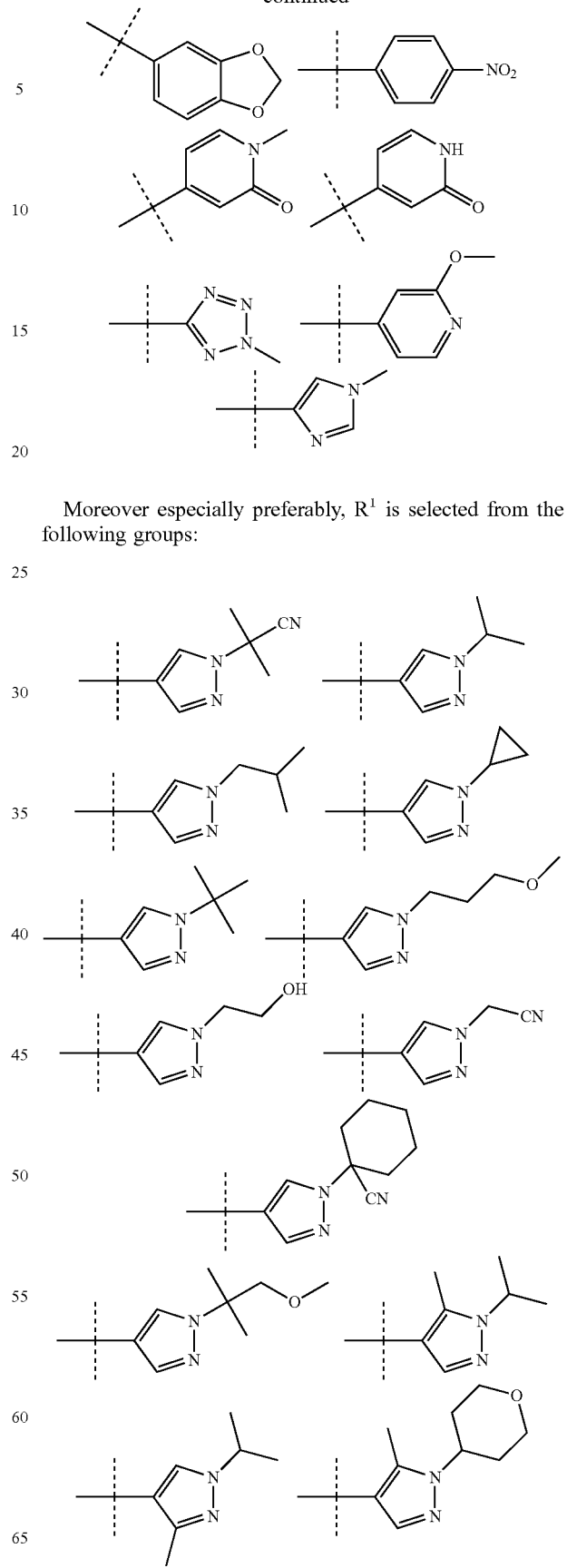

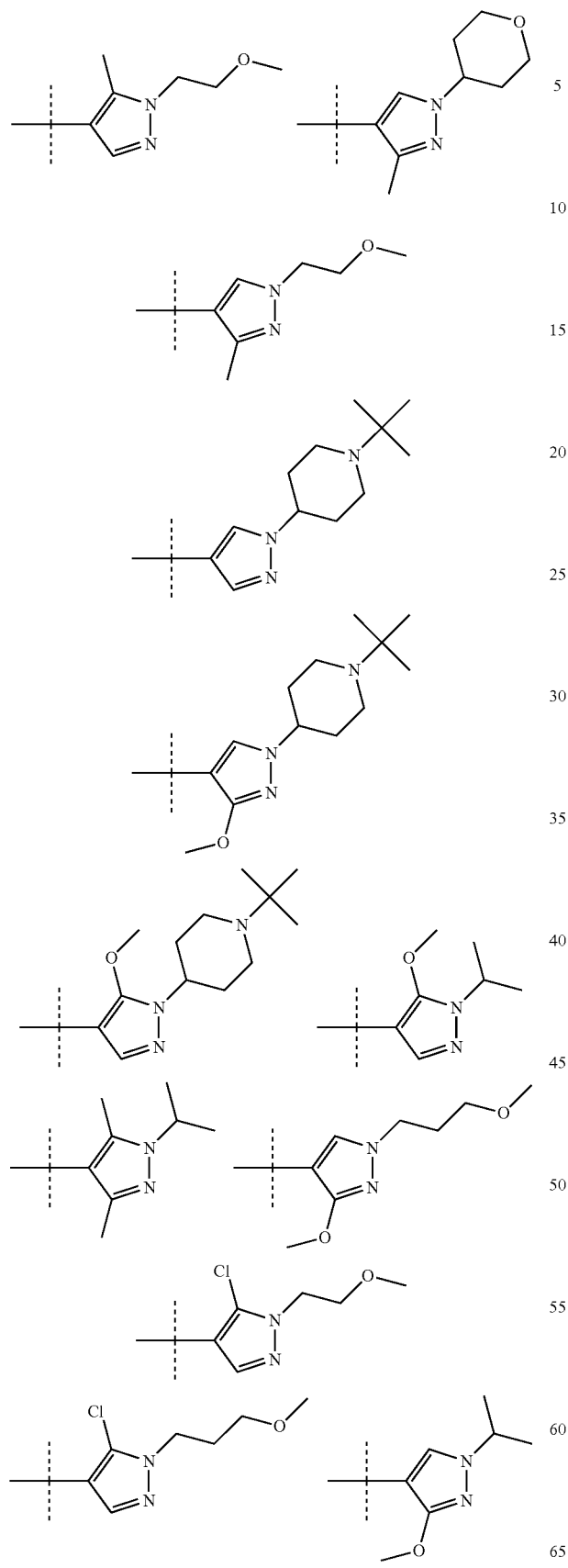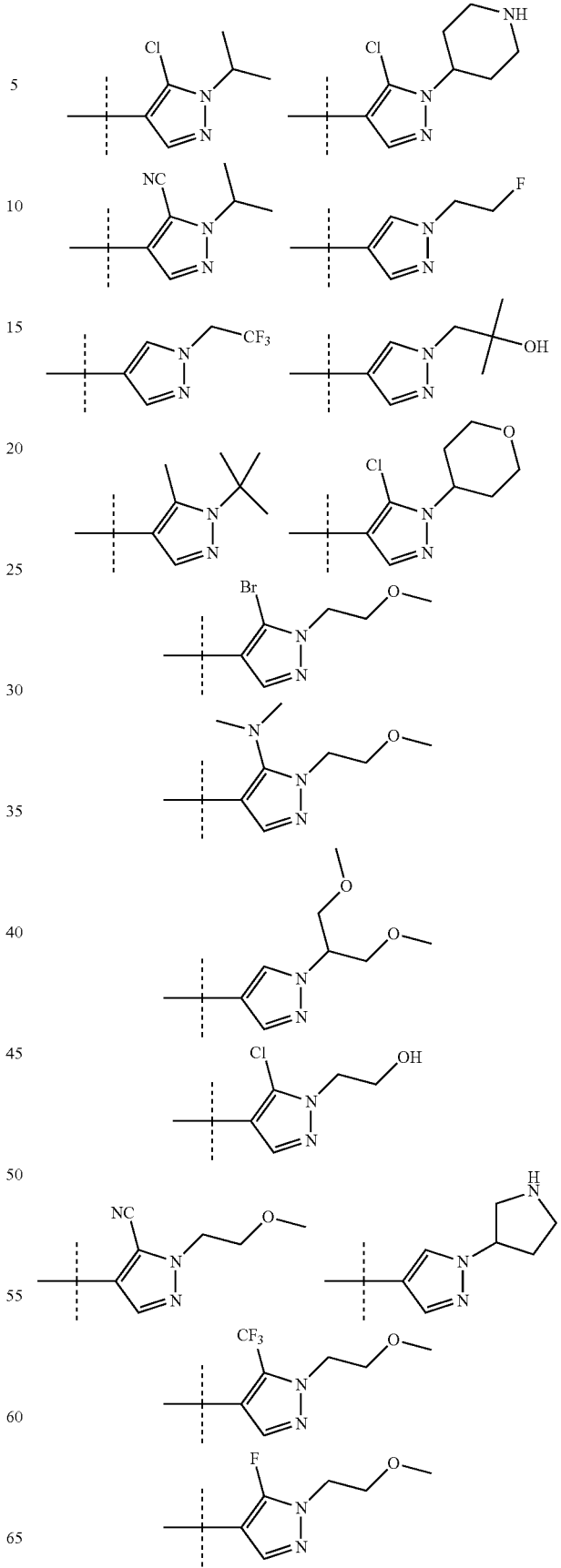

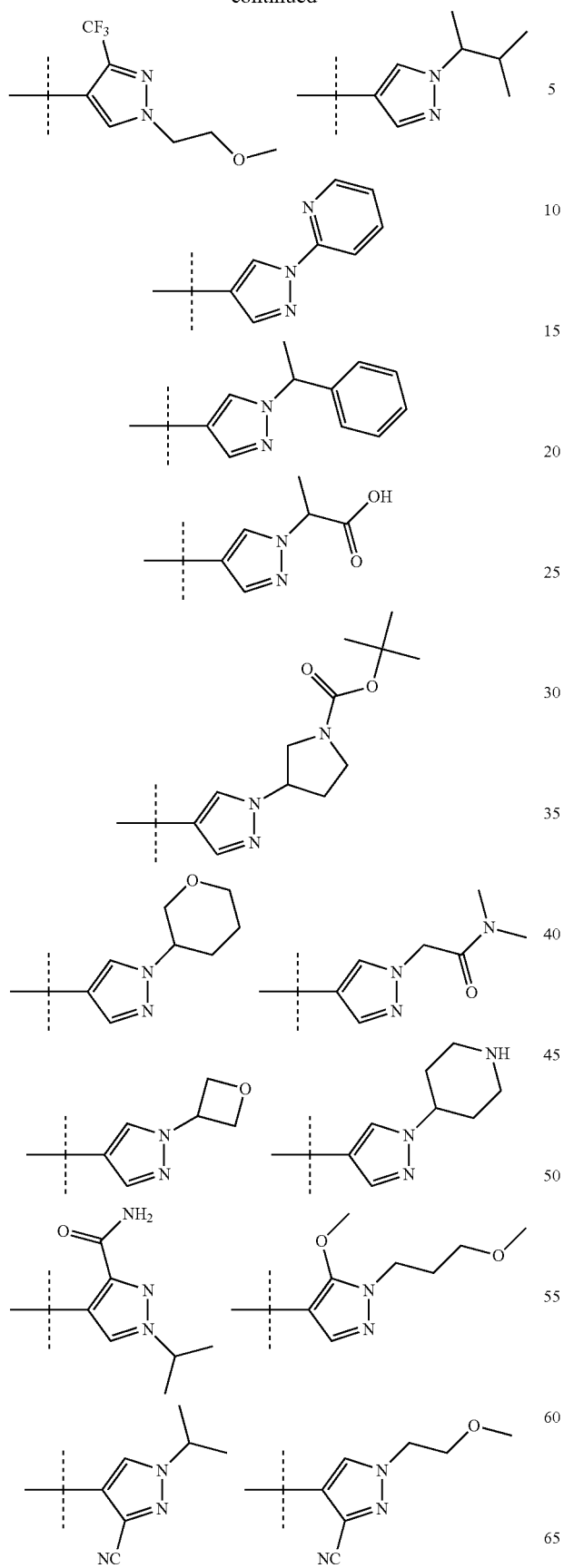
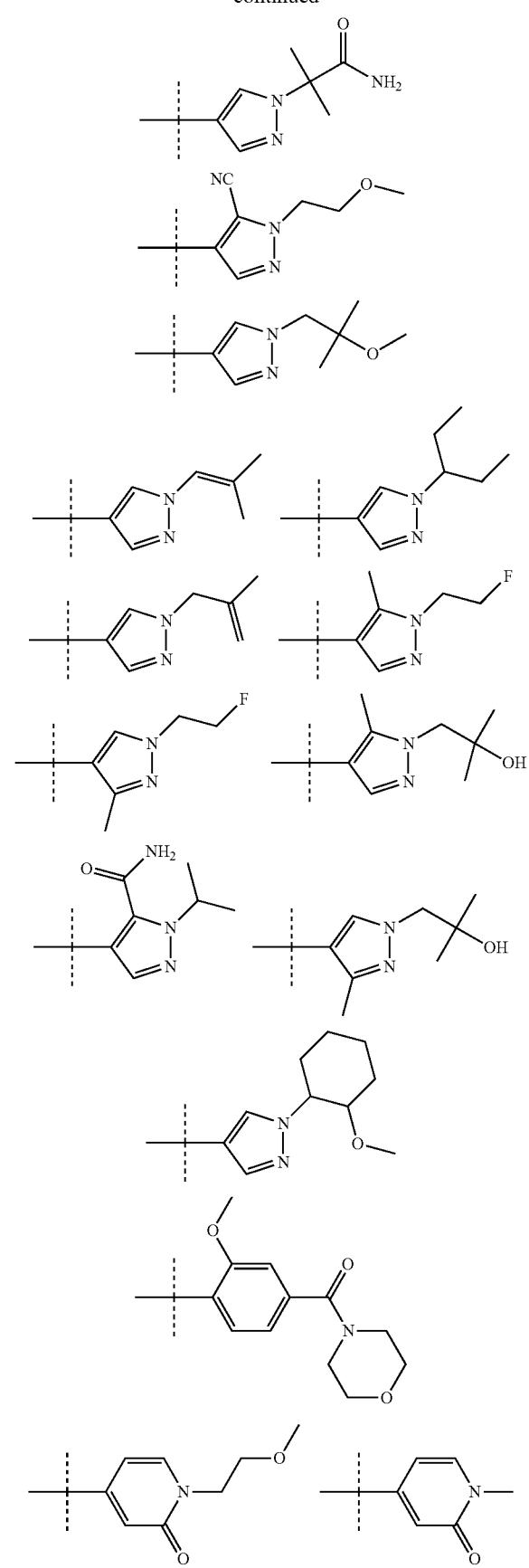

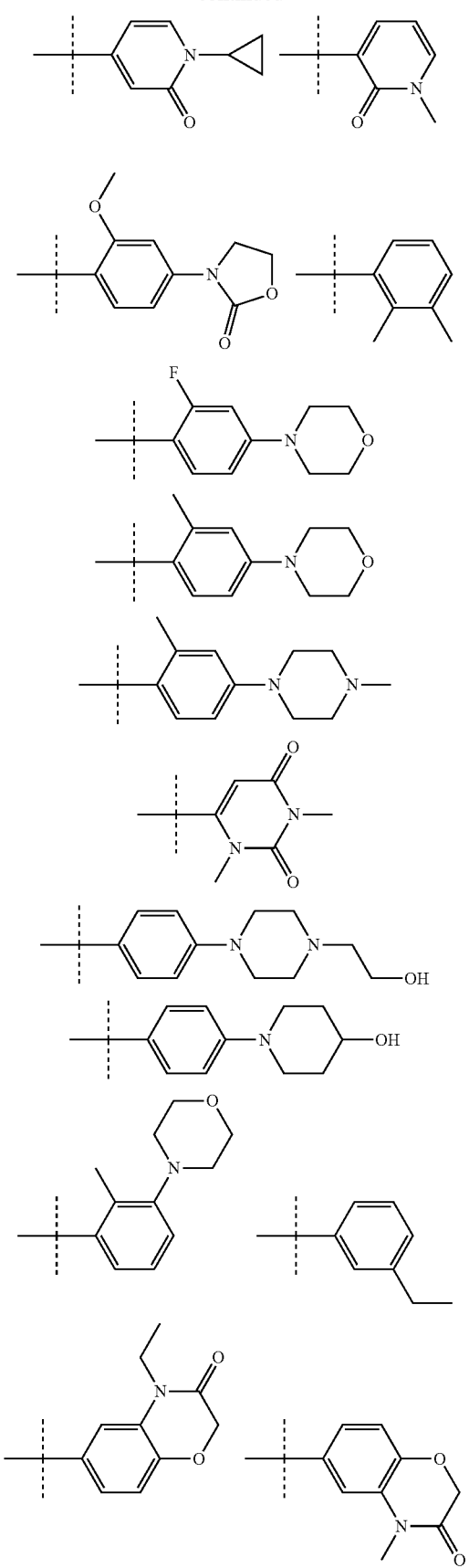
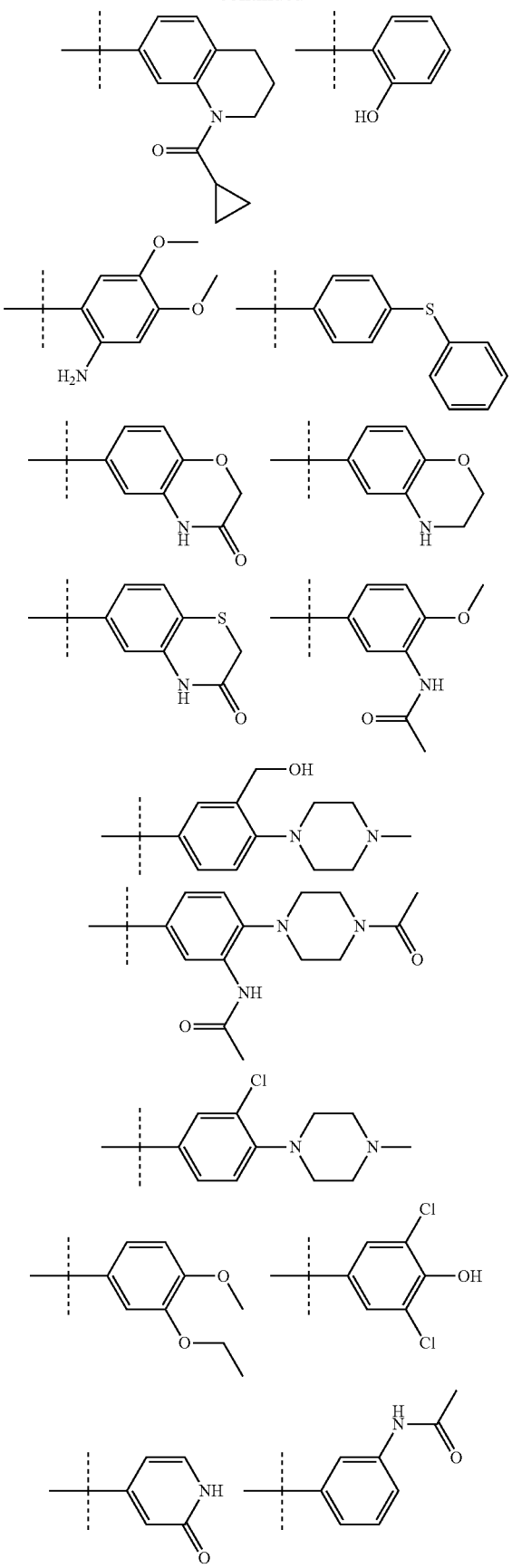

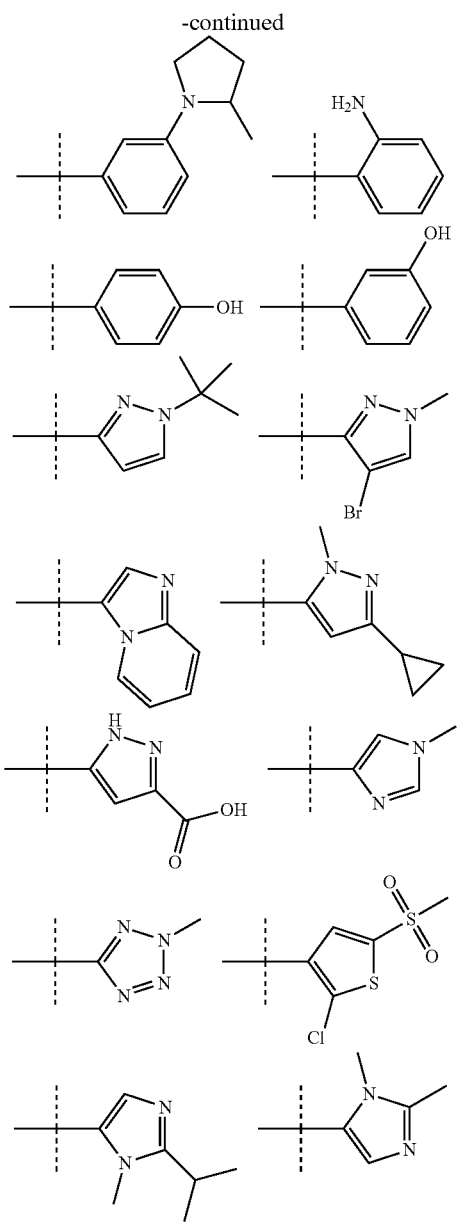

Further preferred are compounds of formula (I) wherein $R^1$ has the following structure:

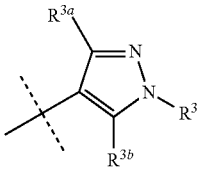

wherein $R^3$ is hydrogen or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

$R^{3a}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen); and $R^{3b}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen).

Further especially preferred are compounds of formula (I) wherein $R^1$ has the following structure:

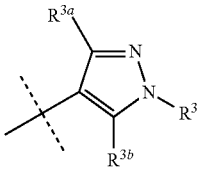

wherein $R^3$ is hydrogen or a $C_1$-$C_6$ alkyl; a $C_2$-$C_6$ alkenyl; a $C_2$-$C_6$ alkynyl, a $C_1$-$C_6$ alkoxy-$C_1$-$C_6$ alkyl, a $C_1$-$C_6$ heteroalkyl; a $C_3$-$C_7$ cycloalkyl; a $C_1$-$C_4$ alkyl-$C_3$-$C_7$ cycloalkyl; a $C_1$-$C_4$ heteroalkyl-$C_3$-$C_7$ cycloalkyl; a phenyl; a $C_1$-$C_4$ alkyl-phenyl or a $C_1$-$C_4$ heteroalkyl-phenyl group; or a heteroaryl group containing 5 or 6 ring atoms and 1, 2, 3 or 4 heteroatoms selected from O, S and N; a $C_1$-$C_4$ alkyl-heteroaryl or a $C_1$-$C_4$ heteroalkyl-heteroaryl group wherein the heteroaryl group contains 5 or 6 ring atoms and 1, 2, 3 or 4 heteroatoms selected from 0, S and N; or a heterocycloalkyl group containing 3, 4, 5, 6 or 7 ring atoms and 1, 2, 3 or 4 heteroatoms selected from O, S and N; or a $C_1$-$C_4$ alkyl-heterocycloalkyl or a $C_1$-$C_4$ heteroalkyl-heterocycloalkyl group wherein the heterocycloalkyl group contains 3, 4, 5, 6 or 7 ring atoms and 1, 2, 3 or 4 heteroatoms selected from O, S and N; all of which groups may optionally be substituted (especially preferably by a halogen or an OH, an =O, a CN, a phenyl, a $C_1$-$C_6$ alkyl or a $C_1$-$C_6$ heteroalkyl (such as e.g. COOH, $CONH_2$ or $OCH_3$) group);

$R^{3a}$ is hydrogen, halogen, a $C_1$-$C_6$ alkyl group (such as e.g. $CH_3$ or $CF_3$), a $C_1$-$C_6$ heteroalkyl group (such as e.g. $OCH_3$, $N(CH_3)_2$, CN or $CONH_2$) or an optionally substituted $C_3$-$C_7$ cycloalkyl group; and $R^{3b}$ is hydrogen, halogen, a $C_1$-$C_6$ alkyl group (such as e.g. $CH_3$ or $CF_3$), a $C_1$-$C_6$ heteroalkyl group (such as e.g. $OCH_3$, $N(CH_3)_2$, CN or $CONH_2$) or an optionally substituted $C_3$-$C_7$ cycloalkyl group.

Moreover preferred are compounds of formula (I) wherein $R^1$ has the following structure:

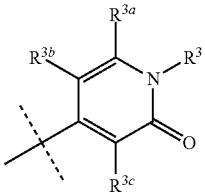

wherein $R^3$ is hydrogen or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group;

$R^{3a}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen);

$R^{3b}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen); and $R^{3c}$ is hydrogen, halogen, OH, SH, $NH_2$, or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group (preferably hydrogen or methyl; especially preferably hydrogen).

Especially preferred are compounds of formula (I) wherein $R^1$ has the following structure:

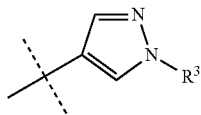

wherein $R^3$ is hydrogen or an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group.

Preferably, $R^3$ is an optionally substituted alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl group.

Moreover preferably, $R^3$ is an optionally substituted alkyl, heteroalkyl, cycloalkyl, heterocycloalkyl, alkylcycloalkyl or heteroalkylcycloalkyl group.

Especially preferably, $R^3$ is selected from the following groups:

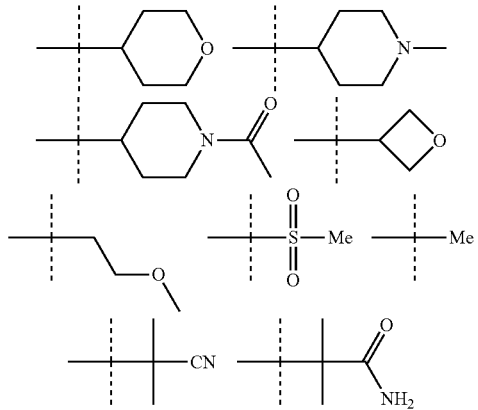

Especially preferred are compounds of formula (I), wherein $R^1$ is derived from the following amines:

m-toluidine; 3-(trifluoromethyl)aniline; 3,4,5-trimethoxyaniline; 1H-indazol-5-amine; aniline; 1H-indazol-6-amine; 3-chloroaniline; 7-methyl-1H-indazol-5-amine; 2-methoxyethan-1-amine; thiophen-2-ylmethanamine; 6-methyl-1H-indazol-5-amine; 2H-indazol-6-amine; methyl 4-aminobenzoate; 1H-benzo[d]imidazol-5-amine; 2H-indazol-7-amine; (1-methyl-1H-pyrrol-2-yl)methanamine; benzo[d][1,3]dioxol-5-amine; pyridin-3-amine; 1-methyl-1H-indazol-6-amine; 6-methoxypyridin-3-amine; 4-(4-methylpiperazin-1-yl)aniline; 4-(4-methyl-1,4-diazepan-1-yl)aniline; pyridin-2-amine; 5-bromopyridin-2-amine; isoquinolin-3-amine; 4-methylpyridin-2-amine; 4,6-dimethylpyridin-2-amine; 1H-indazol-7-amine; benzene-1,3-diamine; 6-amino-2H-benzo[b][1,4]oxazin-3(4H)-one; 1H-benzo[d][1,2,3]triazol-5-amine; 3-aminobenzimidamide; 4-(piperidin-1-yl)aniline; N1,N1-dimethylbenzene-1,4-diamine; 3-aminobenzamide; 3,4-dimethoxyaniline; 4-morpholinoaniline; 2-methyl-1H-benzo[d]imidazol-6-amine; 4-aminobenzoic acid; 4-aminobenzamide; 4-aminobenzonitrile; 3-methoxyaniline; 4-methoxyaniline; 3-aminobenzonitrile; benzo[c][1,2,5]thiadiazol-5-amine; 3-aminopyridin-2(1H)-one; 2-ethoxyaniline; 1H-pyrazol-3-amine; 5-amino-1H-pyrazole-4-carboxamide; 2-phenoxyaniline; 3-phenoxyaniline; 5-amino-1H-benzo[d]imnidazol-2(3H)-one; 1H-indol-5-amine; 4-(aminomethyl)aniline; 1H-indol-6-amine; N1,N1-dimethylbenzene-1,3-diamine; 3-phenyl-1H-pyrazol-5-amine; N1,N1-diethylbenzene-1,4-diamine; 4-(pyrrolidin-1-yl)aniline; 4H-1,2,4-triazole-3,5-diamine; 3-morpholinoaniline; 3-cyclobutyl-1H-pyrazol-5-amine; 4-(4,5-dihydro-1H-imidazol-2-yl)aniline; 4-(4-aminophenyl)morpholin-3-one; 2,2-dimethyl-3,4-dihydro-2H-benzo[b][1,4]thiazin-6-amine; 7-amino-3,4-dihydroquinolin-2(1H)-one; 6-amino-2H-benzo[b][1,4]thiazin-3(4H)-one; 5-(tert-butyl)-1H-pyrazol-3-amine; 3-methyl-1H-pyrazol-5-amine; 5-cyclopropyl-1H-pyrazol-3-amine; 4-(1H-tetrazol-5-yl)aniline; 2,3-dihydrobenzo[b][1,4]dioxin-6-amine; 4-(1-methylpiperidin-4-yl)aniline; 6-morpholinopyridin-3-amine; 4-(2-methoxyethoxy)aniline; 4-ethoxy-3-methoxyaniline; 1-(4-aminophenyl)pyrrolidin-2-one; 4-thiomorpholinoaniline; 5-aminobenzo[d]oxazol-2(3H)-one; 3,4-dihydro-2H-benzo[b][1,4]oxazin-6-amine; 7-aminoquinazolin-4-ol; 4-(4-aminophenyl)thiomorpholine 1,1-dioxide; 2-(4-aminophenyl)acetamide; 3-aminophenol; 3,4-diethoxyaniline; 6-amino-1H-benzo[d][1,3]oxazine-2,4-dione; 5-amino-2-methoxyphenol; 3-methoxy-N-methylaniline; N-(3-aminophenyl)acetamide; 1H-pyrazol-4-amine; 4-fluoro-3-methoxyaniline; 3-fluoro-4-methoxyaniline; 1-methyl-1H-benzo[d]imidazol-5-amine; 1-(3-aminophenyl)ethan-1-one; N-(4-aminophenyl)acetamide; 1H-pyrrolo[2,3-b]pyridin-6-amine; 3-aminobenzenesulfonamide; 4-aminobenzenesulfonamide; pyridine-2,6-diamine; 1,2,3-trimethyl-1H-indol-5-amine; pyrimidine-2,4-diamine; 5-(methylthio)-4H-1,2,4-triazol-3-amine; 5-cyclopropyl-4H-1,2,4-triazol-3-amine; N-(5-amino-2-methoxyphenyl)acetamide; 1H-benzo[d]imidazol-2-amine; 1H-imidazol-2-amine; 1-(4-aminophenyl)ethan-1-one; 4H-benzo[d][1,3]dioxin-6-amine; 1,3-dihydroisobenzofuran-5-amine; 1-methyl-1H-benzo[d]imidazol-6-amine; 4,5-dimethylthiazol-2-amine; 2-methyl-4-(4-methylpiperazin-1-yl)aniline; 6-methylpyridin-2-amine; 4-methylthiazol-2-amine; 4,5,6,7-tetrahydrobenzo[d]thiazol-2-amine; 4-phenoxyaniline; 2-methyl-1,2,3,4-tetrahydrobenzo[4,5]imidazo[1,2-a]pyrazin-8-amine; 4-(pyridin-4-ylmethyl)aniline; 4-aminobenzene-1,2-diol; 4-((1-methylpiperidin-4-yl)oxy)aniline; 1-(4-(4-aminophenyl)piperazin-1-yl)ethan-1-one; 6-(4-methylpiperazin-1-yl)pyridin-3-amine; N1,N1,2-trimethylbenzene-1,4-diamine; 4-(4-cyclopropylpiperazin-1-yl)aniline; ammonia; 3-fluoro-4-morpholinoaniline; 7-aminoquinoxalin-2(1H)-one; 3-methyl-4-(4-methylpiperazin-1-yl)aniline; 4-(piperazin-1-yl)aniline; 4-((dimethylamino)methyl)aniline; 2-fluoro-4-morpholinoaniline; 4-(4-ethylpiperazin-1-yl)aniline; 8-amino-4,5-dihydro-1H-benzo[b]azepin-2(3H)-one; 5-amino-1,3-dimethyl-1H-benzo[d]imidazol-2(3H)-one; 4-benzylaniline; 2-methyl-4-morpholinoaniline; N1-methyl-N-(1-methylpiperidin-4-yl)benzene-1,4-diamine; 4-(2-morpholinoethyl)aniline; 3-chloro-4-(4-methylpiperazin-1-yl)aniline; 1,2,3,4-tetrahydroquinolin-7-amine; cyclohexane-1,2-diamine; pyridin-4-amine; 2-(4-aminophenyl)-N-(4-methoxyphenethyl)acetamide; 3-(piperazin-1-yl)aniline; 4-amino-N-(2-(diethylamino)ethyl)benzamide; 2-(4-methylpiperazin-1-yl)pyrimidin-5-amine; 7-amino-2H-benzo[b][1,4]oxazin-3(4H)-one; 3,4-dihydro-2H-benzo[b][1,4]oxazin-7-amine; 3-(4-methylpiperazin-1-yl)aniline; 3-(2-(piperazin-1-yl)ethoxy)aniline; 6-methyl-5,6,7,8-tetrahydro-1,6-naphthyridin-3-amine; (4-aminophenyl)(pyrrolidin-1-yl)methanone; (4-aminophenyl)(morpholino)methanone; 4-(pyrrolidin-1-ylmethyl)aniline; (4-aminophenyl)(4-methylpiperazin-1-yl)methanone; N2-(2-(dimethylamino)ethyl)pyrimidine-2,5-diamine; 4-(morpholinomethyl)aniline; 4-((4-methylpiperazin-1-yl)methyl)aniline; 4-(4-ethylpiperazin-1-yl)-3-fluoroaniline; 4-(2-(4-benzylpiperidin-1-yl)ethyl)aniline; 4-((4-benzylpiperidin-1-yl)methyl)aniline; p-toluidine; 6-(2-(dimethylamino)ethoxy)pyridin-3-amine; 2-methyl-1H-benzo[d]imidazol-5-amine; N2-(3-(dimethylamino)propyl)pyridine-2,5-diamine; N2-(2-(dimethylamino)ethyl)pyridine-2,5-diamine; 6-((1-methylpiperidin-4-yl)oxy)pyridin-3-amine; 4-(4-cyclopentylpiperazin-1-yl)aniline; 4-(4-isobutylpiperazin-1-yl)aniline; 4-(4-isopropylpiperazin-1-yl)aniline; 4-(4-(cyclopropylmethyl)piperazin-1-yl)aniline; 4-(4-(tert-butyl)piperazin-1-yl)aniline; 2-(4-(4-aminophenyl)piperazin-1-yl)acetic acid; 2-(4-amino-2-methoxyphenoxy)acetic acid; (4-aminophenyl)methanol; 4-(4-(2-(dimethylamino)ethyl)piperazin-1-yl)aniline; 2-(4-aminophenyl)acetic acid; 6-amino-2-naphthoic acid; 3-aminobenzoic acid; 4'-amino-[1,1'-biphenyl]-4-carboxylic acid; 1-(4-aminophenyl)-3-(m-tolyl)urea; 2-(4-aminophenoxy)acetic acid; 2-methylisoindolin-5-amine; (4-amino-3-methoxyphenyl)(4-(4-methylpiperazin-1-yl)piperidin-1-yl)methanone; 4-amino-N-(2-(dimethylamino)ethyl)-N-methylbenzamide; (4-aminophenyl)(2-(methoxymethyl)pyrrolidin-1-yl)methanone; (4-aminophenyl)(azetidin-1-yl)methanone; 4-amino-N,N-dimethylbenzamide; (4-aminophenyl)(4-methyl-1,4-diazepan-1-yl)methanone; 1-(4-aminobenzoyl)piperidin-4-one; (4-aminophenyl)(1,4-dioxa-8-azaspiro[4.5]decan-8-yl)methanone; (4-aminophenyl)(3-(dimethylamino)pyrrolidin-1-yl)methanone; 1-methyl-1,2,3,4-tetrahydroquinolin-6-amine; 3-aminophenylsulphur pentafluoride; 4-fluoroaniline; 3,4-difluoroaniline; N-(4-aminophenyl)-2,2,2-trifluoroacetamide; 3-((6-amino-2H-benzo[b][1,4]oxazin-3-yl)amino)propan-1-ol; N3-phenethyl-2H-benzo[b][1,4]oxazine-3,6-diamine; 3,5-difluoroaniline; 3-fluoro-4-methylaniline; 3,4,5-trifluoroaniline; 4-nitroaniline; 3-methoxy-4-morpholinoaniline; 3-(methylsulfonyl)aniline; 2-(4-aminophenyl)-1,1,1,3,3,3-hexafluoropropan-2-ol; 4-(difluoromethoxy)-3-methoxyaniline; 3-fluoro-4-(trifluoromethyl)aniline; 3-fluoro-4-(trifluoromethoxy)aniline; 2,3-dimethoxyaniline; 2,4-dimethoxyaniline; 3,5-dimethoxyaniline; 4-amino-N,N-dimethylbenzenesulfonamide; 3-amino-N-cyclopropylbenzenesulfonamide; 4-(2H-1,2,3-triazol-2-yl)aniline; 3-(methylsulfinyl)aniline; 3-(2H-1,2,3-triazol-2-yl)aniline; 3-amino-N-methylbenzenesulfonamide; 3-(morpholinosulfonyl)aniline; 3-((trifluoromethyl)sulfonyl)aniline; 2-((3-aminophenyl)sulfonyl)ethan-1-ol; N-(4-aminophenyl)-4-fluorobenzamide; 4-morpholino-3-nitroaniline; 2,4-difluoroaniline; 2-aminobenzamide; 4-chloroaniline; N1,N1-dimethylethane-1,2-diamine; (1-methylpiperidin-4-yl)methanamine; 1-methyl-1,2,3,4-tetrahydroquinolin-7-amine; 2-(4-aminophenyl)-2-methylpropanenitrile; 4-aminophenylsulphur pentafluoride; 3-amino-N,N-dimethylbenzenesulfonamide; 2-(methylsulfonyl)aniline; 4-(4-(4-methylpiperazin-1-yl)piperidin-1-yl)aniline; 3-((dimethylamino)methyl)aniline; (4-aminophenyl)(4-(4-methylpiperazin-1-yl)piperidin-1-yl)methanone.

Furthermore preferably, $R^1$ can be derived from the following amines:

formamide; 2-aminoethan-1-ol; prop-2-yn-1-amine; N1-methylethane-1,2-diamine; 2-aminoacetonitrile; 3-aminopropan-1-ol; butan-1-amine; cyclopropanamine; propan-2-amine; 3-aminopropanenitrile; 4-aminobutan-1-ol; cyclobutanamine; 2-aminopropan-1-ol; acetamide; cyclopropylmethanamine; 5-aminopentan-1-ol; 2-aminoacetamide; isoxazol-3-amine; thiazol-2-amine; 3-aminopropane-1,2-diol; cyclopentanamine; piperidin-4-amine; piperidin-3-amine; pyrimidin-2-amine; 2-aminocyclopentanol; 3-aminopropanamide; tetrahydro-2H-pyran-4-amine; 2-methylpropan-2-amine; o-toluidine; 2,2,2-trifluoroethan-1-amine; phenylmethanamine; piperidin-4-ylmethanamine; 2-aminocyclohexanol; 4-aminobutanamide; piperidin-3-ylmethanamine; 1-methyl-1H-pyrazol-4-amine; 2-methoxyaniline; 2-chloroaniline; 2-aminopropanamide; 4-methylthiophen-2-amine; 2-phenylethan-1-amine; 1H-pyrazol-5-amine; 5-methylisoxazol-3-amine; 2-morpholinoethan-1-amine; 1-(aminomethyl)-N-methylcyclopropanamine; 1-methyl-1H-pyrrol-3-amine; 5-methylthiazol-2-amine; 5-methylthiophen-2-amine; 4-aminophenol; 3-fluoroaniline; 3,5-dimethylisoxazol-4-amine; 3-morpholinopropan-1-amine; 2-aminobutanamide; 4-iodoaniline; (3-aminophenyl)methanol; 2-aminothiazole-4-carbaldehyde; 3-bromoaniline; 2,6-dimethylaniline; 4-ethylaniline; 3-amino-2-methylphenol; 4-(methylthio)aniline; 3-ethylaniline; 1-phenylethan-1-amine; 2-(4-aminophenyl)ethan-1-ol; 5-aminonicotinaldehyde; 6-aminonicotinaldehyde; 4-aminobenzaldehyde; 3-aminobenzaldehyde; indolin-6-amine; 4-amino-2-methoxyphenol; 2-aminopyrimidine-5-carbaldehyde; 5-aminopyrazine-2-carbaldehyde; 5-aminopicolinaldehyde; 3-methoxy-4-methylaniline; 6-aminopyrazine-2-carbaldehyde; N1,6-dimethylbenzene-1,3-diamine; 5-methyl-1H-pyrazol-3-amine; 4-ethoxyaniline; 2,3-dihydrobenzofuran-5-amine; 3-ethoxyaniline; benzo[d]thiazol-5-amine; benzo[d]thiazol-6-amine; piperidine-3-carboxamide; imidazo[1,2-a]pyridin-6-amine; piperidine-4-carboxamide; benzo[d]thiazol-7-amine; benzo[d]isoxazol-5-amine; 4-methoxy-3-methylaniline; benzo[d]thiazol-2-amine; 4-vinylaniline; benzo[c][1,2,5]thiadiazol-4-amine; 1-aminocyclopropanecarboxamide; 2-phenylcyclopropanamine; 2-aminocyclopentanecarboxamide; 3-vinylaniline; (5-amino-2-methoxyphenyl)methanol; 2-(4-aminophenoxy)ethan-1-ol; 1,2,3,4-tetrahydroisoquinolin-6-amine; (4-amino-2-methoxyphenyl)methanol; 2-amino-4-methylpyrimidine-5-carbaldehyde; 6-amino-4-methylnicotinaldehyde; 2-isopropoxyaniline; 6-amino-2-methylnicotinaldehyde; 4-amino-2-methylphenol; 5-amino-2-methylphenol; 3-chloro-4-methoxyaniline; 3,5-dimethylaniline; N-(3-aminophenyl)formamide; 2-(3-aminophenoxy)ethan-1-ol; N-(6-aminopyridin-2-yl)formamide; 4-amino-2-fluorophenol; 5-amino-2-hydroxybenzonitrile; 4-amino-3-fluorophenol; N-(4-aminophenyl)formamide; 2,4-dimethylaniline; 3,4-dimethylaniline; 2-fluoro-5-methylaniline; 2,5-dimethylaniline; quinoxalin-6-amine; quinolin-6-amine; 2-amino-3-methylbutanamide; quinoxalin-5-amine; naphthalen-1-amine; naphthalen-2-amine; 4-fluoro-3-methylaniline; quinolin-5-amine; quinolin-8-amine; 2,6-dimethylpyrimidin-4-amine; 1-(4-aminophenyl)ethan-1-ol; 2,3,4,5-tetrahydrobenzo[b][1,4]oxazepin-7-amine; 3-methoxy-4-(methoxymethyl)aniline; 2-fluoro-4-methoxyaniline; 5-amino-6-methoxypyrazine-2-carbaldehyde; 2-amino-4-methoxypyrimidine-5-carbaldehyde; 6-amino-5-methoxynicotinaldehyde; 3-chloro-4-fluoroaniline; 4H-benzo[b][1,4]

oxazin-6-amine; 4-isopropylaniline; 4-amino-2,5-dimethylphenol; 4-amino-2-chlorophenol; 4H-benzo[b][1,4]oxazin-7-amine; 3-(2-methoxyethoxy)aniline; 4-methoxy-2-methylaniline; 5-methoxy-2-methylaniline; 3-(2-(methylamino)ethoxy)aniline; 3-isopropylaniline; 4-amino-2,3-dimethylphenol; N-(5-amino-2-methylphenyl)formamide; 2-amino-4-methylpentanamide; 4-chloro-3-methylaniline; 3-aminocyclopentanecarboxamide; 2-chloro-5-fluoropyrimidin-4-amine; 3,4-dihydroquinolin-6-amine; 2-amino-4-methylpentanethioamide; 2-(isopentyloxy)aniline; 6-amino-5-methylnicotinaldehyde; 5-amino-6-methylpyrazine-2-carbaldehyde; 2-amino-6-methylpyrimidine-4-carbaldehyde; 2-methyl-2H-indazol-6-amine; 5-amino-6-methylpicolinaldehyde; 5-amino-4-methylpicolinaldehyde; 4-isopropoxyaniline; 1-methyl-1H-indazol-5-amine; 3,5-dichloroaniline; 3,4-dichloroaniline; [1,1'-biphenyl]-2-amine; 2,6-dimethoxypyridin-3-amine; 4-methoxy-3,5-dimethylaniline; 2-methyl-2H-indazol-5-amine; 3-(ethyl(hydroxy)amino)aniline; 3-isopropoxyaniline; N1-isopropylbenzene-1,3-diamine; 4-amino-5-chloro-2-methylphenol; 1-methyl-1H-indol-4-amine; 1H-indazol-4-amine; 1-methyl-1H-indazol-4-amine; 2-methyl-2H-indazol-4-amine; 1H-indol-4-amine; 1H-benzo[d]imidazol-6-amine; 1H-benzo[d][1,2,3]triazol-6-amine; 2-methylbenzo[d]thiazol-6-amine; 4-(methylsulfinyl)aniline; 1-methyl-1H-indol-5-amine; 3-(2-aminophenyl)propanamide; 2-((2-aminocyclohexyl)amino)acetic acid; (2,3,6-trifluorophenyl)methanamine; 5-bromo-2-chloropyrimidin-4-amine; 1-methyl-1H-indazol-7-amine; 1-methyl-1H-benzo[d]imidazol-4-amine; 2-methyl-2H-indazol-7-amine; 2-methylbenzo[d]oxazol-7-amine; 4-methyl-3,4-dihydro-2H-benzo[b][1,4]oxazin-7-amine; 4-methyl-3,4-dihydro-2H-benzo[b][1,4]oxazin-6-amine; 4-(4H-1,2,4-triazol-4-yl)aniline; 4-(1H-imidazol-1-yl)aniline; 4-(1H-pyrazol-1-yl)aniline; 5-aminoindolin-2-one; 6-aminoindolin-2-one; 3-methoxy-4-(2-methoxyethoxy)aniline; 3-(4-amino-2-methoxyphenoxy)propan-1-ol; 2-((4-aminophenyl)(methyl)amino)ethan-1-ol; 2-methyl-1,2,3,4-tetrahydroisoquinolin-6-amine; 4-amino-N-methylbenzamide; 3-amino-N-methylbenzamide; 1-(piperidin-4-yl)-1H-pyrazol-4-amine; 4-(oxazol-4-yl)aniline; 4-(pyrrolidin-3-yl)aniline; 2-(trifluoromethoxy)aniline; 3-chloro-4-methoxy-5-methylaniline; 2-((2-aminophenyl)imino)acetic acid; 3-(oxazol-5-yl)aniline; (5-aminobenzofuran-2-yl)methanol; 3,4,5-trimethylaniline; N-(5-amino-2-fluorophenyl)formamide; methyl 4-amino-1-methyl-1H-pyrrole-2-carboxylate; methyl 3-aminobenzoate; N-(3-amino-4-ethoxyphenyl)formamide; 2-((3-aminophenyl)amino)propan-1-ol; 2-methyl-2,3-dihydrobenzo[b][1,4]dioxin-6-amine; 4-(1H-1,2,4-triazol-1-yl)aniline; 3-(1H-pyrazol-1-yl)aniline; 2-amino-2-phenylacetamide; 4-(thiazol-4-yl)aniline; 1,2-dimethyl-1H-indol-4-amine; 4-(oxazol-5-yl)aniline; 1-ethyl-1H-indol-4-amine; 3-(thiazol-2-yl)aniline; 4-(1,2,3-thiadiazol-4-yl)aniline; 3-(isoxazol-3-yl)aniline; 4-(isoxazol-3-yl)aniline; 4-(isoxazol-5-yl)aniline; 4-(thiophen-2-yl)aniline; 3-(1H-tetrazol-1-yl)aniline; 4-(1H-tetrazol-1-yl)aniline; 3-(1H-imidazol-1-yl)aniline; 5-aminobenzofuran-2(3H)-one; 8-methylquinolin-4-amine; 2-amino-2-(pyridin-3-yl)acetamide; 1-phenyl-1H-pyrazol-4-amine; 1-phenyl-1H-pyrrol-3-amine; 3-(2H-tetrazol-2-yl)aniline; 3-(1H-1,2,4-triazol-1-yl)aniline; 3-(1H-1,2,3-triazol-1-yl)aniline; 4-(1H-1,2,3-triazol-1-yl)aniline; 3-(pyrrolidin-1-yl)aniline; 3-(1H-pyrrol-1-yl)aniline; 4-(1H-pyrrol-1-yl)aniline; 4-(1,3,4-oxadiazol-2-yl)aniline; 4-(thiazol-2-yl)aniline; 3-(thiazol-4-yl)aniline; 3-(oxazol-4-yl)aniline; 3-(thiazol-5-yl)aniline; 4-(thiazol-5-yl)aniline; 6-fluoronaphthalen-2-amine; methyl 2-((2-aminocyclohexyl)amino)acetate; 4-isobutoxyaniline; 2-methylquinolin-6-amine; 2-methylquinolin-8-amine; 3-methylcinnolin-5-amine; 2-(4-aminophenyl)propan-2-ol; 2-((4-aminophenyl)(ethyl)amino)ethan-1-ol; 4-(2-(dimethylamino)ethoxy)aniline; 4-(tetrahydro-2H-pyran-4-yl)aniline; 3-methoxy-4-((2-methoxyethoxy)methyl)aniline; N1-(2-methoxyethyl)-N1-methylbenzene-1,4-diamine; 4-isopropoxy-3-methoxyaniline; 4-amino-2-methoxybenzoic acid; 4-(piperidin-4-yl)aniline; 4-amino-N,2-dimethylbenzamide; 6-(tetrahydro-2H-pyran-4-yl)pyridin-3-amine; 6-(piperidin-4-yl)pyridin-3-amine; 4-(3-(dimethylamino)propyl)aniline; 4-(pyridin-3-yl)aniline; 4-(piperidin-3-yl)aniline; 2-ethyl-1,2,3,4-tetrahydroisoquinolin-6-amine; 3,5-dichloro-4-methoxyaniline; 4-amino-2-chloro-6-methylphenol; 3-(4-aminophenoxy)propane-1,2-diol; 3-(tert-butyl)aniline; 2-(5-amino-1H-indazol-1-yl)ethan-1-ol; 2-(6-amino-1H-indazol-1-yl)ethan-1-ol; 4-chloro-2,5-dimethoxyaniline; ethyl 3-aminobenzoate; 4-(tert-butyl)aniline; 4-chloro-3,5-dimethylaniline; N-(3-amino-5-chlorophenyl)formamide; 4-(trifluoromethyl)aniline; [1,1'-biphenyl]-3-amine; 6-amino-2H-chromen-2-one; 7-amino-2H-chromen-2-one; methyl 2-(4-aminophenyl)acetate; methyl 2-(3-aminophenyl)acetate; methyl 5-amino-2-hydroxybenzoate; methyl 4-amino-2-hydroxybenzoate; 5-amino-2-methoxybenzoic acid; 3-(2-(dimethylamino)ethoxy)aniline; 4-methyl-4H-benzo[b][1,4]oxazin-7-amine; 3-amino-4-isopropylphenol; 5-methyl-3-phenylisoxazol-4-amine; 3-(pyrimidin-2-yl)aniline; 3-(pyrimidin-5-yl)aniline; 2,3-dihydro-1H-pyrrolo[1,2-a]indol-8-amine; 4-(pyrimidin-2-yl)aniline; 3-(pyridin-3-yl)aniline; 4-(pyridin-2-yl)aniline; 6-methoxynaphthalen-2-amine; 2-methyl-2H-indol-4-amine; 4-chloronaphthalen-1-amine; 3-(pyridin-4-yl)aniline; 4-amino-2-methoxybenzamide; 3-(5-methyl-1H-tetrazol-1-yl)aniline; 2-fluoro-4-(1H-pyrazol-1-yl)aniline; 2-fluoro-4-(thiazol-4-yl)aniline; 4-(pyrimidin-5-yl)aniline; 3-(pyrazin-2-yl)aniline; 4-(pyrazin-2-yl)aniline; 3-(tetrahydro-2H-pyran-4-yl)aniline; 3-(pyridazin-4-yl)aniline; 4-(pyridazin-4-yl)aniline; 4-(pyridin-4-yl)aniline; 3-(pyridin-2-yl)aniline; [1,1'-biphenyl]-4-amine; 7-chloro-1H-indazol-6-amine; 6-bromonaphthalen-2-amine; 3-(1-methyl-1H-tetrazol-5-yl)aniline; 4-(4-methyl-4H-1,2,4-triazol-3-yl)aniline; 4-(1-methyl-1H-imidazol-2-yl)aniline; 3-(1-methyl-1H-imidazol-2-yl)aniline; 4-(2-methyl-1H-imidazol-1-yl)aniline; 3-(2-methyl-1H-imidazol-1-yl)aniline; 2-(4-aminophenyl)-2-methylpropan-1-ol; 1-(4-aminophenyl)azetidin-3-ol; 2-aminoquinazoline-6-carbaldehyde; 1-(4-aminophenyl)-2-methylpropan-2-ol; 2-(4-aminophenoxy)-N-methylacetamide; 4-(1,4-oxazepan-4-yl)aniline; 3-methoxy-4-(pyrrolidin-1-yl)aniline; 4-amino-N-propylbenzamide; 3-aminoquinoline-6-carbaldehyde; 4-((tetrahydrofuran-2-yl)methoxy)aniline; 4-((tetrahydro-2H-pyran-4-yl)oxy)aniline; 4-(pyridin-4-yloxy)aniline; 4-(3-fluoroazetidin-1-yl)aniline; 4-amino-N-(2-hydroxyethyl)benzamide; 1-(4-aminophenyl)cyclobutanol; 2-aminoquinoline-6-carbaldehyde; 4-(2-methoxypropan-2-yl)aniline; 2-((4-amino-2-methoxyphenyl)(methyl)amino)ethan-1-ol; 4-methoxy-3-(pyrrolidin-1-yl)aniline; 4-(3-methylazetidin-1-yl)aniline; 2,3-dimethyl-2H-indazol-6-amine; 4-(trifluoromethoxy)aniline; 3-methyl-1H-indazol-6-amine; 1-(2-morpholinoethyl)-1H-pyrazol-4-amine; 3-(trifluoromethoxy)aniline; 4-amino-N-ethoxybenzamide; 3-amino-N-propylbenzamide; 4-((2-methyl-1H-imidazol-1-yl)methyl)aniline; 3-(5-amino-1H-indazol-1-yl)propan-1-ol; 4-amino-2,6-dichlorophenol; 3-(6-amino-1H-indazol-1-yl)propan-1-ol; 2-((3-aminophenyl)imino)acetamide; methyl 5-amino-2-methoxybenzoate; ethyl 2-((2-aminophenyl)imino)acetate; 4-((trifluoromethyl)thio)aniline; 5-amino-2-hydroxybenzoic acid; 4-amino-2-hydroxybenzoic acid; 2-((3-aminophenyl)imino)acetic acid; 2,2'-((3-aminophenyl)azanediyl)bis(ethan-1-ol); 2,2-difluorobenzo[d][1,3]dioxol-5-amine; 2-((methylamino)methylene)-2,3-dihydrobenzofuran-5-amine; 3-aminophenyl ethylcarbamate; 1-(4-aminophenyl)-3-ethylurea; 1-(3-aminophenyl)-3-ethylurea; 6-amino-2-methyl-2H-benzo[b][1,4]oxazin-3(4H)-one; 4-methyl-[1,1'-biphenyl]-3-amine; 2-methyl-1H-indol-4-amine; 3-(4-aminopiperidin-1-yl)-3-oxopropanenitrile; 4-(pyridin-3-yloxy)aniline; 1-(3-aminophenyl)pyrrolidin-2-one; 4-(5,6-dihydro-4H-1,3-oxazin-2-yl)aniline; 4-(3,6-dihydro-2H-pyran-4-yl)aniline; 6-aminoquinoline-2-carbonitrile; 2-chloro-5-cyclopropylpyrimidin-4-amine; 3-(3-aminopiperidin-1-yl)-3-oxopropanenitrile; 3-((tetrahydro-2H-pyran-4-yl)oxy)aniline; 3-(3,6-dihydro-2H-pyran-4-yl)aniline; dibenzo[b,d]furan-2-amine; 3-methoxy-4-(oxazol-5-yl)aniline; 4-methoxy-3-(2H-1,2,3-triazol-2-yl)aniline; 1-(4-aminophenyl)pyrrolidin-3-ol; 1-(4-aminophenoxy)-2-methylpropan-2-ol; 4-((tetrahydro-2H-pyran-4-yl)methoxy)aniline; (4-(4-aminophenyl)morpholin-3-yl)methanol; 4-(2H-tetrazol-5-yl)aniline; 2-methoxy-N1-(2-methoxyethyl)-N1-methylbenzene-1,4-diamine; 4-(1-methoxy-2-methylpropan-2-yl)aniline; 5-amino-1-methyl-6-oxo-1,6-dihydropyridine-3-carbaldehyde; 2-((4-amino-2-ethoxyphenyl)(methyl)amino)ethan-1-ol; 4-(2-(pyrrolidin-1-yl)ethoxy)aniline; 4-(1-methyl-1H-pyrazol-4-yl)aniline; 4-(1H-imidazol-4-yl)aniline; 4-(methylsulfonyl)aniline; 2-methoxy-[1,1'-biphenyl]-4-amine; 4-(1-methylpyrrolidin-3-yl)aniline; 5-amino-2-methylisoindolin-1-one; 6-amino-2-methylisoindolin-1-one; 3-(2-(pyrrolidin-1-yl)ethoxy)aniline; 2-(2-methoxyethyl)-1,2,3,4-tetrahydroisoquinolin-6-amine; 4-methoxy-3-(trifluoromethyl)aniline; 2-((3-aminophenyl)imino)-N-methylacetamide; 3-(1H-tetrazol-5-yl)aniline; N-(4-aminophenyl)-N-methylacetamide; 3-(benzyloxy)aniline; 3-(1H-pyrazol-3-yl)aniline; 2-amino-7-oxabicyclo[4.2.0]octa-1,3,5-triene-8-carboxylic acid; (5-amino-1H-indol-2-yl)methanol; 6-methoxy-[1,1'-biphenyl]-3-amine; 4-methoxy-[1,1'-biphenyl]-3-amine; ethyl (4-amino-2-hydroxyphenyl)carbamate; 3-fluoro-4-(thiazol-4-yl)aniline; 3-fluoro-4-(1H-pyrazol-1-yl)aniline; 4-amino-N-(3-hydroxypropyl)benzamide; 3-fluoro-4-(1H-imidazol-1-yl)aniline; 1-(4-aminophenyl)pyridin-2(1H)-one; 1-(4-aminophenyl)-1-methylurea; butyl 4-aminobenzoate; 4-(5-methyl-1,2,4-oxadiazol-3-yl)aniline; 3-(2-methylthiazol-4-yl)aniline; 4-(3-methyl-1H-pyrazol-1-yl)aniline; 3-methyl-5-(2H-1,2,3-triazol-2-yl)aniline; 4-methyl-3-(2H-1,2,3-triazol-2-yl)aniline; 2-amino-2-(3-hydroxyphenyl)acetamide; 2-amino-2-(3-fluorophenyl)acetamide; 3-fluoro-5-(2H-1,2,3-triazol-2-yl)aniline; 4-fluoro-3-(2H-1,2,3-triazol-2-yl)aniline; 4-amino-2-(2H-1,2,3-triazol-2-yl)benzonitrile; 3-fluoro-4-(2H-1,2,3-triazol-2-yl)aniline; 3-(2H-tetrazol-5-yl)aniline; 3-chloro-1H-indazol-5-amine; 4-(methylthio)-7H-pyrrolo[2,3-d]pyrimidin-2-amine; 4-(2-(methoxymethyl)pyrrolidin-1-yl)aniline; 2'-methoxy-[1,1'-biphenyl]-3-amine; 4-(1-methyl-1H-pyrazol-3-yl)aniline; 3-(1-methyl-1H-pyrazol-3-yl)aniline; 3-(1-methyl-1H-pyrazol-4-yl)aniline; 4-(5-methyl-1,3,4-thiadiazol-2-yl)aniline; 3-(5-methyl-1,2,4-oxadiazol-3-yl)aniline; 3-(4-methyl-2H-1,2,3-triazol-2-yl)aniline; 3-(4-methyl-1H-1,2,3-triazol-1-yl)aniline; 3-(5-methylisoxazol-3-yl)aniline; 3-methyl-5-(2H-tetrazol-2-yl)aniline; 3-methyl-4-(2H-1,2,3-triazol-2-yl)aniline; 3-methyl-4-(1H-pyrazol-1-yl)aniline; 3-(5-methylfuran-2-yl)aniline; 2-amino-2-(m-tolyl)acetamide; 2-amino-2-(p-tolyl)acetamide; 3-amino-1H-indazole-6-carbaldehyde; 3-ethoxy-4-morpholinoaniline; 3-amino-1H-indazole-5-carbaldehyde; 1-(4-aminophenyl)piperidin-3-ol; 3-methoxy-4-((tetrahydro-2H-pyran-4-yl)oxy)aniline; 2-(4-amino-2-methoxyphenoxy)-N-methylacetamide; 2-amino-1H-benzo[d]imidazole-6-carbaldehyde; 2-(4-aminophenoxy)-N-(2-hydroxyethyl)acetamide; 5-amino-2-morpholinobenzonitrile; 1-(4-aminophenyl)piperidin-4-ol; (1-(4-aminophenyl)pyrrolidin-3-yl)methanol; 4-(4-fluoropiperidin-1-yl)aniline; 3-(methoxymethyl)-4-morpholinoaniline; 3-methoxy-4-((tetrahydrofuran-2-yl)methoxy)aniline; 4-(3-(dimethylamino)propoxy)-3-methoxyaniline; 1-(4-amino-2-methoxyphenyl)azetidin-3-ol; 4-amino-N-(2-hydroxyethyl)-2-methoxybenzamide; 1-(4-amino-2-methoxyphenyl)-2-methylpropan-2-ol; 3-(4-aminophenoxy)-2,2-dimethylpropan-1-ol; 4-(2-methylmorpholino)aniline; 6-(2-methylmorpholino)pyridin-3-amine; 3-methyl-4-(piperidin-4-yl)aniline; 4-(2-morpholinoethoxy)aniline; 3-(2-morpholinoethoxy)aniline; 3-methyl-4-morpholinoaniline; (1-(4-aminophenethyl)pyrrolidin-2-yl)methanol; 4-(2-methylpyridin-4-yl)aniline; 6-(1-methylpiperidin-4-yl)pyridin-3-amine; 2-(2-methylmorpholino)pyrimidin-5-amine; 3-methyl-4-(tetrahydro-2H-pyran-4-yl)aniline; 4-amino-N-cyclopropylbenzamide; 4-(1-methylpiperidin-3-yl)aniline; 4-(1-ethylpyrrolidin-3-yl)aniline; 5-methyl-6-morpholinopyridin-3-amine; 4-methyl-3-(trifluoromethyl)aniline; 5-aminobenzofuran-2-carboxylic acid; 2-((dimethylamino)methyl)benzofuran-5-amine; ethyl 2-((3-aminophenyl)imino)acetate; 3-fluoro-5-(trifluoromethyl)aniline; 4-amino-2-(trifluoromethyl)phenol; 5-amino-2,3-dihydrobenzofuran-2-carboxylic acid; N-(4-aminophenyl)methanesulfonamide; 7-amino-4-methyl-2H-benzo[b][1,4]oxazin-3(4H)-one; 6-amino-4-methyl-2H-benzo[b][1,4]oxazin-3(4H)-one; 3-methyl-5-(trifluoromethyl)aniline; 6-amino-1-methyl-3,4-dihydroquinolin-2(1H)-one; methyl (4-aminophenyl)(methyl)carbamate; N-(4-aminophenyl)-2-hydroxy-N-methylacetamide; 6-aminoquinolin-2(1H)-one; 6-amino-1-methylquinolin-2(1H)-one; 4-(ethylsulfonyl)aniline; N-(4-aminophenyl)-N-methylpropionamide; 4-(3,5-dimethyl-1H-pyrazol-1-yl)aniline; 2-amino-2-(3-chlorophenyl)acetamide; 5-fluoro-4-(piperazin-1-yl)pyrimidin-2-amine; 4-(2-(piperidin-1-yl)ethoxy)aniline; 3-chloro-5-(2H-1,2,3-triazol-2-yl)aniline; 4-chloro-3-(2H-1,2,3-triazol-2-yl)aniline; (1-(4-aminophenyl)-1H-1,2,3-triazol-4-yl)methanol; 3-(5-fluoropyrimidin-2-yl)aniline; 4'-fluoro-[1,1'-biphenyl]-3-amine; 3'-fluoro-[1,1'-biphenyl]-3-amine; 4-bromo-3-(2H-1,2,3-triazol-2-yl)aniline; dibenzo[b,d]furan-3-amine; 3-bromo-5-(2H-1,2,3-triazol-2-yl)aniline; 3-methoxy-5-(2H-1,2,3-triazol-2-yl)aniline; 3-methoxy-5-(1H-tetrazol-1-yl)aniline; 2-amino-2-(4-methoxyphenyl)acetamide; 1-(4-aminophenyl)-3-methylazetidin-3-ol; (4-(4-aminophenyl)morpholin-2-yl)methanol; 1-(4-amino-2-methoxyphenyl)pyrrolidin-3-ol; 2-(5-amino-2-morpholinophenoxy)ethan-1-ol; (1-(4-aminophenyl)piperidin-4-yl)methanol; 4-(4-aminophenoxy)cyclohexanol; 4-(4-aminophenyl)piperazin-2-one; 4-(3,3-difluoroazetidin-1-yl)aniline; 2-(1-(4-aminophenyl)pyrrolidin-3-yl)ethan-1-ol; 4-amino-N-(oxetan-3-yl)benzamide; 1-(4-aminophenyl)-2,2,2-trifluoroethan-1-ol; 1-(4-amino-2-methoxyphenoxy)-2-methylpropan-2-ol; 3-methoxy-4-((tetrahydro-2H-pyran-4-yl)methoxy)aniline; 4-amino-N-(2-hydroxyethyl)-N-methylbenzamide; 2-(4-aminophenoxy)-N,N-dimethylacetamide; 4-(3-fluoro-3-methylazetidin-1-yl)aniline; 3-methyl-4-(2-methylmorpholino)aniline; 4-(1-ethylpiperidin-4-yl)aniline; 3-fluoro-4-(2-methylmorpholino)aniline; 3-methyl-4-(1-methylpiperidin-4-yl)aniline; 4-(2,3-dihydroimidazo[2,1-b]thiazol-6-yl)aniline; 3-fluoro-4-(1-methylpiperidin-4-yl)aniline; 5-methyl-6-(2-methylmorpholino)pyridin-3-amine; 3-fluoro-4-(piperazin-1-ylmethyl)aniline; 4'-methoxy-[1,1'-biphenyl]-4-amine; 1-(6-amino-3,4-dihydroisoquinolin-2

(1H)-yl)ethan-1-one; 4-amino-N,N-diethylbenzamide; 5-(4-ethylpiperazin-1-yl)pyridin-2-amine; 2-(isopropylsulfonyl)aniline; 3-methyl-4-(1,2,3,6-tetrahydropyridin-4-yl)aniline; 2-methyl-5-(2-morpholinoethoxy)aniline; methyl 5-aminobenzofuran-2-carboxylate; 5-amino-N-methyl-2,3-dihydrobenzofuran-2-carboxamide; methyl 5-amino-2,3-dihydrobenzofuran-2-carboxylate; 3-methoxy-5-(trifluoromethyl)aniline; 5-amino-N-methylbenzofuran-2-carboxamide; 2-((3-aminophenyl)imino)-N-(2-hydroxyethyl)acetamide; 4-chloro-3-(trifluoromethyl)aniline; 3-nitroaniline; methyl 4-amino-2,3-dihydrobenzofuran-7-carboxylate; 6-amino-N-methyl-1H-indole-1-carboxamide; ethyl 2-amino-7-oxabicyclo[4.2.0]octa-1 (6),2,4-triene-8-carboxylate; 3-aminophenyl isopropylcarbamate; 3-chloro-4-morpholinoaniline; 2-(6-amino-1H-indazol-1-yl)acetamide; 1-(4-aminophenyl)azetidine-2-carboxamide; 6-amino-2-naphthamide; 3-amino-5-(2H-1,2,3-triazol-2-yl)benzonitrile; 3-amino-5-(1H-1,2,3-triazol-1-yl)benzonitrile; 4-amino-N-cyclobutylbenzamide; 3-(4-methoxypyrimidin-2-yl)aniline; 4-(6-methoxypyridin-3-yl)aniline; 3-(6-methoxypyridin-2-yl)aniline; 3-(6-methoxypyridin-3-yl)aniline; 3'-methoxy-[1,1'-biphenyl]-3-amine; 4'-methoxy-[1,1'-biphenyl]-3-amine; N-(4-aminophenyl)-3-hydroxy-N-methylpropanamide; 9-methyl-9H-carbazol-3-amine; 2-(1-(4-aminophenyl)piperidin-4-yl)ethan-1-ol; 1-(4-amino-2-methoxyphenyl)piperidin-3-ol; 1-(4-aminophenyl)-3-methylpyrrolidin-3-ol; 2-(4-(4-aminophenyl)piperazin-1-yl)ethan-1-ol; 4-(3,3-difluoropyrrolidin-1-yl)aniline; 4-(2-oxa-6-azaspiro[3.3]heptan-6-yl)aniline; 3-(2-methoxyethoxy)-4-morpholinoaniline; 3-(4-amino-2-methoxyphenoxy)-2,2-dimethylpropan-1-ol; 1-(4-amino-2-methoxyphenyl)piperidin-4-ol; (1-(4-amino-2-methoxyphenyl)pyrrolidin-3-yl)methanol; 4-(3-methoxy-3-methylazetidin-1-yl)aniline; 1-(4-amino-2-ethoxyphenoxy)-2-methylpropan-2-ol; 1-(4-amino-2-ethoxyphenyl)pyrrolidin-3-ol; 4-amino-N-ethyl-N-(2-hydroxyethyl)benzamide; 4-((4-ethylpiperazin-1-yl)methyl)aniline; 1-(4-aminophenyl)-3-ethylazetidin-3-ol; 3-methyl-4-(2-(pyrrolidin-1-yl)ethoxy)aniline; 4-methyl-3-(2-(pyrrolidin-1-yl)ethoxy)aniline; 1-(4-aminophenethyl)piperidin-4-ol; 2-(4-(4-aminophenyl)piperidin-1-yl)ethan-1-ol; 3-methyl-4-((1-methylpiperidin-4-yl)oxy)aniline; 2-methoxy-5-methyl-4-(piperidin-4-yl)aniline; 4-(1-(2-methoxyethyl)-1H-pyrazol-4-yl)aniline; 3-fluoro-4-(2-(pyrrolidin-1-yl)ethoxy)aniline; 4-amino-N-cyclopentylbenzamide; 4-(1-(2-methoxyethyl)pyrrolidin-3-yl)aniline; 2-methoxy-4-(4-methylpiperazin-1-yl)aniline; 2-(4-(4-amino-1H-pyrazol-1-yl)piperidin-1-yl)acetonitrile; (4-aminophenyl)(piperazin-1-yl)methanone; 1-(1-(2-methoxyethyl)piperidin-4-yl)-1H-pyrazol-4-amine; 4-(2-(4-methylpiperazin-1-yl)ethyl)aniline; 4-(1,2-dimethylpiperidin-4-yl)-3-fluoroaniline; methyl 2-(5-amino-1H-indazol-1-yl)acetate; methyl 2-(6-amino-1H-indazol-1-yl)acetate; 2-(5-amino-1H-indazol-1-yl)-N-methylacetamide; 3-chloro-4-(trifluoromethoxy)aniline; 4-(4,5-dichloro-1H-imidazol-1-yl)aniline; 2-(6-amino-1H-indazol-1-yl)-N-methylacetamide; (3-aminophenyl)(phenyl)methanone; methyl 3-amino-5-formamidobenzoate; 5-methoxy-2-methyl-[1,1'-biphenyl]-4-amine; 2-((3-aminophenyl)imino)-N,N-dimethylacetamide; 2-((3-aminophenyl)imino)-N-(2-(methylamino)ethyl)acetamide; ethyl 5-aminobenzofuran-2-carboxylate; 1-(4-aminophenyl)pyrrolidine-2-carboxamide; (1-(2-amino-5-fluoropyrimidin-4-yl)piperidin-4-yl)methanol; 4-amino-N-(2-hydroxyethyl)benzenesulfonamide; 4-(2-amino-5-fluoropyrimidin-4-yl)piperazin-2-one; 3-(1H-benzo[d][1,2,3]triazol-1-yl)aniline; 3-(1H-indazol-1-yl)aniline; 3-(2H-benzo[d][1,2,3]triazol-2-yl)aniline; 3-(1H-benzo[d]imidazol-1-yl)aniline; 3-(2H-indazol-2-yl)aniline; 3-(imidazo[1,2-a]pyridin-2-yl)aniline; 3-(4-aminophenyl)pyridin-2(1H)-one; 3-(benzo[d][1,3]dioxol-4-yl)aniline; 3-(benzo[d][1,3]dioxol-5-yl)aniline; 3-(2,3-dihydrobenzofuran-5-yl)aniline; 3-(imidazo[1,2-a]pyridin-6-yl)aniline; 4-(imidazo[1,2-a]pyridin-6-yl)aniline; 6-amino-N-methyl-2-naphthamide; 3-fluoro-4-(4-methyl-1H-pyrazol-1-yl)aniline; 1-(4-aminophenyl)-4-methylpiperidin-4-ol; 1-(4-amino-2-methoxyphenyl)-3-methylazetidin-3-ol; (4-(4-amino-2-methoxyphenyl)morpholin-2-yl)methanol; 2-(4-(4-aminophenyl)piperazin-1-yl)acetaldehyde; 4-(4-(3-fluoropropyl)piperazin-1-yl)aniline; 4-(4,4-difluoropiperidin-1-yl)aniline; 4-(3,3-difluoropiperidin-1-yl)aniline; 4-(8-oxa-3-azabicyclo[3.2.1]octan-3-yl)aniline; 4-amino-N-(tetrahydro-2H-pyran-4-yl)benzamide; (4-aminophenyl)(3-hydroxyazetidin-1-yl)methanone; 3-(4-amino-2-ethoxyphenoxy)-2,2-dimethylpropan-1-ol; 4-(4-ethylpiperazin-1-yl)-3-methoxyaniline; 4-(2,6-dimethylmorpholino)aniline; 1-(4-aminophenyl)-3-methylpiperidin-3-ol; 2-(4-aminophenyl)-N,2-dimethylpropanamide; 4-(1-(2-methoxyethyl)piperidin-4-yl)aniline; 4-(1-(3-fluoropropyl)piperidin-4-yl)aniline; 4-(2-(4-ethylpiperazin-1-yl)ethyl)aniline; 4-amino-N-phenylbenzamide; 3-((dimethylamino)methyl)-1H-indazol-6-amine; 1-(4-aminophenyl)-N,N-dimethylpyrrolidin-3-amine; 4-(4-ethoxypiperidin-1-yl)-3-fluoroaniline; 6-(2,6-dimethylmorpholino)pyridin-3-amine; 6-(1-(2-methoxyethyl)piperidin-4-yl)pyridin-3-amine; 4-methyl-3-(2-morpholinoethoxy)aniline; 6-amino-2,2-dimethyl-2H-benzo[b][1,4]oxazin-3(4H)-one; 3-(5-amino-1H-indazol-1-yl)-N-methylpropanamide; 3-(6-amino-1H-indazol-1-yl)-N-methylpropanamide; 5-amino-N-(2-hydroxyethyl)benzofuran-2-carboxamide; 3-(5-amino-2H-indazol-2-yl)-N-methylpropanamide; N-(3-amino-5-(trifluoromethyl)phenyl)formamide; 4-(benzyloxy)-3-chloroaniline; 6-amino-2,2-difluoro-2H-benzo[b][1,4]oxazin-3(4H)-one; 5-amino-N-(2-hydroxyethyl)-2,3-dihydrobenzofuran-2-carboxamide; 5-amino-1H-indole-2-carboxylic acid; methyl 5-amino-3-oxo-2,3-dihydrobenzofuran-2-carboxylate; methyl 2-amino-8-methyl-7-oxabicyclo[4.2.0]octa-1,3,5-triene-5-carboxylate; 2-methoxy-5-nitroaniline; N-(3-aminophenyl)pivalamide; N-(4-aminophenyl)-N-methylcyclopropanecarboxamide; N-(4-amino-2-chlorophenyl)-N-methylacetamide; 3-((4-aminophenyl)sulfonyl)propanenitrile; 2-morpholinoquinolin-6-amine; 4-amino-N-(2-methoxyethyl)benzenesulfonamide; 4-amino-N-cyclopropyl-N-methylbenzamide; tert-butyl 4-aminopiperidine-1-carboxylate; 1-(4-aminophenyl)piperidine-2-carboxamide; 3,5-difluoro-4-morpholinoaniline; 4-(4-aminophenyl)thiomorpholine-2,3-dione; 3-(2H-benzo[b][1,4]oxazin-4(3H)-yl)aniline; 3-(quinolin-3-yl)aniline; 3-(quinolin-4-yl)aniline; 3',4'-difluoro-[1,1'-biphenyl]-3-amine; 3-(quinolin-5-yl)aniline; 3-(quinolin-8-yl)aniline; 3-(2,3-dihydrobenzo[b][1,4]dioxin-6-yl)aniline; 4-(2,3-dihydrobenzo[b][1,4]dioxin-6-yl)aniline; 3-(quinolin-6-yl)aniline; 4-(methylsulfinyl)-7H-pyrrolo[2,3-d]pyrimidin-2-amine; 4-(4-(2-methoxyethyl)piperazin-1-yl)aniline; 2',4'-dimethoxy-[1,1'-biphenyl]-3-amine; 2',3'-dimethoxy-[1,1'-biphenyl]-3-amine; 3',4'-dimethoxy-[1,1'-biphenyl]-3-amine; 1-(4-aminophenyl)-N-methylpyrrolidine-2-carboxamide; tert-butyl 3-aminopiperidine-1-carboxylate; 2-(4-(4-amino-2-methoxyphenyl)piperazin-1-yl)ethan-1-ol; 1-(4-amino-2-ethoxyphenyl)-3-methylazetidin-3-ol; 4-(2-oxa-7-azaspiro[3.5]nonan-7-yl)aniline; 4-(7-oxa-2-azaspiro[3.5]nonan-2-yl)aniline; 1-(4-amino-2-methoxyphenyl)-3-methylpyrrolidin-3-ol; 1-(4-aminophenyl)-N,N-dimethylpiperidin-4-amine; 2-(4-aminophenyl)-1,1,1-trifluoropropan-2-ol; 1-(4-amino-2-fluorophenyl)-3- methylazetidin-3-ol; 4-(1-cyclopropylpiperidin-4-yl) aniline; 4-(1-(2-methoxyethyl)piperidin-4-yl)-3-methylaniline; 3-(4-(4-aminophenyl)piperidin-1-yl) propanenitrile; 4-amino-N-(3-methoxypropyl) benzenesulfonamide; 2-fluoro-5-methyl-4-(1-methylpiperidin-4-yl)aniline; 4-(1-isopropylpiperidin-4-yl) aniline; 2-(3-aminophenoxy)-1-morpholinoethan-1-one; 2-(4-(4-amino-2-methylphenyl)piperidin-1-yl)acetonitrile; 4-(1-(3-fluoropropyl)piperidin-4-yl)-3-methylaniline; ethyl 3-(5-amino-1H-indazol-1-yl)propanoate; ethyl 3-(6-amino-1H-indazol-1-yl)propanoate; 5-amino-N,N-dimethyl-2,3-dihydrobenzofuran-2-carboxamide; ethyl 2-(4-aminophenyl)-2-methylpropanoate; ethyl 3-(5-amino-2H-indazol-2-yl) propanoate; 4-fluoro-3-nitroaniline; 2-fluoro-5-nitroaniline; methyl 5-amino-1H-indole-2-carboxylate; tert-butyl (4-aminophenyl)carbamate; tert-butyl (3-aminophenyl)carbamate; 4-methyl-3-nitroaniline; 2-methyl-5-nitroaniline; 1-(4-aminophenyl)-N-methylpiperidine-2-carboxamide; tert-butyl 4-(aminomethyl)piperidine-1-carboxylate; isopropyl (4-aminophenyl)(methyl)carbamate; 2-(morpholinomethyl)quinolin-6-amine; 4-(pyrrolidin-1-yl)-7H-pyrrolo[2,3-d]pyrimidin-2-amine; benzyl 4-aminocyclohexanecarboxylate; 4-amino-N-cyclobutyl-N-methylbenzamide; 1-(4-aminophenyl)-1H-1,2,3-triazole-4-carboxamide; 2-(4-aminophenoxy)-1-morpholinoethan-1-one; 4-amino-N-cyclopropylbenzenesulfonamide; 2'-(pyrrolidin-3-yl)-[1,1'-biphenyl]-3-amine; 1-(methylsulfonyl)-1H-indazol-6-amine; N-(4-aminophenyl)-2-(dimethylamino)-N-methylacetamide; 5-(4-aminophenyl)-N,N-dimethylpyridin-2-amine; 4-(2-methyl-1-morpholinopropan-2-yl)aniline; 1-(4-amino-2-methoxyphenyl)-4-methylpiperidin-4-ol; 5-amino-2-morpholinobenzamide; (4-aminophenyl)(4-hydroxypiperidin-1-yl)methanone; 3-methoxy-4-(4-(2-methoxyethyl)piperazin-1-yl)aniline; 1-(4-amino-2-methoxyphenyl)-3-methylpiperidin-3-ol; 3-(4-aminophenyl)-1,4-dimethylpiperazin-2-one; 1-(4-(4-aminophenyl)piperidin-1-yl)ethan-1-one; 4-(2-(4-(2-methoxyethyl)piperazin-1-yl)ethyl)aniline; 4-amino-N-(2-morpholinoethyl)benzamide; 2-(methylsulfonyl)-1,2,3,4-tetrahydroisoquinolin-6-amine; 1-(4-aminophenethyl)-N,N-dimethylpyrrolidin-3-amine; 3-methyl-4-(3-(4-methylpiperazin-1-yl)propoxy)aniline; 3-(4-(4-amino-2-methylphenyl)piperidin-1-yl)propanenitrile; 3-chloro-4-(2,6-dimethylmorpholino)aniline; ethyl 5-amino-1H-indole-2-carboxylate; 2-((3-aminophenyl)imino)-1-morpholinoethan-1-one; 2-((3-aminophenyl)imino)-N-(2,3-dihydroxypropyl)acetamide; 2-((3-aminophenyl)imino)-1-(piperazin-1-yl)ethan-1-one; 4-chloro-3-nitroaniline; 4-(pyrrolidin-1-ylsulfonyl)aniline; 2,2,3,3-tetrafluoro-2,3-dihydrobenzo[b][1,4]dioxin-6-amine; methyl 5-amino-2-(trifluoromethoxy)benzoate; ethyl 7-amino-1H-indole-2-carboxylate; 5-amino-N-isopropyl-2,3-dihydrobenzofuran-2-carboxamide; 1-(4-(5-aminopyridin-2-yl)piperazin-1-yl) ethan-1-one; benzyl 3-(aminomethyl)piperidine-1-carboxylate; 6-amino-N,N-dimethyl-2-naphthamide; 4-(4-aminophenyl)piperazine-1-carboxamide; 1-(4-aminophenyl)piperidine-3-carboxamide; 4-(piperidin-1-yl)-7H-pyrrolo[2,3-d]pyrimidin-2-amine; 4-amino-N-cyclobutylbenzenesulfonamide; 1-(4-aminophenyl)piperidine-4-carboxylic acid; 1-(4-aminophenyl)-4-hydroxypyrrolidine-2-carboxamide; 1-(4-aminophenyl)piperidine-4-carboxamide; 2'-(piperidin-4-yl)-[1,1'-biphenyl]-3-amine; 2'-(piperidin-3-yl)-[1,1'-biphenyl]-3-amine; 2-phenyl-1H-indol-4-amine; 2',5'-dimethoxy-[1,1'-biphenyl]-3-amine; 1-(4-aminophenyl)-N-methylpyrrolidine-3-carboxamide; tert-butyl 2-(4-aminophenoxy)acetate; (4-aminophenyl)(2-(hydroxymethyl)morpholino)methanone; 4-amino-N-methyl-N-(tetrahydro-2H-pyran-4-yl)benzamide; 1-(4-amino-2-ethoxyphenyl)-4-methylpiperidin-4-ol; (4-aminophenyl)(3-hydroxy-3-methylazetidin-1-yl)methanone; 3-(4-(4-aminophenyl)piperidin-1-yl)propane-1,2-diol; 1-(4-aminophenethyl)-N,N-dimethylpiperidin-4-amine; 4-(2,2-dimethylmorpholino)-3-methylaniline; 4-amino-N-(1-methylpiperidin-4-yl)benzamide; 4-(2-(tetrahydro-2H-pyran-4-yl)thiazol-4-yl)aniline; 4-(2-(piperidin-3-yl)thiazol-4-yl)aniline; 4-(2-(pyridin-3-yl)thiazol-4-yl)aniline; 4-(1-(piperidin-4-yl)-1H-pyrazol-4-yl)aniline; 4-(1-cyclopentylpiperidin-4-yl)aniline; 3-(1,2,3,6-tetrahydropyridin-4-yl)-1H-indazol-6-amine; 4-(1-ethylpiperidin-4-yl)-2-methoxy-5-methylaniline; methyl 4-(4-aminophenyl) piperazine-1-carboxylate; tert-butyl 2-((3-aminophenyl) imino)acetate; (5-aminobenzofuran-2-yl)(pyrrolidin-1-yl) methanone; methyl 3-amino-5-(trifluoromethyl)benzoate; 2-((3-aminophenyl)imino)-N-(3-(dimethylamino)propyl)acetamide; ethyl 6-amino-4H-benzo[b]imidazo[1,5-d][1,4]oxazine-3-carboxylate; 1-(2-amino-5-fluoropyrimidin-4-yl)piperidine-3-carboxamide; 1-(4-(4-aminophenyl)piperazin-1-yl)propan-1-one; 2-amino-4-(m-tolyl)pyrimidine-5-carboxamide; 2-amino-4-(2-(2-hydroxyethyl)piperidin-1-yl)pyrimidine-5-carboxamide; 4-(morpholinosulfonyl) aniline; 4-((thiazol-4-ylmethyl)sulfonyl)aniline; 4-((tetrahydro-2H-pyran-4-yl)sulfonyl)aniline; 3-(2H-1,2,3-triazol-2-yl)-5-(trifluoromethyl)aniline; 1-(aminophenyl)-N-methylpiperidine-3-carboxamide; 1-(4-aminophenyl)-N-methylpiperidine-4-carboxamide; 6-amino-2,2,4-trimethyl-2H-benzo[b][1,4]oxazin-3(4H)-one; 1-(4-(4-aminophenyl)-3-methylpiperazin-1-yl)ethan-1-one; 2-(4-aminophenylsulfonamido)acetamide; 4-(phenylsulfonyl) aniline; 3-(2H-1,2,3-triazol-2-yl)-4-(trifluoromethyl)aniline; 3-morpholino-4-(1H-pyrazol-1-yl)aniline; 3-(1H-1,2,3-triazol-1-yl)-4-(trifluoromethyl)aniline; 4-(3-(trifluoromethyl)-1H-pyrazol-1-yl)aniline; 2-(6-amino-2-oxo-3,4-dihydroquinolin-1(2H)-yl)acetic acid; 1-(4-aminophenyl)-4-hydroxy-N-methylpyrrolidine-2-carboxamide; 1-(4-aminophenyl)-N,N-dimethylpyrrolidine-2-carboxamide; 4-(4-((dimethylamino)methyl)piperidin-1-yl)-5-fluoropyrimidin-2-amine; 7-amino-2,2,4-trimethyl-2H-benzo[b][1,4]oxazin-3(4H)-one; 3-(4-methyl-3,4-dihydro-2H-benzo[b][1,4]oxazin-7-yl)aniline; N-(1-(4-aminophenyl)piperidin-4-yl)acetamide; 1-(4-(4-aminophenyl)-1,4-diazepan-1-yl) ethan-1-one; 1-(4-(4-aminophenyl)-5,6-dihydropyridin-1(2H)-yl)ethan-1-one; 1-(4-(4-aminophenyl)-1,2,3,6-tetrahydropyridin-2-yl)ethan-1-one; 2-(1-(4-aminophenyl) piperidin-4-yl)propan-2-ol; 4-(piperidin-4-yl)-3-(trifluoromethyl)aniline; 4-(1-cyclopropylpiperidin-4-yl)-3-methylaniline; 4-(piperazin-1-yl)-3-(trifluoromethyl) aniline; 1-(4-aminophenethyl)piperidine-3-carboxylic acid; 1-(4-aminophenethyl)piperidine-4-carboxylic acid; 4-morpholino-3-(trifluoromethyl)aniline; 4-amino-N-(4-chlorophenyl)benzamide; 4-(4-(4-aminophenyl)piperidin-1-yl)butan-2-one; 4-(4-aminophenyl)-N-ethylpiperidine-1-carboxamide; 4-(1-isopropylpiperidin-4-yl)-3-methylaniline; 2-(4-(4-amino-2-methylphenyl)piperidin-1-yl)acetamide; (5-aminobenzofuran-2-yl)(morpholino) methanone; 5-amino-N-(2,3-dihydroxypropyl)-2,3-dihydrobenzofuran-2-carboxamide; 5-amino-N-(2,3-dihydroxypropyl)benzofuran-2-carboxamide; 5-amino-N-(1,3-dihydroxypropan-2-yl)benzofuran-2-carboxamide; 2-amino-4-(3-methoxyphenyl)pyrimidine-5-carboxamide; 3-amino-N-methoxy-N-phenylbenzamide; 1-(4-aminophenyl)-N,N-dimethylpiperidine-2-carboxamide; 2-amino-4-(3-ethylphenyl)pyrimidine-5-carboxamide; 1-(1-(2-amino-5-fluoropyrimidin-4-yl)piperidin-4-yl)urea; 2-(1-(2-amino- 5-fluoropyrimidin-4-yl)piperidin-4-yl)acetamide; 2-amino-4-(3-(hydroxymethyl)piperidin-1-yl)pyrimidine-5-carboxamide; 4-(4-(pyridin-2-yl)piperazin-1-yl)aniline; 3-(4-phenylpiperazin-1-yl)aniline; 3'-morpholino-[1,1'-biphenyl]-3-amine; 4'-morpholino-[1,1'-biphenyl]-3-amine; 3'-morpholino-[1,1'-biphenyl]-4-amine; 4'-morpholino-[1,1'-biphenyl]-4-amine; 2'-(methylsulfonyl)-[1,1'-biphenyl]-3-amine; 1-(4-(4-aminophenyl)piperazin-1-yl)-2-methoxyethan-1-one; 2',3',4'-trimethoxy-[1,1'-biphenyl]-3-amine; 4-acetyl-1-(4-aminophenyl)piperazin-2-one; (2-aminocyclohexyl)(tert-butyl)carbamate; 4-(4-(1-methylcyclopropyl)piperazin-1-yl)aniline; 2-(4-aminophenoxy)-1-(3-hydroxy-3-methylazetidin-1-yl)ethan-1-one; (4-aminophenyl)(4-hydroxy-4-methylpiperidin-1-yl)methanone; 4-(2-(4-(pyrrolidin-1-yl)piperidin-1-yl)ethyl)aniline; 1-(4-(4-amino-2-methylphenyl)piperidin-1-yl)ethan-1-one; 4-(1-(methylsulfonyl)pyrrolidin-3-yl)aniline; 4-(1-(2-morpholinoethyl)-1H-pyrazol-4-yl)aniline; 4-(1-methylpiperidin-4-yl)-3-(trifluoromethyl)aniline; 1-(4-(4-aminophenyl)piperidin-1-yl)-2-(ethylamino)ethan-1-one; 4-(1-(2,2,2-trifluoroethyl)piperidin-4-yl)aniline; 4-(4-aminophenyl)piperidine-1-carboxylate; 1-(4-(4-amino-2-methylphenyl)piperidin-1-yl)-3-methoxypropan-2-ol; 2-(4-(4-amino-2-methylphenyl)piperidin-1-yl)-N-methylacetamide; 4-(4-benzylpiperazin-1-yl)aniline; 2-((3-aminophenyl)imino)-1-(4-methylpiperazin-1-yl)ethan-1-one; 2-((3-aminophenyl)imino)-N-(2-morpholinoethyl)acetamide; (5-aminobenzofuran-2-yl)(1,4-diazepan-1-yl)methanone; (6-aminonaphthalen-2-yl)(morpholino)methanone; 1-(4-(4-amino-3-methylphenyl)piperazin-1-yl)ethan-1-one; 1-((1-(2-amino-5-fluoropyrimidin-4-yl)piperidin-4-yl)methyl)urea; 4-(2-amino-5-fluoropyrimidin-4-yl)piperazine-1-carboxamide; 1-(4-(4-amino-2-fluorophenyl)piperazin-1-yl)ethan-1-one; 1-(4-(4-aminophenyl)-2-methylpiperazin-1-yl)ethan-1-one; 4-(1-(methylsulfonyl)piperidin-4-yl)aniline; 4-(2-(4-morpholinopiperidin-1-yl)ethyl)aniline; 3-methyl-4-(1-(piperidin-4-yl)-1H-pyrazol-4-yl)aniline; 4-(1-(methylsulfonyl)piperidin-3-yl)aniline; 1-(4-(4-amino-2-methylphenyl)piperidin-1-yl)-2-(ethylamino)ethan-1-one; 1-(3-(4-aminophenyl)pyrrolidin-1-yl)-2-(dimethylamino)ethan-1-one; ethyl 3-(4-(4-aminophenyl)piperidin-1-yl)propanoate; tert-butyl 6-amino-3,4-dihydroisoquinoline-2(1H)-carboxylate; 4-(benzyloxy)-3-(trifluoromethyl)aniline; 5-amino-N-(1-hydroxy-2-methylpropan-2-yl)benzofuran-2-carboxamide; 1-((4-aminophenyl)sulfonyl)piperidin-4-ol; 4-(4-(methylsulfonyl)piperazin-1-yl)aniline; 1-(4-aminophenyl)-N,N-dimethylpiperidine-4-carboxamide; 2-amino-4-(4-(2-hydroxyethyl)-1,4-diazepan-1-yl)pyrimidine-5-carboxamide; 4-(4-aminophenyl)-N,N-dimethylpiperazine-1-carboxamide; 1-(4-(4-amino-2-chlorophenyl)piperazin-1-yl)ethan-1-one; 3-(2-amino-5-nitrophenyl)propanamide; 3-(4-(2-amino-5-fluoropyrimidin-4-yl)piperazin-1-yl)-3-oxopropanenitrile; 3-fluoro-4-(3-(trifluoromethyl)-1H-pyrazol-1-yl)aniline; (4-(4-aminophenyl)piperazin-1-yl)(cyclopropyl)methanone; 1-(3'-amino-[1,1'-biphenyl]-4-yl)piperidin-2-one; 1-(3'-amino-[1,1'-biphenyl]-3-yl)pyridin-2(1H)-one; 1-(3'-amino-[1,1'-biphenyl]-4-yl)pyridin-2(1H)-one; 4-(methylsulfonyl)-3-morpholinoaniline; 3'-(methylsulfonyl)-[1,1'-biphenyl]-4-amine; 4'-(methylsulfonyl)-[1,1'-biphenyl]-4-amine; 3'-(methylsulfonyl)-[1,1'-biphenyl]-3-amine; 4'-(methylsulfonyl)-[1,1'-biphenyl]-3-amine; methyl 4-(4-aminophenyl)-3-methylpiperazine-1-carboxylate; N-(4-aminophenyl)-2-(benzyloxy)-N-methylacetamide; 2-(4-amino-N-methylphenylsulfonamido)acetic acid; 1-(4-aminophenyl)-4-hydroxy-N,N-dimethylpyrrolidine-2-carboxamide; 1-(4-aminophenyl)-N,N-dimethylpiperidine-3-carboxamide; N-(1-(4-aminophenyl)piperidin-4-yl)-N-methylacetamide; 1-(4-(4-aminophenyl)piperidin-1-yl)-2-(dimethylamino)ethan-1-one; 4-(1-(4,4,4-trifluorobutyl)piperidin-4-yl)aniline; 3-methyl-4-(6-(piperazin-1-yl)pyridin-3-yl)aniline; 1-(1-(2-(methylsulfonyl)ethyl)piperidin-4-yl)-1H-pyrazol-4-amine; 1-(4-(5-aminopyridin-2-yl)piperidin-1-yl)-2-(dimethylamino)ethan-1-one; 4-(1-(ethylsulfonyl)piperidin-4-yl)aniline; 2-((3-aminophenyl)imino)-N-(2-(benzylamino)ethyl)acetamide; 1-(4-(4-aminophenyl)-3-methylpiperazin-1-yl)-2-methoxyethan-1-one; N-(1-(2-amino-5-fluoropyrimidin-4-yl)piperidin-4-yl)-2-cyanoacetamide; 4-((4-(methylsulfonyl)piperazin-1-yl)methyl)aniline; 4-(4-(methylsulfonyl)-1,4-diazepan-1-yl)aniline; 4-(1-(methylsulfonyl)-1,2,3,6-tetrahydropyridin-4-yl)aniline; 4-(2-(methylsulfonyl)-1,2,3,6-tetrahydropyridin-4-yl)aniline; 2-amino-4-(methyl(1-methylpiperidin-4-yl)amino)pyrimidine-5-carboxamide; 4-(4-(ethylsulfonyl)piperazin-1-yl)aniline; 1-(4-(4-aminobenzoyl)piperazin-1-yl)ethan-1-one; 4-(2-methyl-4-(methylsulfonyl)piperazin-1-yl)aniline; 2,6-diisopropyl-4-phenoxyaniline; 2-methyl-4-(4-(methylsulfonyl)piperazin-1-yl)aniline; 3-methyl-4-(1-(2-morpholinoethyl)-1H-pyrazol-4-yl)aniline; 4-(1-(2-(methylsulfonyl)ethyl)piperidin-4-yl)aniline; 4-(4-amino-2-methylphenyl)piperidin-1-yl)-2-(dimethylamino)ethan-1-one; 5-amino-2-(morpholine-4-carbonyl)benzofuran-3(2H)-one; tert-butyl (6-amino-4H-chromen-4-yl)carbamate; 2-amino-4-(3,5-dimethylphenyl)pyrimidine-5-carboxamide; (1-(4-aminophenyl)piperidin-4-yl)(pyrrolidin-1-yl)methanone; 4-acetyl-1-(4-aminophenyl)piperazine-2-carboxamide; 3-(4-(4-aminophenyl)piperidin-1-yl)-1,1,1-trifluoropropan-2-ol; tert-butyl 3-(4-aminophenyl)pyrrolidine-1-carboxylate; ethyl 1-(3-aminobenzoyl)piperidine-4-carboxylate; (1-(4-aminophenyl)piperidin-4-yl)(morpholino)methanone; (1-(4-aminophenyl)piperidin-4-yl)(piperidin-1-yl)methanone; 4-acetyl-1-(4-aminophenyl)-N-methylpiperazine-2-carboxamide; tert-butyl 4-(4-aminophenyl)piperidine-1-carboxylate; butyl 2-(4-amino-N-methylphenylsulfonamido)acetate; 4-(4-(cyclopropylsulfonyl)piperazin-1-yl)aniline; N-(1-(4-aminophenyl)piperidin-4-yl)-N-methylmethanesulfonamide; 4-(4-(ethylsulfonyl)-2-methylpiperazin-1-yl)aniline; 3-methyl-4-(1-(2-(methylsulfonyl)ethyl)piperidin-4-yl)aniline; (4-aminophenyl)(4-(methylsulfonyl)piperazin-1-yl)methanone; 4-(4-(cyclopropylsulfonyl)-2-methylpiperazin-1-yl)aniline; 1-(4-(4-aminophenyl)piperidin-4-yl)-2-(methylsulfonyl)ethan-1-one; methyl 4-((6-amino-2H-indazol-2-yl)methyl)-3-methoxybenzoate; methyl 4-((6-amino-1H-indazol-1-yl)methyl)-3-methoxybenzoate; 4-((6-amino-1H-indazol-1-yl)methyl)-3-methoxy-N-methylbenzamide; 2-isopropyl-5-methylcyclohexyl 5-amino-2,3-dihydrobenzofuran-2-carboxylate; ethyl 4-amino-3-(2-amino-5-nitrobenzyl)-4-oxobutanoate; 3,4-bis(3-(trifluoromethyl)-1H-pyrazol-1-yl)aniline.

Especially preferably, $R^1$ can be derived from the following amines:

4-(4-(4-methylpiperazin-1-yl)piperidin-1-yl)aniline; 3-fluoro-4-morpholinoaniline; 4-fluoro-3-(methylsulfonyl)aniline; 3-((dimethylamino)methyl)aniline; (4-aminophenyl)(4-(4-methylpiperazin-1-yl)piperidin-1-yl)methanone; (3-aminophenyl)(morpholino)methanone; 3-(tert-butyl)aniline; 4-morpholinoaniline; 4-(4-cyclopropylpiperazin-1-yl)aniline; 6-morpholinopyridin-3-amine; 6-amino-2,3-dihydrobenzo[b]thiophene 1,1-dioxide; 6-aminobenzo[b]thiophene 1,1-dioxide; (4-aminophenyl)(morpholino)methanone; 4-(morpholinomethyl)aniline; 3-methoxy-4-morpholinoaniline; 1,3-dihydroisobenzofuran-5-amine;

4-((4-(4-methylpiperazin-1-yl)piperidin-1-yl)methyl)aniline; 3-(morpholinomethyl)aniline; 2-(3-aminophenyl)-2-methylpropanenitrile; 3-(4-aminophenyl)oxazolidin-2-one; 5-cyclopropyl-1H-pyrazol-3-amine; (4-amino-2-fluorophenyl)(morpholino)methanone; (4-amino-2-nitrophenyl)(morpholino)methanone; 4-(oxazol-2-yl)aniline; 4-(oxazol-5-yl)aniline; 4-(4-(tert-butyl)piperazin-1-yl)aniline; pyridazin-4-amine; 3-(methylsulfonyl)-4-nitroaniline; 3-(methylsulfonyl)aniline; 3,4-dimethoxyaniline; 1-(4-(4-aminophenyl)piperazin-1-yl)ethan-1-one; 7-amino-3,4-dihydroquinolin-2(1H)-one; 4-((dimethylamino)methyl)aniline; 2-methylisoindolin-5-amine; 2-(methylthio)-1H-benzo[d]imidazol-5-amine; 4-(4-(methylsulfonyl)piperazin-1-yl)aniline; 4-(4-aminophenyl)morpholin-3-one; (4-aminophenyl)(pyrrolidin-1-yl)methanone; (4-aminophenyl)(4-methylpiperazin-1-yl)methanone; 4-aminobenzamide; 1-(4-aminophenyl)pyrrolidin-2-one; 5-amino-2-morpholinobenzonitrile; 8-amino-4,5-dihydro-1H-benzo[b]azepin-2(3H)-one; 6-(4-methylpiperazin-1-yl)pyridin-3-amine; cyclopropanamine; 1-methyl-1H-pyrazol-4-amine; 5-(4-aminophenyl)-1,3,4-oxadiazole-2-thiol; 1-(tetrahydro-2H-pyran-4-yl)-1H-pyrazol-4-amine; 4-(4-morpholinopiperidin-1-yl)aniline; N2,N2-dimethylpyridine-2,5-diamine; 3-(methylsulfonyl)-4-morpholinoaniline; 1-(4-(5-aminopyridin-2-yl)piperazin-1-yl)ethan-1-one; 6-(4-(4-methylpiperazin-1-yl)piperidin-1-yl)pyridin-3-amine; 1,5-dimethyl-1H-pyrazol-4-amine; 1,3-dimethyl-1H-pyrazol-4-amine; 2-((4-aminophenyl)amino)ethan-1-ol; 1-(2-methoxyethyl)-1H-pyrazol-4-amine; 1-(methylsulfonyl)-1H-pyrazol-4-amine; 1-(1-methylpiperidin-4-yl)-1H-pyrazol-4-amine; 1-(4-(4-amino-1H-pyrazol-1-yl)piperidin-1-yl)ethan-1-one; 1-methyl-1H-1,2,3-triazol-4-amine; 2-methyl-2H-1,2,3-triazol-4-amine; 1-methyl-1H-pyrazol-3-amine.

Furthermore preferably, $R^1$ can be derived from the following amines:

methanamine; 2-aminoethane-1-thiol; ethane-1,2-diamine; 2-methylpropan-1-amine; furan-2-ylmethanamine; pyrimidin-4-amine; pyridin-4-ylmethanamine; pyridin-2-ylmethanamine; pyridin-3-ylmethanamine; 2-fluoroaniline; 3-methylpyridin-4-amine; 2-(pyridin-4-yl)ethan-1-amine; 1-methyl-1H-pyrazol-3-amine; (2-methoxyphenyl)methanamine; 4-aminocyclohexanol; 6-fluoropyridin-2-amine; (S)-butane-1,2-diamine; 1-amino-3-methylbut-3-en-1-ol; benzene-1,4-diamine; 5-aminopyridin-2-ol; 2-aminobenzonitrile; 2-(1H-imidazol-5-yl)ethan-1-amine; 2-(methylthio)pyrimidin-4-amine; (2-ethoxyphenyl)methanamine; 2,6-difluoroaniline; 6-chloropyridin-3-amine; 2-methoxypyridin-4-amine; 6-methoxypyridazin-3-amine; 1-ethyl-5-methyl-1H-pyrazol-3-amine; (4-methoxyphenyl)methanamine; (4-chlorophenyl)methanamine; (3-chlorophenyl)methanamine; 2-chloro-6-methylaniline; benzo[d]isoxazol-6-amine; benzo[d]oxazol-6-amine; 4-((methylamino)methyl)aniline; 3-ethynylaniline; 3-aminopicolinamide; 2-aminonicotinamide; N1-isopropyl-2-methylpropane-1,2-diamine; 2-fluoro-6-methylpyrimidin-4-amine; 4-chloro-3-methoxyaniline; 4-aminonicotinic acid; 2-aminobenzoic acid; 2-((5-aminopyridin-2-yl)oxy)ethan-1-ol; (3-amino-1H-pyrazol-5-yl)methanol; 4-(2-(methylamino)ethyl)aniline; 2-aminothiazole-4-carboxamide; methyl 2-aminonicotinate; 1-(3-aminophenyl)ethan-1-ol; 2-((4-aminobenzyl)amino)ethan-1-ol; methyl 4-aminonicotinate; methyl 2-aminobenzoate; 6-(2-methoxyethoxy)pyridin-3-amine; 4-(2-(methylamino)ethoxy)aniline; 3-ethoxy-4-methoxyaniline; 6-((2-aminoethyl)amino)nicotinonitrile; 5-aminopicolinamide; 6-aminopicolinamide; 2-(methylsulfinyl)pyrimidin-4-amine; 2-methylbenzo[d]oxazol-5-amine; 2-(4-amino-2-methoxyphenoxy)ethan-1-ol; 4-aminobenzimidamide; 3-methoxy-4-propoxyaniline; 4-(((2-methoxyethyl)amino)methyl)aniline; 2,5-dimethoxyaniline; ethyl 2-aminobenzoate; 2-amino-6-((2-aminoethyl)amino)nicotinonitrile; (R)-1-phenylethan-1-amine; 3-cyclopropyl-1H-pyrazol-5-amine; 2-((5-aminopyridin-2-yl)(methyl)amino)ethan-1-ol; 4-amino-N-methylbenzimidamide; 2-(3-aminophenyl)acetic acid; 2-((6-aminopyridin-3-yl)(methyl)amino)ethan-1-ol; 2-(4-amino-2-methoxyphenoxy)acetonitrile; 4-amino-N-hydroxybenzamide; 2,4,6-trifluoroaniline; 4-((2-methoxyethoxy)methoxy)aniline; N2,N2-diethylpyridine-2,5-diamine; 4-((ethyl(methyl)amino)methyl)aniline; ethyl 4-aminobenzoate; 4-amino-2-((2-aminoethyl)amino)thiazole-5-carbonitrile; 2-aminobenzenesulfonamide; ethyl 6-aminonicotinate; 5-morpholinopyridin-2-amine; 4-amino-N,N'-dimethylbenzimidamide; N-(5-amino-2-hydroxyphenyl)acetamide; ethyl 4-aminobenzimidate; 3-(4-aminophenyl)propanoic acid; 2-((4-aminobenzyl)(methyl)amino)ethan-1-ol; 2-morpholinopyrimidin-5-amine; 6-morpholinopyridazin-3-amine; 6-(piperazin-1-yl)pyridin-3-amine; 4-((1H-imidazol-1-yl)methyl)aniline; 4-amino-N-methoxybenzamide; N5-(2-methoxyethyl)-N5-methylpyridine-2,5-diamine; N2-(2-methoxyethyl)-N2-methylpyridine-2,5-diamine; 2-(4-aminophenyl)-N-methylacetimidamide; 3-amino-N,2-dimethylbenzamide; 2,4-diaminobenzamide; 6-((1-aminopropan-2-yl)amino)nicotinonitrile; 6-((2-aminopropyl)amino)nicotinonitrile; (4-aminophenyl)dimethylphosphine oxide; 1-(5-aminopyridin-2-yl)azetidin-3-ol; 3-methyl-1H-indazol-5-amine; 4-amino-N-cyclopropylnicotinamide; 2-(5-aminopyridin-2-yl)-2-methylpropan-1-ol; 4-amino-3-methylbenzamide; 4-amino-3-methylbenzimidamide; 1-(6-aminopyridin-3-yl)azetidin-3-ol; 4-(1,4-diazepan-1-yl)aniline; 4-(piperazin-1-ylmethyl)aniline; methyl 4-amino-2-methoxybenzoate; 4-(((2-methoxyethyl)(methyl)amino)methyl)aniline; 2-(4-aminophenyl)-N,N'-dimethylacetimidamide; 2-amino-5-methoxybenzamide; 1-(6-aminopyridin-2-yl)pyrrolidin-3-ol; 2-(methylsulfonyl)pyrimidin-4-amine; 4-(2-(dimethylamino)ethoxy)-3-methoxyaniline; 4-((1,4-diazepan-1-yl)methyl)aniline; 4-(1H-imidazol-2-yl)aniline; 2-(3-aminophenyl)propanoic acid; 4-amino-N-(4-aminophenyl)butanamide; 4-amino-N-(3-aminophenyl)butanamide; 1-((5-aminopyridin-2-yl)oxy)-2-methylpropan-2-ol; 1-((6-aminopyridin-3-yl)oxy)-2-methylpropan-2-ol; 4-amino-N,N-dimethylbenzimidamide; 2-(4-aminophenyl)propanoic acid; 4-amino-N,3-dimethylbenzamide; (3,4,5-trimethoxyphenyl)methanamine; N2-phenethylpyrimidine-2,4-diamine; N1-(5-(trifluoromethyl)pyridin-2-yl)ethane-1,2-diamine; 4-amino-N-methylbenzenesulfonamide; 3-methoxy-4-(piperidin-4-yloxy)aniline; 3-methyl-4-(piperazin-1-yl)aniline; 4-(3-methylpiperazin-1-yl)aniline; N-(4-aminobenzyl)-N-methylacetamide; 2-(3-aminophenyl)-N,N-dimethylacetamide; 2-(4-aminophenyl)-N,N-dimethylacetimidamide; 4-((1H-tetrazol-5-yl)methyl)aniline; 2-amino-5-isopropylthiazole-4-carboxamide; 1-(4-aminophenyl)-3-methylazetidin-3-amine; (2-aminopropyl)(tert-butyl)carbamic acid; 1-(5-aminopyridin-2-yl)-3-methylazetidin-3-ol; 3-methoxy-4-(1H-pyrazol-5-yl)aniline; 1-(4-aminophenyl)piperidin-4-one; 1-(6-aminopyridin-3-yl)-3-methylazetidin-3-ol; 4-(4-aminophenyl)thiomorpholine 1-oxide; N1-(4-aminobenzyl)-N1,N2,N2-trimethylethane-1,2-diamine; ethyl 2-(4-aminophenyl)propanoate; 4-((3-methylpiperazin-1-yl)methyl)aniline; 3-((3-methylpiperazin-1-yl)methyl)aniline; (6-aminopyridin-3-yl)(morpholino)methanone; 1-(2-amino-6-((2-aminoethyl)amino)pyridin-3-yl)propan-1- one; methyl 2-amino-6-((2-aminoethyl)amino)nicotinate; 4-(4-aminobenzyl)piperazin-2-one; N-(3-aminophenyl)tetrahydrofuran-2-carboxamide; 4-(1H-imidazol-2-yl)-3-methylaniline; 2-(4-aminobenzamido)acetic acid; 2-(4-aminophenyl)-N-(2-hydroxyethyl)-N-methylacetamide; N-(2-(4-aminophenoxy)ethyl)-N-methylacetamide; 4-(((((methylsulfonyl)methyl)amino)methyl)aniline; N-(3-aminophenyl)furan-2-carboxamide; N-(4-aminophenyl)furan-2-carboxamide; 4-(imino(morpholino)methyl)aniline; 4-((4-methyl-1,4-diazepan-1-yl)methyl)aniline; (S)-1-(4-aminophenyl)pyrrolidin-3-ol; (S)-2-(3-aminopyrrolidin-1-yl)pyrimidin-4-amine; (S)-4-((tetrahydrofuran-2-yl)methoxy)aniline; N1-(5-nitrothiazol-2-yl)ethane-1,2-diamine; (S)-1-(4-aminopyrimidin-2-yl)pyrrolidin-3-ol; ethyl 2-amino-6-((2-aminoethyl)amino)nicotinate; N2-(1-phenylpropan-2-yl)pyrimidine-2,4-diamine; 1-(5-aminopyridin-2-yl)-4-methylpiperidin-4-ol; 2-(3-aminophenyl)-1-morpholinoethan-1-one; 2-(4-aminophenyl)-1-morpholinoethan-1-one; 2-(3-amino-1H-pyrazol-5-yl)-N-cyclopropylacetamide; 1-(5-aminopyridin-2-yl)-3-methylpiperidin-3-ol; N-(4-aminophenyl)isonicotinamide; N-(4-aminophenyl)benzamide; 4-(3,5-dimethylpiperazin-1-yl)aniline; (4-aminophenyl)(1,4-diazepan-1-yl)methanone; 4-((5,6-dihydroimidazo[1,2-a]pyrazin-7(8H)-yl)methyl)aniline; 1-(4-aminobenzyl)pyrrolidine-2-carboxylic acid; 4-(2-imino-2-morpholinoethyl)aniline; methyl 2-(4-aminobenzamido)acetate; (S)-1-(4-aminophenyl)piperidin-3-ol; (S)-(1-(4-aminophenyl)pyrrolidin-3-yl)methanol; (R)-(4-(4-aminophenyl)morpholin-3-yl)methanol; 2-amino-4-(trifluoromethyl)thiazole-5-carboxamide; N1-(5-nitropyridin-2-yl)ethane-1,2-diamine; 6,6-diphenylhex-5-en-1-amine; tert-butyl (4-aminophenyl)carbamate; methyl 1-(4-aminobenzyl)pyrrolidine-2-carboxylate; (4-amino-2-methoxyphenyl)(morpholino)methanone; 6-(4-isopropylpiperazin-1-yl)pyridin-3-amine; tert-butyl (3-aminophenyl)carbamate; 2-amino-N-(4-aminophenyl)benzamide; 4-amino-N-benzylbenzamide; 3-((3,5-dimethylpiperazin-1-yl)methyl)aniline; (S)-(4-(4-aminophenyl)morpholin-2-yl)methanol; (S)-1-(4-amino-2-methoxyphenyl)pyrrolidin-3-ol; N2-(2-aminoethyl)-5-nitropyridine-2,6-diamine; 6-((2-aminoethyl)thio)-3-nitropyridin-2-amine; (S)-3-methoxy-4-((tetrahydrofuran-2-yl)methoxy)aniline; 6-(2-aminoethoxy)-3-nitropyridin-2-amine; (6-aminopyridin-3-yl)(4-methylpiperazin-1-yl)methanone; (S)-(4-(5-aminopyridin-2-yl)morpholin-2-yl)methanol; 1-(4-aminobenzyl)-3-isopropyl-1-methylurea; (S)-1-(4-amino-2-methoxyphenyl)piperidin-3-ol; (R)-1-(4-aminophenyl)-3-methylpyrrolidin-3-ol; (R)—N2-(1-phenylethyl)pyrimidine-2,4-diamine; (S)-(1-(4-amino-2-methoxyphenyl)pyrrolidin-3-yl)methanol; (S)-1-(4-amino-2-ethoxyphenyl)pyrrolidin-3-ol; N2-(3-aminopropyl)-5-nitropyridine-2,6-diamine; 1-(4-(4-aminobenzyl)piperazin-1-yl)ethan-1-one; 4-(4-aminobenzoyl)piperazin-2-one; 4-amino-N-(4-aminophenyl)benzamide; 2-(4-aminophenyl)-N-cyclooctylacetamide; 5-(aminomethyl)-N-(4-aminophenyl)furan-2-carboxamide; 4-((3-methyl-5,6-dihydro-[1,2,4]triazolo[4,3-a]pyrazin-7(8H)-yl)methyl)aniline; 2-(4-aminophenyl)-1-morpholinopropan-1-one; 2-(4-aminophenyl)-1-(4-methylpiperazin-1-yl)ethan-1-one; 2-(3-aminophenyl)-1-(4-methylpiperazin-1-yl)ethan-1-one; (4-aminophenyl)(4-ethylpiperazin-1-yl)methanone; (R)-1-(4-aminophenyl)-3-methylpiperidin-3-ol; (S)-(4-(4-amino-2-methoxyphenyl)morpholin-2-yl)methanol; 4-(aminomethyl)-N-(4-aminophenyl)benzamide; (R)-1-(5-aminopyridin-2-yl)-3-methylpiperidin-3-ol; (4-aminophenyl)(5,6-dihydroimidazo[1,2-a]pyrazin-7(8H)-yl)methanone; N-(aminomethyl)-N-(4-aminophenyl)benzamide; 2-(aminomethyl)-N-(4-aminophenyl)isonicotinamide; 5-(aminomethyl)-N-(4-aminophenyl)nicotinamide; 4-(aminomethyl)-N-(4-aminophenyl)picolinamide; 5-(aminomethyl)-N-(4-aminophenyl)picolinamide; 6-(aminomethyl)-N-(4-aminophenyl)picolinamide; 6-(aminomethyl)-N-(4-aminophenyl)nicotinamide; 3-(aminomethyl)-N-(4-aminophenyl)benzamide; 3-(aminomethyl)-N-(3-aminophenyl)benzamide; 4-(aminomethyl)-N-(3-aminophenyl)benzamide; N4-((1H-indol-5-yl)methyl)pyrimidine-2,4-diamine; ethyl 4-(4-aminophenyl)piperazine-1-carboxylate; 1-(2-amino-6-((2-aminoethyl)amino)pyridin-3-yl)-2,2,2-trifluoroethan-1-one; (R)-1-(4-amino-2-methoxyphenyl)-3-methylpyrrolidin-3-ol; N2-(2-aminopropyl)-5-nitropyridine-2,6-diamine; 2-((1R,4S)-2,5-diazabicyclo[2.2.1]heptan-2-yl)pyrimidin-4-amine; N2-(1-aminopropan-2-yl)-5-nitropyridine-2,6-diamine; 4-(2-aminoethyl)-N-(4-aminophenyl)benzamide; 4-(2-aminoethyl)-N-(3-aminophenyl)benzamide; N-(4-aminophenyl)-2-(3-chlorophenyl)acetamide; (4-aminophenyl)(hexahydro-1H-pyrido[1,2-a]pyrazin-2(6H)-yl)methanone; 2-(4-aminophenyl)-N,N-diisopropylacetamide; N-(4-aminophenyl)-2-(4-methoxyphenyl)acetamide; N-(3-aminophenyl)-2-(4-methoxyphenyl)acetamide; N-(4-aminophenyl)-4-((methylamino)methyl)benzamide; N-(3-aminophenyl)-4-((methylamino)methyl)benzamide; (R)—N2-methyl-N2-(1-phenylethyl)pyrimidine-2,4-diamine; N-(4-aminophenyl)-1,2,3,4-tetrahydroisoquinoline-6-carboxamide; 4'-fluoro-5-(trifluoromethoxy)-[1,1'-biphenyl]-2-amine; N-(3-aminophenyl)-1,2,3,4-tetrahydroisoquinoline-6-carboxamide; N-(3-aminophenyl)-1,2,3,4-tetrahydroisoquinoline-7-carboxamide; N-(4-aminophenyl)-1,2,3,4-tetrahydroisoquinoline-7-carboxamide; (S)-3-(4-aminophenyl)-1,4-dimethylpiperazin-2-one; (4-aminophenyl)(3-methyl-5,6-dihydro-[1,2,4]triazolo[4,3-a]pyrazin-7(8)-yl)methanone; N-(4-aminophenyl)-4-(((2-hydroxyethyl)amino)methyl)benzamide; 4-(aminomethyl)-N-(4-aminophenyl)-2-fluorobenzamide; 4-(aminomethyl)-N-(3-aminophenyl)-2-fluorobenzamide; N-(4-aminophenyl)-3,4-dichlorobenzamide; N-(4-aminophenyl)-4-((dimethylamino)methyl)benzamide; 4-((2R,6R)-2,6-dimethylmorpholino)aniline; N-(4-aminophenyl)-4-guanidinobenzamide; 2-(4-aminophenyl)-1-(hexahydro-1H-pyrido[1,2-a]pyrazin-2(6H)-yl)propan-1-one; tert-butyl 4-(4-aminophenyl)piperazine-1-carboxylate; N-(3-aminophenyl)-4-(2-aminopropan-2-yl)benzamide; N-(4-aminophenyl)-4-(2-aminopropan-2-yl)benzamide; N-(3-aminophenyl)-4-(tert-butyl)benzamide; N-(4-aminophenyl)-4-(tert-butyl)benzamide; N-(3-aminophenyl)-4-(piperidin-3-yl)benzamide; 3-amino-4-methyl-N-(3-(trifluoromethyl)phenyl)benzamide; N-(3-amino-4-methylphenyl)-3-(trifluoromethyl)benzamide; 3-amino-N-(3-aminophenyl)-2-(3,4-dichlorophenyl)propanamide; 4-amino-N-(4-aminophenyl)-2-(3,4-dichlorophenyl)butanamide; N-(4-aminophenyl)-4-((4-methylpiperazin-1-yl)methyl)benzamide; N-(3-amino-4-methylphenyl)-4-methoxy-3-(trifluoromethyl)benzamide; N-(4-aminophenyl)-4-(((2-(methylsulfonyl)ethyl)amino)methyl)benzamide; tert-butyl ((5-((4-aminophenyl)carbamoyl)furan-2-yl)methyl)carbamate; tert-butyl (4-((4-aminophenyl)carbamoyl)benzyl)carbamate; tert-butyl ((2-((4-aminophenyl)carbamoyl)pyridin-4-yl)methyl)carbamate; tert-butyl (4-((4-aminophenyl)carbamoyl)phenethyl)carbamate; tert-butyl 6-((4-aminophenyl)carbamoyl)-3,4-dihydroisoquinoline-2(1H)-carboxylate; tert-butyl (2-(4-((3-aminophenyl)carbamoyl)phenyl)propan-2-yl)carbamate; tert-butyl (3-((3-aminophenyl)amino)-2-(3,4-dichlorophenyl)-3-oxopropyl)carbamate; tert-butyl (4-((4-aminophenyl)amino)-3-(3,4-dichlorophenyl)-4-oxobutyl)carbamate; tert-butyl (4-((4-aminophenyl)carbamoyl)benzyl)(2-((tetrahydro-2H-pyran-2-yl)oxy)ethyl)carbamate.

Furthermore preferably, $R^1$ can be derived from the following compounds (e.g. ureas, amides):

urea; 1-methylurea; propionamide; 1-ethylurea; 1-(2-hydroxyethyl)urea; 1-propylurea; cyclopropanecarboxamide; 1-(3-hydroxypropyl)urea; 1-isopropylurea; 1-(2-cyanoethyl)urea; ethanesulfonamide; thiazole-4-carboxamide; furan-2-carboxamide; 1,2,3-thiadiazole-4-carboxamide; thiazole-5-carboxamide; isoxazole-3-carboxamide; 1-isobutylurea; thiophene-3-carboxamide; furan-3-carboxamide; picolinamide; cyclohexanecarboxamide; 1-methyl-1H-pyrazole-5-carboxamide; nicotinamide; 1-methyl-1H-imidazole-2-carboxamide; 1-methyl-1H-pyrrole-2-carboxamide; benzamide; 1-methyl-1H-1,2,4-triazole-5-carboxamide; 2-methylfuran-3-carboxamide; 1-(3-(dimethylamino)propyl)urea; 2-morpholinoacetamide; 3-fluoropicolinamide; 3-methylpicolinamide; 2-methylnicotinamide; 2-methylbenzamide; 1-(tert-butyl)urea; 2-(pyridin-2-yl)acetamide; 5-bromothiazole-4-carboxamide; 2-fluorobenzamide; 4-methoxythiophene-3-carboxamide; 2-(piperidin-1-yl)acetamide; 2-(tetrahydro-2H-pyran-4-yl)acetamide; 2-chlorofuran-3-carboxamide; 1-ethyl-1H-pyrazole-5-carboxamide; 2-methylthiazole-4-carboxamide; 3-phenylpropanamide; 3-chloropicolinamide; 3-bromopicolinamide; 1H-pyrazole-3-carboxamide; 2-methoxynicotinamide; 3-methoxypicolinamide; 1H-imidazole-2-carboxamide; 1-(2-fluoroethyl)-1H-pyrazole-5-carboxamide; 1-methyl-1H-1,2,4-triazole-3-carboxamide; 1-methyl-1H-imidazole-4-carboxamide; 2-methyloxazole-4-carboxamide; 4-methylthiophene-2-carboxamide; 1H-imidazole-4-carboxamide; 1H-pyrazole-5-carboxamide; 2-methoxybenzamide; 1-methyl-1H-pyrazole-3-carboxamide; 1-vinyl-1H-pyrazole-5-carboxamide; 5-methylisoxazole-3-carboxamide; 5-methylfuran-2-carboxamide; 6-methylpicolinamide; 6-fluoropicolinamide; 4-methylmorpholine-2-carboxamide; 5-methylpicolinamide; 5-oxopyrrolidine-3-carboxamide; 1-(3-(1H-imidazol-1-yl)propyl)urea; 5-chlorofuran-2-carboxamide; 5-fluoropicolinamide; 1,3-dimethyl-1H-pyrazole-5-carboxamide; 2-ethoxynicotinamide; 2-ethoxybenzamide; 1-ethyl-1H-pyrazole-3-carboxamide; 2-(3-methyl-1H-pyrazol-1-yl)acetamide; 3-methylbenzamide; 4-morpholinobutanamide; 1,4-dimethyl-1H-pyrazole-5-carboxamide; 1-methylpiperidine-4-carboxamide; 1-isopropyl-1H-pyrazole-5-carboxamide; 6-(methylamino)picolinamide; 5-isopropylthiazole-4-carboxamide; 4-(methylamino)picolinamide; 1-isopropyl-1H-1,2,4-triazole-5-carboxamide; 1-isopropyl-1H-1,2,3-triazole-5-carboxamide; 6-methoxypicolinamide; 6-chloropicolinamide; 5-bromopicolinamide; 1-(3-thiomorpholinopropyl)urea; 5-isopropyloxazole-4-carboxamide; 1-isopropyl-1H-imidazole-2-carboxamide; 5-isopropylisoxazole-4-carboxamide; 1-(difluoromethyl)-1H-pyrazole-5-carboxamide; 1-(2-fluoroethyl)-1H-pyrazole-3-carboxamide; 2,3-difluorobenzamide; 6-methoxypyrazine-2-carboxamide; 4-chloro-1-methyl-1H-pyrazole-5-carboxamide; 6-bromopicolinamide; 1-(3-morpholinopropyl)urea; 2,6-difluorobenzamide; 1-ethyl-4-fluoro-1H-pyrazole-5-carboxamide; 1-ethyl-3-methyl-1H-pyrazole-5-carboxamide; 1,4-dimethyl-1H-pyrazole-3-carboxamide; 4-chloro-1-ethyl-1H-pyrazole-5-carboxamide; 2,5-dimethyloxazole-4-carboxamide; 3-isopropylpicolinamide; 6-(ethylamino)picolinamide; 1,5-dimethyl-1H-pyrazole-3-carboxamide; 4-cyanobenzamide; 2-methoxy-3-methylbenzamide; 2-methoxy-4-methylbenzamide; 2-methoxy-5-methylbenzamide; 4-fluoro-1-methyl-1H-pyrazole-3-carboxamide; 2,5-dimethylthiazole-4-carboxamide; 5-methyl-1H-pyrazole-3-carboxamide; pyrazolo[1,5-a]pyridine-2-carboxamide; 3-methyl-1H-pyrazole-5-carboxamide; 2-isopropyl-2H-1,2,3-triazole-4-carboxamide; 3-(prop-1-en-2-yl)picolinamide; isoquinoline-1-carboxamide; 4-chloro-1H-pyrazole-5-carboxamide; 3,5-difluoropicolinamide; 2,5-difluorobenzamide; 2,4-difluorobenzamide; 3-ethyl-1H-pyrazole-5-carboxamide; 1-isopropyl-1H-pyrazole-3-carboxamide; 2-(difluoromethoxy)benzamide; 3-(dimethylamino)benzamide; 6-(dimethylamino)picolinamide; 6-chloro-3-fluoropicolinamide; 4-bromo-1,3-dimethyl-1H-pyrazole-5-carboxamide; 2-acetylthiazole-4-carboxamide; 3-cyclopropyl-1-methyl-1H-pyrazole-5-carboxamide; 6-oxo-1,6-dihydropyridine-2-carboxamide; 5-((dimethylamino)methyl)furan-2-carboxamide; 1-(3-(4-methylpiperazin-1-yl)propyl)urea; 4-fluoro-1-isopropyl-1H-pyrazole-5-carboxamide; 1H-indazole-1-carboxamide; 4-(trifluoromethyl)thiazole-5-carboxamide; 6-(cyclopropylamino)picolinamide; 6-((dimethylamino)methyl)picolinamide; 6-(isopropylamino)picolinamide; 1H-benzo[d]imidazole-2-carboxamide; 1-(2,2,2-trifluoroethyl)-1H-pyrazole-5-carboxamide; 1H-indole-2-carboxamide; 3,6-dichloropicolinamide; 4-chloro-1-isopropyl-1H-pyrazole-3-carboxamide; 1-acetylpiperidine-4-carboxamide; 4-((dimethylamino)methyl)-5-methylisoxazole-3-carboxamide; 4-acetylmorpholine-2-carboxamide; 1-ethyl-3-isopropyl-1H-pyrazole-5-carboxamide; 4-chloro-1-isopropyl-1H-pyrazole-5-carboxamide; 1-((tetrahydro-2H-pyran-4-yl)methyl)-1H-pyrazole-5-carboxamide; 2-(pyrrolidin-1-yl)isonicotinamide; 6-(pyrrolidin-1-yl)picolinamide; 6-(diethylamino)picolinamide; 3-isopropyl-1-methyl-1H-pyrazole-5-carboxamide; 5-isopropyl-2-methylthiazole-4-carboxamide; 2-(trifluoromethyl)thiazole-4-carboxamide; 2-phenylthiazole-4-carboxamide; 5-(trifluoromethyl)furan-2-carboxamide; 1-ethyl-3-isobutyl-1H-pyrazole-5-carboxamide; 5-(pyrrolidin-1-ylmethyl)furan-2-carboxamide; 3-isopropyl-1H-pyrazole-5-carboxamide; 2-(piperidin-1-ylmethyl)thiazole-4-carboxamide; 2-(morpholinomethyl)thiazole-4-carboxamide; 5-(morpholinomethyl)isoxazole-3-carboxamide; 1-methyl-4-(trifluoromethyl)-1H-pyrazole-5-carboxamide; 3-(methylsulfonyl)picolinamide; 6-morpholinopicolinamide; 5-morpholinopicolinamide; 5-(piperidin-1-yl)picolinamide; 2-benzylthiazole-4-carboxamide; 1-isopropyl-5-oxopyrrolidine-3-carboxamide; 1-methyl-3-(trifluoromethyl)-1H-pyrazole-5-carboxamide; 3-(tert-butyl)-1-methyl-1H-pyrazole-5-carboxamide; 1-((tetrahydro-2H-pyran-4-yl)methyl)-1H-pyrazole-3-carboxamide; 2'-chloro-[1,1'-biphenyl]-2-carboxamide; 2-chloro-5-isopropylthiazole-4-carboxamide; 3-isobutyl-1-methyl-1H-pyrazole-5-carboxamide; 5-acetyl-2-methylthiazole-4-carboxamide; 5-methyl-4-(pyrrolidin-1-ylmethyl)isoxazole-3-carboxamide; 3-isobutyl-1H-pyrazole-5-carboxamide; 6-(morpholinomethyl)picolinamide; 6-(piperidin-1-ylmethyl)picolinamide; 6-((tetrahydro-2H-pyran-4-yl)oxy)picolinamide; 3-(dimethylamino)-6-(methylamino)picolinamide; 2-((1,4-oxazepan-4-yl)methyl)thiazole-4-carboxamide; 6-((tetrahydro-2H-pyran-4-yl)amino)picolinamide; 3-chloro-6-(dimethylamino)picolinamide; 6-chloro-3-(dimethylamino)picolinamide; 5-(2-methylthiazol-4-yl)isoxazole-3-carboxamide; 5-methyl-4-(morpholinomethyl)isoxazole-3-carboxamide; 1-methyl-3-(morpholinomethyl)-1H-pyrazole-5-carboxamide; 5-methyl-4-(piperidin-1-ylmethyl)isoxazole-3-carboxamide; 3-chloro-6-morpholinopicolinamide; 3-chloro-6-(piperidin-1-yl)picolinamide; 3-(dimethylamino)-6-(ethylamino)picolinamide; 1-(methylsulfonyl)piperidine-4-carboxamide;

2-methyl-5-(trifluoromethyl)oxazole-4-carboxamide; 1-(tert-butyl)-3-methyl-1H-pyrazole-5-carboxamide; 2-((2-methylmorpholino)methyl)thiazole-4-carboxamide; 6-(4-methylpiperazin-1-yl)picolinamide; 1-methyl-5-(morpholinomethyl)-1H-pyrazole-3-carboxamide; 6-((1-methylpiperidin-4-yl)amino)picolinamide; 2-((2-ethylmorpholino)methyl)thiazole-4-carboxamide; 6-(methyl(tetrahydro-2H-pyran-4-yl)amino)picolinamide; 6-((4-methylpiperazin-1-yl)methyl)picolinamide; 6-chloro-3-morpholinopicolinamide; 6-chloro-3-(piperidin-1-yl)picolinamide; (1R,2S)-2-phenylcyclopropanecarboxamide; 5-isopropyl-2-(morpholinomethyl)thiazole-4-carboxamide; 6-(2-methoxy-5-methylphenyl)picolinamide; 3-(dimethylamino)-6-morpholinopicolinamide; 3-(dimethylamino)-6-(piperidin-1-yl)picolinamide; 1-isopropyl-3-(morpholinomethyl)-1H-pyrazole-5-carboxamide; 2-((hexahydro-2H-benzo[b][1,4]oxazin-4(3H)-yl)methyl)thiazole-4-carboxamide; 6-((4-methyl-3-oxopiperazin-1-yl)methyl)picolinamide; 2-((2,2-dimethylmorpholino)methyl)thiazole-4-carboxamide; 2-((hexahydro-1H-pyrido[1,2-a]pyrazin-2(6H)-yl)methyl)thiazole-4-carboxamide; 2-((3,3-dimethylpiperidin-1-yl)methyl)thiazole-4-carboxamide; 2-((4,4-dimethylpiperidin-1-yl)methyl)thiazole-4-carboxamide; tert-butyl 4-carbamoyl-3-methyl-1H-pyrazole-1-carboxylate; 1-(3-(4-(methylsulfonyl)piperazin-1-yl)propyl)urea; 2-((4-isopropylpiperazin-1-yl)methyl)thiazole-4-carboxamide; 6-((4,4-difluoropiperidin-1-yl)methyl)picolinamide; 6-((hexahydro-2H-benzo[b][1,4]oxazin-4(3H)-yl)methyl)picolinamide; 6-((hexahydro-1H-pyrido[1,2-a]pyrazin-2(6H)-yl)methyl)picolinamide; 6-((3,3-dimethylpiperidin-1-yl)methyl)picolinamide; 6-((4,4-dimethylpiperidin-1-yl)methyl)picolinamide; 1-methyl-3-(morpholine-4-carbonyl)-1H-pyrazole-5-carboxamide; 1-isopropyl-5-(morpholinomethyl)-1H-pyrazole-3-carboxamide; 6-((4-isopropylpiperazin-1-yl)methyl)picolinamide; 2-((4-isopropyl-3-methylpiperazin-1-yl)methyl)thiazole-4-carboxamide; 2-((2-isobutylmorpholino)methyl)thiazole-4-carboxamide; 6-((4-isopropylpiperidin-1-yl)methyl)picolinamide; 2-(6-oxa-9-azaspiro[4.5]decan-9-ylmethyl)thiazole-4-carboxamide; 2-((4-isobutylpiperazin-1-yl)methyl)thiazole-4-carboxamide; 2-((1,1-dioxidothiomorpholino)methyl)thiazole-4-carboxamide; 6-((4-isopropyl-3-methylpiperazin-1-yl)methyl)picolinamide; 6-((1,1-dioxidothiomorpholino)methyl)picolinamide; 6-((4-isobutylpiperazin-1-yl)methyl)picolinamide; 6-((2-isobutylmorpholino)methyl)picolinamide; benzyl 3-carbamoyl-4-hydroxypyrrolidine-1-carboxylate; 2-((4-cyclopentylpiperazin-1-yl)methyl)thiazole-4-carboxamide; 2-((3-(pyridin-3-yl)pyrrolidin-1-yl)methyl)thiazole-4-carboxamide; 6-((4-acetylpiperazin-1-yl)methyl)picolinamide; 2-(1-benzamidoethyl)thiazole-4-carboxamide; 2-((4-(pentan-3-yl)piperazin-1-yl)methyl)thiazole-4-carboxamide; 6-((4-cyclopentylpiperazin-1-yl)methyl)picolinamide; 6-((4-(pentan-3-yl)piperazin-1-yl)methyl)picolinamide; 2-((2-(pyrrolidin-1-ylmethyl)morpholino)methyl)thiazole-4-carboxamide; tert-butyl 4-carbamoyl-3-cyclopropyl-1H-pyrazole-1-carboxylate; 6-((2-(pyrrolidin-1-ylmethyl)morpholino)methyl)picolinamide; 6-((3-phenylpiperidin-1-yl)methyl)picolinamide; 2-(((6S)-2,6-dimethylmorphoino)methy)thiazole-4-carboxamide; 2-((3-(benzyloxy)piperidin-1-yl)methyl)thiazole-4-carboxamide; 2-((4-(2-morpholinoethyl)piperazin-1-yl)methyl)thiazole-4-carboxamide; 6-((4-(methylsulfonyl)piperazin-1-yl)methyl)picolinamide; 6-((2-(phenoxymethyl)morpholino)methyl)picolinamide; 6-((3-(benzyloxy)piperidin-1-yl)methyl)picolinamide; 6-((4-(2-morpholinoethyl)piperazin-1-yl)methyl)picolinamide; 2-((4-(4-fluorophenyl)piperazin-1-yl)methyl)thiazole-4-carboxamide; 2-(((2R,6R)-2,6-dimethylmorpholino)methyl)thiazole-4-carboxamide; 6-((4-(4-fluorophenyl)piperazin-1-yl)methyl)picolinamide; 2-(((2R,6S)-2,6-dimethylmorpholino)methyl)thiazole-4-carboxamide; 6-(((2R,6R)-2,6-dimethylmorpholino)methyl)picolinamide; 6-(((2R,6S)-2,6-dimethylmorpholino)methyl)picolinamide.

Moreover especially preferably, $R^1$ can be derived from the following amines:

1-ethyl-1H-pyrazol-4-amine; 1,5-dimethyl-1H-pyrazol-4-amine; 3-methyl-1H-pyrazol-4-amine; 2-(4-amino-1H-pyrazol-1-yl)ethan-1-ol; 1-propyl-1H-pyrazol-4-amine; 1-(2-fluoroethyl)-1H-pyrazol-4-amine; 1-ethyl-5-methyl-1H-pyrazol-4-amine; 5-methoxy-1-methyl-1H-pyrazol-4-amine; N5,1-dimethyl-1H-pyrazole-4,5-diamine; 5-chloro-1-methyl-1H-pyrazol-4-amine; 5-(fluoromethyl)-1-methyl-1H-pyrazol-4-amine; 3-(4-amino-1H-pyrazol-1-yl)propan-1-ol; 1-(2-methoxyethyl)-1H-pyrazol-4-amine; 1,3-dimethyl-1H-pyrazol-4-amine; 1-butyl-1H-pyrazol-4-amine; 5-methyl-1-propyl-1H-pyrazol-4-amine; 4-amino-1-methyl-1H-pyrazole-5-carbonitrile; 5-chloro-1-ethyl-1H-pyrazol-4-amine; 1-(2-fluoroethyl)-5-methyl-1H-pyrazol-4-amine; 1-isopropyl-1H-pyrazol-4-amine; 1-(difluoromethyl)-1H-pyrazol-4-amine; 3-(4-amino-1H-pyrazol-1-yl)propanenitrile; 1-ethyl-3-methyl-1H-pyrazol-4-amine; 1-cyclopropyl-1H-pyrazol-4-amine; 1-(2-methoxyethyl)-5-methyl-1H-pyrazol-4-amine; 1,3,5-trimethyl-1H-pyrazol-4-amine; 1-butyl-5-methyl-1H-pyrazol-4-amine; 1-(oxetan-3-yl)-1H-pyrazol-4-amine; 1-(cyclopropylmethyl)-1H-pyrazol-4-amine; 1-isopropyl-3-methyl-1H-pyrazol-4-amine; 1-(difluoromethyl)-3-methyl-1H-pyrazol-4-amine; 1-(difluoromethyl)-5-methyl-1H-pyrazol-4-amine; 3-methyl-1-propyl-1H-pyrazol-4-amine; 1-isopropyl-5-methyl-1H-pyrazol-4-amine; 5-cyclopropyl-1-methyl-1H-pyrazol-4-amine; 1-(2-fluoroethyl)-3-methyl-1H-pyrazol-4-amine; N5,N5,1-trimethyl-1H-pyrazole-4,5-diamine; 5-isopropyl-1-methyl-1H-pyrazol-4-amine; 3-(4-amino-5-methyl-1H-pyrazol-1-yl)propanenitrile; 1-(tetrahydrofuran-3-yl)-1H-pyrazol-4-amine; 3-methyl-1-(oxetan-3-yl)-1H-pyrazol-4-amine; 1-(2-methoxyethyl)-3-methyl-1H-pyrazol-4-amine; 1-(1-methoxypropan-2-yl)-1H-pyrazol-4-amine; 1-(2-methoxypropyl)-1H-pyrazol-4-amine; 5-cyclobutyl-1-methyl-1H-pyrazol-4-amine; 5-methyl-1-(oxetan-3-yl)-1H-pyrazol-4-amine; 1-(cyclopropylmethyl)-3-methyl-1H-pyrazol-4-amine; 5-chloro-1-cyclopropyl-1H-pyrazol-4-amine; 5-chloro-1-isopropyl-1H-pyrazol-4-amine; 1-(cyclopropylmethyl)-5-methyl-1H-pyrazol-4-amine; 1-(tetrahydro-2H-pyran-4-yl)-1H-pyrazol-4-amine; 1-(pyridin-2-yl)-1H-pyrazol-4-amine; 2-(4-amino-1H-pyrazol-1-yl)cyclopentanol; 1-(pyrimidin-5-yl)-1H-pyrazol-4-amine; 1-(tetrahydro-2H-pyran-3-yl)-1H-pyrazol-4-amine; 2-(4-amino-1H-pyrazol-1-yl)-N-methylacetamide; 1-(pyrimidin-2-yl)-1H-pyrazol-4-amine; 1-(piperidin-3-yl)-1H-pyrazol-4-amine; 3-(4-amino-3-methyl-1H-pyrazol-1-yl)propanenitrile; 5-methyl-1-(tetrahydrofuran-3-yl)-1H-pyrazol-4-amine; 3-methyl-1-(tetrahydrofuran-3-yl)-1H-pyrazol-4-amine; 3-isopropyl-1-methyl-1H-pyrazol-4-amine; 3-cyclopropyl-1-methyl-1H-pyrazol-4-amine; 5-chloro-1-(cyclopropylmethyl)-1H-pyrazol-4-amine; 5-chloro-1-(oxetan-3-yl)-1H-pyrazol-4-amine; 1-(4-amino-1H-pyrazol-1-yl)-2-methylpropan-2-ol; 1-(2,2,2-trifluoroethyl)-1H-pyrazol-4-amine; 2-(4-amino-1H-pyrazol-1-yl)-2-methylpropan-1-ol; 1-(pyridin-3-ylmethyl)-1H-pyrazol-4-amine; 1-(pyrimidin-2-ylmethyl)-1H-pyrazol-4-amine; 1-(pyrazin-2-ylmethyl)-1H-pyrazol-4-amine; 1-(pyrimidin-4-ylmethyl)-1H-pyrazol-4-amine; 1-(pyridazin-3-ylmethyl)-1H-pyrazol-4-amine; 1-(pyridin- 2-ylmethyl)-1H-pyrazol-4-amine; 1-(3-methylpyridin-4-yl)-1H-pyrazol-4-amine; 3-methyl-1-(tetrahydro-2H-pyran-4-yl)-1H-pyrazol-4-amine; 5-methyl-1-(tetrahydro-2H-pyran-4-yl)-1H-pyrazol-4-amine; 5-methyl-1-phenyl-1H-pyrazol-4-amine; 3-methyl-1-phenyl-1H-pyrazol-4-amine; 1-(3-fluoropiperidin-4-yl)-1H-pyrazol-4-amine; 1-(2-methoxycyclopentyl)-1H-pyrazol-4-amine; 3-methyl-1-(pyridin-2-yl)-1H-pyrazol-4-amine; 3-cyclobutyl-1-methyl-1H-pyrazol-4-amine; 5-methyl-1-(tetrahydro-2H-pyran-3-yl)-1H-pyrazol-4-amine; 3-methyl-1-(pyrimidin-2-yl)-1H-pyrazol-4-amine; 3-methyl-1-(pyrimidin-5-yl)-1H-pyrazol-4-amine; 3-methyl-1-(tetrahydro-2H-pyran-3-yl)-1H-pyrazol-4-amine; 3-methyl-1-(piperidin-3-yl)-1H-pyrazol-4-amine; 2-(4-amino-5-methyl-1H-pyrazol-1-yl)-N-methylacetamide; 2-(4-amino-1H-pyrazol-1-yl)-2-methylpropanenitrile; 1-(methylsulfonyl)-1H-pyrazol-4-amine; 1-((3-methyloxetan-3-yl)methyl)-1H-pyrazol-4-amine; 1-(1-methoxy-2-methylpropan-2-yl)-1H-pyrazol-4-amine; 1-(4-amino-1H-pyrazol-1-yl)cyclopropanecarbonitrile; 1-(4-amino-1H-pyrazol-1-yl)-3-methylbutan-2-ol; 1'-methyl-1H-[1,4'-bipyrazol]-4-amine; 2-(4-amino-1H-pyrazol-1-yl)pentan-3-ol; 1-(4-amino-3-methyl-1H-pyrazol-1-yl)-2-methylpropan-2-ol; 3-methyl-1-(2,2,2-trifluoroethyl)-1H-pyrazol-4-amine; 1-(2-methoxy-2-methylpropyl)-1H-pyrazol-4-amine; 1-(1-methylpyrrolidin-3-yl)-1H-pyrazol-4-amine; 5-chloro-1-(tetrahydro-2H-pyran-4-yl)-1H-pyrazol-4-amine; 5-methyl-1-(2,2,2-trifluoroethyl)-1H-pyrazol-4-amine; 1-(4-amino-5-methyl-1H-pyrazol-1-yl)-2-methylpropan-2-ol; 5-methyl-1-(pyrimidin-2-ylmethyl)-1H-pyrazol-4-amine; 5-methyl-1-(pyrazin-2-ylmethyl)-1H-pyrazol-4-amine; 5-methyl-1-(pyrimidin-4-ylmethyl)-1H-pyrazol-4-amine; 5-methyl-1-(pyridazin-3-ylmethyl)-1H-pyrazol-4-amine; 5-methyl-1-(pyridin-3-ylmethyl)-1H-pyrazol-4-amine; 5-methyl-1-(pyridin-2-ylmethyl)-1H-pyrazol-4-amine; 3-methyl-1-(pyrimidin-2-ylmethyl)-1H-pyrazol-4-amine; 3-methyl-1-(pyrazin-2-ylmethyl)-1H-pyrazol-4-amine; 3-methyl-1-(pyrimidin-4-ylmethyl)-1H-pyrazol-4-amine; 3-methyl-1-(pyridazin-3-ylmethyl)-1H-pyrazol-4-amine; 3-methyl-1-(pyridin-3-ylmethyl)-1H-pyrazol-4-amine; 3-methyl-1-(pyridin-2-ylmethyl)-1H-pyrazol-4-amine; 1-(1-methylpiperidin-4-yl)-1H-pyrazol-4-amine; 1-(4-fluorophenyl)-1H-pyrazol-4-amine; 3-(4-amino-1H-pyrazol-1-yl)-2,2-dimethylpropanenitrile; 1-(2-methylpyridin-4-yl)-1H-pyrazol-4-amine; 1-(ethylsulfonyl)-1H-pyrazol-4-amine; (R)-1-(2-methoxypropyl)-1H-pyrazol-4-amine; 1-(4-amino-1H-pyrazol-1-yl)cyclobutanecarbonitrile; 1-((1-methyl-1H-pyrazol-3-yl)methyl)-1H-pyrazol-4-amine; 1-(1-methylpiperidin-3-yl)-1H-pyrazol-4-amine; 3-methyl-1-(methylsulfonyl)-1H-pyrazol-4-amine; 2-(4-amino-1H-pyrazol-1-yl)-N,N-dimethylacetamide; 3-methyl-1-((3-methyloxetan-3-yl)methyl)-1H-pyrazol-4-amine; 1-(3-methoxycyclopentyl)-1H-pyrazol-4-amine; 2-(4-amino-3-methyl-1H-pyrazol-1-yl)cyclopentanol; 2-(4-amino-5-methyl-1H-pyrazol-1-yl)-2-methylpropanenitrile; 5-methyl-1-((3-methyloxetan-3-yl)methyl)-1H-pyrazol-4-amine; 1-(4-amino-3-chloro-1H-pyrazol-1-yl)-2-methylpropan-2-ol; 1-(4-amino-5-chloro-1H-pyrazol-1-yl)-2-methylpropan-2-ol; 1-(4-amino-5-methyl-1H-pyrazol-1-yl)-3-methylbutan-2-ol; 2-(4-amino-5-chloro-1H-pyrazol-1-yl)-2-methylpropan-1-ol; 5-methyl-1-(methylsulfonyl)-1H-pyrazol-4-amine; 1-(1-methoxy-2-methylpropan-2-yl)-5-methyl-1H-pyrazol-4-amine; 2-(4-amino-3-methyl-1H-pyrazol-1-yl)-N-methylacetamide; 1',5-dimethyl-1H-[1,4'-bipyrazol]-4-amine; 2-(4-amino-5-methyl-1H-pyrazol-1-yl)pentan-3-ol; 1-(4-chlorophenyl)-1H-pyrazol-4-amine; 5-(4-amino-1H-pyrazol-1-yl)piperidin-2-one; (S)-1-(1-methoxypropan-2-yl)-1H-pyrazol-4-amine; (S)-2-(4-amino-1H-pyrazol-1-yl)propanenitrile; 1-(1-(pyridin-2-yl)ethyl)-1H-pyrazol-4-amine; 1-((6-methylpyridin-2-yl)methyl)-1H-pyrazol-4-amine; (S)-2-(4-amino-5-methyl-1H-pyrazol-1-yl)propanenitrile; 1-(4-amino-5-methyl-1H-pyrazol-1-yl)cyclobutanecarbonitrile; 1-(4-fluorophenyl)-5-methyl-1H-pyrazol-4-amine; (R)-1-(2-methoxypropyl)-5-methyl-1H-pyrazol-4-amine; 5-methyl-1-(1-methylpiperidin-4-yl)-1H-pyrazol-4-amine; 1-(ethylsulfonyl)-5-methyl-1H-pyrazol-4-amine; 3-methyl-1-(3-methylpyridin-4-yl)-1H-pyrazol-4-amine; 2-(4-amino-5-chloro-1H-pyrazol-1-yl)-2-methylpropanenitrile; 3-(4-amino-5-methyl-1H-pyrazol-1-yl)-2,2-dimethylpropanenitrile; 1-(4-amino-5-chloro-1H-pyrazol-1-yl)cyclopropanecarbonitrile; 1-(3-fluoropiperidin-4-yl)-3-methyl-1H-pyrazol-4-amine; 1-(2-methoxycyclopentyl)-3-methyl-1H-pyrazol-4-amine; 5-methyl-1-((1-methyl-1H-pyrazol-3-yl)methyl)-1H-pyrazol-4-amine; 5-methyl-1-(1-methylpiperidin-3-yl)-1H-pyrazol-4-amine; 5-chloro-1-((3-methyloxetan-3-yl)methyl)-1H-pyrazol-4-amine; 2-(4-amino-3-ethyl-1H-pyrazol-1-yl)-2-methylpropanenitrile; 5-methyl-1-(2-methylpyridin-4-yl)-1H-pyrazol-4-amine; 4-(4-amino-1H-pyrazol-1-yl)benzonitrile; 1-(1-(2-fluoroethyl)piperidin-4-yl)-1H-pyrazol-4-amine; 2-(4-amino-1H-pyrazol-1-yl)-2-methylpropanamide; 1-(1-isopropylazetidin-3-yl)-1H-pyrazol-4-amine; 2-(4-amino-3-methyl-1H-pyrazol-1-yl)-2-methylpropanenitrile; 3-(4-amino-5-chloro-1H-pyrazol-1-yl)-2,2-dimethylpropanenitrile; 1-(4-chlorophenyl)-5-methyl-1H-pyrazol-4-amine; (S)-1-(1-methoxypropan-2-yl)-5-methyl-1H-pyrazol-4-amine; 5-(4-amino-5-methyl-1H-pyrazol-1-yl)piperidin-2-one; 1-(4-amino-3-methyl-1H-pyrazol-1-yl)cyclopropanecarbonitrile; 5-methyl-1-(1-(pyridin-2-yl)ethyl)-1H-pyrazol-4-amine; 3-methyl-1-(1-(pyridin-2-yl)ethyl)-1H-pyrazol-4-amine; 1-(1-methoxy-2-methylpropan-2-yl)-3-methyl-1H-pyrazol-4-amine; 1',3-dimethyl-1'H-[1,4'-bipyrazol]-4-amine; 2-(4-amino-3-methyl-1H-pyrazol-1-yl)pentan-3-ol; 1-(4-amino-3-methyl-1H-pyrazol-1-yl)-3-methylbutan-2-ol; 5-methyl-1-((6-methylpyridin-2-yl)methyl)-1H-pyrazol-4-amine; 2-(4-amino-1H-pyrazol-1-yl)-N,2-dimethylpropanamide; 1-(isopropylsulfonyl)-1H-pyrazol-4-amine; 1-(cyclopropylsulfonyl)-1H-pyrazol-4-amine; 1-(3,5-difluorophenyl)-1H-pyrazol-4-amine; methyl 2-(4-amino-1H-pyrazol-1-yl)-2-methylpropanoate; 1-(3-fluoro-1-methylpiperidin-4-yl)-1H-pyrazol-4-amine; 1-(2,2-dimethyl-1,3-dioxan-5-yl)-1H-pyrazol-4-amine; 1-(2,6-dimethyltetrahydro-2H-pyran-4-yl)-1H-pyrazol-4-amine; 1-(4,4-difluorocyclohexyl)-1H-pyrazol-4-amine; 4-(4-amino-5-methyl-1H-pyrazol-1-yl)benzonitrile; 1-(1-(oxetan-3-yl)azetidin-3-yl)-1H-pyrazol-4-amine; 1-(4-amino-3-cyclopropyl-1H-pyrazol-1-yl)-2-methylpropan-2-ol; 1-(1-(2-fluoroethyl)piperidin-4-yl)-5-methyl-1H-pyrazol-4-amine; 1-(4-fluorophenyl)-3-methyl-1H-pyrazol-4-amine; (R)-1-(2-methoxypropyl)-3-methyl-1H-pyrazol-4-amine; (S)-1-(1-methoxypropan-2-yl)-3-methyl-1H-pyrazol-4-amine; 3-methyl-1-(1-methylpiperidin-4-yl)-1H-pyrazol-4-amine; 1-(ethylsulfonyl)-3-methyl-1H-pyrazol-4-amine; 2-(4-amino-3-methyl-1H-pyrazol-1-yl)-N,N-dimethylacetamide; (S)-2-(4-amino-3-methyl-1H-pyrazol-1-yl)propanenitrile; 2-(4-amino-3-chloro-1H-pyrazol-1-yl)-2-methylpropanenitrile; 3-(4-amino-3-methyl-1H-pyrazol-1-yl)-2,2-dimethylpropanenitrile; 1-(4-amino-3-methyl-1H-pyrazol-1-yl)cyclobutanecarbonitrile; 2-(4-amino-3-methyl-1H-pyrazol-1-yl)-2-methylpropanamide; 1-(3-methoxycyclopentyl)-3-methyl-1H-pyrazol-4-amine; 3-methyl-1-((1-methyl-1H-pyrazol-3-yl)methyl)-1H-pyrazol-4-amine; 3-methyl-1-(1-methylpiperidin-3-yl)-1H-pyrazol-4-amine; 1-(1- isopropylazetidin-3-yl)-5-methyl-1H-pyrazol-4-amine; 3-methyl-1-(2-methylpyridin-4-yl)-1H-pyrazol-4-amine; 2-(4-amino-1H-pyrazol-1-yl)-N-ethyl-2-methylpropanamide; 1-(1-ethyl-3-fluoropiperidin-4-yl)-1H-pyrazol-4-amine; 1-(sec-butylsulfonyl)-1H-pyrazol-4-amine; 1-(2-(1-methyl-1H-pyrazol-5-yl)propan-2-yl)-1H-pyrazol-4-amine; 5-(4-amino-1H-pyrazol-1-yl)-1-methylpiperidin-2-one; (R)-1-(1-methylpiperidin-3-yl)-1H-pyrazol-4-amine; 1-(cyclopropylsulfonyl)-3-methyl-1H-pyrazol-4-amine; 1-(2-(4-methyl-4H-1,2,4-triazol-3-yl)propan-2-yl)-1H-pyrazol-4-amine; methyl 2-(4-amino-5-methyl-1H-pyrazol-1-yl)-2-methylpropanoate; 1-(4-chlorophenyl)-3-methyl-1H-pyrazol-4-amine; 1-(isopropylsulfonyl)-5-methyl-1H-pyrazol-4-amine; 1-(isopropylsulfonyl)-3-methyl-1H-pyrazol-4-amine; 1-(3,5-difluorophenyl)-5-methyl-1H-pyrazol-4-amine; 1-(1-(2-methoxyethyl)piperidin-4-yl)-5-methyl-1H-pyrazol-4-amine; 2-(4-amino-5-methyl-1H-pyrazol-1-yl)-N,2-dimethylpropanamide; 5-(4-amino-3-methyl-1H-pyrazol-1-yl)piperidin-2-one; 3-(4-amino-3-chloro-1H-pyrazol-1-yl)-2,2-dimethylpropanenitrile; 1-(cyclopropylsulfonyl)-5-methyl-1H-pyrazol-4-amine; 1-(2,2-dimethyl-1,3-dioxan-5-yl)-3-methyl-1H-pyrazol-4-amine; 3-methyl-1-(1-(oxetan-3-yl)azetidin-3-yl)-1H-pyrazol-4-amine; 1-(4,4-difluorocyclohexyl)-3-methyl-1H-pyrazol-4-amine; 1-(2,6-dimethyltetrahydro-2H-pyran-4-yl)-5-methyl-1H-pyrazol-4-amine; 1-(4,4-difluorocyclohexyl)-5-methyl-1H-pyrazol-4-amine; 3-methyl-1-((6-methylpyridin-2-yl)methyl)-1H-pyrazol-4-amine; 1-(4-(4-amino-1H-pyrazol-1-yl)piperidin-1-yl)ethan-1-one; 1-(1-(oxetan-3-yl)piperidin-4-yl)-1H-pyrazol-4-amine; 1-(2-methyl-2-morpholinopropyl)-1H-pyrazol-4-amine; 1-(2-methyl-1-morpholinopropan-2-yl)-1H-pyrazol-4-amine; 4-(4-amino-3-methyl-1H-pyrazol-1-yl)benzonitrile; 4-(4-amino-1H-pyrazol-1-yl)tetrahydro-2H-thiopyran 1,1-dioxide; 1-(4-amino-1H-pyrazol-1-yl)-N-ethylcyclobutanecarboxamide; 1-(1-isobutylpiperidin-4-yl)-1H-pyrazol-4-amine; 3-methyl-1-(2-(1-methyl-1H-pyrazol-5-yl)propan-2-yl)-1H-pyrazol-4-amine; 1-(1-(2-fluoroethyl)piperidin-4-yl)-3-methyl-1H-pyrazol-4-amine; 5-chloro-1-(3-fluoro-1-methylpiperidin-4-yl)-1H-pyrazol-4-amine; 3-methyl-1-(2-(4-methyl-4H-1,2,4-triazol-3-yl)propan-2-yl)-1H-pyrazol-4-amine; 2-(4-amino-5-chloro-1H-pyrazol-1-yl)-N,2-dimethylpropanamide; (R)-5-methyl-1-(1-methylpiperidin-3-yl)-1H-pyrazol-4-amine; 1-(1-isopropylazetidin-3-yl)-3-methyl-1H-pyrazol-4-amine; 1-(sec-butylsulfonyl)-5-methyl-1H-pyrazol-4-amine; 2-(4-amino-5-ethyl-1H-pyrazol-1-yl)-N,2-dimethylpropanamide; 1-(3-fluoro-1-(oxetan-3-yl)piperidin-4-yl)-1H-pyrazol-4-amine; 1-(2-(4H-1,2,4-triazol-3-yl)propan-2-yl)-1H-pyrazol-4-amine; 1-(1-((1,3-dioxolan-2-yl)methyl)pyrrolidin-3-yl)-1H-pyrazol-4-amine; 1-(2-(1-methyl-1H-pyrazol-4-yl)propan-2-yl)-1H-pyrazol-4-amine; 1-(2-(1-methyl-1H-pyrazol-3-yl)propan-2-yl)-1H-pyrazol-4-amine; 2-(4-amino-3-methyl-1H-pyrazol-1-yl)-N,2-dimethylpropanamide; 2-(4-amino-1H-pyrazol-1-yl)-N,N,2-trimethylpropanamide; 1-(2-(5-methyl-1,3,4-oxadiazol-2-yl)propan-2-yl)-1H-pyrazol-4-amine; 1-(2-(1-methyl-1H-1,2,4-triazol-3-yl)propan-2-yl)-1H-pyrazol-4-amine; 1-(1-(2,2,2-trifluoroethyl)azetidin-3-yl)-1H-pyrazol-4-amine; 2-(4-amino-3-cyclopropyl-1H-pyrazol-1-yl)-2-methylpropanenitrile; 3-methyl-1-(2-methyl-1-morpholinopropan-2-yl)-1H-pyrazol-4-amine; 1-(3,5-difluorophenyl)-3-methyl-1H-pyrazol-4-amine; methyl 2-(4-amino-3-methyl-1H-pyrazol-1-yl)-2-methylpropanoate; 1-(1-(2-methoxyethyl)piperidin-4-yl)-3-methyl-1H-pyrazol-4-amine; 1-(4-amino-5-(trifluoromethyl)-1H-pyrazol-1-yl)-2-methylpropan-2-ol; 1-(4-amino-3-(trifluoromethyl)-1H-pyrazol-1-yl)-2-methylpropan-2-ol; 3-methyl-1-(2-methyl-2-morpholinopropyl)-1H-pyrazol-4-amine; 1-(4-amino-3-(tert-butyl)-1H-pyrazol-1-yl)-2-methylpropan-2-ol; 3-methyl-1-(1-(oxetan-3-yl)piperidin-4-yl)-1H-pyrazol-4-amine; 1-(3-fluoro-1-methylpiperidin-4-yl)-3-methyl-1H-pyrazol-4-amine; 1-(4-(4-amino-5-methyl-1H-pyrazol-1-yl)piperidin-1-yl)ethan-1-one; 2-(4-amino-5-ethyl-1H-pyrazol-1-yl)-N-ethyl-2-methylpropanamide; 1-(4-amino-5-methyl-1H-pyrazol-1-yl)-N-ethylcyclobutanecarboxamide; 5-chloro-1-(1-ethyl-3-fluoropiperidin-4-yl)-1H-pyrazol-4-amine; 1-(1-isobutylpiperidin-4-yl)-5-methyl-1H-pyrazol-4-amine; 1-(2,6-dimethyltetrahydro-2H-pyran-4-yl)-3-methyl-1H-pyrazol-4-amine; 5-methyl-1-(2-methyl-2-morpholinopropyl)-1H-pyrazol-4-amine; 4-(4-amino-5-methyl-1H-pyrazol-1-yl)tetrahydro-2H-thiopyran 1,1-dioxide; 5-methyl-1-(1-(oxetan-3-yl)piperidin-4-yl)-1H-pyrazol-4-amine; (R)-2-(4-amino-1H-pyrazol-1-yl)-N,N-dimethylpropanamide; 1-(1-((1,3-dioxolan-2-yl)methyl)piperidin-4-yl)-1H-pyrazol-4-amine; 2-(4-amino-H-pyrazol-1-yl)-N-isopropyl-2-methylpropanamide; 1-(2-(4H-1,2,4-triazol-3-yl)propan-2-yl)-3-methyl-1H-pyrazol-4-amine; 1-(1-(methylsulfonyl)azetidin-3-yl)-1H-pyrazol-4-amine; 2-(4-amino-3-methyl-1H-pyrazol-1-yl)-N-ethyl-2-methylpropanamide; 1-(1-((1,3-dioxolan-2-yl)methyl)pyrrolidin-3-yl)-5-methyl-1H-pyrazol-4-amine; 2-(4-amino-5-methyl-1H-pyrazol-1-yl)-N,N,2-trimethylpropanamide; 3-methyl-1-(1-(2,2,2-trifluoroethyl)azetidin-3-yl)-1H-pyrazol-4-amine; 1-(1-((1,3-dioxolan-2-yl)methyl)pyrrolidin-3-yl)-3-methyl-1H-pyrazol-4-amine; 5-methyl-1-(2-(1-methyl-1H-pyrazol-4-yl)propan-2-yl)-1H-pyrazol-4-amine; (R)-3-methyl-1-(1-methylpiperidin-3-yl)-1H-pyrazol-4-amine; 1-(sec-butylsulfonyl)-3-methyl-1H-pyrazol-4-amine; 1-(1-(2,2,2-trifluoroethyl)piperidin-4-yl)-1H-pyrazol-4-amine; 2-(4-amino-1H-pyrazol-1-yl)-N-(cyclopropylmethyl)-2-methylpropanamide; 2-(4-amino-1H-pyrazol-1-yl)-2-methyl-1-(pyrrolidin-1-yl)propan-1-one; 5-chloro-1-(3-fluoro-1-(oxetan-3-yl)piperidin-4-yl)-1H-pyrazol-4-amine; 1-(1-((1,3-dioxolan-2-yl)methyl)piperidin-4-yl)-5-methyl-1H-pyrazol-4-amine; 3-methyl-1-(1-(methylsulfonyl)azetidin-3-yl)-1H-pyrazol-4-amine; 1-(1-((1,3-dioxolan-2-yl)methyl)piperidin-4-yl)-3-methyl-1H-pyrazol-4-amine; 3-cyclopropyl-1-(cyclopropylsulfonyl)-1H-pyrazol-4-amine; 1-(4-(4-amino-3-methyl-1H-pyrazol-1-yl)piperidin-1-yl)ethan-1-one; 2-(4-amino-5-methyl-1H-pyrazol-1-yl)-N-isopropyl-2-methylpropanamide; (4-(4-amino-1H-pyrazol-1-yl)piperidin-1-yl)(cyclopropyl)methanone; 1-(4-(methylsulfonyl)phenyl)-1H-pyrazol-4-amine; 1-(4-(4-amino-1H-pyrazol-1-yl)piperidin-1-yl)-2-methylpropan-1-one; (R)-1-(1-(oxetan-3-yl)pyrrolidin-3-yl)-1H-pyrazol-4-amine; 4-(4-amino-1H-pyrazol-1-yl)-N,N-dimethylbenzamide; (R)-2-(4-amino-1H-pyrazol-1-yl)-1-(pyrrolidin-1-yl)propan-1-one; 1-(2-(5-methyl-4H-1,2,4-triazol-3-yl)propan-2-yl)-1H-pyrazol-4-amine; 3-methyl-1-(1-(2,2,2-trifluoroethyl)piperidin-4-yl)-1H-pyrazol-4-amine; 5-methyl-1-(1-(2,2,2-trifluoroethyl)piperidin-4-yl)-1H-pyrazol-4-amine; 1-(3-fluoro-1-(oxetan-3-yl)piperidin-4-yl)-3-methyl-1H-pyrazol-4-amine; (R)-2-(4-amino-5-methyl-1H-pyrazol-1-yl)-N,N-dimethylpropanamide; 3-methyl-1-(2-(1-methyl-1H-pyrazol-3-yl)propan-2-yl)-1H-pyrazol-4-amine; 2-(4-amino-5-methyl-1H-pyrazol-1-yl)-N-(cyclopropylmethyl)-2-methylpropanamide; 2-(4-amino-3-methyl-1H-pyrazol-1-yl)-N-(cyclopropylmethyl)-2-methylpropanamide; 2-(4-amino-5-methyl-1H-pyrazol-1-yl)-2-methyl-1-(pyrrolidin-1-yl)propan-1-one; 3-methyl-1-(2-(1-methyl-1H-pyrazol-4-yl)propan-2-yl)-1H-pyrazol-4-amine; 3-methyl-1-(2-(1-methyl-1H-1,2,4-triazol-3-yl)propan-2-yl)-1H-pyrazol-4-amine; 2-(4-amino-3-ethyl-1H- pyrazol-1-yl)-N-isopropyl-2-methylpropanamide; 3-methyl-1-(2-(5-methyl-1,3,4-oxadiazol-2-yl)propan-2-yl)-1H-pyrazol-4-amine; (R)-1-(1-(oxetan-3-yl)piperidin-3-yl)-1H-pyrazol-4-amine; 2-(4-amino-1H-pyrazol-1-yl)-N-(tert-butyl)-2-methylpropanamide; 5-methyl-1-(4-(methylsulfonyl)phenyl)-1H-pyrazol-4-amine; 3-methyl-1-(4-(methylsulfonyl)phenyl)-1H-pyrazol-4-amine; 1-(4-(4-amino-5-methyl-1H-pyrazol-1-yl)piperidin-1-yl)-2-methylpropan-1-one; 4-(4-amino-5-methyl-1H-pyrazol-1-yl)-N,N-dimethylbenzamide; (4-(4-amino-5-methyl-1H-pyrazol-1-yl)piperidin-1-yl)(cyclopropyl)methanone; (R)-2-(4-amino-5-methyl-1H-pyrazol-1-yl)-1-(pyrrolidin-1-yl)propan-1-one; (R)-5-methyl-1-(1-(oxetan-3-yl)pyrrolidin-3-yl)-1H-pyrazol-4-amine; (R)-3-methyl-1-(1-(oxetan-3-yl)pyrrolidin-3-yl)-1H-pyrazol-4-amine; (R)-2-(4-amino-3-methyl-1H-pyrazol-1-yl)-N,N-dimethylpropanamide; 2-(4-amino-1H-pyrazol-1-yl)-2-methyl-N-(2,2,2-trifluoroethyl)propanamide; (R)-5-methyl-1-(1-(oxetan-3-yl)piperidin-3-yl)-1H-pyrazol-4-amine; (R)-3-methyl-1-(1-(oxetan-3-yl)piperidin-3-yl)-1H-pyrazol-4-amine; 2-(4-amino-5-methyl-1H-pyrazol-1-yl)-N-(tert-butyl)-2-methylpropanamide; 2-(4-amino-3-methyl-1H-pyrazol-1-yl)-N-(tert-butyl)-2-methylpropanamide; (4-(4-amino-1H-pyrazol-1-yl)piperidin-1-yl)(1-methylcyclopropyl)methanone; 1-((1R,5R)-8-oxabicyclo[3.2.1]octan-3-yl)-1H-pyrazol-4-amine; 1-(4-(4-amino-3-methyl-1H-pyrazol-1-yl)piperidin-1-yl)-2-methylpropan-1-one; (4-(4-amino-3-methyl-1H-pyrazol-1-yl)piperidin-1-yl)(cyclopropyl)methanone; 4-(4-amino-3-methyl-1H-pyrazol-1-yl)-N,N-dimethylbenzamide; 2-(4-amino-5-methyl-1H-pyrazol-1-yl)-2-methyl-N-(2,2,2-trifluoroethyl)propanamide; 3-methyl-1-(2-(5-methyl-4H-1,2,4-triazol-3-yl)propan-2-yl)-1H-pyrazol-4-amine; 1-(4-(cyclopropylsulfonyl)phenyl)-1H-pyrazol-4-amine; (R)-2-(4-amino-3-methyl-1H-pyrazol-1-yl)-1-(pyrrolidin-1-yl)propan-1-one; (4-(4-amino-3-methyl-1H-pyrazol-1-yl)piperidin-1-yl)(1-methylcyclopropyl)methanone; 1-((1R,5R)-8-oxabicyclo[3.2.1]octan-3-yl)-3-methyl-1H-pyrazol-4-amine; (4-(4-amino-5-methyl-1H-pyrazol-1-yl)piperidin-1-yl)(1-methylcyclopropyl)methanone; 1-(4-(cyclopropylsulfonyl)phenyl)-3-methyl-1H-pyrazol-4-amine; 1-(4-(cyclopropylsulfonyl)phenyl)-5-methyl-1H-pyrazol-4-amine.

Further preferred, $R^1$ can be derived from the following compounds (e.g. amines):

thiazol-5-amine; isothiazol-4-amine; pyrimidin-5-amine; pyridazin-4-amine; 3-methylisothiazol-5-amine; 3-methylisoxazol-5-amine; 6-methylpyridin-3-amine; 2-fluoropyridin-4-amine; 4-iodo-3-methylisothiazol-5-amine; 2-methylpyridin-4-amine; 5-fluoropyridin-3-amine; 3-ethylisothiazol-5-amine; 5-methylpyridin-3-amine; 6-fluoropyridin-3-amine; 4-fluoro-3-methylisothiazol-5-amine; 3,4-dimethylisothiazol-5-amine; (5-aminoisothiazol-3-yl)methanol; 3-(aminomethyl)aniline; 6-ethylpyridin-3-amine; thieno[2,3-c]isothiazol-3-amine; 5-chloropyridin-3-amine; 3-(methoxymethyl)isothiazol-5-amine; 5-methoxypyridin-3-amine; thieno[3,2-c]isothiazol-3-amine; 4-bromo-3-methylisothiazol-5-amine; 2-ethylpyridin-4-amine; 4-chloro-3-methylisothiazol-5-amine; 2-methoxypyrimidin-5-amine; 2,3-dimethylaniline; thieno[2,3-b]pyridin-3-amine; pyrazolo[1,5-a]pyridin-3-amine; 2,3-dihydro-1H-inden-5-amine; 6-methoxy-5-methylpyridin-3-amine; isothiazolo[3,4-b]pyridin-3-amine; 6-ethoxypyridin-3-amine; benzo[c]isothiazol-3-amine; isothiazolo[3,4-b]pyrazin-3-amine; imidazo[1,2-a]pyridin-7-amine; 5-aminopicolinonitrile; thiazolo[5,4-b]pyridin-6-amine; p-toluidine; 3-methoxypyridine-2,6-diamine; benzo[b]thiophen-5-amine; thieno[3,2-c]pyridin-3-amine; 3-(4-aminophenyl)propan-1-ol; 4-(2-aminoethoxy)aniline; 4-(3-fluoropropyl)aniline; isoquinolin-7-amine; 1,5-naphthyridin-3-amine; quinolin-7-amine; 1,8-naphthyridin-4-amine; quinolin-3-amine; isoquinolin-6-amine; 3-cyclopropylisothiazol-5-amine; 2,6-dimethylpyridin-4-amine; 1,8-naphthyridin-3-amine; quinolin-4-amine; isoquinolin-5-amine; 1,6-naphthyridin-3-amine; 3-isopropylisothiazol-5-amine; quinazolin-6-amine; 3-cyclopropylisoxazol-5-amine; isoquinolin-8-amine; isoquinolin-4-amine; isochroman-7-amine; isochroman-6-amine; 2-(4-aminophenyl)acetonitrile; 5-amino-2-fluorobenzonitrile; quinolin-2-amine; 5-amino-2-methylbenzonitrile; 1,2,3,4-tetrahydroquinolin-6-amine; 3,4-diaminopicolinonitrile; 5,6-dimethoxypyridin-2-amine; 3-fluoro-5-methylaniline; pyrido[2,3-b]pyrazin-7-amine; 5-methoxyindolin-6-amine; 4-(prop-2-yn-1-yloxy)aniline; 3-(4-aminophenoxy)propan-1-ol; N2,N2-dimethylpyridine-2,5-diamine; N2,N2-dimethylpyridine-2,4-diamine; 2-cyclopropylpyridin-4-amine; 6-cyclopropylpyridin-3-amine; (3-amino-5-iodophenyl)methanol; 3-bromo-5-methylaniline; 4-(4-aminophenyl)butan-1-ol; 2-(3-aminophenoxy)acetonitrile; 2-(4-aminophenoxy)acetonitrile; 3-(4-aminophenyl)propanenitrile; 4-(4-fluorobutyl)aniline; N1-(prop-2-yn-1-yl)benzene-1,4-diamine; 3-(prop-2-yn-1-yloxy)aniline; 4-amino-6-chloronicotinonitrile; 3-amino-5-bromopicolinonitrile; 3-fluoro-5-methoxyaniline; 3-chloro-5-fluoroaniline; 4-(difluoromethoxy)aniline; 6-(azetidin-1-yl)pyridin-3-amine; 5-aminopicolinic acid; 3,5-dibromoaniline; 2-(4-amino-2-methylphenoxy)acetonitrile; methyl 5-aminothiophene-2-carboxylate; 3-fluoro-4-(prop-2-yn-1-yloxy)aniline; 3-(4-amino-2-fluorophenyl)propanenitrile; 3-methyl-4-(prop-2-yn-1-yloxy)aniline; 2-(4-amino-2-fluorophenoxy)acetonitrile; 3-(4-amino-2-methylphenyl)propanenitrile; 4-(but-2-yn-1-yloxy)aniline; 1-methyl-1H-pyrrolo[2,3-b]pyridin-4-amine; 6-aminobenzo[d]thiazol-2-ol; 3-(difluoromethoxy)aniline; 1H-pyrrolo[3,2-b]pyridin-6-amine; 6-fluoroquinolin-3-amine; 3-(oxazol-2-yl)aniline; 8-fluoroquinolin-6-amine; 7-fluoroquinolin-3-amine; 8-fluoroquinolin-3-amine; 2,3-dibromo-4-methylaniline; 3-(tert-butyl)isothiazol-5-amine; 4-(oxazol-2-yl)aniline; 2-cyclobutoxypyridin-4-amine; 3-phenylisothiazol-5-amine; 3-phenylisoxazol-5-amine; 5-aminobicyclo[4.2.0]octa-1,3,5-triene-2-carbonitrile; 2-(4-amino-2-(hydroxymethyl)phenoxy)acetonitrile; 2-(4-amino-2-chlorophenoxy)acetonitrile; 3-chloro-4-(prop-2-yn-1-yloxy)aniline; 3-(4-amino-2-chlorophenyl)propanenitrile; 5-(1H-pyrazol-1-yl)pyridin-3-amine; 5-chlorothiazolo[5,4-d]pyrimidin-7-amine; 6-chloro-[1,2,4]triazolo[1,5-a]pyridin-8-amine; 5-(2H-1,2,3-triazol-2-yl)pyridin-3-amine; 5-(1H-imidazol-1-yl)pyridin-3-amine; 6-(1H-pyrazol-1-yl)pyridin-3-amine; 2-(1H-pyrazol-1-yl)pyridin-4-amine; 5-(thiazol-2-yl)pyridin-3-amine; 6-chloroimidazo[1,2-a]pyridin-8-amine; 6-amino-3,4-dihydroquinolin-2(1H)-one; 6-amino-2H-pyrido[3,2-b][1,4]oxazin-3(4H)-one; [2,3'-bipyridin]-5-amine; N2,N2,3-trimethylpyridine-2,5-diamine; 5-(pyrimidin-2-yl)pyridin-3-amine; 3-methyl-4-(pyrimidin-5-yl)isothiazol-5-amine; 2-(trifluoromethyl)pyridin-4-amine; 3-methyl-4-(pyridin-3-yl)isothiazol-5-amine; 3-(morpholinomethyl)isothiazol-5-amine; 5-(trifluoromethyl)pyridin-3-amine; 3-methyl-4-phenylisothiazol-5-amine; 6-(trifluoromethyl)pyridin-3-amine; 1-(3-aminobenzyl)urea; 2-(4-aminophenoxy)propanenitrile; 2-(3-aminophenoxy)acetamide; 4-aminopyridine-3-sulfonamide; 1-(4-aminobenzyl)urea; 5-aminobenzofuran-2-carbonitrile; 2-(4-aminophenoxy)acetamide; 2-(4-aminophenyl)-2-oxoethanethial; 3-(2,3-dihydro-1H-1,2,3-triazol-1-yl)aniline; 4-amino-1-methylindolin-2-one; 3-amino-N'-(2-aminoethyl)picolinohydrazide; N3-(1-aminobutan-2-yl)

pyridine-3,5-diamine; 2-amino-N,N-dimethylbenzamide; 4-(pyrimidin-4-yl)aniline; 3-(pyrimidin-4-yl)aniline; 1-isopropyl-1H-indol-4-amine; 6-bromo-5-methylimidazo[1,2-a]pyridin-8-amine; 4-amino-2,6-dibromophenol; 2,2'-((4-aminophenyl)azanediyl)bis(ethan-1-ol); 4-(piperidin-4-yloxy)aniline; 1-(2-(piperazin-1-yl)ethyl)-1H-pyrazol-4-amine; 3-(5-aminopyridin-2-yl)oxazolidin-2-one; 2-(2-methylmorpholino)aniline; 3-(4-aminophenyl)oxazolidin-2-one; 5-amino-N,N-dimethylisothiazole-3-carboxamide; 3-(morpholinomethyl)aniline; 3-methyl-1H-pyrazolo[3,4-b]pyridin-5-amine; 3-bromo-5-(difluoromethyl)aniline; 1-(2-methoxyethyl)-1H-indazol-5-amine; 2-(4-amino-2,6-dimethylphenoxy)acetonitrile; 3-aminobenzyl methylcarbamate; 4-aminophenethyl carbamate; 1-(prop-2-yn-1-yl)-1H-indol-6-amine; N-(4-aminobenzyl)propionamide; 1-(4-aminophenethyl)urea; 2-(4-amino-2-fluorophenoxy)acetamide; 1-(prop-2-yn-1-yl)-1H-indol-5-amine; 2-(4-amino-2-methylphenoxy)acetamide; 2-(4-amino-2-methylphenoxy)propanenitrile; 2-((1-methylpyrrolidin-3-yl)oxy)aniline; methyl 2-(4-aminophenoxy)acetate; 3-(1,4,5,6-tetrahydropyrimidin-2-yl)aniline; 3,5-diaminopicolinamide; 2-amino-N-cyclopropylbenzamide; 6-bromo-5-chloroimidazo[1,2-a]pyridin-8-amine; 2-methoxy-4-(piperidin-1-yl)aniline; 2-methoxy-4-(piperidin-4-yl)aniline; 2-methoxy-5-(piperazin-1-yl)aniline; 2-(5-aminoindolin-3-ylidene)acetonitrile; 4-(4-aminophenoxy)butanoic acid; 4-(2-(diethylamino)ethoxy)aniline; 2-(4-aminophenoxy)-2-methylpropan-1-ol; 4-(2-(piperazin-1-yl)ethyl)aniline; 6-(3-methylenemorpholino)pyridin-3-amine; 5-methoxy-6-morpholinopyridin-3-amine; 6-(3-methoxyazetidin-1-yl)pyridin-3-amine; 4-((3-aminopyridin-4-yl)amino)cyclohexanol; N2,N2-dimethylbenzo[d]oxazole-2,6-diamine; 6-(2,2,2-trifluoroethoxy)pyridin-3-amine; 5-amino-N,N-dimethylpicolinamide; 3-amino-5-methylpyridine 1-oxide; 3-amino-N,N-dimethylbenzamide; 1-(4-aminophenyl)piperidin-2-one; 5-amino-1-methylindolin-2-one; 3-methyl-5-(thiazol-5-yl)aniline; 3-(1H-pyrazol-5-yl)aniline; 2-(4-amino-2-methoxyphenoxy)acetamide; 2-(4-amino-2-chlorophenoxy)acetamide; 2-(4-amino-2-fluorophenoxy)-N-methylacetamide; N-(4-aminophenyl)-2-cyanoacetamide; 4-aminophenethyl methylcarbamate; 1-(3-aminobenzyl)-3-ethylurea; 6-amino-4-methylquinolin-2-ol; 1-(3-methoxypropyl)-1H-indazol-5-amine; 2-(6-aminoindolin-3-ylidene)acetonitrile; 4-(pyridin-3-ylmethoxy)aniline; 2-(7-aminoindolin-3-ylidene)acetonitrile; 1-(4-aminobenzyl)-3-ethylurea; 2-(4-amino-2-(hydroxymethyl)phenoxy)acetamide; 2-(3-aminophenyl)-2H-1,2,3-triazol-4-ol; 3-(2-(methoxyethoxymethyl)pyrrolidin-1-yl)aniline; (2-aminophenyl)(pyrrolidin-1-yl)methanone; 3-amino-5-fluoropyridine 1-oxide; 2-(4-amino-3-methoxyphenyl)propane-1,3-diol; (3-aminophenyl)methanesulfonamide; 6-(2-(piperazin-1-yl)ethoxy)pyridin-3-amine; 4-(2-(piperazin-1-yl)ethoxy)aniline; 4-(2-ethyl-2H-tetrazol-5-yl)aniline; 1-(5-aminopyridin-2-yl)piperidin-3-ol; 4-(2-(piperidin-4-yl)ethoxy)aniline; 1-(5-aminopyridin-2-yl)piperidin-4-ol; 4-(3-(piperazin-1-yl)propyl)aniline; 5-fluoro-6-morpholinopyridin-3-amine; 1-(4-aminophenyl)piperidin-4-amine; (4-(4-amino-2-fluorophenyl)morpholin-3-yl)methanol; (5-aminopyridin-2-yl)(azetidin-1-yl)methanone; 4-((methylsulfonyl)methyl)aniline; 2-(azetidin-1-yl)benzo[d]oxazol-6-amine; (3-aminophenyl)(azetidin-1-yl)methanone; 3-bromo-5-(thiazol-5-yl)aniline; 4-((aminomethyl)-1H-1,2,3-triazol-1-yl)aniline; 4-(4-aminophenyl)pyridin-2-amine; 6-amino-4-methyl-2H-benzo[b][1,4]thiazin-3(4H)-one; 1-(4-aminophenethyl)-3-ethylurea; 4-((1H-1,2,4-triazol-3-yl)methyl)aniline; 2-(4-aminophenoxy)propanamide; 2-(4-amino-2-chlorophenoxy)-N-methylacetamide; 5-aminobenzofuran-2-carboxamide; 2-(5-amino-2,3-dimethoxyphenoxy)acetonitrile; 2-(4-aminophenoxy)-2-methylpropanenitrile; 4-((1H-1,2,3-triazol-4-yl)methyl)aniline; N1,N1-di(prop-2-yn-1-yl)benzene-1,4-diamine; 2-amino-6-methylbenzenesulfonamide; 1-isobutyl-1H-indol-4-amine; 6-bromo-5-ethylimidazo[1,2-a]pyridin-8-amine; 2-(4-amino-3-methoxybenzyl)propane-1,3-diol; 1-(4-aminophenyl)-N-methylmethanesulfonamide; prop-2-yn-1-yl (4-aminobenzyl)carbamate; 6-amino-5-fluoro-1,3-dihydrobenzo[c]isothiazole 2,2-dioxide; 6-(4-ethylpiperazin-1-yl)pyridin-3-amine; 4-(2-(1,4-diazepan-1-yl)ethoxy)aniline; 1-(2-(4-methylpiperazin-1-yl)ethyl)-1H-pyrazol-4-amine; (1-(4-aminophenyl)piperidin-3-yl)methanol; 4-(3-(piperazin-1-yl)propoxy)aniline; 2-(5-(4-aminophenyl)-2H-tetrazol-2-yl)ethan-1-ol; 4-(4-methoxypiperidin-1-yl)aniline; N2-methyl-N2-(tetrahydro-2H-pyran-4-yl)pyridine-2,5-diamine; 6-(4-methoxypiperidin-1-yl)pyridin-3-amine; 2,4,4a,5-tetrahydro-1H-benzo[b][1,4]oxazino[4,3-d][1,4]oxazin-8-amine; 6-(3-(ethoxymethyl)morpholino)pyridin-3-amine; (3-aminophenyl)(pyrrolidin-1-yl)methanone; 3-amino-4-methoxy-N,N-dimethylbenzamide; 5-amino-2-methoxy-N,N-dimethylbenzamide; (R)-2-methyl-2H-indol-4-amine; 4-(4-(aminomethyl)piperidin-1-yl)aniline; N2-cyclopropylquinoline-2,6-diamine; 4-amino-2-methoxybenzenesulfonamide; 2-(7-amino-1H-indol-3-yl)acetonitrile; 2-(5-amino-2H-indol-2-ylidene)acetonitrile; 5-amino-N,2-dimethylbenzenesulfonamide; 2-(4-amino-2,6-dimethylphenoxy)propanenitrile; N-(4-amino-2-chlorophenyl)-2-cyanoacetamide; 2-(6-amino-1H-indol-3-yl)acetonitrile; 4-((5-methyl-1,2,4-oxadiazol-3-yl)methoxy)aniline; 5-amino-2-methoxybenzenesulfonamide; 2-(5-amino-1H-indol-3-yl)acetonitrile; N-(3-aminobenzyl)cyclopropanecarboxamide; 6-amino-1,2-dihydrobenzo[b]cyclobuta[d]thiophene-1-carbonitrile; N-(4-aminobenzyl)cyclopropanecarboxamide; 2-(4-amino-2,6-dimethylphenoxy)acetamide; 4-((1-methylpiperidin-3-yl)oxy)aniline; 2-(4-amino-2-methylphenoxy)propanamide; 3-((1-methylpiperidin-3-yl)oxy)aniline; N-(4-amino-3-methylphenyl)acrylamide; 3-((1-methylpiperidin-4-yl)oxy)aniline; 2-(5-amino-1-methyl-1H-indol-3-yl)acetonitrile; 3-chloro-4-(trifluoromethyl)aniline; N-allyl-2-(4-aminophenoxy)acetamide; 4-((5-methyl-1,3,4-oxadiazol-2-yl)methoxy)aniline; 2-amino-6-methoxybenzenesulfonamide; 2-amino-N,N-dimethylbenzenesulfonamide; 1-(6-amino-5-methoxyindolin-1-yl)ethan-1-one; N-(4-aminobenzyl)ethanesulfonamide; 5-amino-2-methylbenzenesulfonamide; N-(3-aminobenzyl)ethanesulfonamide; 4-(4-(2-aminoethyl)piperazin-1-yl)aniline; 4-(4-(2-fluoroethyl)piperazin-1-yl)aniline; 4-(4-(2-fluoroethyl)piperidin-1-yl)aniline; 2-(1-(5-aminopyridin-2-yl)piperidin-4-yl)ethan-1-ol; 2-(1-(4-aminophenyl)piperidin-3-yl)ethan-1-ol; 1-(2-(4-ethylpiperazin-1-yl)ethyl)-1H-pyrazol-4-amine; 1-(4-aminophenyl)piperidine-4-carbonitrile; 6-(1,4-diazabicyclo[3.2.2]nonan-4-yl)pyridin-3-amine; 6-(4-ethoxypiperidin-1-yl)pyridin-3-amine; 2-(4-(4-aminophenyl)morpholin-2-yl)ethan-1-ol; (R)-6-(3-methylmorpholino)pyridin-3-amine; 6-amino-4-propyl-2H-pyrido[3,2-b][1,4]oxazin-3(4H)-one; 4-(4-(methoxymethyl)piperidin-1-yl)aniline; 4-(4-ethoxypiperidin-1-yl)aniline; 5-amino-2-fluoro-N,N-dimethylbenzamide; 4-(4-amino-2-fluorophenyl)morpholin-3-one; 3-amino-4-fluoro-N,N-dimethylbenzamide; 3-amino-N-(isoxazol-3-yl)benzamide; 2-(5-amino-3-chloro-2-methyl-1H-indol-1-yl)ethan-1-ol; 3-chloro-2-methyl-1-propyl-1H-indol-5-amine; 5-amino-2-fluorobenzenesulfonamide; (4-aminophenyl)(thiomorpholino)methanone; 4-amino-2-methoxy-N-methylbenzenesulfonamide; 4-aminophenethyl dimethylcarbamate; S-(2-(4-aminophenyl)-2-oxoethyl) ethanethioate; 3-methyl-4-(pyridin-2-ylmethoxy)aniline; 2-((4-aminobenzyl)amino)butanamide; N-(4-aminophenyl)-2-cyano-N-methylacetamide; 4-(methylsulfonyl)benzene-1,3-diamine; (R)-4-((tetrahydrofuran-2-yl)methoxy)aniline; 2,4-dichloro-5-(2H-1,2,3-triazol-2-yl)aniline; (S)-3-(2-methylpyrrolidin-1-yl)aniline; N-(3-amino-4-methoxyphenyl)-2-(dimethylamino)acetamide; N-(4-aminophenethyl)ethanesulfonamide; 2-(1-(4-aminophenyl)piperidin-4-yl)acetonitrile; 4-(4-aminophenyl)-1-ethylpiperazin-2-one; 2-(4-(4-aminophenoxy)piperidin-1-yl)ethan-1-ol; 1-(2-(4-aminophenoxy)ethyl)piperidin-4-ol; 1-(3-(4-aminophenyl)propyl)piperidin-4-ol; 2-(4-(4-aminophenyl)-1,4-diazepan-1-yl)ethan-1-ol; 2-(4-(4-aminophenyl)piperazin-1-yl)acetonitrile; 3-(4-(4-aminophenyl)piperazin-1-yl)propan-1-ol; 3-(1-(4-aminophenyl)piperidin-4-yl)propan-1-ol; 2-(1-(5-aminopyridin-2-yl)piperidin-4-yl)acetonitrile; 2-(4-aminophenoxy)-2-methylpropanoic acid; 4-(2-(4-methylpiperazin-1-yl)ethoxy)aniline; (S)-6-(3-methylmorpholino)pyridin-3-amine; 6-amino-2,2-dimethyl-2H-pyrido[3,2-b][1,4]oxazin-3(4H)-one; 6-(2,2-dimethylmorpholino)pyridin-3-amine; (S)-2-(2-methylmorpholino)aniline; (S)-4-(3-methylmorpholino)aniline; 4-(2,2-dimethylmorpholino)aniline; 3-(difluoromethoxy)-4-morpholinoaniline; 3-isopropoxy-4-morpholinoaniline; (S)-1-(5-aminopyridin-2-yl)pyrrolidin-3-ol; 6-(2,5-dimethylmorpholino)pyridin-3-amine; 4-amino-2-chloro-N,N-dimethylbenzamide; 3-cyclopropyl-5-(thiazol-5-yl)aniline; 3-amino-N-phenylbenzamide; 5-amino-2-chlorobenzenesulfonamide; 3-amino-N-(prop-2-yn-1-yl)benzenesulfonamide; 3-amino-N-butylbenzenesulfonamide; 5-(3-methyl-1,2,4-oxadiazol-5-yl)bicyclo[4.2.0]octa-1,3,5-trien-2-amine; 2-(4-aminophenoxy)-2-methylpropanamide; 2-(6-amino-3-oxo-2H-benzo[b][1,4]oxazin-4(3H)-yl)acetonitrile; 2-(6-amino-3-oxo-2H-benzo[b][1,4]thiazin-4(3H)-yl)acetonitrile; 3-chloro-4-((1-methylpiperidin-3-yl)oxy)aniline; 4-amino-N-(prop-2-yn-1-yl)benzenesulfonamide; 6-amino-1H-indole-3-carboxamide; 3-chloro-4-((1-methylpiperidin-4-yl)oxy)aniline; (S)-(4-(4-aminophenyl)morpholin-3-yl)methanol; 1-(2,2,2-trifluoroethyl)indolin-4-amine; 2-(3-aminophenyl)-2H-1,2,3-triazole 1-oxide; 2-(pyrrolidin-1-ylsulfonyl)aniline; 2-(4-(4-aminophenethyl)piperazin-1-yl)ethan-1-ol; 4-(2-(4-aminophenoxy)ethyl)piperazin-2-one; 4-(2-(4-ethylpiperazin-1-yl)ethoxy)aniline; (1-(2-(4-aminophenoxy)ethyl)piperidin-4-yl)methanol; (R)-6-(3-fluoropyrrolidin-1-yl)pyridin-3-amine; 1-(5-aminopyridin-2-yl)pyrrolidine-3-carboxamide; (R)-6-(2-methylmorpholino)pyridin-3-amine; (R)-4-(2-methylmorpholino)aniline; (R)-1-(5-aminopyridin-2-yl)pyrrolidin-3-ol; 5-fluoro-N2-(6-methylpyridin-3-yl)pyrimidine-2,4-diamine; (S)-(1-(5-aminopyridin-2-yl)pyrrolidin-3-yl)methanol; (3-amino-4-fluorophenyl)(pyrrolidin-1-yl)methanone; 5-amino-2-methoxy-3-methylbenzenesulfonamide; 2-(4-amino-2-fluorophenoxy)-N,N-dimethylacetamide; (4-aminophenyl)(pyridin-4-yl)methanolate; (R)-1-(4-aminophenyl)pyrrolidin-3-ol; (R)-3-methoxy-4-((tetrahydrofuran-2-yl)methoxy)aniline; 3-ethoxy-4-(4-ethylpiperazin-1-yl)aniline; 4-(((3-(ethylsulfonyl)propyl)amino)methyl)aniline; N-(6-amino-2,3-dihydro-1H-inden-1-yl)methanesulfonamide; N-(4-aminobenzyl)cyclopropanesulfonamide; 7-amino-3,4-dihydroisoquinoline-2(1H)-sulfonamide; 4-(2-oxa-7-azaspiro[3.5]nonan-7-ylmethyl)aniline; 2-(4-(4-aminophenethyl)piperazin-1-yl)ethan-1-ol; 2-(5-(4-aminophenyl)-2H-tetrazol-2-yl)acetic acid; (6-(4-aminophenyl)-6-azaspiro[2.5]octan-1-yl)methanol; 4-(2-(diisopropylamino)ethoxy)aniline; 1-(4-aminophenethyl)-4-methylpiperidin-4-ol; 4-(2-((dimethylamino)methyl)morpholino)aniline; (S)-6-(2-methylmorpholino)pyridin-3-amine; 4-(4-isopropoxypiperidin-1-yl)aniline; 2-(pyridin-4-yl)-1H-benzo[d]imidazol-6-amine; N2-(1-((R)-tetrahydrofuran-2-yl)ethyl)pyridine-2,5-diamine; 6-(3-(diethylamino)pyrrolidin-1-yl)pyridin-3-amine; 6-(2-oxa-8-azaspiro[4.5]decan-8-yl)pyridin-3-amine; ethyl 4-(2-aminophenyl)piperazine-1-carboxylate; 4-(1-oxa-8-azaspiro[4.5]decan-8-yl)aniline; 4-(2-oxa-8-azaspiro[4.5]decan-8-yl)aniline; (R)-6-(3-methoxypyrrolidin-1-yl)pyridin-3-amine; 3,5-di(1H-pyrazol-1-yl)aniline; 3,5-di(1H-1,2,3-triazol-1-yl)aniline; 3-(1H-pyrazol-1-yl)-5-(2H-1,2,3-triazol-2-yl)aniline; 1-(5-aminopicolinoyl)azetidine-3-carbonitrile; 3-(1H-1,2,3-triazol-1-yl)-5-(2H-1,2,3-triazol-2-yl)aniline; 3,5-di(2H-1,2,3-triazol-2-yl)aniline; 7-amino-5-methyl-2H-benzo[e][1,2,4]thiadiazine 1,1-dioxide; N-(6-amino-3-methoxypyridin-2-yl)pivalamide; 5-amino-2-fluoro-3-methylbenzenesulfonamide; 4-(pyridin-3-ylmethyl)-4H-benzo[b][1,4]oxazin-7-amine; 2-(4-amino-2-chlorophenoxy)-N,N-dimethylacetamide; (R)-1-(4-aminophenyl)piperidin-3-ol; (S)-1-(4-aminophenyl)-3-methylpyrrolidin-3-ol; (R)-(1-(4-aminophenyl)pyrrolidin-3-yl)methanol; methyl 8-amino-6-bromoimidazo[1,2-a]pyridine-5-carboxylate; (S)-1-(4-aminophenyl)pyrrolidine-2-carboxamide; 5-(9-oxa-3,7-diazabicyclo[3.3.1]nonan-3-yl)-2-methoxyaniline; 1-(6-amino-5-methoxyindolin-1-yl)-2-(methylamino)ethan-1-one; 2-(4-(4-amino-3-methoxyphenyl)piperazin-1-yl)ethan-1-ol; 4-(9-oxa-3,7-diazabicyclo[3.3.1]nonan-3-yl)-2-methoxyaniline; N-(4-aminophenethyl)cyclopropanesulfonamide; 2-amino-1-(4-(4-aminophenyl)piperazin-1-yl)ethan-1-one; 3-(4-(4-aminophenyl)piperazin-1-yl)propane-1,2-diol; 2-(1-(5-aminopyridin-2-yl)piperidin-3-yl)acetic acid; 2-(1-(4-aminophenyl)piperidin-4-yl)acetic acid; 2-(1-(5-aminopyridin-2-yl)piperidin-4-yl)acetic acid; 2-(4-(4-aminophenyl)cyclohexyl)acetic acid; 1-(4-aminobenzyl)piperidine-4-carboxylic acid; 2-(4-(4-aminophenyl)piperidin-1-yl)acetic acid; 2-(1-(4-aminophenyl)piperidin-3-yl)acetic acid; 2-(1-(5-aminopyridin-2-yl)piperidin-4-yl)acetamide; 1-(2-(4-aminophenoxy)ethyl)-4-methylpiperidin-4-ol; 2-(4-(5-aminopyridin-2-yl)piperazin-1-yl)acetic acid; 2-(1-(4-aminophenyl)piperidin-4-yl)acetamide; 6-(2,2-dimethylmorpholino)-5-methylpyridin-3-amine; 6-(2,2-dimethylmorpholino)-5-fluoropyridin-3-amine; 6-(4-(diethylamino)piperidin-1-yl)pyridin-3-amine; 6-(3-morpholinopyrrolidin-1-yl)pyridin-3-amine; N2-(1-((S)-tetrahydrofuran-2-yl)ethyl)pyridine-2,5-diamine; 4-(4,4-difluoropiperidin-1-yl)-3-fluoroaniline; 1-(4-aminophenyl)-N,N-diethylpiperidin-4-amine; (R)-6-(3-(ethylamino)pyrrolidin-1-yl)pyridin-3-amine; (R)-6-(2-(fluoromethyl)morpholino)pyridin-3-amine; (R)-6-(3-ethoxypyrrolidin-1-yl)pyridin-3-amine; 1-(4-(4-aminophenyl)piperidin-1-yl)propan-1-one; 3-morpholino-5-(1H-pyrazol-1-yl)aniline; 3-morpholino-5-(2H-1,2,3-triazol-2-yl)aniline; 3-(1H-pyrazol-1-yl)-5-(pyrimidin-2-yl)aniline; 3-(pyrimidin-2-yl)-5-(2H-1,2,3-triazol-2-yl)aniline; (5-aminopyridin-2-yl)(3,3-difluoroazetidin-1-yl)methanone; 3-(pyrimidin-2-yl)-5-(1H-1,2,4-triazol-1-yl)aniline; 3-amino-N-(3-fluorophenyl)benzamide; 5-amino-2-isopropylbenzenesulfonamide; 5-amino-3-chloro-2-methylbenzenesulfonamide; 5-amino-2-chloro-3-methylbenzenesulfonamide; 2-(4-amino-2,6-dimethylphenoxy)propanamide; 3-(piperidin-1-ylsulfonyl)aniline; 4-(4-aminobenzyl)thiomorpholine 1,1-dioxide; N-((3-aminophenyl)sulfonyl)propionamide; 2-(ethylsulfonyl)-1,2,3,4-tetrahydroisoquinolin-6-amine; N-((4-aminophenyl)sulfonyl)propionamide; (S)-1-(4-aminophenyl)-3- methylpiperidin-3-ol; (R)-(4-(4-aminophenyl)morpholin-2-yl)methanol; (R)-1-(4-amino-2-methoxyphenyl)pyrrolidin-3-ol; (S)-1-(5-aminopyridin-2-yl)-3-methylpiperidin-3-ol; (R)-(4-(5-aminopyridin-2-yl)morpholin-2-yl)methanol; (S)-3-methoxy-5-(2-methylpyrrolidin-1-yl)aniline; 1-(6-amino-5-methoxyindolin-1-yl)-2-(dimethylamino)ethan-1-one; 1-(4-(4-amino-3-methoxyphenyl)piperazin-1-yl)ethan-1-one; 1-(4-(4-amino-3-methoxyphenyl)piperidin-1-yl)ethan-1-one; 2-(1-(4-aminobenzyl)piperidin-4-yl)acetic acid; 3-(1-(4-aminophenyl)piperidin-4-yl)propanoic acid; 3-(4-(4-aminophenyl)piperazin-1-yl)propanoic acid; 2-(4-aminophenoxy)-1-(4-methylpiperazin-1-yl)ethan-1-one; 2-(4-(4-aminophenoxy)piperidin-1-yl)acetic acid; 2-(4-(4-aminophenyl)-1,4-diazepan-1-yl)acetic acid; (S)-4-(2-(ethoxymethyl)morpholino)aniline; 4-(4-morpholinopiperidin-1-yl)aniline; 6-(4-morpholinopiperidin-1-yl)pyridin-3-amine; (S)-6-(2-(ethoxymethyl)morpholino)pyridin-3-amine; 3,5-di(pyrimidin-2-yl)aniline; 4-amino-N-methyl-N-(2,2,2-trifluoroethyl)benzamide; 3-morpholino-5-(pyrimidin-2-yl)aniline; 2'-amino-[1,1'-biphenyl]-4-sulfonamide; 3-amino-N-(3-chlorophenyl)benzamide; 3-amino-N-(4-chlorophenyl)benzamide; N-((5-amino-2-methylphenyl)sulfonyl)propionamide; 2-(4-amino-2-(1-(cyanomethyl)-1H-pyrazol-3-yl)phenoxy)acetonitrile; 5-amino-N,N-diethyl-2-methoxybenzenesulfonamide; (R)-1-(4-amino-2-methoxyphenyl)piperidin-3-ol; (S)-1-(4-amino-2-methoxyphenyl)-3-methylpyrrolidin-3-ol; (R)-1-(4-amino-2-ethoxyphenyl)pyrrolidin-3-ol; N-(4-aminobenzyl)pyridine-3-sulfonamide; 2-(4-aminophenoxy)-1-(4-ethylpiperazin-1-yl)ethan-1-one; 2-(4-(4-aminophenyl)piperazin-1-yl)-2-methylpropan-1-ol; 3-(4-(4-aminophenyl)piperazin-1-yl)-3-oxopropanenitrile; 7-(4-aminophenyl)-1,7-diazaspiro[3.5]nonan-2-one; 1-(2-(4-aminophenoxy)ethyl)piperidine-4-carboxylic acid; 3-(4-(5-aminopyridin-2-yl)piperazin-1-yl)-3-oxopropanenitrile; (R)-6-(2-(ethoxymethyl)morpholino)pyridin-3-amine; N2-(6-(dimethylamino)pyridin-3-yl)-5-fluoropyrimidine-2,4-diamine; 4-morpholino-3-(trifluoromethoxy)aniline; 3-methyl-4-(2-oxa-8-azaspiro[4.5]decan-8-yl)aniline; 5-amino-N,N-dimethylisoindoline-2-sulfonamide; methyl 2-(((3-aminophenyl)sulfonyl)imino)acetate; 3-((4-aminophenoxy)methyl)-1H-1,2,4-triazol-5(4H)-one; (R)-(4-(4-amino-2-methoxyphenyl)morpholin-2-yl)methanol; 2-(2-(3-aminophenyl)-2H-1,2,3-triazol-4-yl)acetate; 4-amino-3-(pyrrolidin-1-yl)phenol; 4-fluoro-2-(pyrrolidin-1-ylsulfonyl)aniline; 1-(4-(4-amino-2-methylphenyl)piperazin-1-yl)ethan-1-one; N-(6-amino-2,3-dihydro-1H-inden-1-yl)cyclopropanesulfonamide; (S)—N-(6-amino-2,3-dihydro-1H-inden-1-yl)methanesulfonamide; 6-(4-aminophenyl)-6-azaspiro[2.5]octane-1-carboxylic acid; 2-(1-(4-aminophenyl)piperidin-4-yl)-N-(2-hydroxyethyl)acetamide; 6-(5-aminopyridin-2-yl)-6-azaspiro[2.5]octane-1-carboxylic acid; 2-(4-(2-(4-aminophenoxy)ethyl)piperazin-1-yl)acetic acid; 2-(1-(2-(4-aminophenoxy)ethyl)piperidin-4-yl)acetic acid; 6-(4-aminophenyl)spiro[2.5]octane-1-carboxylic acid; 2-(4-(4-aminophenyl)-1,4-diazepan-1-yl)-2-methylpropan-1-ol; 2-(1-(4-aminophenyl)piperidin-4-yl)-2-methylpropanenitrile; 2-(4-(4-aminophenyl)piperazin-1-yl)-2-methylpropanenitrile; 4-((1S,4S)-2-oxa-5-azabicyclo[2.2.1]heptan-5-yl)aniline; (R)-3-(5-aminopyridin-2-yl)-4-isopropyloxazolidin-2-one; 6-((1S,4S)-2-oxa-5-azabicyclo[2.2.1]heptan-5-yl)pyridin-3-amine; 7-amino-N,N-dimethyl-3,4-dihydroisoquinoline-2(1H)-sulfonamide; 4-((1-methylpiperidin-4-yl)oxy)-3-(trifluoromethyl)aniline; 4-((4-methylpiperidin-1-yl)sulfonyl)aniline; 3-((4-methylpiperazin-1-yl)sulfonyl)aniline; (5-amino-2-methyl-7-oxabicyclo[4.2.0]octa-1(6),2,4-trien-8-yl)(morpholino)methanone; N-((5-amino-2-chlorophenyl)sulfonyl)acetamide; (R)-3-(4-aminophenyl)-1,4-dimethylpiperazin-2-one; 4-fluoro-2-(morpholinosulfonyl)aniline; 4-chloro-2-(pyrrolidin-1-ylsulfonyl)aniline; 4-(4-aminophenyl)-1-methylpiperidine 1-oxide; (3-aminobenzyl)(tert-butyl)carbamate; 2-(4-(4-amino-3-methoxyphenyl)piperazin-1-yl)-2-methylpropan-1-ol; 1-(4-(4-amino-3-methoxyphenyl)piperidin-1-yl)-2-hydroxyethan-1-one; 1-(4-(4-amino-3-methoxyphenyl)piperazin-1-yl)-2-hydroxyethan-1-one; (R)—N-(6-amino-2,3-dihydro-1H-inden-1-yl)methanesulfonamide; 6-(4-((2H-tetrazol-5-yl)methyl)piperidin-1-yl)pyridin-3-amine; 4-(4-((2H-tetrazol-5-yl)methyl)piperidin-1-yl)aniline; 4-((4-((2H-tetrazol-5-yl)piperidin-1-yl)methyl)aniline; 6-(4-aminobenzyl)-6-azaspiro[2.5]octane-1-carboxylic acid; 2-(1-(4-aminophenyl)piperidin-4-yl)cyclopropanecarboxylic acid; 2-(1-(3-(4-aminophenoxy)propyl)piperidin-4-yl)acetic acid; (S)-3-(5-aminopyridin-2-yl)-4-isopropyloxazolidin-2-one; (6-amino-3-oxo-2H-pyrido[3,2-b][1,4]oxazin-4(3H)-yl) methyl dihydrogen phosphate; (5-amino-2-(pyrrolidin-1-yl)phenyl)(pyrrolidin-1-yl)methanone; (4-aminophenyl)(1,1-dioxidothiomorpholino)methanone; 5-amino-2-(4-methylpiperazin-1-yl)benzenesulfonamide; 3-amino-N-(4-methylpiperidin-1-yl)benzenesulfonamide; tert-butyl (6-aminochroman-4-yl)carbamate; (S)-1-(4-aminophenyl)-N-methylpiperidine-3-carboxamide; 1-(4-(3-amino-4-methoxyphenyl)piperazin-1-yl)-2-(methylamino)ethan-1-one; 1-(4-(4-amino-3-methoxyphenyl)piperazin-1-yl)-2-(methylamino)ethan-1-one; 1-(4-(4-amino-3-methoxyphenyl)piperidin-1-yl)-2-(methylamino)ethan-1-one; 4-((4-(((2H-tetrazol-5-yl)methyl)piperidin-1-yl)methyl)aniline; ethyl 6-(4-aminophenyl)-6-azaspiro[2.5]octane-1-carboxylate; 4-((2S,6R)-2,6-dimethylmorpholino)aniline; 6-((2S,6R)-2,6-dimethylmorpholino)pyridin-3-amine; 5-amino-2-methyl-N-(1-methylpiperidin-4-yl)benzenesulfonamide; 3-((1R,5S)-8-oxa-3-azabicyclo[3.2.1]octan-3-yl)aniline; 1-(4-(3-amino-4-methoxyphenyl)piperazin-1-yl)-2-(dimethylamino)ethan-1-one; 6-(2-(4-aminophenoxy)ethyl)-6-azaspiro[2.5]octane-1-carboxylic acid; 1-(4-(4-aminophenyl)piperazin-1-yl)-2-hydroxy-2-methylpropan-1-one; 1-(4-(5-aminopyridin-2-yl)piperazin-1-yl)-2-hydroxy-2-methylpropan-1-one; 2-(4-(4-aminophenyl)piperazin-1-yl)-2-methylpropanoic acid; 2-(4-(2-(4-aminophenoxy)ethyl)piperazin-1-yl)-2-methylpropanenitrile; 2-(1-(4-aminophenyl)piperidin-4-yl)-2-methylpropanoic acid; 6-(4-amino-2-fluorophenyl)-6-azaspiro[2.5]octane-1-carboxylic acid; ((2S,5S)-5-((4-aminophenoxy)methyl)-1,4-dioxan-2-yl)methanol; 1-(1-(4-aminophenyl)piperidin-4-yl)-2-hydroxy-2-methylpropan-1-one; 2-(4-(4-aminophenyl)piperazin-1-yl)-2-methylpropanamide; 6-(4-aminophenyl)-6-azaspiro[2.5]octane-1-carboxylate; 4-((1S,4S)-2-oxa-5-azabicyclo[2.2.1]heptan-5-yl)-3-methylaniline; (S)-1-(3-(4-amino-3-methoxyphenyl)azetidin-1-yl)-2-hydroxypropan-1-one; 1-(4-(4-aminobenzyl)piperazin-1-yl)-2-hydroxy-2-methylpropan-1-one; 3-fluoro-5-(4,4,5,5-tetramethyl-1,3,2-dioxaborolan-2-yl)aniline; 3-methyl-5-(4,4,5,5-tetramethyl-1,3,2-dioxaborolan-2-yl)aniline; (R)-1-(3-(4-amino-3-methoxyphenyl)azetidin-1-yl)-2-hydroxypropan-1-one; 2-(1-(4-aminophenyl)piperidin-4-yl)-N,N-bis(2-hydroxyethyl)acetamide; tert-butyl 4-(4-aminobenzyl)piperazine-1-carboxylate; 2-((1s,4s)-4-(4-aminophenyl)cyclohexyl)acetic acid; 3-bromo-5-(4,4,5,5-tetramethyl-1,3,2-dioxaborolan-2-yl)aniline; 6-amino-2,2,4-trimethyl-2H-benzo[b][1,4]thiazin-3(4H)-one 1,1-dioxide; (S)-1-(4-(4-amino-3-methoxyphenyl)piperazin-1-yl)-2-hydroxypropan-1-one; (S)-1-(4-(4-amino-3-methoxyphenyl)piperidin-1-yl)-2-hydroxypropan-1-one; 1-(4-(2-(4-aminophenoxy)ethyl)

piperazin-1-yl)-2-hydroxy-2-methylpropan-1-one; 2-((1r,4r)-4-(4-aminophenyl)cyclohexyl)acetic acid; 6-amino-4-(4-methoxybenzyl)-2-methyl-2H-benzo[b][1,4]oxazin-3(4H)-one; (R)-1-(4-(4-amino-3-methoxyphenyl)piperazin-1-yl)-2-hydroxypropan-1-one; (R)-1-(4-(4-amino-3-methoxyphenyl)piperazin-1-yl)-2-hydroxypropan-1-one; (2R,5S)-5-((4-aminophenoxy)methyl)-1,4-dioxane-2-carboxylic acid; (6-amino-2,2-dimethyl-3-oxo-2H-pyrido[3,2-b][1,4]oxazin-4(3H)-yl)methyl dihydrogen phosphate; 3-(difluoromethyl)-5-(4,4,5,5-tetramethyl-1,3,2-dioxaborolan-2-yl)aniline; 4-((5-(3-amino-5-methylphenyl)thiazol-2-yl)methyl)cyclohexanecarboxylic acid; (phosphonooxy)methyl 6-(4-aminophenyl)-6-azaspiro[2.5]octane-1-carboxylate; ethyl 4-((5-(3-amino-5-methylphenyl)thiazol-2-yl)methyl)cyclohexanecarboxylate; 4-((5-(3-amino-5-methylphenyl)thiazol-2-yl)(hydroxy)methyl)-3,3-dimethylcyclohexanol; (R)-6-amino-4-(4-methoxybenzyl)-2-methyl-2H-benzo[b][1,4]thiazin-3(4H)-one; ethyl 4-((5-(3-amino-5-methylphenyl)thiazol-2-yl)methylene)cyclohexanecarboxylate; 4-(amino(5-(3-amino-5-methylphenyl)thiazol-2-yl)methyl)cyclohexanecarboxylic acid; (5-(3-amino-5-methylphenyl)-4-(1,2-dioxaspiro[4.5]decan-8-yl)thiazol-2-yl)methanol; 4-((5-(3-amino-5-methylphenyl)thiazol-2-yl)(hydroxy)methyl)cyclohexanecarboxylic acid; 4-((5-(3-amino-5-methylphenyl)thiazol-2-yl)methyl)-4-hydroxycyclohexanecarboxylic acid; 5-(3-amino-5-methylphenyl)-4-(1,2-dioxaspiro[4.5]decan-8-yl)thiazole-2-carbaldehyde; methyl 4-((5-(3-amino-5-methylphenyl)thiazol-2-yl)(hydroxy)methyl)cyclohexanecarboxylate; 4-(1-(5-(3-amino-5-methylphenyl)thiazol-2-yl)-1-hydroxyethyl)-1-methylcyclohexanol; 4-(3-(5-(3-aminophenyl)thiazol-2-yl)-1-hydroxy-2-methylpropyl)cyclohexanecarboxylic acid; 4-((5-(3-amino-5-methylphenyl)thiazol-2-yl)(hydroxy)methyl)-4-hydroxycyclohexanecarboxylic acid; 4-(1-(5-(3-amino-5-methylphenyl)thiazol-2-yl)-1,2-dihydroxyethyl)cyclohexanecarboxylic acid; 4-(1-(5-(3-amino-5-methylphenyl)thiazol-2-yl)-2-fluoro-1-hydroxyethyl)cyclohexanecarboxylic acid; butyl 4-(1-(5-(3-aminophenyl)thiazol-2-yl)-1-hydroxyethyl)cyclohexanecarboxylate; 4-(1-(5-(3-aminophenyl)thiazol-2-yl)-1-hydroxy-2-methylpropyl)cyclohexanecarboxylic acid; 3-(1-(5-(3-amino-5-methylphenyl)thiazol-2-yl)-1-hydroxyethyl)bicyclo[3.1.0]hexane-6-carboxylic acid; 4-(5-(3-amino-5-methylphenyl)thiazol-2-yl)-2,2-dimethylcyclohex-3-enecarboxylate; 4-(3-(5-(3-amino-5-methylphenyl)thiazol-2-yl)-3,4-dihydroxybutyl)cyclohexanecarboxylic acid; 4-(1-(5-(3-amino-5-methylphenyl)thiazol-2-yl)-1-hydroxyethyl)cyclohexanecarboxylate; 4-(1-(5-(3-amino-5-methylphenyl)thiazol-2-yl)-3,4-dihydroxybutyl)cyclohexanecarboxylic acid; 7-(5-(3-amino-5-methylphenyl)thiazol-2-yl)-3-ethylbicyclo[4.1.0]heptane-3-carboxylate; butyl 4-(1-(5-(3-amino-5-methylphenyl)thiazol-2-yl)-1-hydroxyethyl)cyclohexanecarboxylate; 4-(1-(5-(3-amino-5-methylphenyl)thiazol-2-yl)-2,2,2-trifluoro-1-hydroxyethyl)cyclohexanecarboxylic acid; 3-(((tert-butyldiethylsilyl)oxy)methyl)-5-(4,4,5,5-tetramethyl-1,3,2-dioxaborolan-2-yl)aniline.

Furthermore especially preferably, $R^1$ can be derived from the following compounds (e.g. amines):

2-(4-amino-1H-pyrazol-1-yl)-2-methylpropanenitrile; 4-amino-1-methylpyridin-2(1H)-one; 1-(tert-butyl)-1H-pyrazol-4-amine; 1-(4-amino-1H-pyrazol-1-yl)cyclohexanecarbonitrile; 1-isopropyl-1H-pyrazol-4-amine; 1-(3-methoxypropyl)-1H-pyrazol-4-amine; 4-amino-1-(2-methoxyethyl)pyridin-2(1H)-one; (4-amino-3-methoxyphenyl)(morpholino)methanone; 1-isobutyl-1H-pyrazol-4-amine; 2-(4-amino-1H-pyrazol-1-yl)ethan-1-ol; 2-(4-amino-1H-pyrazol-1-yl)acetonitrile; 1-cyclopropyl-1H-pyrazol-4-amine; 3-amino-1-methylpyridin-2(1H)-one; 1-(tert-butyl)-1H-pyrazol-3-amine; 4-bromo-1-methyl-1H-pyrazol-3-amine; 1-(1-methoxy-2-methylpropan-2-yl)-1H-pyrazol-4-amine; 1-(2-methoxyethyl)-3-methyl-1H-pyrazol-4-amine; 1-(2-methoxyethyl)-5-methyl-1H-pyrazol-4-amine; 1-isopropyl-3-methyl-1H-pyrazol-4-amine; 1-isopropyl-5-methyl-1H-pyrazol-4-amine; 1-(1-(tert-butyl)piperidin-4-yl)-1H-pyrazol-4-amine; 3-methyl-1-(tetrahydro-2H-pyran-4-yl)-1H-pyrazol-4-amine; 5-methyl-1-(tetrahydro-2H-pyran-4-yl)-1H-pyrazol-4-amine; 4-amino-1-cyclopropylpyridin-2(1H)-one; 5-chloro-1-isopropyl-1H-pyrazol-4-amine; 1-isopropyl-3-methoxy-1H-pyrazol-4-amine; 1-(1-(tert-butyl)piperidin-4-yl)-3-methoxy-1H-pyrazol-4-amine; 1-isopropyl-5-methoxy-1H-pyrazol-4-amine; 1-(1-(tert-butyl)piperidin-4-yl)-5-methoxy-1H-pyrazol-4-amine; 5-chloro-1-(3-methoxypropyl)-1H-pyrazol-4-amine; 1-isopropyl-3,5-dimethyl-1H-pyrazol-4-amine; imidazo[1,2-a]pyridin-3-amine; 3-cyclopropyl-1-methyl-1H-pyrazol-5-amine; 3-(4-amino-3-methoxyphenyl)oxazolidin-2-one; 3-methoxy-1-(3-methoxypropyl)-1H-pyrazol-4-amine; 5-chloro-1-(2-methoxyethyl)-1H-pyrazol-4-amine; 1-(tert-butyl)-5-methyl-1H-pyrazol-4-amine; 6-amino-1,3-dimethylpyrimidine-2,4(1H,3H)-dione; 1-(2-fluoroethyl)-1H-pyrazol-4-amine; 5-chloro-1-(piperidin-4-yl)-1H-pyrazol-4-amine; 5-chloro-1-(tetrahydro-2H-pyran-4-yl)-1H-pyrazol-4-amine; 1-(4-amino-1H-pyrazol-1-yl)-2-methylpropan-2-ol; 2-fluoro-4-morpholinoaniline; 2,3-dimethylaniline; 2-methyl-4-morpholinoaniline; 2-methyl-4-(4-methylpiperazin-1-yl)aniline; 1-(2,2,2-trifluoroethyl)-1H-pyrazol-4-amine; 4-amino-1-isopropyl-1H-pyrazole-5-carbonitrile; 1-(2-methoxyethyl)-3-(trifluoromethyl)-1H-pyrazol-4-amine; 1-(2-methoxyethyl)-5-(trifluoromethyl)-1H-pyrazol-4-amine; 2-(4-amino-5-chloro-1H-pyrazol-1-yl)ethan-1-ol; 5-bromo-1-(2-methoxyethyl)-1H-pyrazol-4-amine; 5-fluoro-1-(2-methoxyethyl)-1H-pyrazol-4-amine; 2-methyl-3-morpholinoaniline; 5-ethynyl-1-(2-methoxyethyl)-1H-pyrazol-4-amine; 1-(2-methoxyethyl)-N5,N5-dimethyl-1H-pyrazole-4,5-diamine; 2-(4-(4-aminophenyl)piperazin-1-yl)ethan-1-ol; 1-(4-aminophenyl)piperidin-4-ol; 1-(pyrrolidin-3-yl)-1H-pyrazol-4-amine; 1-(1,3-dimethoxypropan-2-yl)-1H-pyrazol-4-amine; 2-(4-amino-1H-pyrazol-1-yl)-N,N-dimethylacetamide; tert-butyl 3-(4-amino-1H-pyrazol-1-yl)pyrrolidine-1-carboxylate; 1-(pyridin-2-yl)-1H-pyrazol-4-amine; 1-(3-methylbutan-2-yl)-1H-pyrazol-4-amine; 6-amino-4-methyl-2H-benzo[b][1,4]oxazin-3(4H)-one; 6-amino-4-ethyl-2H-benzo[b][1,4]oxazin-3(4H)-one; 1-(1-phenylethyl)-1H-pyrazol-4-amine; 3-ethylaniline; (7-amino-3,4-dihydroquinolin-1(2H)-yl)(cyclopropyl)methanone; 1-(tetrahydro-2H-pyran-3-yl)-1H-pyrazol-4-amine; 2-(4-amino-1H-pyrazol-1-yl)propanoic acid; 5-amino-1H-pyrazole-3-carboxylic acid; 2-aminophenol; 4,5-dimethoxybenzene-1,2-diamine; 4-(phenylthio)aniline; 6-amino-2H-benzo[b][1,4]oxazin-3(4H)-one; 6-amino-2H-benzo[b][1,4]thiazin-3(4H)-one; N-(5-amino-2-methoxyphenyl)acetamide; (5-amino-2-(4-methylpiperazin-1-yl)phenyl)methanol; 3,4-dihydro-2H-benzo[b][1,4]oxazin-6-amine; N-(2-(4-acetylpiperazin-1-yl)-5-aminophenyl)acetamide; 3-chloro-4-(4-methylpiperazin-1-yl)aniline; 4-amino-2,6-dichlorophenol; 3-ethoxy-4-methoxyaniline; 2-(4-amino-1H-pyrazol-1-yl)-2-methylpropanamide; 2-methyl-2H-tetrazol-5-amine; 1-methyl-1H-imidazol-4-amine; 1-(oxetan-3-yl)-1H-pyrazol-4-amine; 4-aminopyridin-2(1H)-one; 2-chloro-5-(methylsulfonyl)thiophen-3-amine; 5-methoxy-1-(3-methoxypropyl)-1H-pyrazol-4-amine; 1-(piperidin-4-yl)-1H-pyrazol-4-amine; 4-amino-1-isopropyl-1H-pyrazole-3-carbonitrile; 4-amino-1-(2- methoxyethyl)-1H-pyrazole-3-carbonitrile; 4-amino-1-(2-methoxyethyl)-1H-pyrazole-5-carbonitrile; 4-amino-1-isopropyl-1H-pyrazole-3-carboxamide; 4-amino-1-isopropyl-1H-pyrazole-5-carboxamide; 1-(2-methylallyl)-1H-pyrazol-4-amine; 1-(2-methylprop-1-en-1-yl)-1H-pyrazol-4-amine; 1,2-dimethyl-1H-imidazol-5-amine; 1-(2-fluoroethyl)-3-methyl-1H-pyrazol-4-amine; 1-(2-fluoroethyl)-5-methyl-1H-pyrazol-4-amine; 2-isopropyl-1-methyl-1H-imidazol-5-amine; 1-(2-methoxy-2-methylpropyl)-1H-pyrazol-4-amine; 1-(4-amino-3-methyl-1H-pyrazol-1-yl)-2-methylpropan-2-ol; 1-(4-amino-5-methyl-1H-pyrazol-1-yl)-2-methylpropan-2-ol; 1-(pentan-3-yl)-1H-pyrazol-4-amine; N-(3-aminophenyl)acetamide; 3-(2-methylpyrrolidin-1-yl)aniline; benzene-1,2-diamine; 4-aminophenol; 1-(2-methoxycyclohexyl)-1H-pyrazol-4-amine.

Further preferred, $R^1$ can be derived from the following compounds (e.g. amines):

1-methyl-1H-pyrazol-5-amine; 1-ethyl-1H-pyrazol-3-amine; 4-methyl-1H-pyrazol-5-amine; 1-isopropyl-1H-pyrazol-5-amine; 1-isopropyl-1H-pyrazol-3-amine; 4-bromo-2-methoxyaniline; 6-chloro-4-methoxypyridin-3-amine; 3-cyclopropyl-1-methyl-1H-pyrazol-5-amine; 4-amino-3-methoxybenzonitrile; 5-amino-1-methyl-1H-pyrazole-3-carboxylic acid; 3-isopropyl-1-methyl-1H-pyrazol-5-amine; 4-amino-3-chlorobenzonitrile; 4-amino-3-methoxybenzoic acid; 4-amino-3-methoxy-2-methylbenzonitrile; 4-amino-2-fluoro-5-methoxybenzonitrile; 4-amino-5-methoxy-2-methylbenzonitrile; 4-amino-5-chloro-2-methylbenzonitrile; 4-bromo-2-chloro-5-methoxyaniline; 4-amino-3-methoxybenzamide; methyl 5-amino-1-methyl-H-pyrazole-3-carboxylate; 4-methoxy-6-(thiazol-4-yl)pyridin-3-amine; 4-methoxy-6-(thiazol-5-yl)pyridin-3-amine; 4-methoxy-6-(oxazol-2-yl)pyridin-3-amine; 4-(isoxazol-4-yl)-2-methoxyaniline; 4-amino-3-ethoxybenzoic acid; 2-methoxy-4-(trifluoromethyl)aniline; 2-methoxy-4-morpholinoaniline; 2-methoxy-4-(1-methyl-1H-imidazol-5-yl)aniline; 2-chloro-4-(1-methyl-1H-tetrazol-5-yl)aniline; 2-methoxy-4-(1-methyl-1H-tetrazol-5-yl)aniline; 2-methoxy-4-(4-methyl-4H-1,2,4-triazol-3-yl)aniline; 2-methoxy-4-(1-methyl-1H-imidazol-2-yl)aniline; 2-methoxy-4-(1-methyl-H-pyrazol-5-yl)aniline; 2-bromo-4-morpholinoaniline; (R)-1-(1-methoxypropan-2-yl)-5-methyl-1H-pyrazol-4-amine; 3-(5-amino-1-methyl-1H-pyrazol-3-yl)morpholine-4-carbaldehyde; 5-fluoro-2-methoxy-4-(oxetan-3-yl)aniline; 4-amino-3-methoxy-N-methylbenzamide; 4-amino-2-fluoro-5-methoxybenzoic acid; (R)-2-(4-amino-5-methyl-1H-pyrazol-1-yl)propanenitrile; (S)-1-(2-methoxypropyl)-5-methyl-1H-pyrazol-4-amine; 2-methoxy-4-(methylsulfonyl)aniline; 4-amino-2-chloro-5-methoxybenzoic acid; 2-ethoxy-4-(morpholinomethyl)aniline; 2-chloro-4-(methylsulfonyl)aniline; 2-methoxy-4-(1-methyl-1H-pyrazol-4-yl)aniline; 4-amino-5-chloro-2-methoxybenzoic acid; 2-chloro-4-(2H-tetrazol-5-yl)aniline; 2-methoxy-4-(2-methyl-2H-tetrazol-5-yl)aniline; 4-(2-fluoroethoxy)-6-morpholinopyridin-3-amine; 4-amino-N-ethyl-3-methoxybenzamide; 4-amino-3-methoxy-N,N-dimethylbenzamide; 4-amino-5-chloro-2-methoxybenzamide; 4-amino-3-(difluoromethoxy)benzoic acid; 4-amino-2-fluoro-5-methoxy-N-methylbenzamide; 6-amino-4-chloro-3-methylbenzo[d]oxazol-2(3H)-one; 6-amino-5-chloro-3-methylbenzo[d]oxazol-2(3H)-one; 5-amino-6-chloro-2-methylisoindolin-1-one; 5-amino-6-methoxy-2-methylisoindolin-1-one; 6-amino-5-methoxy-2-methylisoindolin-1-one; 1-(4-amino-3-isopropyl-1H-pyrazol-1-yl)-2-methylpropan-2-ol; 4-methyl-1-(1-methylpiperidin-4-yl)-1H-pyrazol-3-amine; 5-(4-amino-5-methyl-1H-pyrazol-1-yl)-1-methylpiperidin-2-one; 2-(2-fluoroethoxy)-4-(morpholinomethyl)aniline; 5-fluoro-2-methoxy-4-(1-methyl-1H-tetrazol-5-yl)aniline; 5-fluoro-2-methoxy-4-(5-methyl-1H-tetrazol-1-yl)aniline; 4-(3,5-dimethylisoxazol-4-yl)-2-methoxyaniline; 4-(1,5-dimethyl-1H-pyrazol-4-yl)-2-methoxyaniline; 4-(1,3-dimethyl-1H-pyrazol-4-yl)-2-methoxyaniline; 4-amino-N-isopropyl-3-methoxybenzamide; 4-amino-5-chloro-2-methoxy-N-methylbenzamide; (4-amino-3-methoxyphenyl)(azetidin-1-yl)methanone; 4-amino-N,N,3-trimethylbenzamide; 4-amino-N-cyclopropyl-3-methoxybenzamide; 6-amino-7-methoxy-2-methyl-1,2-dihydroisoquinolin-3(4H)-one; 5-amino-2-ethyl-4-methoxyisoindolin-1-one; 6-amino-7-methoxy-2-methylphthalazin-1(2H)-one; 8-amino-N-methyl-2,3-dihydrobenzo[b][1,4]dioxine-5-carboxamide; (R)-1-(1-methoxypropan-2-yl)-3-methyl-1H-pyrazol-4-amine; (S)-1-(2-methoxypropyl)-3-methyl-1H-pyrazol-4-amine; 5-fluoro-2-methoxy-4-(morpholinomethyl)aniline; 2-(2-fluoroethoxy)-4-(methylsulfonyl)aniline; 1-(4-amino-2-fluoro-5-methoxyphenyl)pyrrolidin-2-one; 2-chloro-5-methoxy-4-(1-methyl-1H-imidazol-2-yl)aniline; 2-chloro-4-(3-methyl-1,2,4-oxadiazol-5-yl)aniline; 2-chloro-4-(2-methyl-2H-tetrazol-5-yl)aniline; 2-chloro-5-methoxy-4-(1-methyl-1H-pyrazol-5-yl)aniline; 2-chloro-5-methoxy-4-(1-methyl-1H-imidazol-5-yl)aniline; 4-amino-N-(3-aminopropyl)-3-methoxybenzamide; 4-amino-3-methoxy-N-(2-methoxyethyl)benzamide; 5-ethoxy-2-fluoro-4-morpholinoaniline; (4-amino-3-methoxyphenyl)(pyrrolidin-1-yl)methanone; 4-amino-3-methoxy-N-(oxetan-3-yl)benzamide; 4-amino-N-(cyclopropylmethyl)-3-methoxybenzamide; 4-amino-N-(2,2-difluoroethyl)-3-methoxybenzamide; 6-amino-5-chlorobenzo[d]oxazol-2(3H)-one; 5-amino-4-methoxy-2-methylisoindolin-1-one; 8-amino-7-chloro-4-methyl-3,4-dihydrobenzo[f][1,4]oxazepin-5(2H)-one; 8-amino-N-ethyl-2,3-dihydrobenzo[b][1,4]dioxine-5-carboxamide; 5-(4-amino-3-methyl-1H-pyrazol-1-yl)-1-methylpiperidin-2-one; (5-amino-1-methyl-1H-pyrazol-3-yl)(morpholino)methanone; 2-methoxy-5-methyl-4-(methylsulfonyl)aniline; 4-(4-amino-2-fluoro-5-methoxyphenyl)morpholin-3-one; 1-(4-amino-2-fluoro-5-methoxyphenyl)piperidin-2-one; 5-fluoro-2-methoxy-4-(methylsulfonyl)aniline; 5-fluoro-2-methoxy-4-(5-methyl-1,3,4-oxadiazol-2-yl)aniline; 2-methoxy-4-(5-(methoxymethyl)-1H-tetrazol-1-yl)-5-methylaniline; 5-fluoro-2-methoxy-4-(3-methyl-1,2,4-oxadiazol-5-yl)aniline; (4-amino-3-methoxyphenyl)(morpholino)methanone; 4-amino-3-cyclobutoxybenzoic acid; 4-amino-N-ethyl-3-methoxy-N-methylbenzamide; (4-amino-3-methoxyphenyl)(piperidin-1-yl)methanone; (4-amino-3-methoxyphenyl)(2-methylpyrrolidin-1-yl)methanone; 4-amino-2-fluoro-5-methoxy-N,N-dimethylbenzamide; methyl 4-amino-3-(difluoromethoxy)benzoate; 4-amino-5-chloro-N-(2-hydroxyethyl)-2-methoxybenzamide; (4-amino-3-methoxyphenyl)(piperazin-1-yl)methanone; 6-amino-N,N-dimethylbenzofuran-2-carboxamide; 5-amino-6-chloro-1,3-dimethyl-1H-benzo[d]imidazol-2(3H)-one; (S)-5-methyl-1-(1-methylpiperidin-3-yl)-1H-pyrazol-4-amine; 5-fluoro-2-(2-fluoroethoxy)-4-(morpholinomethyl)aniline; 4-(ethylsulfonyl)-2-methoxy-5-methylaniline; 5-chloro-2-methoxy-4-(methylsulfonyl)aniline; 2-isopropoxy-4-(methylsulfonyl)aniline; 2-chloro-5-methoxy-4-(1-methyl-1H-pyrazol-4-yl)aniline; 2-chloro-5-methoxy-4-(5-methyl-1,3,4-oxadiazol-2-yl)aniline; (4-amino-3-hydroxyphenyl)(morpholino)methanone; 4-amino-5-chloro-2-methoxy-N,N-dimethylbenzamide; 4-amino-5-chloro-2-methoxy-N-(2-methoxyethyl)benzamide; 4-amino-3-methoxy-N-

(tetrahydro-2H-pyran-3-yl)benzamide; (4-amino-3-ethoxyphenyl)(morpholino)methanone; 4-amino-N-(tert-butyl)-3-methoxybenzamide; 4-amino-N-isopropyl-3-methoxy-N-methylbenzamide; (4-amino-3-methoxyphenyl)(3-fluoroazetidin-1-yl)methanone; 4-amino-N,N-diethyl-3-methoxybenzamide; (4-amino-3-methylphenyl)(morpholino)methanone; 2-(4-amino-3-methoxyphenyl)-1-morpholinoethan-1-one; 4-amino-N-(3-aminopropyl)-5-chloro-2-methoxybenzamide; (4-amino-3-methoxyphenyl)(2-hydroxypiperidin-1-yl)methanone; (4-amino-3-methoxyphenyl)(2-methylpiperidin-1-yl)methanone; (4-amino-3-fluorophenyl)(morpholino)methanone; (4-amino-3-(2-fluoroethoxy)phenyl)(morpholino)methanone; (4-amino-2-fluoro-5-hydroxyphenyl)(morpholino)methanone; 4-amino-5-(fluoromethoxy)-2-methoxy-N,N-dimethylbenzamide; 4-amino-5-chloro-N-cyclopropyl-2-methoxybenzamide; (4-amino-3-methoxyphenyl)(3-hydroxypyrrolidin-1-yl)methanone; (4-amino-3-chlorophenyl)(morpholino)methanone; (4-amino-3-bromophenyl)(morpholino)methanone; 4-amino-3-methoxy-N-(2-methoxyethyl)-N-methylbenzamide; 6-amino-5-methoxy-N,N-dimethylbenzofuran-3-carboxamide; 5-amino-6-methoxy-2-(oxetan-3-yl)isoindolin-1-one; 6-amino-5-methoxy-N,N-dimethylbenzofuran-2-carboxamide; (4-amino-2,5-dimethylphenyl)(morpholino)methanone; (4-amino-2,3-difluorophenyl)(morpholino)methanone; (4-amino-2,5-difluorophenyl)(morpholino)methanone; (4-amino-5-fluoro-2-methylphenyl)(morpholino)methanone; 8-amino-N-isopropyl-2,3-dihydrobenzo[b][1,4]dioxine-5-carboxamide; (4-amino-2-fluoro-5-methylphenyl)(morpholino)methanone; (S)-3-methyl-1-(1-methylpiperidin-3-yl)-1H-pyrazol-4-amine; (S)-2-(4-amino-5-methyl-1H-pyrazol-1-yl)-N,N-dimethylpropanamide; 5-fluoro-2-methoxy-4-(5-(methoxymethyl)-3-methyl-1H-pyrazol-1-yl)aniline; (4-amino-5-fluoro-2-(fluoromethoxy)phenyl)(pyrrolidin-1-yl)methanone; (4-amino-5-(fluoromethoxy)-2-methylphenyl)(pyrrolidin-1-yl)methanone; (4-amino-2-fluoro-5-methoxyphenyl)(morpholino)methanone; (4-amino-2-fluoro-5-(fluoromethoxy)phenyl)(pyrrolidin-1-yl)methanone; (4-amino-3-methoxyphenyl)(4-methylpiperidin-1-yl)methanone; (4-amino-2-fluoro-3-methoxyphenyl)(morpholino)methanone; 4-amino-5-chloro-2-methoxy-N-(oxetan-3-yl)benzamide; (4-amino-3-methoxyphenyl)(4-fluoropiperidin-1-yl)methanone; 4-amino-5-chloro-N-(2-hydroxyethyl)-2-methoxy-N-methylbenzamide; (4-amino-5-fluoro-2-methoxyphenyl)(morpholino)methanone; (4-amino-3-methoxyphenyl)(4-hydroxypiperidin-1-yl)methanone; 4-amino-2-fluoro-5-methoxy-N-(2-methoxyethyl)-N-methylbenzamide; 4-amino-3-(2,2,2-trifluoroethoxy)benzoic acid; 4-amino-5-chloro-N-(2-hydroxypropyl)-2-methoxybenzamide; (4-amino-5-chloro-2-methoxyphenyl)(pyrrolidin-1-yl)methanone; (4-amino-3-methoxyphenyl)(2-oxa-5-azabicyclo[2.2.1]heptan-5-yl)methanone; (4-amino-3-methoxyphenyl)(4-methylpiperazin-1-yl)methanone; (4-amino-3-methoxyphenyl)(3-methylpiperidin-1-yl)methanone; (4-amino-3-methoxyphenyl)(2-methylmorpholino)methanone; 5-amino-2-cyclopropyl-4-methoxyisoindolin-1-one; (4-amino-5-chloro-2-methylphenyl)(morpholino)methanone; (4-amino-3-chloro-2-fluorophenyl)(morpholino)methanone; (4-amino-5-chloro-2-hydroxyphenyl)(morpholino)methanone; (4-amino-5-methoxy-2-methylphenyl)(morpholino)methanone; (4-amino-3-methoxy-2-methylphenyl)(morpholino)methanone; (4-amino-5-chloro-2-fluorophenyl)(morpholino)methanone; (4-amino-2-chloro-5-methylphenyl)(morpholino)methanone; (4-amino-2-methoxy-5-methylphenyl)(morpholino)methanone; (4-amino-2-chloro-5-fluorophenyl)(morpholino)methanone; (8-amino-2,3-dihydrobenzo[b][1,4]dioxin-5-yl)(pyrrolidin-1-yl)methanone; (S)-5-methyl-1-(1-(oxetan-3-yl)pyrrolidin-3-yl)-1H-pyrazol-4-amine; (S)-3-methyl-1-(1-(oxetan-3-yl)pyrrolidin-3-yl)-1H-pyrazol-4-amine; 2-methoxy-4-(morpholinosulfonyl)aniline; N'-acetyl-4-amino-5-chloro-2-methoxybenzohydrazide; (4-amino-5-(fluoromethoxy)-2-methylphenyl)(morpholino)methanone; (4-amino-2-fluoro-5-(fluoromethoxy)phenyl)(morpholino)methanone; (4-amino-5-chloro-2-(fluoromethoxy)phenyl)(pyrrolidin-1-yl)methanone; (4-amino-5-(fluoromethoxy)-2-methoxyphenyl)(pyrrolidin-1-yl)methanone; (4-amino-3-methoxyphenyl)(3-(hydroxymethyl)morpholino)methanone; (4-amino-5-chloro-2-methoxyphenyl)(morpholino)methanone; (4-amino-2-chloro-5-methoxyphenyl)(morpholino)methanone; (4-amino-3-isopropoxyphenyl)(morpholino)methanone; (4-amino-3-methylphenyl)(4-hydroxypiperidin-1-yl)methanone; (4-amino-5-ethoxy-2-fluorophenyl)(morpholino)methanone; (4-amino-2-ethoxy-5-fluorophenyl)(morpholino)methanone; (4-amino-3-methoxyphenyl)(3-oxa-8-azabicyclo[3.2.1]octan-8-yl)methanone; (4-amino-3-methoxyphenyl)(3,3-dimethylmorpholino)methanone; 4-amino-5-chloro-2-methoxy-N-(2-methoxyethyl)-N-methylbenzamide; (4-amino-3-methoxyphenyl)(3,3-difluoroazetidin-1-yl)methanone; (4-amino-5-chloro-2-methoxyphenyl)(piperazin-1-yl)methanone; 4-amino-3-methoxy-N-(1-methylpiperidin-4-yl)benzamide; 4-amino-N-ethyl-2-fluoro-5-methoxy-N-(2-methoxyethyl)benzamide; (4-amino-3-(difluoromethoxy)phenyl)(morpholino)methanone; 5-amino-4-methoxy-2-(oxetan-3-yl)isoindolin-1-one; 5-amino-2-(2-hydroxypropan-2-yl)-4-methoxyisoindolin-1-one; (4-amino-5-ethoxy-2-methylphenyl)(morpholino)methanone; (4-amino-2,5-dimethoxyphenyl)(morpholino)methanone; (8-amino-2,3-dihydrobenzo[b][1,4]dioxin-5-yl)(morpholino)methanone; (7-amino-5-fluoro-2,3-dihydrobenzofuran-4-yl)(morpholino)methanone; (4-amino-5-bromo-2-methoxyphenyl)(morpholino)methanone; (S)-5-methyl-1-(1-(oxetan-3-yl)piperidin-3-yl)-1H-pyrazol-4-amine; (S)-3-methyl-1-(1-(oxetan-3-yl)piperidin-3-yl)-1H-pyrazol-4-amine; (S)-2-(4-amino-3-methyl-1H-pyrazol-1-yl)-N,N-dimethylpropanamide; 5-fluoro-2-methoxy-4-(1-(oxetan-3-yl)-1H-pyrazol-4-yl)aniline; 2-chloro-5-methoxy-4-(1,3,5-trimethyl-1H-pyrazol-4-yl)aniline; (4-amino-5-(2-fluoroethoxy)-2-methoxyphenyl)(pyrrolidin-1-yl)methanone; (4-amino-5-chloro-2-(fluoromethoxy)phenyl)(morpholino)methanone; (4-amino-5-(2-fluoroethoxy)-2-methylphenyl)(morpholino)methanone; (4-amino-2-fluoro-5-(2-fluoroethoxy)phenyl)(morpholino)methanone; (4-amino-5-(fluoromethoxy)-2-methoxyphenyl)(piperidin-1-yl)methanone; (4-amino-3-methoxyphenyl)(2-oxa-6-azaspiro[3.3]heptan-6-yl)methanone; 2-(4-amino-2,5-dimethoxyphenyl)-1-morpholinoethan-1-one; (4-amino-5-chloro-2-ethoxyphenyl)(morpholino)methanone; (4-amino-3-cyclopropylphenyl)(morpholino)methanone; (4-amino-3-methoxyphenyl)(3,3-difluoropyrrolidin-1-yl)methanone; (R)-(4-amino-3-methoxyphenyl)(3-methylmorpholino)methanone; 4-amino-N-(tert-butyl)-5-chloro-2-methoxybenzamide; (4-amino-5-chloro-2-methoxyphenyl)(3-hydroxyazetidin-1-yl)methanone; 4-amino-N-(3,3-difluorocyclobutyl)-3-methoxybenzamide; (4-amino-5-chloro-2-methoxyphenyl)(1,4-oxazepan-4-yl)methanone; 5-amino-2-(2-hydroxy-2-methylpropyl)-6-methoxyisoindolin-1-one; (6-amino-5-methoxybenzofuran-3-yl)(morpholino)methanone; 4-amino-5-fluoro-N-(2-hydroxy-2-methylpropyl)-2-methoxybenzamide; 4-amino- 2-fluoro-N-(2-hydroxy-2-methylpropyl)-3-methoxybenzamide; 4-amino-2-fluoro-N-(1-(hydroxymethyl)cyclopropyl)-5-methoxybenzamide; 4-amino-2-fluoro-N-(1-hydroxy-2-methylpropan-2-yl)-5-methoxybenzamide; 4-amino-N-(2-hydroxy-2-methylpropyl)-5-methoxy-2-methylbenzamide; 4-amino-2-fluoro-N-(2-hydroxy-2-methylpropyl)-5-methoxybenzamide; 4-amino-2-fluoro-N-((1-hydroxycyclopropyl)methyl)-5-methoxybenzamide; (S)-2-(4-amino-5-methyl-1H-pyrazol-1-yl)-1-(pyrrolidin-1-yl)propan-1-one; (4-amino-3-methoxyphenyl)(4,4-difluoropiperidin-1-yl)methanone; (4-amino-3-methoxyphenyl)(4-ethylpiperazin-1-yl)methanone; (4-amino-3-methoxyphenyl)(3,3-difluoropiperidin-1-yl)methanone; (4-amino-3-methoxyphenyl)(8-oxa-3-azabicyclo[3.2.1]octan-3-yl)methanone; (4-amino-3-methoxyphenyl)(4-(hydroxymethyl)piperidin-1-yl)methanone; (4-amino-3-methoxyphenyl)(2,6-dimethylmorpholino)methanone; 4-amino-5-chloro-N-(2-hydroxy-2-methylpropyl)-2-methoxybenzamide; (4-amino-3-(cyclobutylmethoxy)phenyl)(morpholino)methanone; (4-amino-3-methoxyphenyl)(3,5-dimethylpiperidin-1-yl)methanone; (4-amino-3-methoxyphenyl)(4-methoxypiperidin-1-yl)methanone; (4-amino-2-fluoro-5-methoxyphenyl)(3-methoxypyrrolidin-1-yl)methanone; (S)-(4-amino-3-methoxyphenyl)(3-methylmorpholino)methanone; (4-amino-3-methoxyphenyl)(2-(hydroxymethyl)morpholino)methanone; (4-amino-5-chloro-2-methoxyphenyl)(3-hydroxypyrrolidin-1-yl)methanone; (4-amino-3-methoxyphenyl)(4,4-dimethylpiperidin-1-yl)methanone; (4-amino-3-cyclopropoxyphenyl)(morpholino)methanone; (4-amino-3-methoxyphenyl)(3-methoxypiperidin-1-yl)methanone; (4-amino-3-methoxyphenyl)(hexahydro-1H-pyrido[1,2-a]pyrazin-2(6H)-yl)methanone; (S)-(4-amino-3-methoxyphenyl)(3-fluoropyrrolidin-1-yl)methanone; 4-amino-5-chloro-2-methoxy-N-(1-methylcyclobutyl)benzamide; (4-amino-2,6-difluoro-3-methoxyphenyl)(morpholino)methanone; (4-amino-3-methoxyphenyl)(2,2-dimethylmorpholino)methanone; (S)-2-(4-amino-3-methyl-1H-pyrazol-1-yl)-1-(pyrrolidin-1-yl)propan-1-one; (R)-(4-amino-3-methoxyphenyl)(3-fluoropyrrolidin-1-yl)methanone; (4-amino-3-cyclobutoxyphenyl)(morpholino)methanone; (4-amino-3-methoxyphenyl)(4-(dimethylamino)piperidin-1-yl)methanone; (4-amino-5-chloro-2-methoxyphenyl)(3-methoxypyrrolidin-1-yl)methanone; 1-(4-amino-3-methoxybenzoyl)piperidine-4-carbonitrile; (4-amino-3-(oxetan-3-yloxy)phenyl)(morpholino)methanone; (4-amino-2-fluoro-3-isopropoxyphenyl)(morpholino)methanone; (4-amino-3-methoxyphenyl)(4-(2-hydroxyethyl)piperazin-1-yl)methanone; 1-(4-amino-2-fluoro-5-methoxybenzoyl)pyrrolidine-3-carbonitrile; (4-amino-5-chloro-2-methoxyphenyl)(4-hydroxypiperidin-1-yl)methanone; 4-amino-5-chloro-N-(1-cyanocyclopropyl)-2-methoxybenzamide; (R)-(4-amino-3-methoxyphenyl)(3-hydroxypyrrolidin-1-yl)methanone; (4-amino-3-methoxyphenyl)(4-isopropylpiperazin-1-yl)methanone; (4-amino-3-(cyclopropylmethoxy)phenyl)(morpholino)methanone; 4-amino-N-(4,4-difluorocyclohexyl)-3-methoxybenzamide; (4-amino-5-isopropoxy-2-methylphenyl)(morpholino)methanone; (4-amino-3-fluoro-2,6-dimethoxyphenyl)(morpholino)methanone; (S)-(4-amino-3-fluorophenyl)(3-fluoropyrrolidin-1-yl)methanone; 1-((1S,5S)-8-oxabicyclo[3.2.1]octan-3-yl)-3-methyl-1H-pyrazol-4-amine; (4-amino-3-methoxyphenyl)(4-cyclobutylpiperazin-1-yl)methanone; 1-(4-amino-5-chloro-2-methoxybenzoyl)pyrrolidine-3-carbonitrile; (4-amino-3-methoxyphenyl)(3-morpholinoazetidin-1-yl)methanone; 4-amino-5-chloro-2-methoxy-N-(1-methylpiperidin-4-yl)benzamide; (4-amino-3-methoxyphenyl)(2,2-diethylmorpholino)methanone; 1-(4-(4-amino-3-methoxybenzoyl)piperazin-1-yl)ethan-1-one; (4-amino-3-methoxyphenyl)(2-isobutylmorpholino)methanone; (4-amino-3-methoxyphenyl)(4-(oxetan-3-yl)piperazin-1-yl)methanone; (4-amino-5-chloro-2-methoxyphenyl)(2-(hydroxymethyl)morpholino)methanone; 4-amino-2-fluoro-N-(2-hydroxy-2-methylpropyl)-5-methoxy-N-methylbenzamide; (4-amino-3-(cyclopentyloxy)phenyl)(morpholino)methanone; (6-amino-5-methoxy-1-methyl-1H-indol-3-yl)(morpholino)methanone; (4-amino-5-chloro-2-(difluoromethoxy)phenyl)(morpholino)methanone; (S)-(4-amino-3-chlorophenyl)(3-fluoropyrrolidin-1-yl)methanone; (4-amino-5-(cyclopropylmethoxy)-2-methylphenyl)(morpholino)methanone; 4-amino-5-fluoro-N-(2-hydroxy-2-methylpropyl)-2-methoxy-N-methylbenzamide; (4-amino-3-chloro-2,6-dimethoxyphenyl)(morpholino)methanone; (4-amino-2-fluoro-5-methoxyphenyl)(hexahydropyrrolo[1,2-a]pyrazin-2(1H)-yl)methanone; (4-amino-2-fluoro-5-methoxyphenyl)(1-oxa-6-azaspiro[3.3]heptan-6-yl)methanone; (4-amino-2,5-dimethoxyphenyl)(3,3-difluoropyrrolidin-1-yl)methanone; (4-amino-3-methoxyphenyl)(3-(trifluoromethyl)pyrrolidin-1-yl)methanone; (4-amino-3-(trifluoromethoxy)phenyl)(morpholino)methanone; 4-amino-5-chloro-N-(2-hydroxy-2-methylpropyl)-2-methoxy-N-methylbenzamide; 1-(4-amino-5-chloro-2-methoxybenzoyl)piperidine-4-carbonitrile; (4-amino-3-(difluoromethoxy)phenyl)(4-hydroxypiperidin-1-yl)methanone; (4-amino-2-fluoro-5-methoxyphenyl)(2,2-dimethylmorpholino)methanone; (8-amino-2,3-dihydrobenzo[b][1,4]dioxin-5-yl)(3,3-difluoropyrrolidin-1-yl)methanone; (S)-(4-amino-5-chloro-2-methylphenyl)(3-fluoropyrrolidin-1-yl)methanone; (4-amino-5-chloro-2-methoxyphenyl)(1-oxa-6-azaspiro[3.3]heptan-6-yl)methanone; (4-amino-5-chloro-2-methoxyphenyl)(3,3-difluoropyrrolidin-1-yl)methanone; (S)-(4-amino-5-methoxy-2-methylphenyl)(3-fluoropyrrolidin-1-yl)methanone; (4-amino-5-chloro-2-methoxyphenyl)(2-oxa-6-azaspiro[3.3]heptan-6-yl)methanone; (S)-(4-amino-5-fluoro-2-methoxyphenyl)(3-fluoropyrrolidin-1-yl)methanone; (S)-(4-amino-2-fluoro-5-methoxyphenyl)(3-fluoropyrrolidin-1-yl)methanone; 4-(4-amino-2-fluoro-5-methoxyphenyl)-N,N,1-trimethyl-1H-pyrazole-5-carboxamide; (4-amino-5-(fluoromethoxy)-2-methoxyphenyl)(3,3-difluoropyrrolidin-1-yl)methanone; (4-amino-3-methoxyphenyl)(4-(2-hydroxypropan-2-yl)piperidin-1-yl)methanone; (4-amino-5-chloro-2-methoxyphenyl)(2,6-dimethylmorpholino)methanone; (4-amino-3-methoxyphenyl)(4-(tert-butyl)piperidin-1-yl)methanone; (S)-(4-amino-2-fluoro-5-methoxyphenyl)(2-(methoxymethyl)pyrrolidin-1-yl)methanone; (4-amino-5-chloro-2-methoxyphenyl)(4,4-difluoropiperidin-1-yl)methanone; (4-amino-3-(2,2,2-trifluoroethoxy)phenyl)(morpholino)methanone; (4-amino-3-methoxyphenyl)(4-(piperidin-4-yl)piperazin-1-yl)methanone; (4-amino-3-methoxyphenyl)(3-(trifluoromethyl)piperidin-1-yl)methanone; (S)-(4-amino-5-chloro-2-methoxyphenyl)(3-fluoropyrrolidin-1-yl)methanone; 4-amino-5-chloro-2-methoxy-N-methyl-N-(1-methyl-1H-pyrazol-4-yl)benzamide; (4-amino-5-chloro-2-methoxyphenyl)(4-(2-methoxyethyl)piperazin-1-yl)methanone; 4-amino-2-fluoro-5-methoxy-N-methyl-N-(1-methylpiperidin-4-yl)benzamide; (4-amino-5-methoxy-2-(trifluoromethyl)phenyl)(morpholino)methanone; (4-amino-5-(2-fluoroethoxy)-2-methoxyphenyl)(3,3-difluoropyrrolidin-1-yl)methanone; (4-amino-5-chloro-2-methoxyphenyl)(4-(dimethylamino)piperidin-1-yl)

methanone; (4-amino-3-methoxyphenyl)(4-(2,2,2-trifluoroethyl)piperazin-1-yl)methanone; (4-amino-5-methoxy-2-(trifluoromethoxy)phenyl)(morpholino)methanone; (4-(4-amino-3-methoxybenzoyl)piperazin-1-yl)(cyclopropyl)methanone; (4-amino-3-methoxyphenyl)(2,2,6,6-tetrafluoromorpholino)methanone; (4-amino-3-methoxyphenyl)(4-(methylsulfonyl)piperazin-1-yl)methanone; (4-amino-5-chloro-2-methoxyphenyl)(3-morpholinoazetidin-1-yl)methanone; (4-amino-5-chloro-2-methoxyphenyl)(4-(oxetan-3-yl)piperazin-1-yl)methanone; (4-amino-3-methoxyphenyl)(4-(1-methylpiperidin-4-yl)piperazin-1-yl)methanone; (4-amino-3-(cyclopentyloxy)phenyl)(2-oxa-6-azaspiro[3.3]heptan-6-yl)methanone; (6-amino-5-chloro-1-methyl-1H-indol-3-yl)(4-methylpiperazin-1-yl)methanone; (4-amino-2-fluoro-5-methoxyphenyl)(4-morpholinopiperidin-1-yl)methanone; (4-amino-3-methoxyphenyl)((3S,4S)-3,4-difluoropyrrolidin-1-yl)methanone; (6-amino-5-chloro-1-methyl-1H-indol-3-yl)(4-ethylpiperazin-1-yl)methanone; (4-amino-2-fluoro-3-methoxyphenyl)((1S,4S)-2-oxa-5-azabicyclo[2.2.1]heptan-5-yl)methanone; (4-amino-2-fluoro-5-methoxyphenyl)((1S,4S)-2-oxa-5-azabicyclo[2.2.1]heptan-5-yl)methanone; (4-amino-5-chloro-2-methoxyphenyl)((1S,4S)-2-oxa-5-azabicyclo[2.2.1]heptan-5-yl)methanone; (4-amino-2-fluoro-5-methoxyphenyl)((3 S,4S)-3,4-difluoropyrrolidin-1-yl)methanone; (4-amino-2-fluoro-5-methoxyphenyl)((2S,6R)-2,6-dimethylmorpholino)methanone; (4-amino-2-fluoro-5-methoxyphenyl)((1R,5S)-8-oxa-3-azabicyclo[3.2.1]octan-3-yl)methanone; (4-amino-5-chloro-2-methoxyphenyl)((2S,6R)-2,6-dimethylmorpholino)methanone; (4-amino-5-chloro-2-methoxyphenyl)((3 S,5R)-3,5-dimethylpiperazin-1-yl)methanone; (6-amino-5-chloro-1-methyl-1H-indol-3-yl)((1S,4S)-2-oxa-5-azabicyclo[2.2.1]heptan-5-yl)methanone.

Especially preferred are compounds of formula (I) that are selected from:

9-fluoro-N-(4-(4-(4-methylpiperazin-1-yl)piperidin-1-yl)phenyl)-3H-pyrazolo[3,4-c]quinolin-4-amine; 9-fluoro-N-(3-fluoro-4-morpholinophenyl)-3H-pyrazolo[3,4-c]quinolin-4-amine; 8-methoxy-N-(4-(4-(4-methylpiperazin-1-yl)piperidin-1-yl)phenyl)-2H-pyrazolo[3,4-c]quinolin-4-amine; N-(4-fluoro-3-(methylsulfonyl)phenyl)-8-methoxy-2H-pyrazolo[3,4-c]quinolin-4-amine; N-(3-((dimethylamino)methyl)phenyl)-8-methoxy-2H-pyrazolo[3,4-c]quinolin-4-amine; (4-((8-methoxy-2H-pyrazolo[3,4-c]quinolin-4-yl)amino)phenyl)(4-(4-methylpiperazin-1-yl)piperidin-1-yl)methanone; (3-((8-methoxy-2H-pyrazolo[3,4-c]quinolin-4-yl)amino)phenyl)(morpholino)methanone; N-(3-(tert-butyl)phenyl)-8-methoxy-2H-pyrazolo[3,4-c]quinolin-4-amine; 9-fluoro-N-(4-morpholinophenyl)-3H-pyrazolo[3,4-c]quinolin-4-amine; N-(4-(4-cyclopropylpiperazin-1-yl)phenyl)-9-fluoro-3H-pyrazolo[3,4-c]quinolin-4-amine; 9-fluoro-N-(6-morpholinopyridin-3-yl)-3H-pyrazolo[3,4-c]quinolin-4-amine; 6-((8-methoxy-2H-pyrazolo[3,4-c]quinolin-4-yl)amino)-2,3-dihydrobenzo[b]thiophene 1,1-dioxide; 6-((8-methoxy-2H-pyrazolo[3,4-c]quinolin-4-yl)amino)benzo[b]thiophene 1,1-dioxide; (4-((9-methoxy-3H-pyrazolo[3,4-c]quinolin-4-yl)amino)phenyl)(morpholino)methanone; 9-methoxy-N-(4-(morpholinomethyl)phenyl)-3H-pyrazolo[3,4-c]quinolin-4-amine; 9-methoxy-N-(3-methoxy-4-morpholinophenyl)-3H-pyrazolo[3,4-c]quinolin-4-amine; 9-methoxy-N-(6-morpholinopyridin-3-yl)-3H-pyrazolo[3,4-c]quinolin-4-amine; N-(1,3-dihydroisobenzofuran-5-yl)-9-methoxy-3H-pyrazolo[3,4-c]quinolin-4-amine; 6-((9-methoxy-3H-pyrazolo[3,4-c]quinolin-4-yl)amino)-2,3-dihydrobenzo[b]thiophene 1,1-dioxide; 6-((9-methoxy-3H-pyrazolo[3,4-c]quinolin-4-yl)amino)benzo[b]thiophene 1,1-dioxide; 9-methoxy-N-(4-(4-methylpiperazin-1-yl)piperidin-1-yl)phenyl)-3H-pyrazolo[3,4-c]quinolin-4-amine; 8-methoxy-N-(4-((4-(4-methylpiperazin-1-yl)piperidin-1-yl)methyl)phenyl)-2H-pyrazolo[3,4-c]quinolin-4-amine; 8-methoxy-N-(3-(morpholinomethyl)phenyl)-2H-pyrazolo[3,4-c]quinolin-4-amine; 2-(3-((8-methoxy-2H-pyrazolo[3,4-c]quinolin-4-yl)amino)phenyl)-2-methylpropanenitrile; 3-(4-((8-methoxy-2H-pyrazolo[3,4-c]quinolin-4-yl)amino)phenyl)oxazolidin-2-one; N-(5-cyclopropyl-1H-pyrazol-3-yl)-9-methoxy-3H-pyrazolo[3,4-c]quinolin-4-amine; N-(3-fluoro-4-morpholinophenyl)-9-methoxy-3H-pyrazolo[3,4-c]quinolin-4-amine; N-(3-((dimethylamino)methyl)phenyl)-9-methoxy-3H-pyrazolo[3,4-c]quinolin-4-amine; (4-((9-fluoro-3H-pyrazolo[3,4-c]quinolin-4-yl)amino)phenyl)(morpholino)methanone; 9-fluoro-N-(4-(morpholinomethyl)phenyl)-3H-pyrazolo[3,4-c]quinolin-4-amine; 9-fluoro-N-(3-methoxy-4-morpholinophenyl)-3H-pyrazolo[3,4-c]quinolin-4-amine; N-(4-fluoro-3-(methylsulfonyl)phenyl)-9-methoxy-3H-pyrazolo[3,4-c]quinolin-4-amine; 2-(3-((9-methoxy-3H-pyrazolo[3,4-c]quinolin-4-yl)amino)phenyl)-2-methylpropanenitrile; (2-fluoro-4-((8-methoxy-2H-pyrazolo[3,4-c]quinolin-4-yl)amino)phenyl)(morpholino)methanone; (4-((8-methoxy-2H-pyrazolo[3,4-c]quinolin-4-yl)amino)-2-nitrophenyl)(morpholino)methanone; 8-methoxy-N-(4-(oxazol-2-yl)phenyl)-2H-pyrazolo[3,4-c]quinolin-4-amine; 8-methoxy-N-(4-(oxazol-5-yl)phenyl)-2H-pyrazolo[3,4-c]quinolin-4-amine; N-(4-(4-(tert-butyl)piperazin-1-yl)phenyl)-9-methoxy-3H-pyrazolo[3,4-c]quinolin-4-anine; (4-((9-methoxy-3H-pyrazolo[3,4-c]quinolin-4-yl)amino)phenyl)(4-(4-methylpiperazin-1-yl)piperidin-1-yl)methanone; 3-(4-((9-methoxy-2H-pyrazolo[3,4-c]quinolin-4-yl)amino)phenyl)oxazolidin-2-one; 8-methoxy-N-(pyridazin-4-yl)-2H-pyrazolo[3,4-c]quinolin-4-anine; 8-methoxy-N-(3-(methylsulfonyl)-4-nitrophenyl)-2H-pyrazolo[3,4-c]quinolin-4-anine; 8-(methylthio)-N-(4-morpholinophenyl)-3H-pyrazolo[3,4-c]quinolin-4-amine; N-(3-(methylsulfonyl)phenyl)-8-(methylthio)-3H-pyrazolo[3,4-c]quinolin-4-amine; N-(3,4-dimethoxyphenyl)-8-(methylthio)-3H-pyrazolo[3,4-c]quinolin-4-amine; 1-(4-(4-((8-(methylthio)-3H-pyrazolo[3,4-c]quinolin-4-yl)amino)phenyl)piperazin-1-yl)ethan-1-one; 7-((8-(methylthio)-3H-pyrazolo[3,4-c]quinolin-4-yl)amino)-3,4-dihydroquinolin-2(1H)-one; N-(4-(((dimethylamino)methyl)phenyl)-8-(methylthio)-3H-pyrazolo[3,4-c]quinolin-4-amine; N-(2-methylisoindolin-5-yl)-8-(methylthio)-3H-pyrazolo[3,4-c]quinolin-4-amine; 6-fluoro-N-(4-morpholinophenyl)-3H-pyrazolo[3,4-c]quinolin-4-amine; 6-fluoro-N-(3-(methylsulfonyl)phenyl)-3H-pyrazolo[3,4-c]quinolin-4-amine; N-(3,4-dimethoxyphenyl)-6-fluoro-3H-pyrazolo[3,4-c]quinolin-4-amine; 1-(4-(4-((6-fluoro-3H-pyrazolo[3,4-c]quinolin-4-yl)amino)phenyl)piperazin-1-yl)ethan-1-one; 7-((6-fluoro-3H-pyrazolo[3,4-c]quinolin-4-yl)amino)-3,4-dihydroquinolin-2(1H)-one; 8-(methylsulfonyl)-N-(4-morpholinophenyl)-3H-pyrazolo[3,4-c]quinolin-4-amine; 8-methoxy-N-(2-(methylthio)-1H-benzo[d]imidazol-5-yl)-2H-pyrazolo[3,4-c]quinolin-4-amine; 9-methoxy-N-(4-(oxazol-5-yl)phenyl)-3H-pyrazolo[3,4-c]quinolin-4-amine; 9-methoxy-N-(4-(oxazol-2-yl)phenyl)-3H-pyrazolo[3,4-c]quinolin-4-amine; 9-methoxy-N-(4-(4-(methylsulfonyl)piperazin-1-yl)phenyl)-3H-pyrazolo[3,4-c]quinolin-4-amine; 4-(4-((9-methoxy-3H-pyrazolo[3,4-c]quinolin-4-yl)amino)phenyl)morpholin-3-one; (4-((9-methoxy-3H-pyrazolo[3,4-c]quinolin-4-yl)amino)phenyl)(pyrrolidin-1-yl)methanone; 1-(4-(4-((8-(methylsulfonyl)-3H-pyrazolo[3,4-c]quinolin-4-yl)amino)phenyl)piperazin-1-yl)ethan-1-one; N-(3,4-dimethoxyphenyl)-8-(methylsulfonyl)-3H-pyrazolo[3,4-c]quinolin-4-amine; (4-((8-(methylsulfonyl)-3H-pyrazolo[3,4-c]quinolin-4-yl)amino)phenyl)(morpholino)methanone; (4-methylpiperazin-1-yl)(4-((8-(methylsulfonyl)-3H-pyrazolo[3,4-c]quinolin-4-yl)amino)phenyl)methanone; 4-((8-(methylsulfonyl)-3H-pyrazolo[3,4-c]quinolin-4-yl)amino) benzamide; N-(4-(4-(4-methylpiperazin-1-yl)piperidin-1-yl)phenyl)-8-(methylsulfonyl)-3H-pyrazolo[3,4-c]quinolin-4-amine; 1-(4-((9-methoxy-3H-pyrazolo[3,4-c]quinolin-4-yl)amino)phenyl)pyrrolidin-2-one; (4-((9-methoxy-3H-pyrazolo[3,4-c]quinolin-4-yl)amino)phenyl)(4-methylpiperazin-1-yl)methanone; 8-cyclopropyl-N-(3,4-dimethoxyphenyl)-3H-pyrazolo[3,4-c]quinolin-4-amine; 5-((9-methoxy-3H-pyrazolo[3,4-c]quinolin-4-yl)amino)-2-morpholinobenzonitrile; N-(3,4-dimethoxyphenyl)-8-methyl-3H-pyrazolo[3,4-c]quinolin-4-amine; 1-(4-(4-((8-methyl-3H-pyrazolo[3,4-c]quinolin-4-yl)amino)phenyl) piperazin-1-yl)ethan-1-one; 8-methyl-N-(4-morpholinophenyl)-3H-pyrazolo[3,4-c]quinolin-4-amine; 8-methyl-N-(3-(methylsulfonyl)phenyl)-3H-pyrazolo[3,4-c]quinolin-4-amine; 3-(4-((8-(methylsulfonyl)-3H-pyrazolo[3,4-c]quinolin-4-yl)amino)phenyl)oxazolidin-2-one; 8-((8-(methylsulfonyl)-3H-pyrazolo[3,4-c]quinolin-4-yl)amino)-4,5-dihydro-1H-benzo[b]azepin-2(3H)-one; 8-(methylsulfonyl)-N-(3-(methylsulfonyl)phenyl)-3H-pyrazolo[3,4-c]quinolin-4-amine; 9-methoxy-N-(6-(4-methylpiperazin-1-yl)pyridin-3-yl)-3H-pyrazolo[3,4-c]quinolin-4-amine; N-(4-(4-(tert-butyl)piperazin-1-yl)phenyl)-8-(methylsulfonyl)-3H-pyrazolo[3,4-c]quinolin-4-amine; N-(6-(4-methylpiperazin-1-yl)pyridin-3-yl)-8-(methylsulfonyl)-3H-pyrazolo[3,4-c]quinolin-4-amine; N-cyclopropyl-8-methoxy-3H-pyrazolo[3,4-c]quinolin-4-amine; 8-methoxy-N-(1-methyl-1H-pyrazol-4-yl)-2H-pyrazolo[3,4-c]quinolin-4-amine; 5-(4-((8-methoxy-2H-pyrazolo[3,4-c]quinolin-4-yl)amino)phenyl)-1,3,4-oxadiazole-2-thiol; 8-methoxy-N-(1-(tetrahydro-2H-pyran-4-yl)-1H-pyrazol-4-yl)-2H-pyrazolo[3,4-c]quinolin-4-amine; 8-methoxy-N-(4-(4-morpholinopiperidin-1-yl)phenyl)-2H-pyrazolo[3,4-c]quinolin-4-amine; N5-(8-methoxy-2H-pyrazolo[3,4-c]quinolin-4-yl)-N2,N2-dimethylpyridine-2,5-diamine; 9-methyl-N-(3-(methylsulfonyl)phenyl)-3H-pyrazolo[3,4-c]quinolin-4-amine; 9-methyl-N-(4-morpholinophenyl)-3H-pyrazolo[3,4-c]quinolin-4-amine; 8-methoxy-N-(3-(methylsulfonyl)-4-morpholinophenyl)-2H-pyrazolo[3,4-c]quinolin-4-amine; 1-(4-(5-((8-methoxy-2H-pyrazolo[3,4-c]quinolin-4-yl)amino)pyridin-2-yl)piperazin-1-yl)ethan-1-one; 9-(methylsulfonyl)-N-(4-morpholinophenyl)-3H-pyrazolo[3,4-c]quinolin-4-amine; 1-(4-(4-((9-(methylsulfonyl)-3H-pyrazolo[3,4-c]quinolin-4-yl)amino) phenyl)piperazin-1-yl)ethan-1-one; (4-((9-(methylsulfonyl)-3H-pyrazolo[3,4-c]quinolin-4-yl)amino) phenyl)(morpholino)methanone; N-(4-(4-(tert-butyl) piperazin-1-yl)phenyl)-9-(methylsulfonyl)-3H-pyrazolo[3,4-c]quinolin-4-amine; 8-methoxy-N-(6-(4-(4-methylpiperazin-1-yl)piperidin-1-yl)pyridin-3-yl)-2H-pyrazolo[3,4-c]quinolin-4-amine; N-(4-(4-(4-methylpiperazin-1-yl)piperidin-1-yl)phenyl)-9-(methylsulfonyl)-3H-pyrazolo[3,4-c]quinolin-4-amine; 8-((9-(methylsulfonyl)-3H-pyrazolo[3,4-c]quinolin-4-yl)amino)-4,5-dihydro-1H-benzo[b]azepin-2(3H)-one; N-(3,4-dimethoxyphenyl)-9-(methylsulfonyl)-3H-pyrazolo[3,4-c]quinolin-4-amine; N-(6-(4-methylpiperazin-1-yl)pyridin-3-yl)-9-(methylsulfonyl)-3H-pyrazolo[3,4-c]quinolin-4-amine; 7-(methylsulfonyl)-N-(4-morpholinophenyl)-3H-pyrazolo[3,4-c]quinolin-4-amine; 9-methoxy-N-(1-(tetrahydro-2H-pyran-4-yl)-1H-pyrazol-4-yl)-3H-pyrazolo[3,4-c]quinolin-4-amine; 8-(methylsulfonyl)-N-(1-(tetrahydro-2H-pyran-4-yl)-1H-pyrazol-4-yl)-3H-pyrazolo[3,4-c]quinolin-4-amine; N-(1,5-dimethyl-1H-pyrazol-4-yl)-8-methoxy-2H-pyrazolo[3,4-c]quinolin-4-amine; N-(1,3-dimethyl-1H-pyrazol-4-yl)-8-methoxy-2H-pyrazolo[3,4-c]quinolin-4-amine; 2-((4-((9-(methylsulfonyl)-3H-pyrazolo[3,4-c]quinolin-4-yl)amino)phenyl)amino)ethan-1-ol; 9-(methylsulfonyl)-N-(3-(methylsulfonyl)phenyl)-3H-pyrazolo[3,4-c]quinolin-4-amine; 9-(methylsulfonyl)-N-(1-(tetrahydro-2H-pyran-4-yl)-1H-pyrazol-4-yl)-3H-pyrazolo[3,4-c]quinolin-4-amine; 8-methoxy-N-(1-(2-methoxyethyl)-1H-pyrazol-4-yl)-2H-pyrazolo[3,4-c]quinolin-4-amine; 8-methoxy-N-(1-(methylsulfonyl)-1H-pyrazol-4-yl)-2H-pyrazolo[3,4-c]quinolin-4-amine; 8-methoxy-N-(1-(1-methylpiperidin-4-yl)-1H-pyrazol-4-yl)-2H-pyrazolo[3,4-c]quinolin-4-amine; 1-(4-(4-((8-methoxy-2H-pyrazolo[3,4-c]quinolin-4-yl)amino)-1H-pyrazol-1-yl)piperidin-1-yl)ethan-1-one; N-(1-(2-methoxyethyl)-1H-pyrazol-4-yl)-8-(methylsulfonyl)-3H-pyrazolo[3,4-c]quinolin-4-amine; N-(1-(1-methylpiperidin-4-yl)-1H-pyrazol-4-yl)-8-(methylsulfonyl)-3H-pyrazolo[3,4-c]quinolin-4-amine; 1-(4-(4-((8-(methylsulfonyl)-3H-pyrazolo[3,4-c]quinolin-4-yl)amino)-1H-pyrazol-1-yl) piperidin-1-yl)ethan-1-one; 9-methoxy-N-(1-(2-methoxyethyl)-1H-pyrazol-4-yl)-2H-pyrazolo[3,4-c] quinolin-4-amine; 1-(4-(4-((9-methoxy-3H-pyrazolo[3,4-c]quinolin-4-yl)amino)-1H-pyrazol-1-yl)piperidin-1-yl)ethan-1-one; 9-methoxy-N-(1-(1-methylpiperidin-4-yl)-1H-pyrazol-4-yl)-3H-pyrazolo[3,4-c]quinolin-4-amine; 8-((7-(methylsulfonyl)-3H-pyrazolo[3,4-c]quinolin-4-yl)amino)-4,5-dihydro-1H-benzo[b]azepin-2(3H)-one; 7-(methylsulfonyl)-N-(1-(tetrahydro-2H-pyran-4-yl)-1H-pyrazol-4-yl)-3H-pyrazolo[3,4-c]quinolin-4-amine; 8-methoxy-N-(1-methyl-1H-1,2,3-triazol-4-yl)-2H-pyrazolo[3,4-c]quinolin-4-amine; 8-methoxy-N-(2-methyl-2H-1,2,3-triazol-4-yl)-2H-pyrazolo[3,4-c]quinolin-4-amine; 8-methoxy-N-(1-methyl-1H-pyrazol-3-yl)-2H-pyrazolo[3,4-c]quinolin-4-amine.

Moreover especially preferred are compounds of formula (I) that are selected from:

5-(4-((8-methoxy-2H-pyrazolo[3,4-c]quinolin-4-yl) amino)phenyl)-1,3,4-oxadiazole-2-thiol; 8-methoxy-N-(1-(tetrahydro-2H-pyran-4-yl)-1H-pyrazol-4-yl)-2H-pyrazolo[3,4-c]quinolin-4-amine; 8-methoxy-N-(4-(4-morpholinopiperidin-1-yl)phenyl)-2H-pyrazolo[3,4-c] quinolin-4-amine; N5-(8-methoxy-2H-pyrazolo[3,4-c]quinolin-4-yl)-N2,N2-dimethylpyridine-2,5-diamine; 9-methyl-N-(3-(methylsulfonyl)phenyl)-3H-pyrazolo[3,4-c]quinolin-4-amine; 9-methyl-N-(4-morpholinophenyl)-3H-pyrazolo[3,4-c]quinolin-4-amine; 8-methoxy-N-(3-(methylsulfonyl)-4-morpholinophenyl)-2H-pyrazolo[3,4-c]quinolin-4-amine; 1-(4-(5-((8-methoxy-2H-pyrazolo[3,4-c]quinolin-4-yl)amino)pyridin-2-yl)piperazin-1-yl)ethan-1-one; 9-(methylsulfonyl)-N-(4-morpholinophenyl)-3H-pyrazolo[3,4-c]quinolin-4-amine; 1-(4-(4-((9-(methylsulfonyl)-3H-pyrazolo[3,4-c]quinolin-4-yl)amino) phenyl)piperazin-1-yl)ethan-1-one; (4-((9-(methylsulfonyl)-3H-pyrazolo[3,4-c]quinolin-4-yl)amino) phenyl)(morpholino)methanone; N-(4-(4-(tert-butyl) piperazin-1-yl)phenyl)-9-(methylsulfonyl)-3H-pyrazolo[3,4-c]quinolin-4-amine; 8-methoxy-N-(6-(4-(4-methylpiperazin-1-yl)piperidin-1-yl)pyridin-3-yl)-2H-pyrazolo[3,4-c]quinolin-4-amine; N-(4-(4-(4-methylpiperazin-1-yl)piperidin-1-yl)phenyl)-9-(methylsulfonyl)-3H-pyrazolo[3,4-c]quinolin-4-amine; 8-((9-(methylsulfonyl)-3H-pyrazolo[3,4-c]quinolin-4-yl) amino)-4,5-dihydro-1H-benzo[b]azepin-2(3H)-one; N-(3,4-dimethoxyphenyl)-9-(methylsulfonyl)-3H-pyrazolo[3,4-c]

quinolin-4-amine; N-(6-(4-methylpiperazin-1-yl)pyridin-3-yl)-9-(methylsulfonyl)-3H-pyrazolo[3,4-c]quinolin-4-amine; 7-(methylsulfonyl)-N-(4-morpholinophenyl)-3H-pyrazolo[3,4-c]quinolin-4-amine; 9-methoxy-N-(1-(tetrahydro-2H-pyran-4-yl)-1H-pyrazol-4-yl)-3H-pyrazolo[3,4-c]quinolin-4-amine; 8-(methylsulfonyl)-N-(1-(tetrahydro-2H-pyran-4-yl)-1H-pyrazol-4-yl)-3H-pyrazolo[3,4-c]quinolin-4-amine; N-(1,5-dimethyl-1H-pyrazol-4-yl)-8-methoxy-2H-pyrazolo[3,4-c]quinolin-4-amine; N-(1,3-dimethyl-1H-pyrazol-4-yl)-8-methoxy-2H-pyrazolo[3,4-c]quinolin-4-amine; 2-((4-((9-(methylsulfonyl)-3H-pyrazolo[3,4-c]quinolin-4-yl)amino)phenyl)amino)ethan-1-ol; 9-(methylsulfonyl)-N-(3-(methylsulfonyl)phenyl)-3H-pyrazolo[3,4-c]quinolin-4-amine; 9-(methylsulfonyl)-N-(1-(tetrahydro-2H-pyran-4-yl)-1H-pyrazol-4-yl)-3H-pyrazolo[3,4-c]quinolin-4-amine; 8-methoxy-N-(1-(2-methoxyethyl)-1H-pyrazol-4-yl)-2H-pyrazolo[3,4-c]quinolin-4-amine; 8-methoxy-N-(1-(methylsulfonyl)-1H-pyrazol-4-yl)-2H-pyrazolo[3,4-c]quinolin-4-amine; 8-methoxy-N-(1-(1-methylpiperidin-4-yl)-1H-pyrazol-4-yl)-2H-pyrazolo[3,4-c]quinolin-4-amine; 1-(4-(4-((8-methoxy-2H-pyrazolo[3,4-c]quinolin-4-yl)amino)-1H-pyrazol-1-yl)piperidin-1-yl)ethan-1-one; N-(1-(2-methoxyethyl)-1H-pyrazol-4-yl)-8-(methylsulfonyl)-3H-pyrazolo[3,4-c]quinolin-4-amine; N-(1-(1-methylpiperidin-4-yl)-1H-pyrazol-4-yl)-8-(methylsulfonyl)-3H-pyrazolo[3,4-c]quinolin-4-anine; 1-(4-(4-((8-(methylsulfonyl)-3H-pyrazolo[3,4-c]quinolin-4-yl)amino)-1H-pyrazol-1-yl)piperidin-1-yl)ethan-1-one; 9-methoxy-N-(1-(2-methoxyethyl)-1H-pyrazol-4-yl)-2H-pyrazolo[3,4-c]quinolin-4-amine; 1-(4-(4-((9-methoxy-3H-pyrazolo[3,4-c]quinolin-4-yl)amino)-1H-pyrazol-1-yl)piperidin-1-yl)ethan-1-one; 9-methoxy-N-(1-(1-methylpiperidin-4-yl)-1H-pyrazol-4-yl)-3H-pyrazolo[3,4-c]quinolin-4-amine; 8-((7-(methylsulfonyl)-3H-pyrazolo[3,4-c]quinolin-4-yl)amino)-4,5-dihydro-1H-benzo[b]azepin-2(3H)-one; 7-(methylsulfonyl)-N-(1-(tetrahydro-2H-pyran-4-yl)-1H-pyrazol-4-yl)-3H-pyrazolo[3,4-c]quinolin-4-amine; 8-methoxy-N-(1-methyl-1H-1,2,3-triazol-4-yl)-2H-pyrazolo[3,4-c]quinolin-4-amine; 8-methoxy-N-(2-methyl-2H-1,2,3-triazol-4-yl)-2H-pyrazolo[3,4-c]quinolin-4-amine; 8-methoxy-N-(1-methyl-1H-pyrazol-3-yl)-2H-pyrazolo[3,4-c]quinolin-4-amine; 2-(4-((8-methoxy-2H-pyrazolo[3,4-c]quinolin-4-yl)amino)-1H-pyrazol-1-yl)-2-methylpropanamide; 8-methoxy-N-(2-methyl-2H-tetrazol-5-yl)-2H-pyrazolo[3,4-c]quinolin-4-amine; 8-methoxy-N-(1-methyl-1H-imidazol-4-yl)-2H-pyrazolo[3,4-c]quinolin-4-amine; N-(1-(1-methylpiperidin-4-yl)-1H-pyrazol-4-yl)-7-(methylsulfonyl)-3H-pyrazolo[3,4-c]quinolin-4-amine; 1-(4-(4-((7-(methylsulfonyl)-3H-pyrazolo[3,4-c]quinolin-4-yl)amino)-1H-pyrazol-1-yl)piperidin-1-yl)ethan-1-one; 7-(methylsulfonyl)-N-(1-(tetrahydro-2H-pyran-4-yl)-1H-pyrazol-4-yl)-3H-pyrazolo[3,4-c]quinolin-4-amine; N-(1-(2-methoxyethyl)-1H-pyrazol-4-yl)-7-(methylsulfonyl)-3H-pyrazolo[3,4-c]quinolin-4-amine; N-(1-(2-methoxyethyl)-1H-pyrazol-4-yl)-7-(methylthio)-3H-pyrazolo[3,4-c]quinolin-4-amine; 2-methyl-2-(4-((8-(methylsulfonyl)-3H-pyrazolo[3,4-c]quinolin-4-yl)amino)-1H-pyrazol-1-yl)propanenitrile; 8-(methylsulfonyl)-N-(1-(oxetan-3-yl)-1H-pyrazol-4-yl)-3H-pyrazolo[3,4-c]quinolin-4-amine; (2-fluoro-4-((7-(methylsulfonyl)-3H-pyrazolo[3,4-c]quinolin-4-yl)amino)phenyl)(morpholino)methanone; (2-fluoro-4-((8-(methylsulfonyl)-3H-pyrazolo[3,4-c]quinolin-4-yl)amino)phenyl)(morpholino)methanone; 4-((8-methoxy-2H-pyrazolo[3,4-c]quinolin-4-yl)amino)pyridin-2(1H)-one; 4-((8-methoxy-2H-pyrazolo[3,4-c]quinolin-4-yl)amino)-1-methylpyridin-2(1H)-one; N-(1-(3-methoxypropyl)-1H-pyrazol-4-yl)-8-(methylsulfonyl)-3H-pyrazolo[3,4-c]quinolin-4-amine; 1-(4-((8-(methylsulfonyl)-3H-pyrazolo[3,4-c]quinolin-4-yl)amino)-1H-pyrazol-1-yl)cyclohexanecarbonitrile; N-(1-isopropyl-1H-pyrazol-4-yl)-8-(methylsulfonyl)-3H-pyrazolo[3,4-c]quinolin-4-amine; N-(1-(tert-butyl)-1H-pyrazol-4-yl)-9-methoxy-3H-pyrazolo[3,4-c]quinolin-4-amine; N-(1-isopropyl-1H-pyrazol-4-yl)-9-methoxy-3H-pyrazolo[3,4-c]quinolin-4-amine; 9-methoxy-N-(1-(3-methoxypropyl)-1H-pyrazol-4-yl)-3H-pyrazolo[3,4-c]quinolin-4-amine; 2-(4-((9-methoxy-3H-pyrazolo[3,4-c]quinolin-4-yl)amino)-1H-pyrazol-1-yl)-2-methylpropanenitrile; 1-(4-((9-methoxy-3H-pyrazolo[3,4-c]quinolin-4-yl)amino)-1H-pyrazol-1-yl)cyclohexanecarbonitrile; 2-(4-((8-(methylsulfonyl)-3H-pyrazolo[3,4-c]quinolin-4-yl)amino)-1H-pyrazol-1-yl)ethan-1-ol; N-(1-isobutyl-1H-pyrazol-4-yl)-8-(methylsulfonyl)-3H-pyrazolo[3,4-c]quinolin-4-amine; N-(1-(tert-butyl)-1H-pyrazol-4-yl)-7-(methylsulfonyl)-3H-pyrazolo[3,4-c]quinolin-4-amine; N-(1-isopropyl-1H-pyrazol-4-yl)-7-(methylsulfonyl)-3H-pyrazolo[3,4-c]quinolin-4-amine; N-(1-(3-methoxypropyl)-1H-pyrazol-4-yl)-7-(methylsulfonyl)-3H-pyrazolo[3,4-c]quinolin-4-amine; 2-methyl-2-(4-((7-(methylsulfonyl)-3H-pyrazolo[3,4-c]quinolin-4-yl)amino)-1H-pyrazol-1-yl)propanenitrile; N-(1-isobutyl-1H-pyrazol-4-yl)-7-(methylsulfonyl)-3H-pyrazolo[3,4-c]quinolin-4-amine; 2-(4-((7-(methylsulfonyl)-3H-pyrazolo[3,4-c]quinolin-4-yl)amino)-1H-pyrazol-1-yl)ethan-1-ol; (3-methoxy-4-((7-(methylsulfonyl)-3H-pyrazolo[3,4-c]quinolin-4-yl)amino)phenyl)(morpholino)methanone; N-(1-(tert-butyl)-1H-pyrazol-4-yl)-8-(methylsulfonyl)-3H-pyrazolo[3,4-c]quinolin-4-amine; (3-methoxy-4-((8-(methylsulfonyl)-3H-pyrazolo[3,4-c]quinolin-4-yl)amino)phenyl)(morpholino)methanone; N-(1-cyclopropyl-1H-pyrazol-4-yl)-7-(methylsulfonyl)-3H-pyrazolo[3,4-c]quinolin-4-amine; N-(1-isobutyl-1H-pyrazol-4-yl)-9-methoxy-3H-pyrazolo[3,4-c]quinolin-4-amine; 2-(4-((9-methoxy-3H-pyrazolo[3,4-c]quinolin-4-yl)amino)-1H-pyrazol-1H-yl)ethan-1-ol; (3-methoxy-4-((9-methoxy-3H-pyrazolo[3,4-c]quinolin-4-yl)amino)phenyl)(morpholino)methanone; N-(1-cyclopropyl-1H-pyrazol-4-yl)-9-methoxy-3H-pyrazolo[3,4-c]quinolin-4-amine; 1-methyl-3-((8-(methylsulfonyl)-3H-pyrazolo[3,4-c]quinolin-4-yl)amino)pyridin-2(1H)-one; N-(1-cyclopropyl-1H-pyrazol-4-yl)-8-(methylsulfonyl)-3H-pyrazolo[3,4-c]quinolin-4-amine; 9-methoxy-N-(1-(1-methoxy-2-methylpropan-2-yl)-1H-pyrazol-4-yl)-3H-pyrazolo[3,4-c]quinolin-4-amine; 9-methoxy-N-(1-(2-methoxyethyl)-3-methyl-1H-pyrazol-4-yl)-3H-pyrazolo[3,4-c]quinolin-4-amine; N-(1-(1-(tert-butyl)piperidin-4-yl)-1H-pyrazol-4-yl)-9-methoxy-3H-pyrazolo[3,4-c]quinolin-4-amine; 9-methoxy-N-(3-methyl-1-(tetrahydro-2H-pyran-4-yl)-1H-pyrazol-4-yl)-3H-pyrazolo[3,4-c]quinolin-4-amine; N-(1-(1-methoxy-2-methylpropan-2-yl)-1H-pyrazol-4-yl)-8-(methylsulfonyl)-3H-pyrazolo[3,4-c]quinolin-4-amine; N-(1-(2-methoxyethyl)-3-methyl-1H-pyrazol-4-yl)-8-(methylsulfonyl)-3H-pyrazolo[3,4-c]quinolin-4-amine; N-(1-(2-methoxyethyl)-5-methyl-1H-pyrazol-4-yl)-8-(methylsulfonyl)-3H-pyrazolo[3,4-c]quinolin-4-amine; N-(1-(1-(tert-butyl)piperidin-4-yl)-1H-pyrazol-4-yl)-8-(methylsulfonyl)-3H-pyrazolo[3,4-c]quinolin-4-amine; N-(1-(tert-butyl)-1H-pyrazol-3-yl)-8-(methylsulfonyl)-3H-pyrazolo[3,4-c]quinolin-4-amine; N-(1-isopropyl-3-methyl-1H-pyrazol-4-yl)-8-(methylsulfonyl)-3H-pyrazolo[3,4-c]quinolin-4-amine; N-(1-isopropyl-5-methyl-1H-pyrazol-4-yl)-8-(methylsulfonyl)-3H-pyrazolo[3,4-c]quinolin-4-amine; N-(5-methyl-1-(tetrahydro-2H-pyran-4-yl)-1H-pyrazol-4-yl)-8-(methylsulfonyl)-3H-pyrazolo[3,4-c]

quinolin-4-amine; N-(3-methyl-1-(tetrahydro-2H-pyran-4-yl)-1H-pyrazol-4-yl)-8-(methylsulfonyl)-3H-pyrazolo[3,4-c]quinolin-4-amine; N-(1-isopropyl-3-methyl-1H-pyrazol-4-yl)-8-(methylsulfonyl)-3H-pyrazolo[3,4-c]quinolin-4-amine; N-(1-isopropyl-5-methyl-1H-pyrazol-4-yl)-8-(methylsulfonyl)-3H-pyrazolo[3,4-c]quinolin-4-amine; N-(1-isopropyl-5-methyl-1H-pyrazol-4-yl)-9-methoxy-3H-pyrazolo[3,4-c]quinolin-4-amine; N-(1-isopropyl-3-methyl-1H-pyrazol-4-yl)-9-methoxy-3H-pyrazolo[3,4-c]quinolin-4-amine; N-(1-(2-fluoroethyl)-1H-pyrazol-4-yl)-8-(methylsulfonyl)-3H-pyrazolo[3,4-c]quinolin-4-amine; N-(1-isopropyl-3-methyl-1H-pyrazol-4-yl)-9-methoxy-3H-pyrazolo[3,4-c]quinolin-4-amine; N-(1-isopropyl-5-methyl-1H-pyrazol-4-yl)-9-methoxy-3H-pyrazolo[3,4-c]quinolin-4-amine; N-(1-isopropyl-3-methoxy-1H-pyrazol-4-yl)-9-methoxy-3H-pyrazolo[3,4-c]quinolin-4-amine; N-(1-(1-(tert-butyl)piperidin-4-yl)-3-methoxy-1H-pyrazol-4-yl)-9-methoxy-3H-pyrazolo[3,4-c]quinolin-4-amine; N-(1-isopropyl-3-methoxy-1H-pyrazol-4-yl)-8-(methylsulfonyl)-3H-pyrazolo[3,4-c]quinolin-4-amine; N-(1-isopropyl-5-methoxy-1H-pyrazol-4-yl)-8-(methylsulfonyl)-3H-pyrazolo[3,4-c]quinolin-4-amine; N-(1-(1-(tert-butyl)piperidin-4-yl)-3-methoxy-1H-pyrazol-4-yl)-8-(methylsulfonyl)-3H-pyrazolo[3,4-c]quinolin-4-amine; N-(1-(1-(tert-butyl)piperidin-4-yl)-5-methoxy-1H-pyrazol-4-yl)-8-(methylsulfonyl)-3H-pyrazolo[3,4-c]quinolin-4-amine; N-(2-chloro-5-(methylsulfonyl)thiophen-3-yl)-8-(methylsulfonyl)-3H-pyrazolo[3,4-c]quinolin-4-amine; N-(3-methoxy-1-(3-methoxypropyl)-1H-pyrazol-4-yl)-8-(methylsulfonyl)-3H-pyrazolo[3,4-c]quinolin-4-amine; N-(5-methoxy-1-(3-methoxypropyl)-1H-pyrazol-4-yl)-8-(methylsulfonyl)-3H-pyrazolo[3,4-c]quinolin-4-amine; N-(5-chloro-1-isopropyl-1H-pyrazol-4-yl)-8-(methylsulfonyl)-3H-pyrazolo[3,4-c]quinolin-4-amine; N-(1-isopropyl-3,5-dimethyl-1H-pyrazol-4-yl)-9-methoxy-3H-pyrazolo[3,4-c]quinolin-4-amine; N-(5-chloro-1-(3-methoxypropyl)-1H-pyrazol-4-yl)-9-methoxy-3H-pyrazolo[3,4-c]quinolin-4-amine; 9-methoxy-N-(1-(piperidin-4-yl)-1H-pyrazol-4-yl)-3H-pyrazolo[3,4-c]quinolin-4-amine; N-(5-chloro-1-(3-methoxypropyl)-1H-pyrazol-4-yl)-8-(methylsulfonyl)-3H-pyrazolo[3,4-c]quinolin-4-amine; N-(1-isopropyl-3,5-dimethyl-1H-pyrazol-4-yl)-8-(methylsulfonyl)-3H-pyrazolo[3,4-c]quinolin-4-amine; N-(3-cyclopropyl-1-methyl-1H-pyrazol-5-yl)-8-(methylsulfonyl)-3H-pyrazolo[3,4-c]quinolin-4-amine; 3-(3-methoxy-4-((8-(methylsulfonyl)-3H-pyrazolo[3,4-c]quinolin-4-yl)amino)phenyl)oxazolidin-2-one; N-(5-chloro-1-(2-methoxyethyl)-1H-pyrazol-4-yl)-9-methoxy-3H-pyrazolo[3,4-c]quinolin-4-amine; N-(5-chloro-1-(2-methoxyethyl)-1H-pyrazol-4-yl)-8-(methylsulfonyl)-3H-pyrazolo[3,4-c]quinolin-4-amine; N-(5-chloro-1-(2-methoxyethyl)-1H-pyrazol-4-yl)-7-(methylsulfonyl)-3H-pyrazolo[3,4-c]quinolin-4-amine; N-(1-isopropyl-5-methyl-1H-pyrazol-4-yl)-7-(methylsulfonyl)-3H-pyrazolo[3,4-c]quinolin-4-amine; 6-((9-methoxy-3H-pyrazolo[3,4-c]quinolin-4-yl)amino)-1,3-dimethylpyrimidine-2,4(1H,3H)-dione; 1-isopropyl-4-((8-(methylsulfonyl)-3H-pyrazolo[3,4-c]quinolin-4-yl)amino)-1H-pyrazole-3-carbonitrile; 1-isopropyl-4-((8-(methylsulfonyl)-3H-pyrazolo[3,4-c]quinolin-4-yl)amino)-1H-pyrazole-5-carbonitrile; 1-(2-methoxyethyl)-4-((8-(methylsulfonyl)-3H-pyrazolo[3,4-c]quinolin-4-yl)amino)-1H-pyrazole-3-carbonitrile; 1-(2-methoxyethyl)-4-((8-(methylsulfonyl)-3H-pyrazolo[3,4-c]quinolin-4-yl)amino)-1H-pyrazole-5-carbonitrile; 1-isopropyl-4-((8-(methylsulfonyl)-3H-pyrazolo[3,4-c]quinolin-4-yl)amino)-1H-pyrazole-3-carboxamide; 1-isopropyl-4-((8-(methylsulfonyl)-3H-pyrazolo[3,4-c]quinolin-4-yl)amino)-1H-pyrazole-5-carboxamide; 1,3-dimethyl-6-((8-(methylsulfonyl)-3H-pyrazolo[3,4-c]quinolin-4-yl)amino)pyrimidine-2,4(1H,3H)-dione; N-(1-(2-fluoroethyl)-1H-pyrazol-4-yl)-9-methoxy-3H-pyrazolo[3,4-c]quinolin-4-amine; N-(5-chloro-1-(piperidin-4-yl)-1H-pyrazol-4-yl)-9-methoxy-3H-pyrazolo[3,4-c]quinolin-4-amine; N-(5-chloro-1-(tetrahydro-2H-pyran-4-yl)-1H-pyrazol-4-yl)-9-methoxy-3H-pyrazolo[3,4-c]quinolin-4-amine; 1-(4-((9-methoxy-3H-pyrazolo[3,4-c]quinolin-4-yl)amino)-1H-pyrazol-1-yl)-2-methylpropan-2-ol; 9-methoxy-N-(1-(2,2,2-trifluoroethyl)-1H-pyrazol-4-yl)-3H-pyrazolo[3,4-c]quinolin-4-amine; 9-methoxy-N-(1-(2-methylallyl)-1H-pyrazol-4-yl)-3H-pyrazolo[3,4-c]quinolin-4-amine; 9-methoxy-N-(1-(2-methylprop-1-en-1-YL)-1H-pyrazol-4-yl)-H-pyrazolo[3,4-c]quinolin-4-amine; N-(1,2-dimethyl-1H-imidazol-5-yl)-8-(methylsulfonyl)-3H-pyrazolo[3,4-c]quinolin-4-amine; 8-(methylsulfonyl)-N-(1-(2,2,2-trifluoroethyl)-1H-pyrazol-4-yl)-3H-pyrazolo[3,4-c]quinolin-4-amine; 2-methyl-1-(4-((8-(methylsulfonyl)-3H-pyrazolo[3,4-c]quinolin-4-yl)amino)-1H-pyrazol-1-yl)propan-2-ol; N-(1-(2-methylprop-1-en-1-yl)-1H-pyrazol-4-yl)-8-(methylsulfonyl)-3H-pyrazolo[3,4-c]quinolin-4-amine; N-(1-(2-methylallyl)-1H-pyrazol-4-yl)-8-(methylsulfonyl)-3H-pyrazolo[3,4-c]quinolin-4-amine; N-(5-chloro-1-(tetrahydro-2H-pyran-4-yl)-1H-pyrazol-4-yl)-8-(methylsulfonyl)-3H-pyrazolo[3,4-c]quinolin-4-amine; 1-isopropyl-4-((9-methoxy-3H-pyrazolo[3,4-c]quinolin-4-yl)amino)-1H-pyrazole-5-carboxamide; 9-methoxy-N-(1-(2-methoxyethyl)-3-(trifluoromethyl)-1H-pyrazol-4-yl)-3H-pyrazolo[3,4-c]quinolin-4-amine; 9-methoxy-N-(1-(2-methoxyethyl)-5-(trifluoromethyl)-1H-pyrazol-4-yl)-3H-pyrazolo[3,4-c]quinolin-4-amine; N-(1-(2-fluoroethyl)-3-methyl-1H-pyrazol-4-yl)-8-(methylsulfonyl)-3H-pyrazolo[3,4-c]quinolin-4-amine; N-(1-(2-fluoroethyl)-5-methyl-1H-pyrazol-4-yl)-8-(methylsulfonyl)-3H-pyrazolo[3,4-c]quinolin-4-amine; N-(1-(2-methoxyethyl)-3-(trifluoromethyl)-1H-pyrazol-4-yl)-8-(methylsulfonyl)-3H-pyrazolo[3,4-c]quinolin-4-amine; N-(1-(2-methoxyethyl)-5-(trifluoromethyl)-1H-pyrazol-4-yl)-8-(methylsulfonyl)-3H-pyrazolo[3,4-c]quinolin-4-amine; 1-(2-methoxyethyl)-4-((8-(methylsulfonyl)-3H-pyrazolo[3,4-c]quinolin-4-yl)amino)-1H-pyrazole-5-carbonitrile; 1-(2-methoxyethyl)-4-((8-(methylsulfonyl)-3H-pyrazolo[3,4-c]quinolin-4-yl)amino)-1H-pyrazole-3-carbonitrile; N-(5-bromo-1-(2-methoxyethyl)-1H-pyrazol-4-yl)-9-methoxy-3H-pyrazolo[3,4-c]quinolin-4-amine; N-(5-fluoro-1-(2-methoxyethyl)-1H-pyrazol-4-yl)-9-methoxy-3H-pyrazolo[3,4-c]quinolin-4-amine; N4-(9-methoxy-3H-pyrazolo[3,4-c]quinolin-4-yl)-1-(2-methoxyethyl)-N5,N5-dimethyl-1H-pyrazole-4,5-diamine; N-(2-isopropyl-1-methyl-1H-imidazol-5-yl)-9-methoxy-3H-pyrazolo[3,4-c]quinolin-4-amine; N-(5-bromo-1-(2-methoxyethyl)-1H-pyrazol-4-yl)-8-(methylsulfonyl)-3H-pyrazolo[3,4-c]quinolin-4-amine; 1-(2-meth oxyethyl)-N5,N5-dim ethyl-N4-(8-(methylsulfonyl)-3H-pyrazolo[3,4-c]quinolin-4-yl)-1H-pyrazole-4,5-diamine; N-(5-methyl-1-(tetrahydro-2H-pyran-4-yl)-1H-pyrazol-4-yl)-8-(methylsulfonyl)-3H-pyrazolo[3,4-c]quinolin-4-amine; N-(1-(2-methoxyethyl)-5-methyl-1H-pyrazol-4-yl)-8-(methylsulfonyl)-3H-pyrazolo[3,4-c]quinolin-4-amine; N-(2-methyl-3-morpholinophenyl)-8-(methylsulfonyl)-3H-pyrazolo[3,4-c]quinolin-4-amine; N-(2-isopropyl-1-methyl-1H-imidazol-5-yl)-8-(methylsulfonyl)-3H-pyrazolo[3,4-c]quinolin-4-amine; N-(1-isobutyl-1H-pyrazol-4-yl)-8-methoxy-3H-pyrazolo[3,4-c]quinolin-4-amine; N-(1-(tert-butyl)-1H-pyrazol-4-yl)-8-methoxy-3H-pyrazolo[3,4-c]quinolin-4-amine; 8-methoxy-N-(1-(3-methoxypropyl)-1H-pyrazol-4-yl)-3H-pyrazolo[3,4-c]quinolin-4-amine; 6,8- dimethoxy-N-(4-morpholinophenyl)-3H-pyrazolo[3,4-c]quinolin-4-amine; 6,8-dimethoxy-N-(1-(tetrahydro-2H-pyran-4-yl)-1H-pyrazol-4-yl)-3H-pyrazolo[3,4-c]quinolin-4-amine; 6,8-dimethoxy-N-(1-(3-methoxypropyl)-1H-pyrazol-4-yl)-3H-pyrazolo[3,4-c]quinolin-4-amine; N-(1-(2-fluoroethyl)-1H-pyrazol-4-yl)-8-methoxy-3H-pyrazolo[3,4-c]quinolin-4-amine; N-(1-isopropyl-1H-pyrazol-4-yl)-8-methoxy-3H-pyrazolo[3,4-c]quinolin-4-amine; N-(1-cyclopropyl-1H-pyrazol-4-yl)-8-methoxy-3H-pyrazolo[3,4-c]quinolin-4-amine; N-(1-isopropyl-1H-pyrazol-4-yl)-6,8-dimethoxy-3H-pyrazolo[3,4-c]quinolin-4-amine; N-(1-(1-(tert-butyl)piperidin-4-yl)-1H-pyrazol-4-yl)-6,8-dimethoxy-3H-pyrazolo[3,4-c]quinolin-4-amine; 1-(4-((8-methoxy-3H-pyrazolo[3,4-c]quinolin-4-yl)amino)phenyl)piperidin-4-ol; 2-(4-(4-((8-methoxy-3H-pyrazolo[3,4-c]quinolin-4-yl)amino)phenyl)piperazin-1-yl)ethan-1-ol; 1-(4-((8-methoxy-3H-pyrazolo[3,4-c]quinolin-4-yl)amino)-1H-pyrazol-1-yl)-2-methylpropan-2-ol; N-(1-(tert-butyl)-1H-pyrazol-4-yl)-8-methoxy-3H-pyrazolo[3,4-c]quinolin-4-anine; N-(1-(1-(tert-butyl)piperidin-4-yl)-1H-pyrazol-4-yl)-8-methoxy-3H-pyrazolo[3,4-c]quinolin-4-amine; 2-(4-((8-methoxy-3H-pyrazolo[3,4-c]quinolin-4-yl)amino)-1H-pyrazol-1-yl)-2-methylpropanenitrile; N-(3,4-dimethoxyphenyl)-7-(methylsulfonyl)-3H-pyrazolo[3,4-c]quinolin-4-amine; 2-(4-(4-((7-(methylsulfonyl)-3H-pyrazolo[3,4-c]quinolin-4-yl)amino)phenyl)piperazin-1-yl)ethan-1-ol; 6-methoxy-N-(4-morpholinophenyl)-3H-pyrazolo[3,4-c]quinolin-4-amine; N-(1-isopropyl-1H-pyrazol-4-yl)-6-methoxy-3H-pyrazolo[3,4-c]quinolin-4-amine; 6-methoxy-N-(1-(3-methoxypropyl)-1H-pyrazol-4-yl)-3H-pyrazolo[3,4-c]quinolin-4-amine; 6-methoxy-N-(1-(tetrahydro-2H-pyran-4-yl)-1H-pyrazol-4-yl)-3H-pyrazolo[3,4-c]quinolin-4-amine; (4-((6,8-dimethoxy-3H-pyrazolo[3,4-c]quinolin-4-yl)amino)phenyl)(morpholino)methanone; 2-(4-(4-((8-(methylsulfonyl)-3H-pyrazolo[3,4-c]quinolin-4-yl)amino)phenyl)piperazin-1-yl)ethan-1-ol; N-(1-(1-(tert-butyl)piperidin-4-yl)-1H-pyrazol-4-yl)-8-(methylsulfonyl)-3H-pyrazolo[3,4-c]quinolin-4-amine; 2-(4-((8-methoxy-2H-pyrazolo[3,4-c]quinolin-4-yl)amino)-1H-pyrazol-1-yl)-N,N-dimethylacetamide; 8-methoxy-N-(1-(pyrrolidin-3-yl)-1H-pyrazol-4-yl)-2H-pyrazolo[3,4-c]quinolin-4-amine; N-(1-(1,3-dimethoxypropan-2-yl)-1H-pyrazol-4-yl)-8-methoxy-2H-pyrazolo[3,4-c]quinolin-4-amine; 8-methoxy-N-(1-(tetrahydro-2H-pyran-3-yl)-1H-pyrazol-4-yl)-2H-pyrazolo[3,4-c]quinolin-4-amine; N-(1-(2-methoxy-2-methylpropyl)-1H-pyrazol-4-yl)-8-(methylsulfonyl)-3H-pyrazolo[3,4-c]quinolin-4-amine; 1-(4-((8-(methylsulfonyl)-3H-pyrazolo[3,4-c]quinolin-4-yl)amino)phenyl)piperidin-4-ol; 2-methyl-1-(4-((8-(methylsulfonyl)-3H-pyrazolo[3,4-c]quinolin-4-yl)amino)-1H-pyrazol-1-yl)propan-2-ol; 4-ethyl-6-((8-methoxy-2H-pyrazolo[3,4-c]quinolin-4-yl)amino)-2H-benzo[b][1,4]oxazin-3(4H)-one; 8-methoxy-N-(1-(pyridin-2-yl)-1H-pyrazol-4-yl)-2H-pyrazolo[3,4-c]quinolin-4-amine; 8-methoxy-N-(1-(1-phenylethyl)-1H-pyrazol-4-yl)-2H-pyrazolo[3,4-c]quinolin-4-amine; 8-methoxy-N-(1-(3-methylbutan-2-yl)-1H-pyrazol-4-yl)-2H-pyrazolo[3,4-c]quinolin-4-amine; 6-((8-methoxy-2H-pyrazolo[3,4-c]quinolin-4-yl)amino)-4-methyl-2H-benzo[b][1,4]oxazin-3(4H)-one; 8-(methyl sulfonyl)-N-(1-(tetrahydro-2H-pyran-3-yl)-1H-pyrazol-4-yl)-2H-pyrazolo[3,4-c]quinolin-4-amine; N-(1-(3-methylbutan-2-yl)-1H-pyrazol-4-yl)-8-(methylsulfonyl)-2H-pyrazolo[3,4-c]quinolin-4-amine; 2-methyl-1-(3-methyl-4-((8-(methylsulfonyl)-2H-pyrazolo[3,4-c]quinolin-4-yl)amino)-1H-pyrazol-1-yl)propan-2-ol; 2-methyl-1-(5-methyl-4-((8-(methylsulfonyl)-2H-pyrazolo[3,4-c]quinolin-4-yl)amino)-1H-pyrazol-1-yl)propan-2-ol; 8-(methylsulfonyl)-N-(1-(pyrrolidin-3-yl)-1H-pyrazol-4-yl)-2H-pyrazolo[3,4-c]quinolin-4-amine; 4-methyl-6-((8-(methylsulfonyl)-2H-pyrazolo[3,4-c]quinolin-4-yl)amino)-2H-benzo[b][1,4]oxazin-3(4H)-one; 2-methyl-1-(4-((7-(methylsulfonyl)-3H-pyrazolo[3,4-c]quinolin-4-yl)amino)-1H-pyrazol-1-yl)propan-2-ol; 8-(methylsulfonyl)-N-(1-(pentan-3-yl)-1H-pyrazol-4-yl)-2H-pyrazolo[3,4-c]quinolin-4-amine; N-(3-((8-(methylsulfonyl)-2H-pyrazolo[3,4-c]quinolin-4-yl)amino)phenyl)acetamide; N-(2-methoxy-5-((8-(methylsulfonyl)-2H-pyrazolo[3,4-c]quinolin-4-yl)amino)phenyl)acetamide; N-(3-ethylphenyl)-8-(methylsulfonyl)-2H-pyrazolo[3,4-c]quinolin-4-amine; 2-(4-((8-(methylsulfonyl)-2H-pyrazolo[3,4-c]quinolin-4-yl)amino)-1H-pyrazol-1-yl)propanoic acid; 5-((8-(methylsulfonyl)-2H-pyrazolo[3,4-c]quinolin-4-yl)amino)-1H-pyrazole-3-carboxylic acid; 2-((8-(methylsulfonyl)-2H-pyrazolo[3,4-c]quinolin-4-yl)amino)phenol; (S)—N-(3-(2-methylpyrrolidin-1-yl)phenyl)-8-(methylsulfonyl)-2H-pyrazolo[3,4-c]quinolin-4-amine; (S)-8-methoxy-N-(3-(2-methylpyrrolidin-1-yl)phenyl)-2H-pyrazolo[3,4-c]quinolin-4-amine; 2-(4-((9-methoxy-3H-pyrazolo[3,4-c]quinolin-4-yl)amino)-11-pyrazol-1-yl)-N,N-dimethylacetamide; N-(1-(1,3-dimethoxypropan-2-yl)-1H-pyrazol-4-yl)-9-methoxy-3H-pyrazolo[3,4-c]quinolin-4-amine; 8-(methylsulfonyl)-N-(1-(pyridin-2-yl)-1H-pyrazol-4-yl)-2H-pyrazolo[3,4-c]quinolin-4-amine; 4-ethyl-6-((8-(methylsulfonyl)-2H-pyrazolo[3,4-c]quinolin-4-yl)amino)-2H-benzo[b][1,4]oxazin-3(4H)-one; 6-((8-(methylsulfonyl)-2H-pyrazolo[3,4-c]quinolin-4-yl)amino)-2H-benzo[b][1,4]oxazin-3(4H)-one; 6-((8-(methylsulfonyl)-2H-pyrazolo[3,4-c]quinolin-4-yl)amino)-2H-benzo[b][1,4]thiazin-3(4H)-one; 7-((8-(methylsulfonyl)-2H-pyrazolo[3,4-c]quinolin-4-yl)amino)-3,4-dihydroquinolin-2(1H)-one; N1-(8-(methylsulfonyl)-2H-pyrazolo[3,4-c]quinolin-4-yl)benzene-1,2-diamine; 2-(4-((8-methoxy-2H-pyrazolo[3,4-c]quinolin-4-yl)amino)-1H-pyrazol-1-yl)propanoic acid; 7-bromo-N-(1-(tetrahydro-2H-pyran-4-yl)-1H-pyrazol-4-yl)-2H-pyrazolo[3,4-c]quinolin-4-amine; 4-((8-(methylsulfonyl)-2H-pyrazolo[3,4-c]quinolin-4-yl)amino)phenol; cyclopropyl(7-((8-(methylsulfonyl)-2H-pyrazolo[3,4-c]quinolin-4-yl)amino)-3,4-dihydroquinolin-1(2H)-yl)methanone; 4,5-dimethoxy-N1-(8-(methylsulfonyl)-2H-pyrazolo[3,4-c]quinolin-4-yl)benzene-1,2-diamine; N-(2-(4-acetylpiperazin-1-yl)-5-((8-(methylsulfonyl)-2H-pyrazolo[3,4-c]quinolin-4-yl)amino)phenyl)acetamide; N-(1-((1R,2S)-2-methoxycyclohexyl)-1H-pyrazol-4-yl)-8-(methylsulfonyl)-2H-pyrazolo[3,4-c]quinolin-4-amine; 5-((8-(methylsulfonyl)-2H-pyrazolo[3,4-c]quinolin-4-yl)amino)-2-morpholinobenzonitrile; 6-bromo-N-(1-(tetrahydro-2H-pyran-4-yl)-3H-pyrazolo[3,4-c]quinolin-4-amine.

The present invention further provides pharmaceutical compositions comprising one or more compounds of formula (I) as defined herein or a pharmaceutically acceptable ester, prodrug, hydrate, solvate or salt thereof, optionally in combination with a pharmaceutically acceptable carrier.

It is a further object of the present invention to provide a compound of formula (I) as defined herein or a pharmaceutical composition as defined herein for the preparation of a medicament for the treatment of one or more diseases mentioned herein.

Preferably the compounds of the present invention may be used for the treatment and/or prevention of the following conditions:

respiratory tract/obstructive airways diseases and disorders including:

rhinorrhea, tracheal constriction, airway contraction, acute-, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofulous rhinitis, perennial allergic rhinitis, seasonal rhinitis (including rhinitis nervosa (hay fever) and vasomotor rhinitis), pollinosis, asthma (such as bronchial, atopic, allergic, intrinsic, extrinsic, exercise-induced, cold air-induced, occupational, bacterial infection-induced, and dust asthma particularly chronic or inveterate asthma (e.g. late asthma and airways hyper-responsiveness)), bronchitis (including chronic, acute, arachidic, catarrhal, croupus, phthinoid and eosinophilic bronchitis), cardiobronchitis, pneumoconiosis, chronic inflammatory disease of the lung which result in interstitial fibrosis, such as interstitial lung disease (ILD) (e.g., idiopathic pulmonary fibrosis, or ILD associated with rheumatoid arthritis, or other autoimmune conditions), acute lung injury (ALI), adult respiratory distress syndrome (ARDS), chronic obstructive pulmonary, airways or lung disease (CORD, COAD, COLD or COPD, such as irreversible COPD), chronic sinusitis, conjunctivitis (e.g. allergic conjunctivitis), cystic fibrosis, extrinsic allergic alveolitis (like farmer's lung and related diseases), fibroid lung, hypersensitivity lung diseases, hypersensitivity pneumonitis, idiopathic interstitial pneumonia, nasal congestion, nasal polyposis, otitis media, and cough (chronic cough associated with inflammation or iatrogenic induced), pleurisy, pulmonary congestion, emphysema, bronchiectasis, sarcoidosis, lung fibrosis, including cryptogenic fibrosing alveolitis, fibrosis complicating anti-neoplastic therapy and chronic infection, including tuberculosis and aspergillosis and other fungal infections, vasculitic and thrombotic disorders of the lung vasculature, and pulmonary hypertension, acute viral infection including the common cold, and infection due to respiratory syncytial virus, influenza, coronavirus (including SARS) and adenovirus, allergic bronchopulmonary mycosis, emphysema, diffuse panbronchiolitis, systemic anaphylaxis or hypersensitivity responses, drug allergies (e.g., to penicillin, cephalosporins), insect sting allergies, and food related allergies which may have effects remote from the gut (such as migraine, rhinitis and eczema), anaphylactic shock, vascular spasms;

bone and joint related diseases and disorders including:
osteoporosis, arthritis (including rheumatic, infectious, autoimmune, chronic, malignant), seronegative spondyloarthropathies (such as ankylosing spondylitis, rheumatoid spondylitis, psoriatic arthritis, enthesopathy, Bechet's disease, Marie-Strümpell arthritis, arthritis of inflammatory bowel disease, and Reiter's disease), systemic sclerosis, osteoarthritis, osteoarthrosis, both primary and secondary to e.g. congenital hip dysplasia, cervical and lumbar spondylitis, and low back and neck pain, Still's disease, reactive arthritis and undifferentiated spondarthropathy, septic arthritis and other infection-related arthropathies and bone disorders such as tuberculosis, including Pott's disease and Poncet's syndrome, acute and chronic crystal-induced synovitis including urate gout, calcium pyrophosphate deposition disease, and calcium apatite related tendon, bursar and synovial inflammation, primary and secondary Sjogren's syndrome, systemic sclerosis and limited scleroderma, mixed connective tissue disease, and undifferentiated connective tissue disease, inflammatory myopathies including, polymalgia rheumatica, juvenile arthritis including idiopathic inflammatory arthritides of whatever joint distribution and associated syndromes, other joint disease (such as intervertebral disc degeneration or temporomandibular joint degeneration), rheumatic fever and its systemic complications, vasculitides including giant cell arteritis, Takayasu's arteritis, polyarteritis nodosa, microscopic polyarteritis, and vasculitides to associated with viral infection, hypersensitivity reactions, cryoglobulins, paraproteins, low back pain, Familial Mediterranean fever, Muckle-Wells syndrome, and Familial Hibenian Fever, Kikuchi disease, drug-induced arthalgias, tendonititides, polychondritis, and myopathies, osteoporosis, osteomalacia like osteoporosis, osteopenia, osteogenesis imperfects, osteopetrosis, osteofibrosis, osteonecrosis, Paget's disease of bone, hypophosphatemia, Felty's syndrome, Still's disease, slack of artificial joint implant, sprain or strain of muscle or joint, tendinitis, fasciitis, periarthritis humeroscapularis, cervico-omo-brachial syndrome, tenosynovitis;

skin and eye related diseases and disorders including:
glaucoma, ocular hypertension, cataract, retinal detachment, psoriasis (including psoriasis vulgaris, pustular psoriasis, arthritic psoriasis, erythroderma psoriaticum), palmoplantar pustulosis, xerodoma, eczematous diseases (like atopic dermatitis, ultraviolet radiation dermatitis, contact dermatitis, and seborrheic dermatitis), phytodermatitis, photodermatitis, cutaneous eosinophilias, chronic skin ulcers, cutaneous lupus erythematosus, contact hypersensitivity/allergic contact dermatitis (including sensitivity to poison ivy, sumac, or oak), and eosinophilic folliculitis (Ofuji's disease), pruritus, drug eruptions, urticaria (acute or chronic, allergic or non-allergic), acne, erythema, dermatitis herpetiformis, scleroderma, vitiligo, lichen planus, lichen sclerosus et atrophica, pyodenna gangrenosum, skin sarcoid, pemphigus, ocular pemphigus, pemphigoid, epidennolysis bullosa, angioedema, vasculitides, toxic erythemas, cutaneous eosinophilias, alopecia areata, male-pattern baldness, Sweet's syndrome, Stevens-Johnson syndrome, Weber-Christian syndrome, erythema multiforme, cellulitis, botl, infective and non infective, panniculitis, cutaneous Lymphomas, non-melanoma skin cancer and other dysplastic lesions, blepharitis, iritis, anterior and posterior uveitis, choroiditis, autoimmune, degenerative or inflammatory disorders affecting the retina, ophthalmitis including sympathetic ophthalmitis, sarcoidosis, xerosis infections including viral, fungal, and bacterial, allergic conjunctivitis, increased fibrosis, keloids, keloplasty, post-surgical scars, epidermolysis bullosa, dry eye, ocular inflammation, allergic conjunctivitis, vernal conjunctivitis, vernal keratoconjunctivitis, and giant papillary conjunctivitis, ocular angiogenesis, cornea damage and scar, all forms of macular degeneration, macular edema, macular dystrophy, abnormal wound healing, scleritis, episcleritis, pachydermia, peripheral ulcerative keratitis, fungal keratitis, herpetic keratitis, invasive aspergillosis; conical cornea, dystorphia epithelialis corneae, severe intraocular inflammation;

gastrointestinal tract and abdominal related diseases and disorders including:
celiac/coeliac disease (e.g. celiac sprue), cholecystitis, enteritis (including infectious, ischemic, radiation, drug-induced, and eosinophilic gastroenteritis), eosinophilic esophagitis, eosinophilic gastrointestinal inflammation, allergen induced diarrhea, enteropathy associated with seronegative arthropathies, gastritis, autoimmune atrophic gastritis, ischemic bowel disease, inflammatory bowel disease (Crohn's disease and ulcerative colitis), colitis, Mooren's ulcer, irritable bowel syndrome, necrotizing enterocolitis, gut ischemia, glossitis, gingivitis, periodontitis, oesophagitis, including reflex, proctitis, fibrosis and cirrhosis of the liver, pancreatitis, both acute and chronic, pancreatic fibrosis, pancreatic sclerosis, pancreatolithiasis, hepatic cirrhosis, hepatitis (congestive, autoimmune, acute, fulminant, chronic, drug-induced, alcoholic, lupoid, steatohepatitis and chronic viral), fatty liver, primary biliary cirrhosis, hepatic porphyria, and gastrointestinal related allergic disorders, spastic colon, diverticulitis, gastroenteric bleeding, Behcet's disease; partial liver resection, acute liver necrosis (e.g. necrosis caused by toxins, viral hepatitis, shock or anoxia), hemolytic uremic syndrome;

hematological disorders including:

anemias, coagulation, myeloproliferative disorders, hemorrhagic disorders, leukopenia, eosinophilic disorders, leukemias (e.g. myelogenous, lymphomas, plasma cell dyscrasias, disorders of the spleen, Banti's disease, hemophilia, purpura (including idiopathic thrombocytopenic purpura), Wiskott-Aldrich syndrome;

metabolic disorders including:

obesity, amyloidosis, disturbances of the amino and acid metabolism like branched chain disease, hyperaminoacidemia, hyperaminoaciduria, disturbances of the metabolism of urea, hyperammonemia, mucopolysaccharidoses e.g. Maroteaux-Lamy syndrome, storage disease like glycogen storage diseases and lipid storage diseases, glycogenosis I diseases like Cori's disease, malabsorption diseases like intestinal carbohydrate malabsorption, oligosaccharidase deficiency like maltase-, lactase-, sucrase-insufficiency, disorders of the metabolism of fructose, disorders of the metabolism of galactose, galactosaemia, disturbances of carbohydrate utilization like diabetes, hypoglycemia, disturbances of pyruvate metabolism, hypolipidemia, hypolipoproteinemia, hyperlipidemia, hyperlipoproteinemia, carnitine or carnitine acyltransferase deficiency, disturbances of the porphyrin metabolism, porphyrins, disturbances of the purine metabolism, lysosomal diseases, metabolic diseases of nerves and nervous systems like gangliosidoses, sphingolipidoses, sulfatidoses, leucodystrophies, Lesch-Nyhan syndrome;

cerebellar dysfunction, disturbances of brain metabolism like:

dementia, Alzheimer's disease, Huntington's chores, Parkinson's disease, Pick's disease, toxic encepha-lopathy, demyelinating neuropathies like inflammatory neuropathy, Guillain-Barre syndrome; Meniere's disease and radiculopathy, primary and secondary metabolic disorders associated with hormonal defects like any disorder stemming from either an hyperfunction or hypofunction of some hormone-secreting endocrine gland and any combination thereof. Sipple's syndrome, pituitary gland dysfunction and its effects on other endocrine glands, such as the thyroid, adrenals, ovaries, and testes, acromegaly, hyper- and hypothyroidism, euthyroid goiter, euthyroid sick syndrome, thyroiditis, and thyroid cancer, over or underproduction of the adrenal steroid hormones, adrenogenital syndrome, Cushing's syndrome, Addison's disease of the adrenal cortex, Addison's pernicious anemia, primary and secondary aldosteronism, diabetes insipidus, diabetes mellitus, carcinoid syndrome, disturbances caused by the dysfunction of the parathyroid glands, pancreatic islet cell dysfunction, diabetes, disturbances of the endocrine system of the female like estrogen deficiency, resistant ovary syndrome; muscle weakness, myotonia. Duchenne's and other muscular dystrophies, dystrophia myotonica of Steinert, mitochondrial myopathies like I disturbances of the catabolic metabolism in the muscle, carbohydrate and lipid storage myopathies, glycogenoses, myoglobinuria, malignant hyperthermia, polymyalgia rheumatics, dermatomyositis, multiple myositis, primary myocardial disease, cardiomyopathy; disorders of the ectoderm, neurofibromatosis, scleroderma and polyar teritis, Louis-Bar syndrome, von Hippel-Lindau disease, Sturge-Weber syndrome, tuberous sclerosis, amyloidosis, porphyria; sexual dysfunction of the male and female; confused states and seizures due to inappropriate secretion of antidiuretic hormone from the pituitary gland, Liddle's syndrome, Bartter's syndrome, Fanconi's I syndrome, and renal electrolyte wasting;

transplant rejection related conditions including:

acute and chronic allograft rejection following solid organ transplant, for example, transplantation of kidney, heart, liver, lung, and cornea, chronic graft versus host disease, skin graft rejection, and bone marrow transplant rejection, immunosuppression;

genitourinary related conditions including:

nephritis (interstitial, acute interstitial (allergic), and glomerulonephritis), nephrotic syndrome, cystitis including acute and chronic (interstitial) cystitis and Hunner's ulcer, acute and chronic umethritis, prostatitis, epididymitis, oophoritis, salpingitis, vulvo vaginitis, vulvovaginal candidiasis, Peyronie's disease, and erectile dysfunction, renal disease, renal fibrosis, nephropyelitis, secondary contracted kidney, steroid dependent and steroid-resistant nephrosis, Goodpasture's syndrome;

CNS related diseases and disorders including:

neurodegenerative diseases, Alzheimer's disease and other cementing disorders including CJD and nvCJD, amyloidosis, and other demyelinating syndromes, cerebral atherosclerosis and vasculitis, temporal arteritis, myasthenia gravis, acute and chronic so pain (acute, intermittent or persistent, whether of central or peripheral origin) including post-operative, visceral pain, headache, migraine, neuralgia (including trigeminal), atypical facial pain, joint and bone pain, pain arising from cancer and tumor invasion, neuropathic pain syndromes including diabetic, post-herpetic, and HIV-associated neuropathies, neurosarcoidosis, to brain injuries, cerebrovascular diseases and their consequences, Parkinson's disease, corticobasal degeneration, motor neuron disease, dementia, including ALS (Amyotrophic lateral sclerosis), multiple sclerosis, traumatic brain injury, stroke, post-stroke, post-traumatic brain injury, and small-vessel cerebrovascular disease, dementias, vascular dementia, dementia with Lewy bodies, frontotemporal dementia and Parkinsonism linked 1 to chromosome 17, frontotemporal dementias, including Pick's disease, progressive supranuclear palsy, corticobasal degeneration, Huntington's disease, thalamic degeneration, HIV dementia, schizophrenia with dementia, and Korsakoffs psychosis, within the meaning of the definition are also considered to be CNS disorders central and peripheral nervous system complications of malignant, infectious or autoimmune processes, algesia, cerebral infarction, attack, cerebral ischemia, head injury, spinal cord injury, myelopathic muscular atrophy, Shy-Drager syndrome, Reye's syndrome, progressive multifocal leukoencephalopathy, normal pressure hydrocephalus, sclerosing panencephalitis, frontal lobe type dementia, acute anterior poliomyelitis (poliomyelitis), poliomyelitis neurosis, viral encephalitis, allergic encephalomyelitis, epileptic encephalopathies, Creutzfeldt-Jakob disease, Kuru disease, bovine spongiform encephalopathy (mad cow disease), scrapie, epilepsy, cerebral amyloid angiopathy, depression, mania, manic-depressive psychosis, hereditary cerebellar ataxia, peripheral neuropathy, Nasu-Hakola syndrome, Machado-Joseph disease;

inflammatory or immunological diseases or disorders including:

general inflammation (of the ocular, nasal, pulmonary, and gastrointestinal passages), mastocytosis/mast cell disorders (cutaneous, systemic, mast cell activation syndrome, and pediatric mast cell diseases), mastitis (mammary gland), vaginitis, vasculitis (e.g., necrotizing, cutaneous, and hypersensitivity vasculitis), Wegener granulamatosis, myyositis (including polyinyositis, dermatomyositis), basophil related diseases including basophilic leukemia and basophilic leukocytosis, and eosinophil related diseases such as Churg-Strauss syndrome, eosinophilic granuloma, lupus erythematosus (such as, systemic lupus erythematosus, subacute cutaneous lupus erythematosus, and discoid lupus erythematosus), chronic thyroiditis, Hashimoto's thyroiditis, Grave's disease, type I diabetes, complications arising from diabetes mellitus, other immune disorders, eosinophilia fasciitis, hyper IgE syndrome, Addison's disease, antiphospholipid syndrome, immunodeficiency disease, acquired immune deficiency syndrome (AIDS), leprosy, Sezary syndrome, paraneoplastic syndromes, and other autoimmune disorders, fervescence, myositis, nervous diseases selected from multiple myositis, bursitis, Evans syndrome, leukotriene B4-mediated diseases, idiopathic hypoparathyroidism, nephrotic syndrome lupus, immunosuppression;

cardiovascular diseases and disorders including:

congestive heart failure, myocardial infarction, ischemic diseases of the heart, all kinds of atrial and ventricular arrhythmias, hypertension, cerebral trauma, occlusive vascular disease, stroke, cerebrovascular disorder, atherosclerosis, restenosis, affecting the coronary and peripheral is circulation, pericarditis, myocarditis, inflammatory and auto-immune cardiomyopathies including myocardial sarcoid, endocarditis, valvulitis, and aortitis including infective (e.g. syphilitic), hypertensive vascular diseases, peripheral vascular diseases, and atherosclerosis, vasculitides, disorders of the proximal and peripheral veins including phlebitis and thrombosis, including deep vein thrombosis and complications of varicose veins, aortic aneurism, periarteritis nodosa, cardiac fibrosis, post-myocardial infarction, idiopathic cardiomyopathy; angioplasty;

oncological diseases and disorders including:

common cancers (prostrate, breast, lung, ovarian, pancreatic, bowel and colon, abdomen, stomach (and any other digestive system cancers), liver, pancreas, peritoneum, endocrine glands (adrenal, parathyroid, pituitary, testicles, ovary, thymus, thyroid), eye, head, neck, nervous system (central and peripheral), lymphatic system, blood, pelvic, skin, bone, soft tissue, spleen, thoracic, urogenital, and brain tumors), breast cancer, genitourinary cancer, lung cancer, gastrointestinal cancer, epidermoid cancer, melanoma, ovarian cancer, pancreas cancer, neuroblastoma, malignancies affecting the bone marrow (including the leukaemias) and lymphoproliferative systems, such as Hodgkin's and non-Hodgkin's lymphoma, B-cell lymphoma, follicular lymphoma, metastatic disease and tumour recurrences, and paraneoplastic syndromes, as well as hypergammaglobulinemia, lymphoproliferative diseases, disorders, and/or conditions, paraproteinemias, purpura (including idiopathic thrombocytopenic purpura), Waldenstron's Macroglobulinemia, Gaucher's Disease, histiocytosis, retinoblastoma and any other hyperproliferative disease, sarcomata, cachexia, tumor growth, tumor invasion, metastasis, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia, keratoleukoma and other diseases and disorders including:

pain, migraine, sleep disorders, fever, sepsis, idiopathic thrombocytopenia pupura, post-operative adhesions, flushing, ischemic/reperfusion injury in the heart, brain, peripheral limbs, bacterial infection, viral infection, fungal infection, thrombosis, endotoxin shock, septic shock, thermal regulation including fever, Raynaud's disease, gangrene, diseases requiring anti-coagulation therapy, congestive heart failure, mucus secretion disorders, pulmonary hypotension, prostanoid-induced smooth muscle contract associated with dysmenorrhea and premature labor, premature delivery, reperfusion injury, burn, thermal injury, hemorrhage or traumatic shock, menstrual pain, menstrual cramp, dysmenorrhea, periodontosis, rickettsial infectious disease, protozoal disease, reproduction disease, toothache, pain after tooth extraction, Herpes zoster, Herpes simplex, retroperitoneal fibrosis, various radiation injuries and the like.

The present invention furthermore provides a method of treatment of a disease mediated by kinase-activity comprising the administration, to a patient in need thereof, of a therapeutically effective amount of a compound or a pharmaceutical composition described herein. Preferably, the kinase is selected from SYK (Spleen Tyrosine Kinase), LRRK2 (Leucine-rich repeat kinase 2) and/or Myosin light chain kinase (MYLK or MLCK) or mutants thereof. Further preferably, said treatment is systemic. Moreover preferably, said administration is topical. Moreover preferably, said topical administration is to the skin, the eye or intranasal or by inhalation.

Preferably, the disease is selected from the group consisting of an inflammatory disease, an autoimmune disease, an allergic disorder, and an ocular disorder.

Especially preferably, the disease is selected from the group consisting of pruritus, eczema, asthma, rhinitis, dry eye, ocular inflammation, allergic conjunctivitis, vernal conjunctivitis, vernal keratoconjunctivitis, giant papillary conjunctivitis, fungal keratitis and uveitis.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage may be adjusted to the individual requirements in each particular case including the specific compound being administered, the route of administration, the condition being treated, as well as the patient being treated.

Examples of pharmacologically acceptable salts of sufficiently basic compounds of formula (I) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of formula (I) may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of formula (I). Compounds of formula (I) may be solvated, especially hydrated. The hydratization/hydration may occur during the process of production or as a consequence of the hygroscopic nature of the initially water free compounds of formula (I). The solvates and/or hydrates may e.g. be present in solid or liquid form.

It should be appreciated that certain compounds of formula (I) may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention. Since the compounds of formula (I) may contain asymmetric C-atoms, they may be present either as achiral compounds, mixtures of diastereomers, mixtures of enantiomers or as optically pure compounds. The present invention comprises both all pure enantiomers and all pure diastereomers, and also the mixtures thereof in any mixing ratio.

According to a further embodiment of the present invention, one or more hydrogen atoms of the compounds of the present invention may be replaced by deuterium. Deuterium modification improves the metabolic properties of a drug with little or no change in its intrinsic pharmacology. Deuterium substitution at specific molecular positions improves metabolic stability, reduces formation of toxic metabolites and/or increases the formation of desired active metabolites. Accordingly, the present invention also encompasses the partially and fully deuterated compounds of formula (I). The term hydrogen also encompasses deuterium.

The therapeutic use of compounds according to formula (I), their pharmacologically acceptable salts, solvates and hydrates, respectively, as well as formulations and pharmaceutical compositions also lie within the scope of the present invention.

The pharmaceutical compositions according to the present invention preferably comprise at least one compound of formula (I) as an active ingredient and, optionally, carrier substances and/or adjuvants.

The present invention also relates to pro-drugs which are composed of a compound of formula (I) and at least one pharmacologically acceptable protective group which will be cleaved off under physiological conditions, such as an alkoxy-, arylalkyloxy-, acyl-, acyloxymethyl group (e.g. pivaloyloxymethyl), an 2-alkyl-, 2-aryl- or 2-arylalkyl-oxycarbonyl-2-alkylidene ethyl group or an acyloxy group as defined herein, e.g. ethoxy, benzyloxy, acetyl or acetyloxy or, especially for a compound of formula (I), carrying a hydroxy group (—OH): a sulfate, a phosphate (—OPO$_3$ or —OCH$_2$OPO$_3$) or an ester of an amino acid. Especially preferred are pro-drugs of the hydroxy group of a compound of formula (I).

As used herein, the term pharmaceutically acceptable ester especially refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Preferably, the present invention also relates to a prodrug, a biohydrolyzable ester, a biohydrolyzable amide, a polymorph, tautomer, stereoisomer, metabolite, N-oxide, biohydrolyzable carbamate, biohydrolyzable ether, physiologically functional derivative, atropisomer, or in vivohydrolysable precursor, diastereomer or mixture of diastereomers, chemically protected form, affinity reagent, complex, chelate and a stereoisomer of the compounds of formula (I).

As mentioned above, therapeutically useful agents that contain compounds of formula (I), their solvates, salts or formulations are also comprised in the scope of the present invention. In general, compounds of formula (I) will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 10 mg to about 10,000 mg, preferably from about 20 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

The present invention refers furthermore to compounds of formulas (II), (IIIa) and/or (IIIb) wherein $R^2$ and n are defined as above and PG is a protecting group.

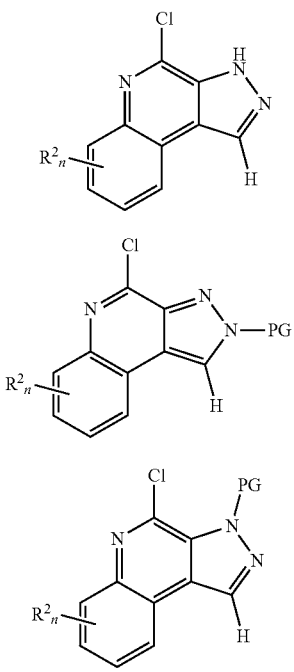

Protecting groups are known to a person skilled in the art and e.g. described in P. J. Kocienski, Protecting Groups, Georg Thieme Verlag, Stuttgart, 1994 and in T. W. Greene, P. G. M. Wuts, Protective Groups in Organic Synthesis, John Wiley & Sons, New York, 1999.

Preferably, PG is a 4-methoxy benzyl group or a Carboxybenzyl (Cbz or Z) group; especially preferably, PG is a 4-methoxy benzyl group.

Preferred compounds of formula (II) are:

4-chloro-9-fluoro-2H-pyrazolo[3,4-c]quinoline; 4-chloro-8-methoxy-2H-pyrazolo[3,4-c]quinoline; 4-chloro-9-methoxy-2H-pyrazolo[3,4-c]quinoline; 4-chloro-8-(methylthio)-2H-pyrazolo[3,4-c]quinoline; 4-chloro-7-(methylthio)-2H-pyrazolo[3,4-c]quinoline; 4-chloro-9-(methylthio)-2H-pyrazolo[3,4-c]quinoline; 4-chloro-6-fluoro-2H-pyrazolo[3,4-c]quinoline; 4-chloro-8-(methylsulfonyl)-2H-pyrazolo[3,4-c]quinoline; 4-chloro-8-iodo-2H-pyrazolo[3,4-c]quinoline; 4-chloro-8-methyl-2H-pyrazolo[3,4-c]quinoline; 4-chloro-9-methyl-2H-pyrazolo[3,4-c]quinoline; 4-chloro-9-(methylsulfonyl)-2H-pyrazolo[3,4-c]quinoline; 4-chloro-7-(methylsulfonyl)-2H-pyrazolo[3,4-c]quinoline.

Further preferred compounds of formula (II) are:

4-chloro-7-(methylthio)-2H-pyrazolo[3,4-c]quinoline; 4-chloro-6,8-dimethoxy-2H-pyrazolo[3,4-c]quinoline; 4-chloro-6-methoxy-2H-pyrazolo[3,4-c]quinoline; 7-bromo-4-chloro-2H-pyrazolo[3,4-c]quinoline; 6-bromo-4-chloro-2H-pyrazolo[3,4-c]quinoline.

Preferred compounds of formula (IIIa) and (IIIb) are:

4-chloro-9-fluoro-2-(4-methoxybenzyl)-2H-pyrazolo[3,4-c]quinoline; 4-chloro-8-methoxy-2-(4-methoxybenzyl)-2H-pyrazolo[3,4-c]quinoline; 4-chloro-9-methoxy-2-(4-methoxybenzyl)-2H-pyrazolo[3,4-c]quinoline; 4-chloro-2-(4-methoxybenzyl)-8-(methylthio)-2H-pyrazolo[3,4-c]quinoline; 4-chloro-2-(4-methoxybenzyl)-7-(methylthio)-2H-pyrazolo[3,4-c]quinoline; 4-chloro-2-(4-methoxybenzyl)-9-(methylthio)-2H-pyrazolo[3,4-c]quinoline; 4-chloro-6-fluoro-2-(4-methoxybenzyl)-2H-pyrazolo[3,4-c]quinoline; 4-chloro-2-(4-methoxybenzyl)-8-(methylsulfonyl)-2H-pyrazolo[3,4-c]quinoline; 4-chloro-8-iodo-2-(4-methoxybenzyl)-2H-pyrazolo[3,4-c]quinoline; 4-chloro-2-(4-methoxybenzyl)-8-methyl-2H-pyrazolo[3,4-c]quinoline; 4-chloro-2-(4-methoxybenzyl)-9-methyl-2H-pyrazolo[3,4-c]quinoline; 4-chloro-2-(4-methoxybenzyl)-9-(methylsulfonyl)-2H-pyrazolo[3,4-c]quinoline; 4-chloro-2-(4-methoxybenzyl)-7-(methylsulfonyl)-2H-pyrazolo[3,4-c]quinoline.

Further preferred compounds of formula (IIIa) and (IIIb) are:

4-chloro-2-(4-methoxybenzyl)-7-(methylthio)-2H-pyrazolo[3,4-c]quinoline; 4-chloro-6,8-dimethoxy-2-(4-methoxybenzyl)-2H-pyrazolo[3,4-c]quinoline; 4-chloro-6-methoxy-2-(4-methoxybenzyl)-2H-pyrazolo[3,4-c]quinoline; 7-bromo-4-chloro-2-(4-methoxybenzyl)-2H-pyrazolo[3,4-c]quinoline; 6-bromo-4-chloro-2-(4-methoxybenzyl)-2H-pyrazolo[3,4-c]quinoline.

General Synthesis

The following routes may be used to provide chloride intermediates (herein, $R^1$ preferably corresponds to $R^2$ in formula (I)). These chloride intermediates may then be used in an amination reaction with various amines and a subsequent deprotection to provide the final products:

Cyclisation:

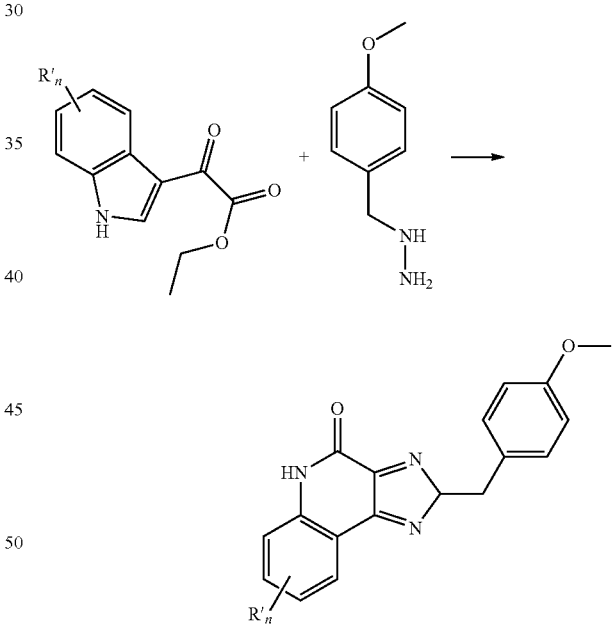

(1H-Indol-3-yl)-oxo-acetic acid ethyl ester (or alternatively methyl ester) is reacted with (4-methoxybenzyl)-hydrazine hydrochloride. This results in the formation of 2-(4-Methoxy-benzyl)-2,5-dihydro-pyrazolo[3,4-c]quinolin-4-one.

In the same way using hydrazine hydrate or hydrazine hydrochloride the corresponding none protected tricycles could be synthesized.

Chlorination:

The provided amides, using e.g. the above routes, may be used in a chlorination step:

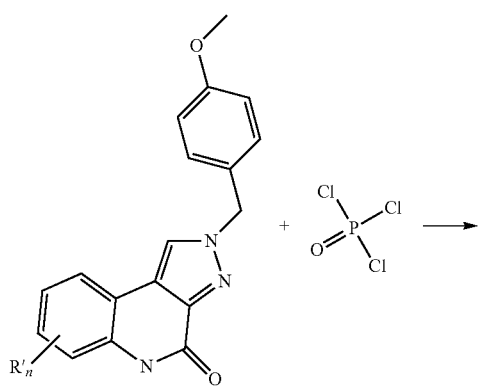

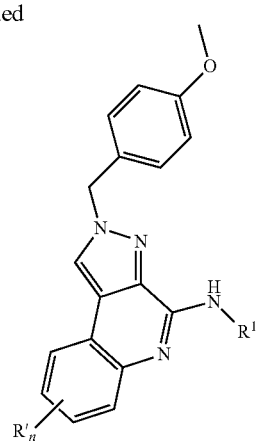

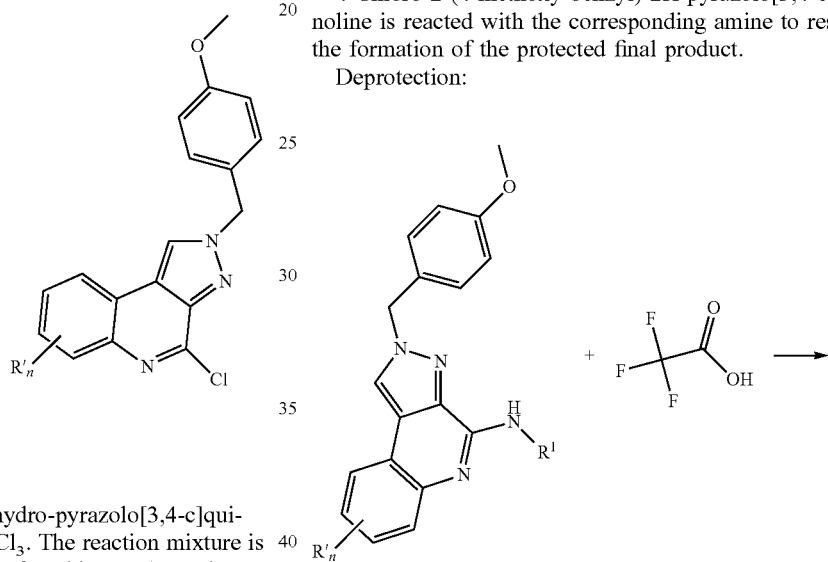

2-(4-Methoxy-benzyl)-2,5-dihydro-pyrazolo[3,4-c]quinolin-4-one is suspended in POCl₃. The reaction mixture is heated resulting in the formation of 4-Chloro-2-(4-methoxy-benzyl)-2H-pyrazolo[3,4-c]quinoline.

Amination:

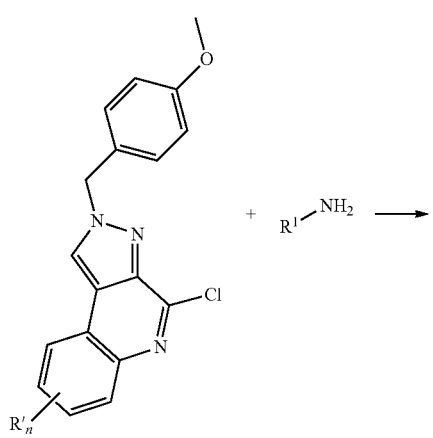

4-Chloro-2-(4-methoxy-benzyl)-2H-pyrazolo[3,4-c]quinoline is reacted with the corresponding amine to result in the formation of the protected final product.

Deprotection:

In a final step the para-methoxy-benzyl protection group is removed with TFA to provide final product for biological characterisation.

EXAMPLES

Materials and Methods
Biological Assays—Protein Kinase Assays
SYK Assay

In the assay OMNIA® KINASE ASSAY by Invitrogen Corporation (Carlsbad) the effect of invention of a compound on the phosphorylation is determined by measurement of fluorescence intensity of a chelation-enhanced fluorophore called SOX. Upon phosphorylation of the peptide by the kinase of interest, Mg2+ is chelated to form a bridge between the SOX moiety and the phosphate group that is transferred to the specific tyrosine on the peptide. The fluorescence intensity is directly proportional to the amount of peptide phosphorylation.

To the wells of an 384 well small volume plate (Greiner, Frickenhausen) are added (i) the compound under test in 5% DMSO/distilled water (2 µl), (ii) 16 µl of the master mix containing ATP, DTT, Kinase Reaction Buffer, Omina Peptide Substrate Tyr 7 resulting in a final concentration of 1 mM ATP, 0.2 mM DTT and 10 µM Peptide Substrate.

The Master Mix and the assay plate was incubated to reaction temperature before the measurement (30° C.). The reaction was started with addition of (iii) 2 µl 4 µg/ml SYK kinase (Invitrogen, Carlsbad). During measurement fluorescence intensity readings were collected using a TECAN M1000 at a wavelength of $\lambda$ex 360/$\lambda$em 485 nm every 30 s for 30 minutes. The reaction velocity was plotted versus the inhibitor concentration to determine the IC50 using XLFit 5.0 (IDBS, Guildford) to fit to a sigmoidal dose response curve.

The ATP dependency was determined according to Lai C-J-, Wu J C A Simple Kinetic Method for Rapid Mechanistic Analysis of Reversible Enzyme Inhibitors. Assays and Drug Dev. Technologies. 2003; 1(4):527-535. To demonstrate a competition effect of the test compounds towards ATP the corresponding test compound was used at the 50% inhibitory concentration. Assay conditions as described previously were maintained. ATP concentrations used was 1000, 333, 100, 33.3, 10, 3.3, 1 µM.

LRRK2-LRRK2 G2019S-Assay

In the assay LanthaScreen™ Eu Kinase Binding Assay by Invitrogen Corporation (Carlsbad) the effect of invention of a compound on the phosphorylation is determined by measurement of fluorescence intensity emission ratio based on the binding and displacement of a proprietary, Alexa Fluor® 647-labeled, ATP-competitive kinase inhibitor scaffold (kinase tracer) to the kinase of interest. Binding of the tracer to the kinase is detected using a europium-labeled anti-tag antibody, which binds to the kinase of interest. Simultaneous binding of both the tracer and antibody to the kinase results in a high degree of FRET (fluorescence resonance energy transfer) from the europium (Eu) donor fluorophore to the Alexa Fluor® 647 acceptor fluorophore on the kinase tracer. Binding of an inhibitor to the kinase competes for binding with the tracer, resulting in a loss of FRET. The fluorescence intensity ratio is directly proportional to the amount of peptide phosphorylation.

To the wells of an 384 well small volume plate (Greiner, Frickenhausen) are added (i) the compound under test in 5% DMSO/distilled water (5 µl), (ii) 5 µl of the kinase antibody mixture resulting in a final concentration 5 nM LRRK2 or their mutants, 2 nM EU-Anti-GST antibody in 1× kinase buffer A. The reaction was started with addition of (iii) 5 µl resulting in a final concentration of 10 nM tracer 236. The assay plate was incubated at RT for 1 h and fluorescence intensity readings were collected using a TECAN M1000 at two wavelengths of $\lambda$ex 340/$\lambda$em 615 nm and $\lambda$ex 340/$\lambda$em 665 nm with a delay time of 100 µs and an integration time of 200 µs after 60 minutes. The emission ratio was calculated by division of the acceptor/tracer emission (665 nM) by the antibody/donor emission (615 nM). The inhibitor concentration was plotted versus the emission ratio to determine the IC50 using XLFit 5.0 (IDBS, Guildford) to fit to a sigmoidal dose response curve with a variable slope.

General Procedures for Synthesis of Compounds
Chromatography

The compound verification via analytical HPLC-MS was done after purification using the following instrumentation, column and method:

Analytical Method for Compound Purity
Instrumentation:
Agilent MSD 1100
Analytical Methods:
Solvents:
A: acetonitrile
B: H2O
C: 2% HCOOH in acetonitrile
D: 0.1% NEt3 in acetonitrile
The following analytical methods were used:
Method A
Column ODS-AQ from YMC 2.1×50 mm 3 m particle size, incl. GuardCol 2.1×10 mm, 3 µm particle size thermostated @ 40° C.
Gradient:

| Time [min] | % B | % C | % D | Flow [mL/min] |
|---|---|---|---|---|
| 0 | 90 | 5 | 0 | 0.6 |
| 10.0 | 10 | 5 | 0 | 0.6 |
| 13.0 | 10 | 5 | 0 | 0.6 |
| 14.0 | 90 | 5 | 0 | 0.6 |

Stop time @ 15 min
MS: ESI positive, Mass scan from 100 to 800
gradient fragmentation: 50 to 125V
UV: detection @ 220 and 254 nm
Method B
Column YMC ODS-AQ 2.1×50 mm, 3 µm particle size incl. GuardCol 2.1×10 mm, 3 µm particle size thermostated@40° C.
Gradient:

| Time[min] | % B | % C | % D | Flow[mL/min] |
|---|---|---|---|---|
| 0 | 99 | 5 | 0 | 0.6 |
| 2.5 | 10 | 5 | 0 | 0.6 |
| 4 | 10 | 5 | 0 | 0.6 |
| 4.5 | 99 | 5 | 0 | 0.6 |
| 6 | 99 | 5 | 0 | 0.6 |

Stoptime@7 min
MS: ESI positive, Mass scan from 100 to 800
gradient fragmentation: 50 to 125V
UV: detection @ 220 and 254 nm
Purification and Characterisation:

The resulting crude reaction products were purified in an automatic process using a semi-preparative HPLC-MS with mass-triggered sampling of the desired peak:
Purification Via Semi-Preparative HPLC-MS
Instrumentation:
2× Varian PrepStar SD-1
1× Dionex P580 Pump 1 Channel (MakeUP I)
1× Dionex AXP-MS (MakeUP II)
1× Dionex MSQ
1× Dionex UVD 340V—Prep Flow Cell
Gilson 215 Liquid Handler
Column:
SunFire Prep C18 OBD 5 µm 19×50 mm
Typical Method:
Column Flow: 30 ml/min
Solvent A: methanol, 0.3% acetic acid
Solvent B: water, 0.3% acetic acid Typical Time table for gradient:

| Time (min) | Solv. A | Solv. B |
|---|---|---|
| 0.0 | 30.00 | 70.00 |
| 10.0 | 100.00 | 0.00 |
| 14.0 | 100.00 | 0.00 |
| 14.4 | 30.00 | 70.00 |
| 16.4 | 30.00 | 70.00 |

Detection:

UV 254 nm, Mass Spectrometer Detector (API-ES, positive)

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different workup or purification techniques. Where reactions are carried out using microwave irradiation, the microwave used is an Initiator 60 supplied by Biotage. The actual power supplied varies during the course of the reaction in order to maintain a constant temperature.

ABBREVIATIONS

DCM=Dichloromethane
DMF=N,N-Dimethylformamide
THF=Tetrahydrofuran
MeOH=Methanol
TFA=Trifluoroacetic acid
TEA=Triethylamine
Lithium bis(trimethylsilyl)amide
rm=Reaction mixture
rt=Room temperature
AcOH=Acetic acid
MeCN=Acetonitrile
EtOH=Ethanol
EtOAc=Ethyl Acetate
LCMS=Mass spectrometry directed high pressure liquid chromatography
UV=Ultraviolet
DMSO=Dimethylsulphoxide

INTERMEDIATES

Intermediate 1

4-chloro-8-methoxy-2-(4-methoxybenzyl)-2H-pyrazolo[3,4-c]quinoline 5-methoxy-(1H-Indol-3-yl)-oxo-acetic acid ethyl ester (10 mmol) was suspended in EtOH (25 mL) and HOAc (3 mL). The p-methoxybenzyl hydrazine hydrochloride (11.5 mmol) was added. The mixture was refluxed for 24 h, then stirred for 16 h at rt. The reaction was monitored by LCMS. The mixture was concentrated, resuspended in EtOH (10 mL). The solid product was collected by filtration, washed with EtOH and Et$_2$O. The filtrated was concentrated and portioned between EtOAc and water. The organic layer was dried (Na$_2$SO$_4$), filtrated and concentrated. The material was pure enough for further reactions.

8-Methoxy-2-(4-Methoxy-benzyl)-2,5-dihydro-pyrazolo[3,4-c]quinolin-4-one (4.4 mmol) was suspended in POCl$_3$. The mixture was heated to 100° C. After 0.5 h LCMS showed reaction completion. The mixture was cooled to rt, and stirred overnight. The mixture was concentrated to dryness, cooled to 0° C., and quenched with ice/water. The mixture was extracted with DCM. The organic layer was washed with NaHCO$_3$ sat. aq. and water, dried (Na$_2$SO$_4$) filtered and concentrated.

The product was used without further purification.

The following intermediates 2-10, and 14-18 were synthesised using the corresponding method described in the synthesis of Intermediate 1:

Intermediate 2: 4-chloro-6-fluoro-2-(4-methoxybenzyl)-2H-pyrazolo[3,4-c]quinoline Intermediate 3: 4-chloro-9-fluoro-2-(4-methoxybenzyl)-2H-pyrazolo[3,4-c]quinoline Intermediate 4: 4-chloro-9-methoxy-2-(4-methoxybenzyl)-2H-pyrazolo[3,4-c]quinoline Intermediate 5: 4-chloro-2-(4-methoxybenzyl)-8-methyl-2H-pyrazolo[3,4-c]quinoline Intermediate 6: 4-chloro-2-(4-methoxybenzyl)-9-methyl-2H-pyrazolo[3,4-c]quinoline Intermediate 7: 4-chloro-2-(4-methoxybenzyl)-7-(methylthio)-2H-pyrazolo[3,4-c]quinoline Intermediate 8: 4-chloro-2-(4-methoxybenzyl)-8-(methylthio)-2H-pyrazolo[3,4-c]quinoline Intermediate 9: 4-chloro-2-(4-methoxybenzyl)-9-(methylthio)-2H-pyrazolo[3,4-c]quinoline Intermediate 10: 4-chloro-8-iodo-2-(4-methoxybenzyl)-2H-pyrazolo[3,4-c]quinoline Intermediate 14: 4-chloro-2-(4-methoxybenzyl)-7-(methylthio)-2H-pyrazolo[3,4-c]quinoline Intermediate 15: 4-chloro-6,8-dimethoxy-2-(4-methoxybenzyl)-2H-pyrazolo[3,4-c]quinoline Intermediate 16: 4-chloro-6-methoxy-2-(4-methoxybenzyl)-2H-pyrazolo[3,4-c]quinoline Intermediate 17: 7-bromo-4-chloro-2-(4-methoxybenzyl)-2H-pyrazolo[3,4-c]quinoline Intermediate 18: 6-bromo-4-chloro-2-(4-methoxybenzyl)-2H-pyrazolo[3,4-c]quinoline Intermediate 11

4-chloro-2-(4-methoxybenzyl)-7-(methylsulfonyl)-2H-pyrazolo[3,4-c]quinoline 7-(methylsulfonyl)-2-(4-Methoxy-benzyl)-2,5-dihydro-pyrazolo[3,4-c]quinolin-4-one (10 mmol) was dissolved in 250 mL DCM and cooled to 0° C. in an ice bath. 3-Chlorobenzenecarboperoxoic acid (1.1 eq., 11 mmol) was carefully added. The ice bath was removed. After 24 h the solvent was evaporated and the resulting solid was suspended in 2M aqueous NaOH, filtered and dried. The material was pure enough for further reactions.

7-(methylsulfonyl)-2-(4-Methoxy-benzyl)-2,5-dihydro-pyrazolo[3,4-c]quinolin-4-one (4.4 mmol) was suspended in POCl$_3$. The mixture was heated to 100° C. After 0.5 h LCMS showed reaction completion. The mixture was cooled to rt, and stirred overnight. The mixture was concentrated to dryness, cooled to 0° C., and quenched with ice/water. The mixture was extracted with DCM. The organic layer was washed with NaHCO$_3$ sat. aq. and water, dried (Na$_2$SO$_4$) filtered and concentrated.

The product was used without further purification.

Intermediate 12 and 13 were synthesised using the corresponding method described in the synthesis of Intermediate 11.

Intermediate 12

4-chloro-2-(4-methoxybenzyl)-8-(methylsulfonyl)-2H-pyrazolo[3,4-c]quinoline

Intermediate 13

4-chloro-2-(4-methoxybenzyl)-9-(methylsulfonyl)-2H-pyrazolo[3,4-c]quinoline

Products

Example 1: 9-fluoro-N-(4-(4-(4-methylpiperazin-1-yl)piperidin-1-yl)phenyl)-3H-pyrazolo[3,4-c]quinolin-4-amine 4-chloro-9-fluoro-2-(4-methoxybenzyl)-2H-pyrazolo[3,4-c]quinoline (0.16 mmol) and 4-(4-(4-methylpiperazin-1-yl)piperidin-1-yl)aniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 459.3025 g/mol
HPLC-MS: analytical method A
rt: 2.90 min—found mass: 460.2 (m/z+H)

The following examples were synthesized according to the protocol of Example 1:

Example 2: 9-fluoro-N-(3-fluoro-4-morpholinophenyl)-3H-pyrazolo[3,4-c]quinolin-4-amine;
Example 3: 8-methoxy-N-(4-(4-(4-methylpiperazin-1-yl)piperidin-1-yl)phenyl)-2H-pyrazolo[3,4-c]quinolin-4-amine;
Example 4: N-(4-fluoro-3-(methylsulfonyl)phenyl)-8-methoxy-2H-pyrazolo[3,4-c]quinolin-4-amine;
Example 5: N-(3-((dimethylamino)methyl)phenyl)-8-methoxy-2H-pyrazolo[3,4-c]quinolin-4-amine
Example 6: (4-((8-methoxy-2H-pyrazolo[3,4-c]quinolin-4-yl)amino)phenyl)(4-(4-methylpiperazin-1-yl)piperidin-1-yl)methanone
Example 7: (3-((8-methoxy-2H-pyrazolo[3,4-c]quinolin-4-yl)amino)phenyl)(morpholino)methanone
Example 8: N-(3-(tert-butyl)phenyl)-8-methoxy-2H-pyrazolo[3,4-c]quinolin-4-amine
Example 9: 9-fluoro-N-(4-morpholinophenyl)-3H-pyrazolo[3,4-c]quinolin-4-amine
Example 10: N-(4-(4-cyclopropylpiperazin-1-yl)phenyl)-9-fluoro-3H-pyrazolo[3,4-c]quinolin-4-amine
Example 11: 9-fluoro-N-(6-morpholinopyridin-3-yl)-3H-pyrazolo[3,4-c]quinolin-4-amine
Example 12: 6-((8-methoxy-2H-pyrazolo[3,4-c]quinolin-4-yl)amino)-2,3-dihydrobenzo[b]thiophene 1,1-dioxide
Example 13: 6-((8-methoxy-2H-pyrazolo[3,4-c]quinolin-4-yl)amino)benzo[b]thiophene 1,1-dioxide
Example 14: (4-((9-methoxy-3H-pyrazolo[3,4-c]quinolin-4-yl)amino)phenyl)(morpholino)methanone
Example 16: 9-methoxy-N-(3-methoxy-4-morpholinophenyl)-3H-pyrazolo[3,4-c]quinolin-4-amine
Example 17: 9-methoxy-N-(6-morpholinopyridin-3-yl)-3H-pyrazolo[3,4-c]quinolin-4-amine
Example 18: N-(1,3-dihydroisobenzofuran-5-yl)-9-methoxy-3H-pyrazolo[3,4-c]quinolin-4-amine
Example 19: 6-((9-methoxy-3H-pyrazolo[3,4-c]quinolin-4-yl)amino)-2,3-dihydrobenzo[b]thiophene 1,1-dioxide
Example 20: 6-((9-methoxy-3H-pyrazolo[3,4-c]quinolin-4-yl)amino)benzo[b]thiophene 1,1-dioxide
Example 21: 9-methoxy-N-(4-(4-(4-methylpiperazin-1-yl)piperidin-1-yl)phenyl)-3H-pyrazolo[3,4-c]quinolin-4-amine
Example 24: 2-(3-((8-methoxy-2H-pyrazolo[3,4-c]quinolin-4-yl)amino)phenyl)-2-methylpropanenitrile
Example 25: 3-(4-((8-methoxy-2H-pyrazolo[3,4-c]quinolin-4-yl)amino)phenyl)oxazolidin-2-one
Example 26: N-(5-cyclopropyl-1H-pyrazol-3-yl)-9-methoxy-3H-pyrazolo[3,4-c]quinolin-4-amine
Example 27: N-(3-fluoro-4-morpholinophenyl)-9-methoxy-3H-pyrazolo[3,4-c]quinolin-4-amine
Example 28: N-(3-((dimethylamino)methyl)phenyl)-9-methoxy-3H-pyrazolo[3,4-c]quinolin-4-amine
Example 29: (4-((9-fluoro-3H-pyrazolo[3,4-c]quinolin-4-yl)amino)phenyl)(morpholino)methanone
Example 31: 9-fluoro-N-(3-methoxy-4-morpholinophenyl)-3H-pyrazolo[3,4-c]quinolin-4-amine
Example 32: N-(4-fluoro-3-(methylsulfonyl)phenyl)-9-methoxy-3H-pyrazolo[3,4-c]quinolin-4-amine
Example 33: 2-(3-((9-methoxy-3H-pyrazolo[3,4-c]quinolin-4-yl)amino)phenyl)-2-methylpropanenitrile
Example 34: (2-fluoro-4-((8-methoxy-2H-pyrazolo[3,4-c]quinolin-4-yl)amino)phenyl)(morpholino)methanone
Example 35: (4-((8-methoxy-2H-pyrazolo[3,4-c]quinolin-4-yl)amino)-2-nitrophenyl)(morpholino)methanone
Example 36: 8-methoxy-N-(4-(oxazol-2-yl)phenyl)-2H-pyrazolo[3,4-c]quinolin-4-amine
Example 37: 8-methoxy-N-(4-(oxazol-5-yl)phenyl)-2H-pyrazolo[3,4-c]quinolin-4-amine
Example 38: N-(4-(4-(tert-butyl)piperazin-1-yl)phenyl)-9-methoxy-3H-pyrazolo[3,4-c]quinolin-4-amine
Example 39: (4-((9-methoxy-3H-pyrazolo[3,4-c]quinolin-4-yl)amino)phenyl)(4-(4-methylpiperazin-1-yl)piperidin-1-yl)methanone
Example 40: 3-(4-((9-methoxy-2H-pyrazolo[3,4-c]quinolin-4-yl)amino)phenyl)oxazolidin-2-one
Example 41: 8-methoxy-N-(pyridazin-4-yl)-2H-pyrazolo[3,4-c]quinolin-4-amine
Example 42: 8-methoxy-N-(3-(methylsulfonyl)-4-nitrophenyl)-2H-pyrazolo[3,4-c]quinolin-4-amine
Example 43: 8-(methylthio)-N-(4-morpholinophenyl)-3H-pyrazolo[3,4-c]quinolin-4-amine
Example 44: N-(3-(methylsulfonyl)phenyl)-8-(methylthio)-3H-pyrazolo[3,4-c]quinolin-4-amine
Example 45: N-(3,4-dimethoxyphenyl)-8-(methylthio)-3H-pyrazolo[3,4-c]quinolin-4-amine
Example 46: 1-(4-(4-((8-(methylthio)-3H-pyrazolo[3,4-c]quinolin-4-yl)amino)phenyl)piperazin-1-yl)ethan-1-one
Example 47: 7-((8-(methylthio)-3H-pyrazolo[3,4-c]quinolin-4-yl)amino)-3,4-dihydroquinolin-2(1H)-one
Example 48: N-(4-((dimethylamino)methyl)phenyl)-8-(methylthio)-3H-pyrazolo[3,4-c]quinolin-4-amine
Example 49: N-(2-methylisoindolin-5-yl)-8-(methylthio)-3H-pyrazolo[3,4-c]quinolin-4-amine
Example 50: 6-fluoro-N-(4-morpholinophenyl)-3H-pyrazolo[3,4-c]quinolin-4-amine Example 51: 6-fluoro-N-(3-(methylsulfonyl)phenyl)-3H-pyrazolo[3,4-c]quinolin-4-amine
Example 52: N-(3,4-dimethoxyphenyl)-6-fluoro-3H-pyrazolo[3,4-c]quinolin-4-amine
Example 53: 1-(4-(4-((6-fluoro-3H-pyrazolo[3,4-c]quinolin-4-yl)amino)phenyl)piperazin-1-yl)ethan-1-one
Example 54: 7-((6-fluoro-3H-pyrazolo[3,4-c]quinolin-4-yl)amino)-3,4-dihydroquinolin-2(1H)-one
Example 55: 8-(methylsulfonyl)-N-(4-morpholinophenyl)-3H-pyrazolo[3,4-c]quinolin-4-amine
Example 56: 8-methoxy-N-(2-(methylthio)-1H-benzo[d]imidazol-5-yl)-2H-pyrazolo[3,4-c]quinolin-4-amine
Example 57: 9-methoxy-N-(4-(oxazol-5-yl)phenyl)-3H-pyrazolo[3,4-c]quinolin-4-amine
Example 58: 9-methoxy-N-(4-(oxazol-2-yl)phenyl)-3H-pyrazolo[3,4-c]quinolin-4-amine
Example 59: 9-methoxy-N-(4-(4-(methylsulfonyl)piperazin-1-yl)phenyl)-3H-pyrazolo[3,4-c]quinolin-4-amine
Example 60: 4-(4-((9-methoxy-3H-pyrazolo[3,4-c]quinolin-4-yl)amino)phenyl)morpholin-3-one
Example 61: (4-((9-methoxy-3H-pyrazolo[3,4-c]quinolin-4-yl)amino)phenyl)(pyrrolidin-1-yl)methanone
Example 62: 1-(4-(4-((8-(methylsulfonyl)-3H-pyrazolo[3,4-c]quinolin-4-yl)amino)phenyl)piperazin-1-yl)ethan-1-one
Example 63: N-(3,4-dimethoxyphenyl)-8-(methylsulfonyl)-3H-pyrazolo[3,4-c]quinolin-4-amine
Example 64: (4-((8-(methylsulfonyl)-3H-pyrazolo[3,4-c]quinolin-4-yl)amino)phenyl)(morpholino)methanone
Example 65: (4-methylpiperazin-1-yl)(4-((8-(methylsulfonyl)-3H-pyrazolo[3,4-c]quinolin-4-yl)amino)phenyl)methanone
Example 66: 4-((8-(methylsulfonyl)-3H-pyrazolo[3,4-c]quinolin-4-yl)amino)benzamide
Example 67: N-(4-(4-(4-methylpiperazin-1-yl)piperidin-1-yl)phenyl)-8-(methylsulfonyl)-3H-pyrazolo[3,4-c]quinolin-4-amine
Example 68: 1-(4-((9-methoxy-3H-pyrazolo[3,4-c]quinolin-4-yl)amino)phenyl)pyrrolidin-2-one
Example 69: (4-((9-methoxy-3H-pyrazolo[3,4-c]quinolin-4-yl)amino)phenyl)(4-methylpiperazin-1-yl)methanone
Example 71: 5-((9-methoxy-3H-pyrazolo[3,4-c]quinolin-4-yl)amino)-2-morpholinobenzonitrile
Example 72: N-(3,4-dimethoxyphenyl)-8-methyl-3H-pyrazolo[3,4-c]quinolin-4-amine
Example 73: 1-(4-(4-((8-methyl-3H-pyrazolo[3,4-c]quinolin-4-yl)amino)phenyl)piperazin-1-yl)ethan-1-one
Example 74: 8-methyl-N-(4-morpholinophenyl)-3H-pyrazolo[3,4-c]quinolin-4-amine
Example 75: 8-methyl-N-(3-(methylsulfonyl)phenyl)-3H-pyrazolo[3,4-c]quinolin-4-amine
Example 76: 3-(4-((8-(methylsulfonyl)-3H-pyrazolo[3,4-c]quinolin-4-yl)amino)phenyl)oxazolidin-2-one
Example 77: 8-((8-(methylsulfonyl)-3H-pyrazolo[3,4-c]quinolin-4-yl)amino)-4,5-dihydro-1H-benzo[b]azepin-2(3H)-one
Example 78: 8-(methylsulfonyl)-N-(3-(methylsulfonyl)phenyl)-3H-pyrazolo[3,4-c]quinolin-4-amine
Example 79: 9-methoxy-N-(6-(4-methylpiperazin-1-yl)pyridin-3-yl)-3H-pyrazolo[3,4-c]quinolin-4-amine
Example 80: N-(4-(4-(tert-butyl)piperazin-1-yl)phenyl)-8-(methylsulfonyl)-3H-pyrazolo[3,4-c]quinolin-4-amine
Example 81: N-(6-(4-methylpiperazin-1-yl)pyridin-3-yl)-8-(methylsulfonyl)-3H-pyrazolo[3,4-c]quinolin-4-amine
Example 82: N-cyclopropyl-8-methoxy-3H-pyrazolo[3,4-c]quinolin-4-amine
Example 83: 8-methoxy-N-(1-methyl-1H-pyrazol-4-yl)-2H-pyrazolo[3,4-c]quinolin-4-amine
Example 84: 5-(4-((8-methoxy-2H-pyrazolo[3,4-c]quinolin-4-yl)amino)phenyl)-1,3,4-oxadiazole-2-thiol
Example 85: 8-methoxy-N-(1-(tetrahydro-2H-pyran-4-yl)-1H-pyrazol-4-yl)-2H-pyrazolo[3,4-c]quinolin-4-amine
Example 86: 8-methoxy-N-(4-(4-morpholinopiperidin-1-yl)phenyl)-2H-pyrazolo[3,4-c]quinolin-4-amine
Example 87: N5-(8-methoxy-2H-pyrazolo[3,4-c]quinolin-4-yl)-N2,N2-dimethylpyridine-2,5-diamine
Example 88: 9-methyl-N-(3-(methylsulfonyl)phenyl)-3H-pyrazolo[3,4-c]quinolin-4-amine
Example 89: 9-methyl-N-(4-morpholinophenyl)-3H-pyrazolo[3,4-c]quinolin-4-amine
Example 90: 8-methoxy-N-(3-(methylsulfonyl)-4-morpholinophenyl)-2H-pyrazolo[3,4-c]quinolin-4-amine
Example 91: 1-(4-(5-((8-methoxy-2H-pyrazolo[3,4-c]quinolin-4-yl)amino)pyridin-2-yl)piperazin-1-yl)ethan-1-one
Example 92: 9-(methylsulfonyl)-N-(4-morpholinophenyl)-3H-pyrazolo[3,4-c]quinolin-4-amine
Example 93: 1-(4-(4-((9-(methylsulfonyl)-3H-pyrazolo[3,4-c]quinolin-4-yl)amino)phenyl)piperazin-1-yl)ethan-1-one
Example 94: (4-((9-(methylsulfonyl)-3H-pyrazolo[3,4-c]quinolin-4-yl)amino)phenyl)(morpholino)methanone
Example 95: N-(4-(4-(tert-butyl)piperazin-1-yl)phenyl)-9-(methylsulfonyl)-3H-pyrazolo[3,4-c]quinolin-4-amine
Example 96: 8-methoxy-N-(6-(4-(4-methylpiperazin-1-yl)piperidin-1-yl)pyridin-3-yl)-2H-pyrazolo[3,4-c]quinolin-4-amine
Example 97: N-(4-(4-(4-methylpiperazin-1-yl)piperidin-1-yl)phenyl)-9-(methylsulfonyl)-3H-pyrazolo[3,4-c]quinolin-4-amine
Example 98: 8-((9-(methylsulfonyl)-3H-pyrazolo[3,4-c]quinolin-4-yl)amino)-4,5-dihydro-1H-benzo[b]azepin-2(3H)-one
Example 99: N-(3,4-dimethoxyphenyl)-9-(methylsulfonyl)-3H-pyrazolo[3,4-c]quinolin-4-amine
Example 100: N-(6-(4-methylpiperazin-1-yl)pyridin-3-yl)-9-(methylsulfonyl)-3H-pyrazolo[3,4-c]quinolin-4-amine
Example 101: 7-(methylsulfonyl)-N-(4-morpholinophenyl)-3H-pyrazolo[3,4-c]quinolin-4-amine
Example 102: 9-methoxy-N-(1-(tetrahydro-2H-pyran-4-yl)-1H-pyrazol-4-yl)-3H-pyrazolo[3,4-c]quinolin-4-amine
Example 103: 8-(methylsulfonyl)-N-(1-(tetrahydro-2H-pyran-4-yl)-1H-pyrazol-4-yl)-3H-pyrazolo[3,4-c]quinolin-4-amine
Example 104: N-(1,5-dimethyl-1H-pyrazol-4-yl)-8-methoxy-2H-pyrazolo[3,4-c]quinolin-4-amine
Example 105: N-(1,3-dimethyl-1H-pyrazol-4-yl)-8-methoxy-2H-pyrazolo[3,4-c]quinolin-4-amine
Example 106: 2-((4-((9-(methylsulfonyl)-3H-pyrazolo[3,4-c]quinolin-4-yl)amino)phenyl)amino)ethan-1-ol
Example 107: 9-(methylsulfonyl)-N-(3-(methylsulfonyl)phenyl)-3H-pyrazolo[3,4-c]quinolin-4-amine
Example 108: 9-(methylsulfonyl)-N-(1-(tetrahydro-2H-pyran-4-yl)-1H-pyrazol-4-yl)-3H-pyrazolo[3,4-c]quinolin-4-amine
Example 109: 8-methoxy-N-(1-(2-methoxyethyl)-1H-pyrazol-4-yl)-2H-pyrazolo[3,4-c]quinolin-4-amine
Example 110: 8-methoxy-N-(1-(methylsulfonyl)-1H-pyrazol-4-yl)-2H-pyrazolo[3,4-c]quinolin-4-amine
Example 111: 8-methoxy-N-(1-(1-methylpiperidin-4-yl)-1H-pyrazol-4-yl)-2H-pyrazolo[3,4-c]quinolin-4-amine Example 112: 1-(4-(4-((8-methoxy-2H-pyrazolo[3,4-c]quinolin-4-yl)amino)-1H-pyrazol-1-yl)piperidin-1-yl)ethan-1-one
Example 113: N-(1-(2-methoxyethyl)-1H-pyrazol-4-yl)-8-(methylsulfonyl)-3H-pyrazolo[3,4-c]quinolin-4-amine
Example 114: N-(1-(1-methylpiperidin-4-yl)-1H-pyrazol-4-yl)-8-(methylsulfonyl)-3H-pyrazolo[3,4-c]quinolin-4-amine
Example 115: 1-(4-(4-((8-(methylsulfonyl)-3H-pyrazolo[3,4-c]quinolin-4-yl)amino)-1H-pyrazol-1-yl)piperidin-1-yl)ethan-1-one
Example 116: 9-methoxy-N-(1-(2-methoxyethyl)-1H-pyrazol-4-yl)-2H-pyrazolo[3,4-c]quinolin-4-amine
Example 117: 1-(4-(4-((9-methoxy-3H-pyrazolo[3,4-c]quinolin-4-yl)amino)-1H-pyrazol-1-yl)piperidin-1-yl)ethan-1-one
Example 118: 9-methoxy-N-(1-(1-methylpiperidin-4-yl)-1H-pyrazol-4-yl)-3H-pyrazolo[3,4-c]quinolin-4-amine
Example 119: 8-((7-(methylsulfonyl)-3H-pyrazolo[3,4-c]quinolin-4-yl)amino)-4,5-dihydro-1H-benzo[b]azepin-2(3H)-one
Example 120: 7-(methylsulfonyl)-N-(1-(tetrahydro-2H-pyran-4-yl)-1H-pyrazol-4-yl)-3H-pyrazolo[3,4-c]quinolin-4-amine
Example 121: 8-methoxy-N-(1-methyl-1H-1,2,3-triazol-4-yl)-2H-pyrazolo[3,4-c]quinolin-4-amine
Example 122: 8-methoxy-N-(2-methyl-2H-1,2,3-triazol-4-yl)-2H-pyrazolo[3,4-c]quinolin-4-amine
Example 123: 8-methoxy-N-(1-methyl-1H-pyrazol-3-yl)-2H-pyrazolo[3,4-c]quinolin-4-amine
Example 124: 5-(4-((8-methoxy-2H-pyrazolo[3,4-c]quinolin-4-yl)amino)phenyl)-1,3,4-oxadiazole-2-thiol
Example 125: 8-methoxy-N-(1-(tetrahydro-2H-pyran-4-yl)-1H-pyrazol-4-yl)-2H-pyrazolo[3,4-c]quinolin-4-amine
Example 126: 8-methoxy-N-(4-(4-morpholinopiperidin-1-yl)phenyl)-2H-pyrazolo[3,4-c]quinolin-4-amine
Example 127: N5-(8-methoxy-2H-pyrazolo[3,4-c]quinolin-4-yl)-N2,N2-dimethylpyridine-2,5-diamine
Example 128: 9-methyl-N-(3-(methylsulfonyl)phenyl)-3H-pyrazolo[3,4-c]quinolin-4-amine
Example 129: 9-methyl-N-(4-morpholinophenyl)-3H-pyrazolo[3,4-c]quinolin-4-amine
Example 130: 8-methoxy-N-(3-(methylsulfonyl)-4-morpholinophenyl)-2H-pyrazolo[3,4-c]quinolin-4-amine
Example 131: 1-(4-(5-((8-methoxy-2H-pyrazolo[3,4-c]quinolin-4-yl)amino)pyridin-2-yl)piperazin-1-yl)ethan-1-one
Example 132: 9-(methylsulfonyl)-N-(4-morpholinophenyl)-3H-pyrazolo[3,4-c]quinolin-4-amine
Example 133: 1-(4-(4-((9-(methylsulfonyl)-3H-pyrazolo[3,4-c]quinolin-4-yl)amino)phenyl)piperazin-1-yl)ethan-1-one
Example 134: (4-((9-(methylsulfonyl)-3H-pyrazolo[3,4-c]quinolin-4-yl)amino)phenyl)(morpholino)methanone
Example 135: N-(4-(4-(tert-butyl)piperazin-1-yl)phenyl)-9-(methylsulfonyl)-3H-pyrazolo[3,4-c]quinolin-4-amine
Example 136: 8-methoxy-N-(6-(4-(4-methylpiperazin-1-yl)piperidin-1-yl)pyridin-3-yl)-2H-pyrazolo[3,4-c]quinolin-4-amine
Example 137: N-(4-(4-(4-methylpiperazin-1-yl)piperidin-1-yl)phenyl)-9-(methylsulfonyl)-3H-pyrazolo[3,4-c]quinolin-4-amine
Example 138: 8-((9-(methylsulfonyl)-3H-pyrazolo[3,4-c]quinolin-4-yl)amino)-4,5-dihydro-1H-benzo[b]azepin-2(3H)-one
Example 139: N-(3,4-dimethoxyphenyl)-9-(methylsulfonyl)-3H-pyrazolo[3,4-c]quinolin-4-amine
Example 140: N-(6-(4-methylpiperazin-1-yl)pyridin-3-yl)-9-(methylsulfonyl)-3H-pyrazolo[3,4-c]quinolin-4-amine
Example 141: 7-(methylsulfonyl)-N-(4-morpholinophenyl)-3H-pyrazolo[3,4-c]quinolin-4-amine
Example 142: 9-methoxy-N-(1-(tetrahydro-2H-pyran-4-yl)-1H-pyrazol-4-yl)-3H-pyrazolo[3,4-c]quinolin-4-amine
Example 143: 8-(methylsulfonyl)-N-(1-(tetrahydro-2H-pyran-4-yl)-1H-pyrazol-4-yl)-3H-pyrazolo[3,4-c]quinolin-4-amine
Example 144: N-(1,5-dimethyl-1H-pyrazol-4-yl)-8-methoxy-2H-pyrazolo[3,4-c]quinolin-4-amine
Example 145: N-(1,3-dimethyl-1H-pyrazol-4-yl)-8-methoxy-2H-pyrazolo[3,4-c]quinolin-4-amine
Example 146: 2-((4-((9-(methylsulfonyl)-3H-pyrazolo[3,4-c]quinolin-4-yl)amino)phenyl)amino)ethan-1-ol
Example 147: 9-(methylsulfonyl)-N-(3-(methylsulfonyl)phenyl)-3H-pyrazolo[3,4-c]quinolin-4-amine
Example 148: 9-(methylsulfonyl)-N-(1-(tetrahydro-2H-pyran-4-yl)-1H-pyrazol-4-yl)-3H-pyrazolo[3,4-c]quinolin-4-amine
Example 149: 8-methoxy-N-(1-(2-methoxyethyl)-1H-pyrazol-4-yl)-2H-pyrazolo[3,4-c]quinolin-4-amine
Example 150: 8-methoxy-N-(1-(methylsulfonyl)-1H-pyrazol-4-yl)-2H-pyrazolo[3,4-c]quinolin-4-amine
Example 151: 8-methoxy-N-(1-(1-methylpiperidin-4-yl)-1H-pyrazol-4-yl)-2H-pyrazolo[3,4-c]quinolin-4-amine
Example 152: 1-(4-(4-((8-methoxy-2H-pyrazolo[3,4-c]quinolin-4-yl)amino)-1H-pyrazol-1-yl)piperidin-1-yl)ethan-1-one
Example 153: N-(1-(2-methoxyethyl)-H-pyrazol-4-yl)-8-(methylsulfonyl)-3H-pyrazolo[3,4-c]quinolin-4-amine
Example 154: N-(1-(1-methylpiperidin-4-yl)-1H-pyrazol-4-yl)-8-(methylsulfonyl)-3H-pyrazolo[3,4-c]quinolin-4-amine
Example 155: 1-(4-(4-((8-(methylsulfonyl)-3H-pyrazolo[3,4-c]quinolin-4-yl)amino)-1H-pyrazol-1-yl)piperidin-1-yl)ethan-1-one
Example 156: 9-methoxy-N-(1-(2-methoxyethyl)-1H-pyrazol-4-yl)-2H-pyrazolo[3,4-c]quinolin-4-amine
Example 157: 1-(4-(4-((9-methoxy-3H-pyrazolo[3,4-c]quinolin-4-yl)amino)-1H-pyrazol-1-yl)piperidin-1-yl)ethan-1-one
Example 158: 9-methoxy-N-(1-(1-methylpiperidin-4-yl)-1H-pyrazol-4-yl)-3H-pyrazolo[3,4-c]quinolin-4-amine
Example 159: 8-((7-(methylsulfonyl)-3H-pyrazolo[3,4-c]quinolin-4-yl)amino)-4,5-dihydro-1H-benzo[b]azepin-2(3H)-one
Example 160: 7-(methylsulfonyl)-N-(1-(tetrahydro-2H-pyran-4-yl)-1H-pyrazol-4-yl)-3H-pyrazolo[3,4-c]quinolin-4-amine
Example 161: 8-methoxy-N-(1-methyl-1H-1,2,3-triazol-4-yl)-2H-pyrazolo[3,4-c]quinolin-4-amine
Example 162: 8-methoxy-N-(2-methyl-2H-1,2,3-triazol-4-yl)-2H-pyrazolo[3,4-c]quinolin-4-amine
Example 163: 8-methoxy-N-(1-methyl-1H-pyrazol-3-yl)-2H-pyrazolo[3,4-c]quinolin-4-amine
Example 164: 2-(4-((8-methoxy-2H-pyrazolo[3,4-c]quinolin-4-yl)amino)-1H-pyrazol-1-yl)-2-methylpropanamide
Example 165: 8-methoxy-N-(2-methyl-2H-tetrazol-5-yl)-2H-pyrazolo[3,4-c]quinolin-4-amine
Example 166: 8-methoxy-N-(1-methyl-1H-imidazol-4-yl)-2H-pyrazolo[3,4-c]quinolin-4-amine
Example 167: N-(1-(1-methylpiperidin-4-yl)-1H-pyrazol-4-yl)-7-(methylsulfonyl)-3H-pyrazolo[3,4-c]quinolin-4-amine Example 168: 1-(4-(4-((7-(methylsulfonyl)-3H-pyrazolo[3,4-c]quinolin-4-yl)amino)-1H-pyrazol-1-yl)piperidin-1-yl)ethan-1-one Example 169: 7-(methylsulfonyl)-N-(1-(tetrahydro-2H-pyran-4-yl)-1H-pyrazol-4-yl)-3H-pyrazolo[3,4-c]quinolin-4-amine Example 170: N-(1-(2-methoxyethyl)-1H-pyrazol-4-yl)-7-(methylsulfonyl)-3H-pyrazolo[3,4-c]quinolin-4-amine Example 171: N-(1-(2-methoxyethyl)-1H-pyrazol-4-yl)-7-(methylthio)-3H-pyrazolo[3,4-c]quinolin-4-amine Example 172: 2-methyl-2-(4-((8-(methylsulfonyl)-3H-pyrazolo[3,4-c]quinolin-4-yl)amino)-1H-pyrazol-1-yl)propanenitrile Example 173: 8-(methylsulfonyl)-N-(1-(oxetan-3-yl)-1H-pyrazol-4-yl)-3H-pyrazolo[3,4-c]quinolin-4-amine Example 174: (2-fluoro-4-((7-(methylsulfonyl)-3H-pyrazolo[3,4-c]quinolin-4-yl)amino)phenyl)(morpholino)methanone Example 175: (2-fluoro-4-((8-(methylsulfonyl)-3H-pyrazolo[3,4-c]quinolin-4-yl)amino)phenyl)(morpholino)methanone Example 176: 4-((8-methoxy-2H-pyrazolo[3,4-c]quinolin-4-yl)amino)pyridin-2(1H)-one Example 177: 4-((8-methoxy-2H-pyrazolo[3,4-c]quinolin-4-yl)amino)-1-methylpyridin-2(1H)-one Example 178: N-(1-(3-methoxypropyl)-1H-pyrazol-4-yl)-8-(methylsulfonyl)-3H-pyrazolo[3,4-c]quinolin-4-amine Example 179: 1-(4-((8-(methylsulfonyl)-3H-pyrazolo[3,4-c]quinolin-4-yl)amino)-1H-pyrazol-1-yl)cyclohexanecarbonitrile Example 180: N-(1-isopropyl-1H-pyrazol-4-yl)-8-(methylsulfonyl)-3H-pyrazolo[3,4-c]quinolin-4-amine Example 181: N-(1-(tert-butyl)-1H-pyrazol-4-yl)-9-methoxy-3H-pyrazolo[3,4-c]quinolin-4-amine Example 182: N-(1-isopropyl-1H-pyrazol-4-yl)-9-methoxy-3H-pyrazolo[3,4-c]quinolin-4-amine Example 183: 9-methoxy-N-(1-(3-methoxypropyl)-1H-pyrazol-4-yl)-3H-pyrazolo[3,4-c]quinolin-4-amine Example 184: 2-(4-((9-methoxy-3H-pyrazolo[3,4-c]quinolin-4-yl)amino)-1H-pyrazol-1-yl)-2-methylpropanenitrile Example 185: 1-(4-((9-methoxy-3H-pyrazolo[3,4-c]quinolin-4-yl)amino)-1H-pyrazol-1-yl)cyclohexanecarbonitrile Example 186: 2-(4-((8-(methylsulfonyl)-3H-pyrazolo[3,4-c]quinolin-4-yl)amino)-1H-pyrazol-1-yl)ethan-1-ol Example 187: N-(1-isobutyl-1H-pyrazol-4-yl)-8-(methylsulfonyl)-3H-pyrazolo[3,4-c]quinolin-4-amine Example 188: N-(1-(tert-butyl)-1H-pyrazol-4-yl)-7-(methylsulfonyl)-3H-pyrazolo[3,4-c]quinolin-4-amine Example 189: N-(1-isopropyl-1H-pyrazol-4-yl)-7-(methylsulfonyl)-3H-pyrazolo[3,4-c]quinolin-4-amine Example 190: N-(1-(3-methoxypropyl)-1H-pyrazol-4-yl)-7-(methylsulfonyl)-3H-pyrazolo[3,4-c]quinolin-4-amine Example 191: 2-methyl-2-(4-((7-(methylsulfonyl)-3H-pyrazolo[3,4-c]quinolin-4-yl)amino)-1H-pyrazol-1-yl)propanenitrile Example 192: N-(1-isobutyl-1H-pyrazol-4-yl)-7-(methylsulfonyl)-3H-pyrazolo[3,4-c]quinolin-4-amine Example 193: 2-(4-((7-(methylsulfonyl)-3H-pyrazolo[3,4-c]quinolin-4-yl)amino)-1H-pyrazol-1-yl)ethan-1-ol Example 194: (3-methoxy-4-((7-(methylsulfonyl)-3H-pyrazolo[3,4-c]quinolin-4-yl)amino)phenyl)(morpholino)methanone Example 195: N-(1-(tert-butyl)-1H-pyrazol-4-yl)-8-(methylsulfonyl)-3H-pyrazolo[3,4-c]quinolin-4-amine Example 196: (3-methoxy-4-((8-(methylsulfonyl)-3H-pyrazolo[3,4-c]quinolin-4-yl)amino)phenyl)(morpholino)methanone Example 197: N-(1-cyclopropyl-1H-pyrazol-4-yl)-7-(methylsulfonyl)-3H-pyrazolo[3,4-c]quinolin-4-amine Example 198: N-(1-isobutyl-1H-pyrazol-4-yl)-9-methoxy-3H-pyrazolo[3,4-c]quinolin-4-amine Example 199: 2-(4-((9-methoxy-3H-pyrazolo[3,4-c]quinolin-4-yl)amino)-1H-pyrazol-1-yl)ethan-1-ol Example 200: (3-methoxy-4-((9-methoxy-3H-pyrazolo[3,4-c]quinolin-4-yl)amino)phenyl)(morpholino)methanone Example 201: N-(1-cyclopropyl-1H-pyrazol-4-yl)-9-methoxy-3H-pyrazolo[3,4-c]quinolin-4-amine Example 202: 1-methyl-3-((8-(methylsulfonyl)-3H-pyrazolo[3,4-c]quinolin-4-yl)amino)pyridin-2(1H)-one Example 203: N-(1-cyclopropyl-1H-pyrazol-4-yl)-8-(methylsulfonyl)-3H-pyrazolo[3,4-c]quinolin-4-amine Example 204: 9-methoxy-N-(1-(1-methoxy-2-methylpropan-2-yl)-1H-pyrazol-4-yl)-3H-pyrazolo[3,4-c]quinolin-4-amine Example 205: 9-methoxy-N-(1-(2-methoxyethyl)-3-methyl-1H-pyrazol-4-yl)-3H-pyrazolo[3,4-c]quinolin-4-amine Example 206: N-(1-(1-(tert-butyl)piperidin-4-yl)-1H-pyrazol-4-yl)-9-methoxy-3H-pyrazolo[3,4-c]quinolin-4-amine Example 207: 9-methoxy-N-(3-methyl-1-(tetrahydro-2H-pyran-4-yl)-1H-pyrazol-4-yl)-3H-pyrazolo[3,4-c]quinolin-4-amine Example 208: N-(1-(1-methoxy-2-methylpropan-2-yl)-1H-pyrazol-4-yl)-8-(methylsulfonyl)-3H-pyrazolo[3,4-c]quinolin-4-amine Example 209: N-(1-(2-methoxyethyl)-3-methyl-1H-pyrazol-4-yl)-8-(methylsulfonyl)-3H-pyrazolo[3,4-c]quinolin-4-amine Example 210: N-(1-(2-methoxyethyl)-5-methyl-1H-pyrazol-4-yl)-8-(methylsulfonyl)-3H-pyrazolo[3,4-c]quinolin-4-amine Example 211: N-(1-(1-(tert-butyl)piperidin-4-yl)-1H-pyrazol-4-yl)-8-(methylsulfonyl)-3H-pyrazolo[3,4-c]quinolin-4-amine Example 212: N-(1-(tert-butyl)-1H-pyrazol-3-yl)-8-(methylsulfonyl)-3H-pyrazolo[3,4-c]quinolin-4-amine Example 213: N-(1-isopropyl-3-methyl-1H-pyrazol-4-yl)-8-(methylsulfonyl)-3H-pyrazolo[3,4-c]quinolin-4-amine Example 214: N-(1-isopropyl-5-methyl-1H-pyrazol-4-yl)-8-(methylsulfonyl)-3H-pyrazolo[3,4-c]quinolin-4-amine Example 215: N-(5-methyl-1-(tetrahydro-2H-pyran-4-yl)-1H-pyrazol-4-yl)-8-(methylsulfonyl)-3H-pyrazolo[3,4-c]quinolin-4-amine Example 216: N-(3-methyl-1-(tetrahydro-2H-pyran-4-yl)-1H-pyrazol-4-yl)-8-(methylsulfonyl)-3H-pyrazolo[3,4-c]quinolin-4-amine Example 217: N-(1-isopropyl-3-methyl-1H-pyrazol-4-yl)-8-(methylsulfonyl)-3H-pyrazolo[3,4-c]quinolin-4-amine Example 218: N-(1-isopropyl-5-methyl-1H-pyrazol-4-yl)-8-(methylsulfonyl)-3H-pyrazolo[3,4-c]quinolin-4-amine Example 219: N-(1-isopropyl-5-methyl-1H-pyrazol-4-yl)-9-methoxy-3H-pyrazolo[3,4-c]quinolin-4-amine Example 220: N-(1-isopropyl-3-methyl-1H-pyrazol-4-yl)-9-methoxy-3H-pyrazolo[3,4-c]quinolin-4-amine Example 221: N-(1-(2-fluoroethyl)-1H-pyrazol-4-yl)-8-(methylsulfonyl)-3H-pyrazolo[3,4-c]quinolin-4-amine Example 222: N-(1-isopropyl-3-methyl-1H-pyrazol-4-yl)-9-methoxy-3H-pyrazolo[3,4-c]quinolin-4-amine Example 223: N-(1-isopropyl-5-methyl-1H-pyrazol-4-yl)-9-methoxy-3H-pyrazolo[3,4-c]quinolin-4-amine Example 224: N-(1-isopropyl-3-methoxy-1H-pyrazol-4-yl)-9-methoxy-3H-pyrazolo[3,4-c]quinolin-4-amine Example 225: N-(1-(1-(tert-butyl)piperidin-4-yl)-3-methoxy-1H-pyrazol-4-yl)-9-methoxy-3H-pyrazolo[3,4-c]quinolin-4-amine Example 226: N-(1-isopropyl-3-methoxy-1H-pyrazol-4-yl)-8-(methylsulfonyl)-3H-pyrazolo[3,4-c]quinolin-4-amine Example 227: N-(1-isopropyl-5-methoxy-1H-pyrazol-4-yl)-8-(methylsulfonyl)-3H-pyrazolo[3,4-c]quinolin-4-amine Example 228: N-(1-(1-(tert-butyl)piperidin-4-yl)-3-methoxy-1H-pyrazol-4-yl)-8-(methylsulfonyl)-3H-pyrazolo[3,4-c]quinolin-4-amine Example 229: N-(1-(1-(tert-butyl)piperidin-4-yl)-5-methoxy-1H-pyrazol-4-yl)-8-(methylsulfonyl)-3H-pyrazolo[3,4-c]quinolin-4-amine Example 230: N-(2-chloro-5-(methylsulfonyl)thiophen-3-yl)-8-(methylsulfonyl)-3H-pyrazolo[3,4-c]quinolin-4-amine Example 231: N-(3-methoxy-1-(3-methoxypropyl)-1H-pyrazol-4-yl)-8-(methylsulfonyl)-3H-pyrazolo[3,4-c]quinolin-4-amine Example 232: N-(5-methoxy-1-(3-methoxypropyl)-1H-pyrazol-4-yl)-8-(methylsulfonyl)-3H-pyrazolo[3,4-c]quinolin-4-amine Example 233: N-(5-chloro-1-isopropyl-1H-pyrazol-4-yl)-8-(methylsulfonyl)-3H-pyrazolo[3,4-c]quinolin-4-amine Example 234: N-(1-isopropyl-3,5-dimethyl-1H-pyrazol-4-yl)-9-methoxy-3H-pyrazolo[3,4-c]quinolin-4-amine Example 235: N-(5-chloro-1-(3-methoxypropyl)-1H-pyrazol-4-yl)-9-methoxy-3H-pyrazolo[3,4-c]quinolin-4-amine Example 236: 9-methoxy-N-(1-(piperidin-4-yl)-1H-pyrazol-4-yl)-3H-pyrazolo[3,4-c]quinolin-4-amine Example 237: N-(5-chloro-1-(3-methoxypropyl)-1H-pyrazol-4-yl)-8-(methylsulfonyl)-3H-pyrazolo[3,4-c]quinolin-4-amine Example 238: N-(1-isopropyl-3,5-dimethyl-1H-pyrazol-4-yl)-8-(methylsulfonyl)-3H-pyrazolo[3,4-c]quinolin-4-amine Example 239: N-(3-cyclopropyl-1-methyl-1H-pyrazol-5-yl)-8-(methylsulfonyl)-3H-pyrazolo[3,4-c]quinolin-4-amine Example 240: 3-(3-methoxy-4-((8-(methylsulfonyl)-3H-pyrazolo[3,4-c]quinolin-4-yl)amino)phenyl)oxazolidin-2-one Example 241: N-(5-chloro-1-(2-methoxyethyl)-1H-pyrazol-4-yl)-9-methoxy-3H-pyrazolo[3,4-c]quinolin-4-amine Example 242: N-(5-chloro-1-(2-methoxyethyl)-1H-pyrazol-4-yl)-8-(methylsulfonyl)-3H-pyrazolo[3,4-c]quinolin-4-amine Example 243: N-(5-chloro-1-(2-methoxyethyl)-1H-pyrazol-4-yl)-7-(methylsulfonyl)-3H-pyrazolo[3,4-c]quinolin-4-amine Example 244: N-(1-isopropyl-5-methyl-1H-pyrazol-4-yl)-7-(methylsulfonyl)-3H-pyrazolo[3,4-c]quinolin-4-amine Example 245: 6-((9-methoxy-3H-pyrazolo[3,4-c]quinolin-4-yl)amino)-1,3-dimethylpyrimidine-2,4(1H,3H)-dione Example 246: 1-isopropyl-4-((8-(methylsulfonyl)-3H-pyrazolo[3,4-c]quinolin-4-yl)amino)-1H-pyrazole-3-carbonitrile Example 247: 1-isopropyl-4-((8-(methylsulfonyl)-3H-pyrazolo[3,4-c]quinolin-4-yl)amino)-1H-pyrazole-5-carbonitrile Example 248: 1-(2-methoxyethyl)-4-((8-(methylsulfonyl)-3H-pyrazolo[3,4-c]quinolin-4-yl)amino)-1H-pyrazole-3-carbonitrile Example 249: 1-(2-methoxyethyl)-4-((8-(methylsulfonyl)-3H-pyrazolo[3,4-c]quinolin-4-yl)amino)-1H-pyrazole-5-carbonitrile Example 250: 1-isopropyl-4-((8-(methylsulfonyl)-3H-pyrazolo[3,4-c]quinolin-4-yl)amino)-1H-pyrazole-3-carboxamide Example 251: 1-isopropyl-4-((8-(methylsulfonyl)-3H-pyrazolo[3,4-c]quinolin-4-yl)amino)-1H-pyrazole-5-carboxamide Example 252: 1,3-dimethyl-6-((8-(methylsulfonyl)-3H-pyrazolo[3,4-c]quinolin-4-yl)amino)pyrimidine-2,4(1H,3H)-dione Example 253: N-(1-(2-fluoroethyl)-1H-pyrazol-4-yl)-9-methoxy-3H-pyrazolo[3,4-c]quinolin-4-amine Example 254: N-(5-chloro-1-(piperidin-4-yl)-1H-pyrazol-4-yl)-9-methoxy-3H-pyrazolo[3,4-c]quinolin-4-amine Example 255: N-(5-chloro-1-(tetrahydro-2H-pyran-4-yl)-1H-pyrazol-4-yl)-9-methoxy-3H-pyrazolo[3,4-c]quinolin-4-amine Example 256: 1-(4-((9-methoxy-3H-pyrazolo[3,4-c]quinolin-4-yl)amino)-1H-pyrazol-1-yl)-2-methylpropan-2-ol Example 257: 9-methoxy-N-(1-(2,2,2-trifluoroethyl)-1H-pyrazol-4-yl)-3H-pyrazolo[3,4-c]quinolin-4-amine Example 258: 9-methoxy-N-(1-(2-methylallyl)-1H-pyrazol-4-yl)-3H-pyrazolo[3,4-c]quinolin-4-amine Example 259: 9-methoxy-N-(1-(2-methylprop-1-en-1-yl)-1H-pyrazol-4-yl)-3H-pyrazolo[3,4-c]quinolin-4-amine Example 260: N-(1,2-dimethyl-1H-imidazol-5-yl)-8-(methylsulfonyl)-3H-pyrazolo[3,4-c]quinolin-4-amine Example 261: 8-(methylsulfonyl)-N-(1-(2,2,2-trifluoroethyl)-1H-pyrazol-4-yl)-3H-pyrazolo[3,4-c]quinolin-4-amine Example 262: 2-methyl-1-(4-((8-(methylsulfonyl)-3H-pyrazolo[3,4-c]quinolin-4-yl)amino)-1H-pyrazol-1-yl)propan-2-ol Example 263: N-(1-(2-methylprop-1-en-1-yl)-1H-pyrazol-4-yl)-8-(methylsulfonyl)-3H-pyrazolo[3,4-c]quinolin-4-amine Example 264: N-(1-(2-methylallyl)-1H-pyrazol-4-yl)-8-(methylsulfonyl)-3H-pyrazolo[3,4-c]quinolin-4-amine Example 265: N-(5-chloro-1-(tetrahydro-2H-pyran-4-yl)-1H-pyrazol-4-yl)-8-(methylsulfonyl)-3H-pyrazolo[3,4-c]quinolin-4-amine Example 266: 1-isopropyl-4-((9-methoxy-3H-pyrazolo[3,4-c]quinolin-4-yl)amino)-1H-pyrazole-5-carboxamide Example 267: 9-methoxy-N-(1-(2-methoxyethyl)-3-(trifluoromethyl)-1H-pyrazol-4-yl)-3H-pyrazolo[3,4-c]quinolin-4-amine Example 268: 9-methoxy-N-(1-(2-methoxyethyl)-5-(trifluoromethyl)-1H-pyrazol-4-yl)-3H-pyrazolo[3,4-c]quinolin-4-amine Example 269: N-(1-(2-fluoroethyl)-3-methyl-1H-pyrazol-4-yl)-8-(methylsulfonyl)-3H-pyrazolo[3,4-c]quinolin-4-amine Example 270: N-(1-(2-fluoroethyl)-5-methyl-1H-pyrazol-4-yl)-8-(methylsulfonyl)-3H-pyrazolo[3,4-c]quinolin-4-amine Example 271: N-(1-(2-methoxyethyl)-3-(trifluoromethyl)-1H-pyrazol-4-yl)-8-(methylsulfonyl)-3H-pyrazolo[3,4-c]quinolin-4-amine Example 272: N-(1-(2-methoxyethyl)-5-(trifluoromethyl)-1H-pyrazol-4-yl)-8-(methylsulfonyl)-3H-pyrazolo[3,4-c]quinolin-4-amine Example 273: 1-(2-methoxyethyl)-4-((8-(methylsulfonyl)-3H-pyrazolo[3,4-c]quinolin-4-yl)amino)-1H-pyrazole-5-carbonitrile Example 274: 1-(2-methoxyethyl)-4-((8-(methylsulfonyl)-3H-pyrazolo[3,4-c]quinolin-4-yl)amino)-1H-pyrazole-3-carbonitrile Example 275: N-(5-bromo-1-(2-methoxyethyl)-1H-pyrazol-4-yl)-9-methoxy-3H-pyrazolo[3,4-c]quinolin-4-amine Example 276: N-(5-fluoro-1-(2-methoxyethyl)-1H-pyrazol-4-yl)-9-methoxy-3H-pyrazolo[3,4-c]quinolin-4-amine Example 277: N4-(9-methoxy-3H-pyrazolo[3,4-c]quinolin-4-yl)-1-(2-methoxyethyl)-N5,N5-dimethyl-1H-pyrazole-4,5-diamine Example 278: N-(2-isopropyl-1-methyl-1H-imidazol-5-yl)-9-methoxy-3H-pyrazolo[3,4-c]quinolin-4-amine Example 279: N-(5-bromo-1-(2-methoxyethyl)-1H-pyrazol-4-yl)-8-(methylsulfonyl)-3H-pyrazolo[3,4-c]quinolin-4-amine Example 280: 1-(2-methoxyethyl)-N5,N5-dimethyl-N4-(8-(methylsulfonyl)-3H-pyrazolo[3,4-c]quinolin-4-yl)-1H-pyrazole-4,5-diamine Example 281: N-(5-methyl-1-(tetrahydro-2H-pyran-4-yl)-1H-pyrazol-4-yl)-8-(methylsulfonyl)-3H-pyrazolo[3,4-c]quinolin-4-amine Example 282: N-(1-(2-methoxyethyl)-5-methyl-1H-pyrazol-4-yl)-8-(methylsulfonyl)-3H-pyrazolo[3,4-c]quinolin-4-amine Example 283: N-(2-methyl-3-morpholinophenyl)-8-(methylsulfonyl)-3H-pyrazolo[3,4-c]quinolin-4-amine Example 284: N-(2-isopropyl-1-methyl-1H-imidazol-5-yl)-8-(methylsulfonyl)-3H-pyrazolo[3,4-c]quinolin-4-amine Example 285: N-(1-isobutyl-1H-pyrazol-4-yl)-8-methoxy-3H-pyrazolo[3,4-c]quinolin-4-amine Example 286: N-(1-(tert-butyl)-1H-pyrazol-4-yl)-8-methoxy-3H-pyrazolo[3,4-c]quinolin-4-amine Example 287: 8-methoxy-N-(1-(3-methoxypropyl)-1H-pyrazol-4-yl)-3H-pyrazolo[3,4-c]quinolin-4-amine Example 288: 6,8-dimethoxy-N-(4-morpholinophenyl)-3H-pyrazolo[3,4-c]quinolin-4-amine Example 289: 6,8-dimethoxy-N-(1-(tetrahydro-2H-pyran-4-yl)-1H-pyrazol-4-yl)-3H-pyrazolo[3,4-c]quinolin-4-amine Example 290: 6,8-dimethoxy-N-(1-(3-methoxypropyl)-1H-pyrazol-4-yl)-3H-pyrazolo[3,4-c]quinolin-4-amine Example 291: N-(1-(2-fluoroethyl)-1H-pyrazol-4-yl)-8-methoxy-3H-pyrazolo[3,4-c]quinolin-4-amine Example 292: N-(1-isopropyl-1H-pyrazol-4-yl)-8-methoxy-3H-pyrazolo[3,4-c]quinolin-4-amine Example 293: N-(1-cyclopropyl-1H-pyrazol-4-yl)-8-methoxy-3H-pyrazolo[3,4-c]quinolin-4-amine Example 294: N-(1-isopropyl-1H-pyrazol-4-yl)-6,8-dimethoxy-3H-pyrazolo[3,4-c]quinolin-4-amine Example 295: N-(1-(1-(tert-butyl)piperidin-4-yl)-1H-pyrazol-4-yl)-6,8-dimethoxy-3H-pyrazolo[3,4-c]quinolin-4-amine Example 296: 1-(4-((8-methoxy-3H-pyrazolo[3,4-c]quinolin-4-yl)amino)phenyl)piperidin-4-ol Example 297: 2-(4-(4-((8-methoxy-3H-pyrazolo[3,4-c]quinolin-4-yl)amino)phenyl)piperazin-1-yl)ethan-1-ol Example 298: 1-(4-((8-methoxy-3H-pyrazolo[3,4-c]quinolin-4-yl)amino)-1H-pyrazol-1-yl)-2-methylpropan-2-ol Example 299: N-(1-(tert-butyl)-1H-pyrazol-4-yl)-8-methoxy-3H-pyrazolo[3,4-c]quinolin-4-amine Example 300: N-(1-(1-(tert-butyl)piperidin-4-yl)-1H-pyrazol-4-yl)-8-methoxy-3H-pyrazolo[3,4-c]quinolin-4-amine Example 301: 2-(4-((8-methoxy-3H-pyrazolo[3,4-c]quinolin-4-yl)amino)-1H-pyrazol-1-yl)-2-methylpropanenitrile Example 302: N-(3,4-dimethoxyphenyl)-7-(methylsulfonyl)-3H-pyrazolo[3,4-c]quinolin-4-amine Example 303: 2-(4-(4-((7-(methylsulfonyl)-3H-pyrazolo[3,4-c]quinolin-4-yl)amino)phenyl)piperazin-1-yl)ethan-1-ol Example 304: 6-methoxy-N-(4-morpholinophenyl)-3H-pyrazolo[3,4-c]quinolin-4-amine Example 305: N-(1-isopropyl-1H-pyrazol-4-yl)-6-methoxy-3H-pyrazolo[3,4-c]quinolin-4-amine Example 306: 6-methoxy-N-(1-(3-methoxypropyl)-1H-pyrazol-4-yl)-3H-pyrazolo[3,4-c]quinolin-4-amine Example 307: 6-methoxy-N-(1-(tetrahydro-2H-pyran-4-yl)-1H-pyrazol-4-yl)-3H-pyrazolo[3,4-c]quinolin-4-amine Example 308: (4-((6,8-dimethoxy-3H-pyrazolo[3,4-c]quinolin-4-yl)amino)phenyl)(morpholino)methanone Example 309: 2-(4-(4-((8-(methylsulfonyl)-3H-pyrazolo[3,4-c]quinolin-4-yl)amino)phenyl)piperazin-1-yl)ethan-1-ol Example 310: N-(1-(1-(tert-butyl)piperidin-4-yl)-1H-pyrazol-4-yl)-8-(methylsulfonyl)-3H-pyrazolo[3,4-c]quinolin-4-amine Example 311: 2-(4-((8-methoxy-2H-pyrazolo[3,4-c]quinolin-4-yl)amino)-1H-pyrazol-1-yl)-N,N-dimethylacetamide Example 312: 8-methoxy-N-(1-(pyrrolidin-3-yl)-1H-pyrazol-4-yl)-2H-pyrazolo[3,4-c]quinolin-4-amine Example 313: N-(1-(1,3-dimethoxypropan-2-yl)-1H-pyrazol-4-yl)-8-methoxy-2H-pyrazolo[3,4-c]quinolin-4-amine Example 314: 8-methoxy-N-(1-(tetrahydro-2H-pyran-3-yl)-1H-pyrazol-4-yl)-2H-pyrazolo[3,4-c]quinolin-4-amine Example 315: N-(1-(2-methoxy-2-methylpropyl)-1H-pyrazol-4-yl)-8-(methylsulfonyl)-3H-pyrazolo[3,4-c]quinolin-4-amine Example 316: 1-(4-((8-(methylsulfonyl)-3H-pyrazolo[3,4-c]quinolin-4-yl)amino)phenyl)piperidin-4-ol Example 317: 2-methyl-1-(4-((8-(methylsulfonyl)-3H-pyrazolo[3,4-c]quinolin-4-yl)amino)-1H-pyrazol-1-yl)propan-2-ol Example 318: 4-ethyl-6-((8-methoxy-2H-pyrazolo[3,4-c]quinolin-4-yl)amino)-2H-benzo[b][1,4]oxazin-3(4H)-one Example 319: 8-methoxy-N-(1-(pyridin-2-yl)-1H-pyrazol-4-yl)-2H-pyrazolo[3,4-c]quinolin-4-amine Example 320: 8-methoxy-N-(1-(1-phenylethyl)-1H-pyrazol-4-yl)-2H-pyrazolo[3,4-c]quinolin-4-amine Example 321: 8-methoxy-N-(1-(3-methylbutan-2-yl)-1H-pyrazol-4-yl)-2H-pyrazolo[3,4-c]quinolin-4-amine Example 322: 6-((8-methoxy-2H-pyrazolo[3,4-c]quinolin-4-yl)amino)-4-methyl-2H-benzo[b][1,4]oxazin-3(4H)-one Example 323: 8-(methylsulfonyl)-N-(1-(tetrahydro-2H-pyran-3-yl)-1H-pyrazol-4-yl)-2H-pyrazolo[3,4-c]quinolin-4-amine Example 324: N-(1-(3-methylbutan-2-yl)-1H-pyrazol-4-yl)-8-(methylsulfonyl)-2H-pyrazolo[3,4-c]quinolin-4-amine Example 325: 2-methyl-1-(3-methyl-4-((8-(methylsulfonyl)-2H-pyrazolo[3,4-c]quinolin-4-yl)amino)-1H-pyrazol-1-yl)propan-2-ol Example 326: 2-methyl-1-(5-methyl-4-((8-(methylsulfonyl)-2H-pyrazolo[3,4-c]quinolin-4-yl)amino)-1H-pyrazol-1-yl)propan-2-ol Example 327: 8-(methylsulfonyl)-N-(1-(pyrrolidin-3-yl)-1H-pyrazol-4-yl)-2H-pyrazolo[3,4-c]quinolin-4-amine Example 328: 4-methyl-6-((8-(methylsulfonyl)-2H-pyrazolo[3,4-c]quinolin-4-yl)amino)-2H-benzo[b][1,4]oxazin-3(4H)-one Example 329: 2-methyl-1-(4-((7-(methylsulfonyl)-3H-pyrazolo[3,4-c]quinolin-4-yl)amino)-1H-pyrazol-1-yl)propan-2-ol Example 330: 8-(methylsulfonyl)-N-(1-(pentan-3-yl)-1H-pyrazol-4-yl)-2H-pyrazolo[3,4-c]quinolin-4-amine Example 331: N-(3-((8-(methylsulfonyl)-2H-pyrazolo[3,4-c]quinolin-4-yl)amino)phenyl)acetamide
Example 332: N-(2-methoxy-5-((8-(methylsulfonyl)-2H-pyrazolo[3,4-c]quinolin-4-yl)amino)phenyl)acetamide
Example 333: N-(3-ethylphenyl)-8-(methylsulfonyl)-2H-pyrazolo[3,4-c]quinolin-4-amine
Example 334: 2-(4-((8-(methylsulfonyl)-2H-pyrazolo[3,4-c]quinolin-4-yl)amino)-1H-pyrazol-1-yl)propanoic acid
Example 335: 5-((8-(methylsulfonyl)-2H-pyrazolo[3,4-c]quinolin-4-yl)amino)-1H-pyrazole-3-carboxylic acid
Example 336: 2-((8-(methylsulfonyl)-2H-pyrazolo[3,4-c]quinolin-4-yl)amino)phenol
Example 337: (S)—N-(3-(2-methylpyrrolidin-1-yl)phenyl)-8-(methylsulfonyl)-2H-pyrazolo[3,4-c]quinolin-4-amine
Example 338: (S)-8-methoxy-N-(3-(2-methylpyrrolidin-1-yl)phenyl)-2H-pyrazolo[3,4-c]quinolin-4-amine
Example 339: 2-(4-((9-methoxy-3H-pyrazolo[3,4-c]quinolin-4-yl)amino)-1H-pyrazol-1-yl)-N,N-dimethylacetamide
Example 340: N-(1-(1,3-dimethoxypropan-2-yl)-1H-pyrazol-4-yl)-9-methoxy-3H-pyrazolo[3,4-c]quinolin-4-amine
Example 341: 8-(methylsulfonyl)-N-(1-(pyridin-2-yl)-1H-pyrazol-4-yl)-2H-pyrazolo[3,4-c]quinolin-4-amine
Example 342: 4-ethyl-6-((8-(methylsulfonyl)-2H-pyrazolo[3,4-c]quinolin-4-yl)amino)-2H-benzo[b][1,4]oxazin-3(4H)-one
Example 343: 6-((8-(methylsulfonyl)-2H-pyrazolo[3,4-c]quinolin-4-yl)amino)-2H-benzo[b][1,4]oxazin-3(4H)-one
Example 344: 6-((8-(methylsulfonyl)-2H-pyrazolo[3,4-c]quinolin-4-yl)amino)-2H-benzo[b][1,4]thiazin-3(4H)-one
Example 345: 7-((8-(methylsulfonyl)-2H-pyrazolo[3,4-c]quinolin-4-yl)amino)-3,4-dihydroquinolin-2(1H)-one
Example 346: N1-8-(methylsulfonyl)-2H-pyrazolo[3,4-c]quinolin-4-yl)benzene-1,2-diamine
Example 347: 2-(4-((8-methoxy-2H-pyrazolo[3,4-c]quinolin-4-yl)amino)-1H-pyrazol-1-yl)propanoic acid
Example 348: 7-bromo-N-(1-(tetrahydro-2H-pyran-4-yl)-1H-pyrazol-4-yl)-2H-pyrazolo[3,4-c]quinolin-4-amine
Example 349: 4-((8-(methylsulfonyl)-2H-pyrazolo[3,4-c]quinolin-4-yl)amino)phenol
Example 350: cyclopropyl(7-((8-(methylsulfonyl)-2H-pyrazolo[3,4-c]quinolin-4-yl)amino)-3,4-dihydroquinolin-1(2H)-yl)methanone
Example 351: 4,5-dimethoxy-N-(8-(methylsulfonyl)-2H-pyrazolo[3,4-c]quinolin-4-yl)benzene-1,2-diamine
Example 352: N-(2-(4-acetylpiperazin-1-yl)-5-((8-(methylsulfonyl)-2H-pyrazolo[3,4-c]quinolin-4-yl)amino)phenyl)acetamide
Example 353: N-(1-((1R,2S)-2-methoxycyclohexyl)-1H-pyrazol-4-yl)-8-(methylsulfonyl)-2H-pyrazolo[3,4-c]quinolin-4-amine
Example 354: 5-((8-(methylsulfonyl)-2H-pyrazolo[3,4-c]quinolin-4-yl)amino)-2-morpholinobenzonitrile
Example 355: 6-bromo-N-(1-(tetrahydro-2H-pyran-4-yl)-1H-pyrazol-4-yl)-3H-pyrazolo[3,4-c]quinolin-4-amine Example 15: 9-methoxy-N-(4-(morpholinomethyl)phenyl)-3H-pyrazolo[3,4-c]quinolin-4-amine 4-chloro-9-methoxy-2-(4-methoxybenzyl)-2H-pyrazolo[3,4-c]quinoline (0.16 mmol) and (4-amino-phenyl)-morpholin-4-yl-methanone (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The residue was dissolved in TFA (3 mL). The reaction mixture was irradiated in a microwave reactor for 5 min at 140° C. The reaction mixture was concentrated and dissolved in THF (dry) LiAlH$_4$ powder was added (excess, 2 by 2 eq) until completion of reaction is observed (by LCMS). The reaction was quenched with water (1 mL per gram LiAlH$_4$), then NaOH (ca. 15% aq., 1 mL per g LiAlH$_4$), water (3 mL per gram LiALH$_4$). The mixture was filtered, washed with THF, MeOH, MeCN (ca. 10 mL each).

The reaction mixture was concentrated and purified by semi-preparative HPLC-MS and freeze dried from water/t-BuOH 4/1.

exact mass: 389.2203 g/mol
HPLC-MS: analytical method B
rt: 2.20 min—found mass: 390.2 (m/z+H)

The following examples were synthesized according to the protocol of Example 15:

Example 22: 8-methoxy-N-(4-((4-(4-methylpiperazin-1-yl)piperidin-1-yl)methyl)phenyl)-2H-pyrazolo[3,4-c]quinolin-4-amine
Example 23: 8-methoxy-N-(3-(morpholinomethyl)phenyl)-2H-pyrazolo[3,4-c]quinolin-4-amine
Example 30: 9-fluoro-N-(4-(morpholinomethyl)phenyl)-3H-pyrazolo[3,4-c]quinolin-4-amine Example 70: 8-cyclopropyl-N-(3,4-dimethoxyphenyl)-3H-pyrazolo[3,4-c]quinolin-4-amine 4-chloro-8-iodo-2-(4-methoxybenzyl)-2H-pyrazolo[3,4-c]quinoline (0.16 mmol) and 3,4-dimethoxyaniline (2 eq., 0.3 mmol) were suspended in MeOH (dry, 3 mL) in a microwave vial (2-5 mL), HCl in dioxane (4M, 3 drops) was added. The reaction mixture was irradiated in a microwave reactor for 5 min at 140° C. The reaction mixture was evaporated and used without further purification. The reaction mixture was dissolved in 4 ml toluone. Cyclopropylboronic acid (1.3 eq.), potassium phosphate (6 eq.), tricyclohexylphosphine (0.2 eq.) and Palladiumacetate (0.1 eq.) was added. The mixture was heated in a microwave reactor for 30 min at 120° C. The reaction mixture was evaporated and used without further purification. The residue was dissolved in TFA (3 mL). The reaction mixture was irradiated in a microwave reactor for 5 min at 140° C. The reaction mixture was concentrated and purified by semi-preparative HPLC-MS and freeze dried from water/t-BuOH 4/1.

exact mass: 360.1883 g/mol
HPLC-MS: analytical method A
rt: 4.97 min—found mass: 361.4 (m/z+H)

Biological Data
SYK Activities:
IC50 lower than 10 nM:
Example 47; Example 55; Example 62; Example 67; Example 77; Example 114; Example 115; Example 154; Example 155; Example 172; Example 173; Example 180; Example 203; Example 211; Example 221; Example 310; Example 312; Example 327; Example 344; Example 349;
IC50 between 10 nM and 100 nM:
Example 48; Example 64; Example 65; Example 66; Example 80; Example 103; Example 111; Example 112; Example 113; Example 118; Example 119; Example 120; Example 143; Example 151; Example 152; Example 153; Example 158; Example 159; Example 160; Example 167; Example 168; Example 169; Example 178; Example 179; Example 182; Example 184; Example 186; Example 187; Example 189; Example 190; Example 192; Example 193;

Example 195; Example 197; Example 206; Example 208; Example 236; Example 261; Example 262; Example 263; Example 264; Example 287; Example 292; Example 293; Example 295; Example 297; Example 301; Example 303; Example 309; Example 314; Example 315; Example 316; Example 317; Example 323; Example 324; Example 329; Example 332; Example 334; Example 348; Example 352; Example 354; Example 355;

IC50 between 100 nM and 1000 nM:

Example 1; Example 3; Example 6; Example 10; Example 21; Example 22; Example 46; Example 49; Example 54; Example 56; Example 57; Example 73; Example 74; Example 76; Example 78; Example 79; Example 81; Example 83; Example 85; Example 86; Example 98; Example 101; Example 102; Example 108; Example 109; Example 116; Example 117; Example 125; Example 126; Example 138; Example 141; Example 142; Example 148; Example 149; Example 156; Example 157; Example 170; Example 171; Example 175; Example 183; Example 188; Example 191; Example 196; Example 198; Example 199; Example 201; Example 204; Example 218; Example 224; Example 226; Example 227; Example 228; Example 229; Example 231; Example 232; Example 233; Example 246; Example 247; Example 248; Example 249; Example 253; Example 256; Example 257; Example 258; Example 259; Example 285; Example 286; Example 288; Example 289; Example 290; Example 291; Example 294; Example 298; Example 299; Example 300; Example 302; Example 307; Example 311; Example 313; Example 321; Example 328; Example 331; Example 333; Example 339; Example 340; Example 341; Example 353;

LRRK2 Activities:

IC50 lower than 10 nM:

Example 40; Example 47; Example 77; Example 102; Example 103; Example 114; Example 115; Example 116; Example 117; Example 118; Example 120; Example 142; Example 143; Example 154; Example 155; Example 156; Example 157; Example 158; Example 160; Example 178; Example 181; Example 182; Example 183; Example 184; Example 185; Example 186; Example 187; Example 193; Example 195; Example 199; Example 201; Example 203; Example 204; Example 208; Example 211; Example 213; Example 214; Example 218; Example 219; Example 220; Example 223; Example 224; Example 226; Example 227; Example 233; Example 247; Example 253; Example 254; Example 255; Example 256; Example 257; Example 261; Example 262; Example 263; Example 264; Example 265; Example 269; Example 270; Example 286; Example 287; Example 299; Example 301; Example 309; Example 310; Example 324; Example 327; Example 340; Example 348; Example 353; Example 37; Example 92; Example 132; Example 179; Example 198; Example 206; Example 221; Example 236; Example 258; Example 259; Example 180;

IC50 between 10 nM and 100 nM:

Example 1; Example 3; Example 6; Example 9; Example 14; Example 15; Example 16; Example 17; Example 18; Example 19; Example 20; Example 21; Example 26; Example 27; Example 32; Example 34; Example 38; Example 39; Example 43; Example 44; Example 46; Example 48; Example 49; Example 55; Example 57; Example 59; Example 61; Example 62; Example 63; Example 64; Example 65; Example 66; Example 67; Example 68; Example 69; Example 71; Example 73; Example 74; Example 76; Example 78; Example 79; Example 80; Example 81; Example 83; Example 84; Example 85; Example 93; Example 98; Example 101; Example 108; Example 109; Example 111; Example 112; Example 113; Example 124; Example 125; Example 133; Example 138; Example 141; Example 148; Example 149; Example 151; Example 152; Example 153; Example 168; Example 169; Example 172; Example 173; Example 175; Example 188; Example 189; Example 190; Example 191; Example 192; Example 196; Example 197; Example 200; Example 205; Example 207; Example 209; Example 210; Example 215; Example 216; Example 217; Example 222; Example 225; Example 228; Example 229; Example 230; Example 231; Example 232; Example 235; Example 237; Example 241; Example 242; Example 243; Example 244; Example 246; Example 248; Example 249; Example 266; Example 271; Example 272; Example 273; Example 274; Example 275; Example 276; Example 279; Example 281; Example 285; Example 288; Example 289; Example 290; Example 292; Example 293; Example 296; Example 297; Example 298; Example 300; Example 305; Example 308; Example 311; Example 312; Example 313; Example 314; Example 315; Example 316; Example 317; Example 319; Example 321; Example 323; Example 328; Example 331; Example 332; Example 333; Example 334; Example 339; Example 342; Example 343; Example 344; Example 349; Example 352;

IC50 between 100 nM and 1000 nM:

Example 2; Example 4; Example 5; Example 7; Example 10; Example 11; Example 12; Example 13; Example 22; Example 23; Example 24; Example 25; Example 28; Example 29; Example 30; Example 31; Example 33; Example 35; Example 36; Example 45; Example 50; Example 53; Example 56; Example 58; Example 60; Example 72; Example 86; Example 87; Example 88; Example 89; Example 90; Example 91; Example 94; Example 95; Example 96; Example 97; Example 99; Example 100; Example 104; Example 105; Example 106; Example 107; Example 119; Example 122; Example 126; Example 127; Example 128; Example 129; Example 130; Example 131; Example 134; Example 135; Example 136; Example 137; Example 139; Example 140; Example 144; Example 145; Example 146; Example 147; Example 159; Example 162; Example 164; Example 167; Example 170; Example 171; Example 174; Example 194; Example 202; Example 234; Example 239; Example 240; Example 250; Example 251; Example 267; Example 268; Example 282; Example 302; Example 303; Example 304; Example 306; Example 307; Example 318; Example 320; Example 322; Example 325; Example 326; Example 329; Example 335; Example 336; Example 337; Example 347; Example 350.

The invention claimed is:

1. A compound of formula (II), (IIIa) and/or (IIIb) wherein n is 1, 2, 3 or 4;
groups $R^2$ are independently selected from —OMe, —SOMe, —SO$_2$Me, cyclopropyl, methyl and —SMe; and PG is a 4-methoxy benzyl group or a carboxybenzyl group

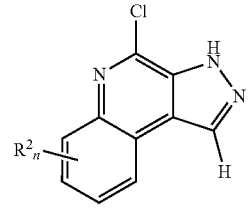

(II)

-continued

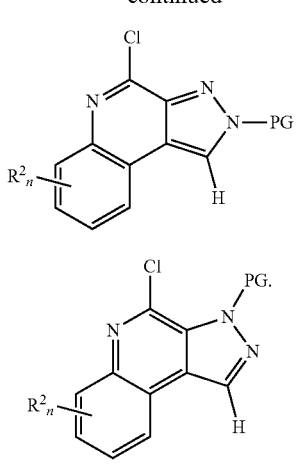

(IIIa)

(IIIb)

2. The compound of claim 1 which is selected from the group consisting of: 4-chloro-8-(methylthio)-2H-pyrazolo[3,4-c]quinoline; 4-chloro-7-(methylthio)-2H-pyrazolo[3,4-c]quinoline; 4-chloro-9-(methylthio)-2H-pyrazolo[3,4-c]quinoline; 4-chloro-8-(methylsulfonyl)-2H-pyrazolo[3,4-c]quinoline; 4-chloro-8-methyl-2H-pyrazolo[3,4-c]quinoline; 4-chloro-9-methyl-2H-pyrazolo[3,4-c]quinoline; 4-chloro-9-(methylsulfonyl)-2H-pyrazolo[3,4-c]quinoline; 4-chloro-7-(methylsulfonyl)-2H-pyrazolo[3,4-c]quinoline; 4-chloro-2-(4-methoxybenzyl)-8-(methylthio)-2H-pyrazolo[3,4-c]quinoline; 4-chloro-2-(4-methoxybenzyl)-7-(methylthio)-2H-pyrazolo[3,4-c]quinoline; 4-chloro-2-(4-methoxybenzyl)-9-(methylthio)-2H-pyrazolo[3,4-c]quinoline; 4-chloro-2-(4-methoxybenzyl)-8-(methylsulfonyl)-2H-pyrazolo[3,4-c]quinoline; 4-chloro-2-(4-methoxybenzyl)-8-methyl-2H-pyrazolo[3,4-c]quinoline; 4-chloro-2-(4-methoxybenzyl)-9-methyl-2H-pyrazolo[3,4-c]quinoline; 4-chloro-2-(4-methoxybenzyl)-9-(methylsulfonyl)-2H-pyrazolo[3,4-c]quinoline; and 4-chloro-2-(4-methoxybenzyl)-7-(methylsulfonyl)-2H-pyrazolo[3,4-c]quinoline.

3. The compound of claim 1 which is selected from the group consisting of: 4-chloro-7-(methylthio)-2H-pyrazolo[3,4-c]quinoline and 4-chloro-2-(4-methoxybenzyl)-7-(methylthio)-2H-pyrazolo[3,4-c]quinoline.

4. The compound of claim 1, wherein n is 1.

5. The compound of claim 1, wherein $R^2$ is selected from —OMe, —SOMe, —SO$_2$Me, cyclopropyl, methyl and —SMe.

6. The compound of claim 1, wherein $R^2$ is selected from —SOMe, —SO$_2$Me, cyclopropyl, methyl and —SMe.

7. The compound of claim 1, wherein $R^2$ is —SO$_2$Me.

* * * * *